United States Patent
Davies et al.

(10) Patent No.: US 11,299,467 B2
(45) Date of Patent: Apr. 12, 2022

(54) CHEMICAL COMPOUNDS

(71) Applicant: Antabio SAS, Labege (FR)

(72) Inventors: David Thomas Davies, Labege (FR); Simon Leiris, Labege (FR); Nicolas Sprynski, Labege (FR); Martin Everett, Labege (FR); Magdalena Zalacain, West Chester, PA (US)

(73) Assignee: ANTABIO SAS, Labege (FR)

( * ) Notice: Subject to any disclaimer, the term of this patent is extended or adjusted under 35 U.S.C. 154(b) by 0 days.

(21) Appl. No.: 16/631,218

(22) PCT Filed: Jul. 20, 2018

(86) PCT No.: PCT/EP2018/069827
§ 371 (c)(1),
(2) Date: Jan. 15, 2020

(87) PCT Pub. No.: WO2019/016393
PCT Pub. Date: Jan. 24, 2019

(65) Prior Publication Data
US 2020/0339526 A1  Oct. 29, 2020

(30) Foreign Application Priority Data

| Jul. 21, 2017 | (EP) | 17305973 |
| Jan. 8, 2018 | (EP) | 18290003 |
| Jan. 9, 2018 | (EP) | 18150903 |

(51) Int. Cl.
C07D 277/587 (2006.01)
A61K 31/407 (2006.01)
A61K 31/437 (2006.01)

(52) U.S. Cl.
CPC ........ C07D 277/587 (2013.01); A61K 31/407 (2013.01); A61K 31/437 (2013.01)

(58) Field of Classification Search
None
See application file for complete search history.

(56) References Cited

U.S. PATENT DOCUMENTS

| 2002/0019527 A1 | 2/2002 | Wang et al. |
| 2004/0259877 A1 | 12/2004 | Muto et al. |
| 2012/0323010 A1 | 12/2012 | Ronsheim et al. |
| 2016/0272641 A1 | 9/2016 | Abe et al. |

FOREIGN PATENT DOCUMENTS

| GB | 2533136 A | 6/2016 |
| WO | 2001081316 A2 | 11/2001 |
| WO | 2002000651 A2 | 1/2002 |
| WO | 2002051810 A2 | 7/2002 |
| WO | 2003097644 A2 | 11/2003 |
| WO | 2005005421 A1 | 1/2005 |
| WO | 2007008917 A2 | 1/2007 |
| WO | 2009030887 A2 | 3/2009 |
| WO | 2009064747 A2 | 5/2009 |
| WO | 2009064752 A2 | 5/2009 |
| WO | 2009091856 A2 | 7/2009 |
| WO | 2009094224 A1 | 7/2009 |
| WO | 2009118596 A2 | 10/2009 |
| WO | 2009152356 A2 | 12/2009 |
| WO | 2010029300 A1 | 3/2010 |
| WO | 2010081172 A1 | 7/2010 |
| WO | 2010084402 A2 | 7/2010 |
| WO | 2011005330 A1 | 1/2011 |
| WO | 2011084882 A2 | 7/2011 |
| WO | 2011121505 A1 | 10/2011 |
| WO | 2013038330 A1 | 3/2013 |
| WO | 2013123444 A1 | 8/2013 |

(Continued)

OTHER PUBLICATIONS

Grant & Hackh's Chemical Dictionary (5th Ed. 1987) at p. 148.*
Chemical Abstract Registry No. 1808893-97-1, indexed in the Registry File on STN CAS Online Sep. 29, 2015.*
Ball et al., "Development of a Manufacturing Route to Avibactam, a beta-Lactamase Inhibitor," Organic Process Research & Development, vol. 20, No. 10, pp. 1799-1805 (2016).
Hamada, Y., "Novel prodrugs with a spontaneous cleavable guanidine moiety," Bioorganic & Medicinal Chemistry Letters, vol. 26, pp. 1685-1689 (2016).

(Continued)

Primary Examiner — Po-Chih Chen
(74) Attorney, Agent, or Firm — Panitch Schwarze Belisario & Nadel LLP; Lars H. Genieser

(57) ABSTRACT

The invention relates to a compound which is a thiazole derivative of Formula (I), or a pharmaceutically acceptable salt thereof, wherein $R^1$, $R^2$, $R^3$, $R^4$, $R^5$, $R^6$, $R^7$, Formula (A), Z, L, X, m, n and p are as defined herein. The compounds are useful in the treatment and prevention of bacterial infection. The invention also relates to combinations of the compound of Formula (I) with further active agents.

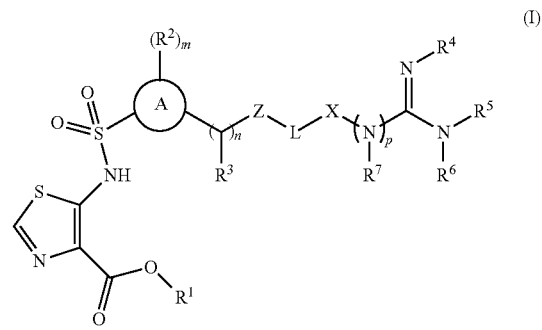

28 Claims, 2 Drawing Sheets

(56) References Cited

FOREIGN PATENT DOCUMENTS

| WO | 2014040077 A1 | 3/2014 |
|----|---------------|--------|
| WO | 2014062938 A1 | 4/2014 |
| WO | 2014091268 A1 | 6/2014 |
| WO | 2014144606 A2 | 9/2014 |
| WO | 2014181287 A1 | 11/2014 |
| WO | 2014190199 A1 | 11/2014 |
| WO | 2014198849 A1 | 12/2014 |
| WO | 2015110885 A1 | 7/2015 |
| WO | 2015114595 A1 | 8/2015 |
| WO | 2015138895 A1 | 9/2015 |

OTHER PUBLICATIONS

Park et al., "Discovery of an Orally Bioavailable Small Molecule Inhibitor of Prosurvival B-Cell Lymphoma 2 Proteins," J. Med. Chem., vol. 51, pp. 6902-6915 (2008).

Patel et al., "Synthesis and antimicrobial evaluation of guanylsulfonamides," Bioorganic & Medicinal Chemistry Letters, vol. 17, pp. 6610-6614 (2007).

Tangden et al., "Global dissemination of extensively drug-resistant carbapenemase-producing Enterobacteriaceae: clinical perspectives on detection, treatment and infection control," Journal of Internal Medicine, vol. 277, pp. 501-512 (2015).

* cited by examiner

CHEMICAL COMPOUNDS

CROSS-REFERENCE TO RELATED APPLICATIONS

This application is a Section 371 of international Application No. PCT/EP2018/069827, filed Jul. 20, 2018, which was published in the English language on Jan. 24, 2019 as International Publication No. WO 2019/016393 A1, which claims priority under 35 U.S.C. § 119(b) to European Application No. 17305973.4, filed Jul. 21, 2017, and European Application No. 18290003.5, filed Jan. 8, 2018, and European Application No. 18150903.5, filed Jan. 9, 2018.

FIELD OF THE INVENTION

The present invention relates to compounds which are thiazole derivatives. The compounds of the invention find use in the prevention or treatment of bacterial infection.

The invention also provides such compounds per se and pharmaceutical compositions comprising such compounds. The compounds of the invention are useful as inhibitors of metallo-β-lactamase (MBL) enzymes. The compounds of the invention can be used in combination therapy, for example in combination with one or more antibiotic agents and optionally with one or more inhibitors of serine-β-lactamase (SBL) enzymes. Such combination therapy has particular applications in prevention or treatment of bacterial infection caused by bacteria which are resistant to treatment by antibiotic agents when administered alone, especially when the resistance is attributable to the presence of metallo-β-lactamase and/or serine-β-lactamase enzymes and treatment with β-lactam antibiotics alone may be unsuccessful. In such cases the combination therapy can rescue the antibacterial activity of the β-lactam antibiotic.

BACKGROUND

Bacteria in both clinical and non-clinical settings are becoming increasingly resistant to conventional antibiotics, and this resistance is becoming a serious clinical and epidemiological problem for human health. For example, it has been shown that single amino acid mutations in bacterial DNA-dependent RNA-polymerase can reduce the binding affinity of this target enzyme for antibiotics, leading to a high frequency of resistance (FoR). One approach to addressing FoR that has been previously considered is to develop a single agent that inhibits two related bacterial enzymes. Examples of such agents include gepotidacin, which inhibits two similar DNA-processing components of Topoisomerase II and IV enzymes, (GyrA and ParC) and zoliflodacin, which inhibits two similar ATP-hydrolysing components of Topoisomerase II and IV enzymes (GyrB and ParE). However, this approach is not always suitable for addressing other forms of resistance, for example when microbial resistance to an antibiotic arises through production of a bacterial enzyme able to deactivate the antibacterial drug.

In Gram-negative bacteria, resistance to antibiotics (particularly β-lactam antibiotics) often arises from the production by the organism of β-lactamases. β-Lactamase enzymes include both metallo-β-lactamases (MBL) and serine-β-lactamases (SBL). Serine β-lactamase enzymes use an active serine to hydrolyse β-lactam rings in a covalent mechanism while the structurally different metallo-β-lactamase enzymes use Zn metal coordination and a hydroxide ion to hydrolyse the β-lactam ring. In the field of bacterial β-lactamase enzymes, in particular the Gram-negative area and more particular the Enterobacteriaceae, the older serine-β-lactamase enzymes have been supplemented by the more recently-evolved metallo-β-lactamases. Resistance of gram-negative bacteria to β-lactam antibiotics therefore especially arises from the production by the organism of two types of β-lactamases.

As discussed above, in gram-negative bacteria, resistance to antibiotics often arises from the production by the organism of β-lactamases, especially metallo-β-lactamases (MBL). MBL are resistance determinants of increasing clinical relevance. In fact, because of their broad range, potent carbapenemase activity and resistance to inhibitors, these enzymes can confer resistance to almost all β-lactam antibiotics.

MBLs were first detected in the mid-1960s as carried by mobile DNA elements in species with only low pathogenic potential. However, genes encoding MBL spread among major Gram-negative bacteria during the 1990s and this has led to a health crisis arising from the international dissemination of carbapenem-resistant Enterobacteriaceae producing the VIM-type and NDM-type metallo-β-lactamases.

Functional features of these Enterobacteriaceae include potent carbapenemase activity and resistance to clinical β-lactamase inhibitors (clavulanate and sulfones). The activity against β-lactams differs between the different metallo-β-lactamases, and substrate specificity might vary from a narrow range (eg, the CphA metallo-β-lactamase of *Aeromonas hydrophila*), to an extended range (eg, the VIM-type metallo-β-lactamases, which can degrade almost all classes of β-lactams apart from the monobactams).

There are three major structural subclasses of MBL which share substantial internal diversity. Members of the different subclasses differ not only in their high degree of sequence diversity, but also in the structure of their active sites. In enzymes of subclasses B1 and B3, the active site contains two zinc ions; in members of subclass B2, the active site contains only one zinc ion.

Acquired metallo-β-lactamases have been detected in strains of Enterobacteriaceae, *Pseudomonas aeruginosa*, *Acinetobacter baumannii*, and other Gram-negative bacteria. Among acquired MBL, almost all the enzymes belong to subclass B1, which indicates an overall higher propensity for members of this subclass to be captured and spread with mobile genetic elements than for members of subclasses B2 and B3.

As an example, the subclass B1 comprises the IMP-type, the VIM-type, and the NDM-type enzymes.

The IMP-type enzymes, including IMP-1, were first detected in Japan in the late 1980s, and have since been reported worldwide in Enterobacteriaceae and in Gram-negative bacteria. The IMP-type enzymes have broad substrate specificity with a high affinity for cephalosporins and carbapenems, but they have little activity against Temocillin.

The VIM-type enzymes, including VIM-2, were first discovered in Europe in the late 1990s and have since been reported worldwide. VIM-type enzymes were initially detected in *P. aeruginosa* and in other Gram-negative bacteria, but have since emerged in Enterobacteriaceae, and have become a major problem in some settings. More than 20 different VIM allotypes are known, each with a defined geographical distribution except for VIM-1 and VIM-2, which share a broader distribution than the IMP-type enzymes. The VIM-type metallo-β-lactamases show even broader substrate specificities than the IMP-types, being able to hydrolyse 6-α-methoxy-penicillins. Furthermore, the VIM-type enzymes are unique in the metallo-β-lactamases in that they have a high affinity for carbapenems.

New Delhi metallo-β-lactamase 1 (NDM-1) is a novel metallo-β-lactamase identified initially in a patient hospitalized in New Delhi with an infection caused by *Klebsiella pneumoniae*. Subsequently, organisms in the Enterobacteriaceae family containing this new β-lactamase have been found widely distributed throughout India, Pakistan, and Bangladesh and are now occurring in the United Kingdom and in many other countries. The New Delhi metallo-β-lactamase 1 (NDM-1) is a polypeptide of 158 amino acids in length (Accession number AB571289) capable of hydrolyzing a wide range of β-lactam antibiotics including penicillins, cephalosporins and carbapenem antibiotics that are a mainstay for the treatment of antibiotic-resistant bacterial infections.

Accordingly, there is an urgent need for new antibacterial compounds and compositions and adjuvant therapies for treating bacterial infection, in particular bacterial infection caused by bacteria which express MBL enzymes. There is also an urgent need for new compositions for treating bacterial infection by bacteria which exhibit high resistance, particularly when resistance to antibiotic agents (especially β-lactam antibiotic agents) arises through production by the bacteria of one or more enzyme able to deactivate the antibacterial drug. The present invention aims to address some or all of these issues.

SUMMARY OF THE INVENTION

Previously, the inventors reported in WO 2014/198849 that certain thiazole derivatives are inhibitors of metallo-β-lactamases, including NDM-1. The inventors have now surprisingly found that compounds of Formula (I) are potent inhibitors of metallo-β-lactamases, including NDM-1, and have improved properties compared to the compounds disclosed in WO 2014/198849. The compounds therefore are useful in treating and preventing bacterial infection, for example by use in combination with β-lactam antibiotics.

The inventors have also found that the compounds of Formula (I) can advantageously be used in combination with inhibitors of serine-β-lactamase enzymes and other antibiotic agents such as β-lactam antibiotics e.g. carbapenem antibiotics. Such combination therapies have particular relevance in the prevention or treatment of bacterial infection caused by bacteria which exhibit a high degree of resistance to the antibiotic agents when administered alone, especially when the bacterial infection is caused by bacteria which produce β-lactamase enzymes.

Accordingly, the invention provides a compound which is a thiazole derivative according to Formula (I), or a pharmaceutically acceptable salt thereof,

[FORMULA (I)]

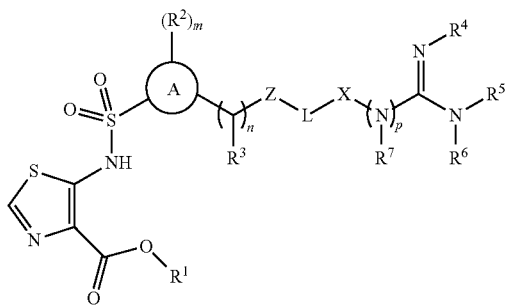

wherein
$R^1$ is selected from H, $R^{1a}$ and —$CH_2OC(O)R^{1a}$, wherein $R^{1a}$ is selected from an unsubstituted $C_1$ to $C_4$ alkyl group and phenyl;

Ⓐ is a cyclic group selected from $C_6$ to $C_{10}$ aryl, 5- to 10-membered heteroaryl, and 4- to 10-membered carbocyclic and heterocyclic groups;

each $R^2$ is independently selected from:
(i) halo or $R^8$.
(ii) $C_{1-3}$ alkyl, $O(C_{1-3}$ alkyl), $S(C_{1-3}$ alkyl), $SO(C_{1-3}$ alkyl) or $SO_2(C_{1-3}$ alkyl), any of which may optionally be substituted with 1, 2 or 3 halo substituents and/or one $R^8$ substituent; and
(iii) $NR^aC(O)R^c$, and $NR^aC(O)NR^bR^c$, wherein each $R^a$ and $R^b$ is independently selected from hydrogen and unsubstituted $C_{1-2}$ alkyl and each $R^c$ is unsubstituted $C_{1-2}$ alkyl;

and
each $R^8$ is independently selected from CN, OH, —$C(O)NR^fR^g$, —$NR^fR^g$, —$NR^{10}C(NR^{11})R^{12}$, —$C(NR^{10})NR^{11}R^{12}$, and —$NR^{10}C(NR^{11})NR^{12}R^{13}$; wherein each of $R^f$ and $R^g$ is independently H or unsubstituted $C_{1-2}$ alkyl;

m is 0, 1, 2 or 3
$R^3$ is selected from hydrogen and a $C_1$ to $C_3$ alkyl group which is unsubstituted or is substituted with 1, 2 or 3 substituents selected from halogen, —$OR^{10}$, and —$NR^{10}R^{11}$;

n is 0 or 1
Z is a bond or is selected from —$NR^{10}C(O)$—, —$C(O)NR^{10}$—, —$NR^{10}C(O)NR^{11}$—, —$NR^{10}C(O)O$—, —$OC(O)NR^{10}$—, —$NR^{10}C(O)S$—, —$SC(O)NR^{10}$—, —$NR^{10}C(NR^{11})$—, —$C(NR^{10})NR^{11}$—, —$NR^{10}C(NR^{11})NR^{12}$—, —$NR^{10}C(N^+R^{11}R^{12})$—, —$C(N^+R^{10}R^{11})NR^{12}$—, —$NR^{10}C(N^+R^{11}R^{12})NR^{13}$—, —$NR^{10}C(NR^{11})O$—, —$OC(NR^{10})NR^{11}$, —$NR^{10}C(N^+R^{11}R^{12})O$—, —$OC(N^+R^{10}R^{11})NR^{12}$—, —$NR^{10}C(NR^{11})S$—, —$SC(NR^{10})NR^{11}$, —$NR^{10}C(N^+R^{11}R^{12})S$—, —$SC(N^+R^{10}R^{11})NR^{12}$—, —$C(O)NR^{15}$—, —$NR^{10}C(O)NR^{15}$—, —$OC(O)NR^{15}$, —$SC(O)NR^{15}$, —$C(NR^{10})NR^{15}$—, —$NR^1C(NR^{11})NR^{15}$—, —$C(N^+R^{10}R^{11})NR^{15}$—, —$NR^{10}C(N^+R^{11}R^{12})NR^{15}$—, —$OC(NR^{10})NR^{15}$, —$OC(N^+R^{10}R^{11})NR^{15}$—, —$SC(NR^{10})NR^{15}$, and —$SC(N^+R^{10}R^{11})NR^{15}$—;

L is a bond or is selected from $C_{1-4}$ alkylene, $C_{2-4}$ alkenylene, $C_{2-4}$ alkynylene, $C_{1-3}$ alkylene-($C_{3-6}$cycloalkylene)-$C_{1-3}$ alkylene, $C_{1-4}$ alkylene-($C_{3-6}$cycloalkylene) and ($C_{3-6}$cycloalkylene)-$C_{1-4}$ alkylene, wherein L is unsubstituted or is substituted with 1 or 2 substituents selected from halogen, —$OR^{10}$, and —$NR^{10}R^{11}$; or L is —$C(R^{10})$=N—;

X is a bond or, when L is other than a bond or —$C(R^{10})$=N—, X is a bond or is selected from —$NR^{10}$—, —O—, —$NR^{10}C(NR^{11})$—, and —$C(NR^{10})$—;

p is 0 or 1;
$R^4$ is selected from H, —CN and $C_1$ to $C_3$ alkyl which is unsubstituted or is substituted with 1, 2 or 3 substituents selected from halogen, —$OR^{10}$, —$NR^{10}R^{11}$, and —CN;

or $R^4$ is joined together with $R^5$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted $C_1$ to $C_2$ alkyl, halogen, —$OR^{10}$, —$NR^{10}R^{11}$, and —CN;

$R^5$ is selected from H, —CN and $C_1$ to $C_3$ alkyl which is unsubstituted or is substituted with 1, 2 or 3 substituents selected from halogen, —$OR^{10}$, —$NR^{10}R^{11}$, and —CN;

or $R^5$ is joined together with $R^4$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted $C_1$ to $C_2$ alkyl, halogen, —$OR^{10}$, —$NR^{10}R^{11}$, and —CN;

or $R^5$ is joined together with $R^6$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted $C_1$ to $C_2$ alkyl, halogen, —$OR^{10}$, —$NR^{10}R^{11}$, and —CN;

$R^6$ is selected from H, —CN and $C_1$ to $C_3$ alkyl which is unsubstituted or is substituted with 1, 2 or 3 substituents selected from halogen, —$OR^{10}$, —$NR^{10}R^{11}$, and —CN;

or $R^6$ is joined together with $R^5$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted $C_1$ to $C_2$ alkyl, halogen, —$OR^{10}$, —$NR^{10}R^{11}$, and —CN;

or $R^6$ is joined together with $R^7$ if present to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted $C_1$ to $C_2$ alkyl, halogen, —$OR^{10}$, —$NR^{10}R^{11}$, and —CN;

$R^7$ if present is selected from H, —CN and $C_1$ to $C_3$ alkyl which is unsubstituted or is substituted with 1, 2 or 3 substituents selected from halogen, —$OR^{10}$, —$NR^{10}R^{11}$, and —CN;

or $R^7$ is joined together with $R^6$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted $C_1$ to $C_2$ alkyl, halogen, —$OR^{10}$, —$NR^{10}R^{11}$, and —CN;

each $R^{10}$, $R^{11}$, $R^{12}$, $R^{13}$ and $R^{14}$ is independently H or methyl;

each $R^{15}$ is independently substituted $C_1$ to $C_4$ alkyl or unsubstituted $C_2$ to $C_4$ alkyl, wherein when $R^{15}$ is a substituted alkyl group the alkyl group is substituted with 1, 2 or 3 substituents independently selected from halogen, CN, $OR^{10}$ and —$NR^{10}R^{11}$.

The invention also provides a compound of Formula (I) wherein $R^1$, (A), $R^2$, m, $R^3$, n, L, X, p, $R^4$, $R^5$, $R^6$, $R^7$ (if present), $R^{10}$, $R^{11}$, $R^{12}$, $R^{13}$ and $R^{14}$ are as defined herein;

Z is a bond or is selected from —$NR^{10}C(O)$—, —$C(O)NR^{10}$—, —$NR^{10}C(O)NR^{11}$—, —$NR^{10}C(O)O$—, —$OC(O)NR^{10}$, —$NR^{10}C(O)S$—, —$SC(O)NR^{10}$, —$NR^{10}C(NR^{11})$—, —$C(NR^{10})NR^{11}$—, —$NR^{10}C(NR^{11})NR^{12}$—, —$NR^{10}C(N^+R^{11}R^{12})$—, —$C(N^+R^{10}R^{11})NR^{12}$—, —$NR^{10}C(N^+R^{11}R^{12})NR^{13}$—, —$NR^{10}C(NR^{11})O$—, —$OC(NR^{10})NR^1$, —$NR^{10}C(N^+R^{11}R^{12})O$—, —$OC(N^+R^{10}R^{11})NR^{12}$—, —$NR^{10}C(NR^{11})S$—, —$SC(NR^{10})NR^{11}$, —$NR^{10}C(N^+R^{11}R^{12})S$—, and —$SC(N^+R^{10}R^{11})NR^{12}$—; and $R^{15}$ is absent.

The present invention also provides a pharmaceutical composition comprising a compound as described herein and optionally further comprising an antibiotic agent. The pharmaceutical composition typically comprises a compound as described herein together with at least one pharmaceutically acceptable carrier or diluent and optionally further comprises (i) an antibiotic agent and/or (ii) a serine-β-lactamase inhibitor. Also provided is a product comprising a compound as described herein in combination with an antibiotic agent.

The invention also provides a compound as described herein for use in the treatment or prevention of bacterial infection in a subject in need thereof. Also provided is a method for treating or preventing bacterial infection in a subject, which method comprises administering to said subject an effective amount of a compound as described herein. Further provided is the use of a compound as described herein in the manufacture of a medicament for use in treating or preventing bacterial infection in a subject.

The invention also provides a product comprising a compound as described herein together with a serine-β-lactamase inhibitor and an antibiotic agent. The product may be used in the treatment or prevention of bacterial infection in a subject in need thereof, particularly when the bacterial infection is caused by bacteria which are resistant to treatment by the antibiotic agent when administered alone, and especially when the resistance is attributable to the presence of metallo-β-lactamase and/or serine-β-lactamase enzymes. In patients suffering from or susceptible to infection by such bacteria, treatment with β-lactam antibiotics alone may be unsuccessful.

DETAILED DESCRIPTION OF THE INVENTION

Definitions

Figure 1:
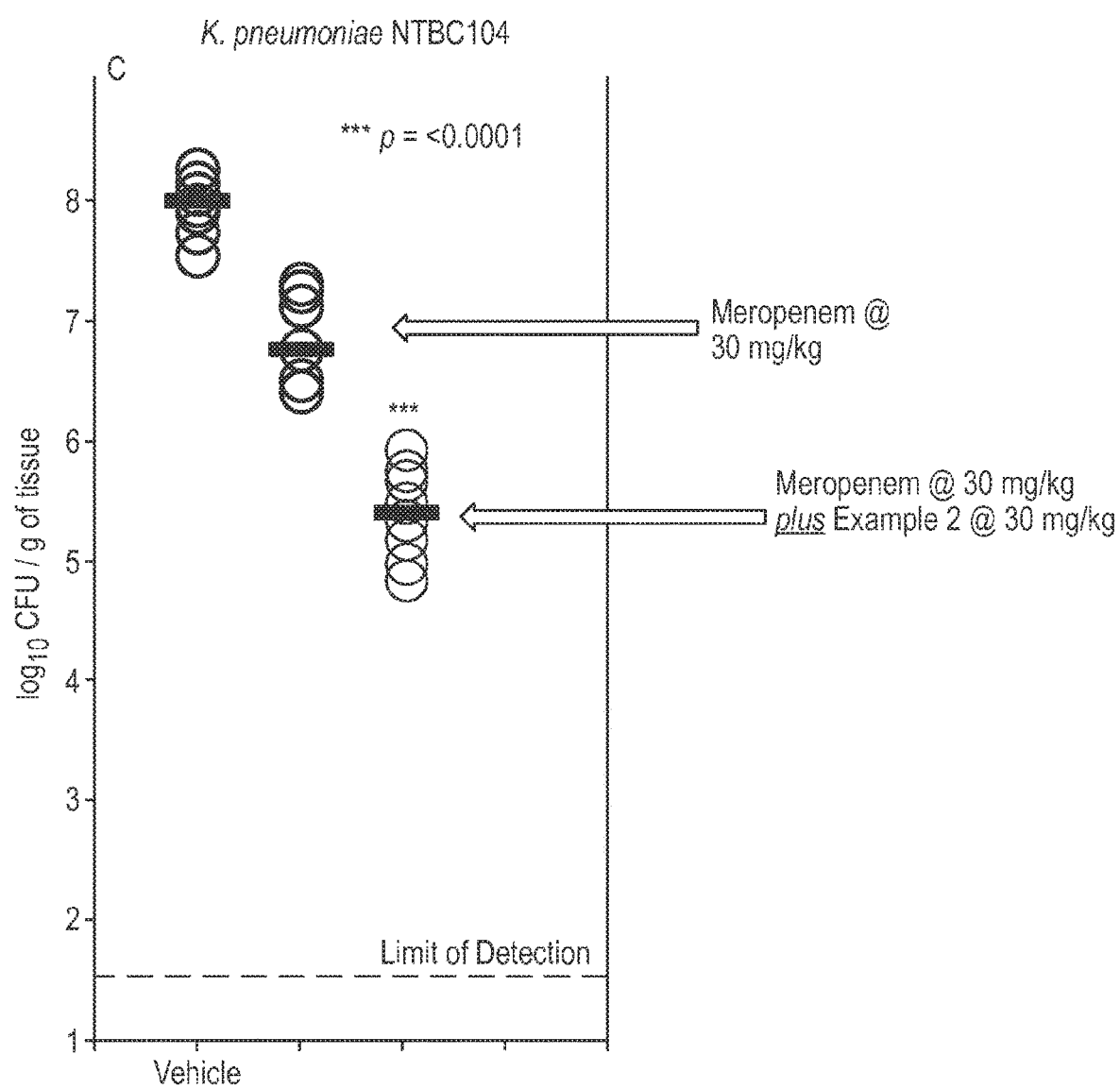
FIG. 1 shows the results of in vivo efficacy studies conducted using the compound of Example 2 described herein in a mouse model. Data show the suppression of bacterial infection by *K. pneumonia* NTBC104 in mice by meropenem alone compared to [meropenem+Example 2]. Meropenem at 30 mg/kg reduced bacterial load slightly whereas meropenem at 30 mg/kg plus Example 2 at 30 mg/kg significantly reduced the bacterial load compared to meropenem alone, showing a 1.6 $Log_{10}$ reduction in CFUs.

As used herein, a $C_1$ to $C_4$ alkyl group is a linear or branched alkyl group containing from 1 to 4 carbon atoms. A $C_1$ to $C_4$ alkyl group is often a $C_1$ to $C_3$ alkyl group or a $C_2$ to $C_4$ alkyl group. Examples of $C_1$ to $C_4$ alkyl groups include methyl, ethyl, n-propyl, iso-propyl, n-butyl, iso-butyl, sec-butyl, and tert-butyl. A $C_1$ to $C_3$ alkyl group is typically a $C_1$ to $C_2$ alkyl group. A $C_1$ to $C_2$ alkyl group is methyl or ethyl, typically methyl. For the avoidance of doubt, where two alkyl groups are present, the alkyl groups may be the same or different.

As used herein, a $C_2$-$C_4$ alkenyl group is a linear or branched alkenyl group containing from 2 to 4 carbon atoms and having one or more, e.g. one or two, typically one double bonds. Typically a $C_2$-$C_4$ alkenyl group is a $C_2$-$C_3$ alkenyl group. Examples of $C_2$-$C_4$ alkenyl groups include ethenyl, propenyl and butenyl. For the avoidance of doubt, where two alkenyl groups are present, the alkenyl groups may be the same or different.

As used herein, a $C_2$-$C_4$ alkynyl group is a linear or branched alkynyl group containing from 2 to 4 carbon atoms and having one or more, e.g. one or two, typically one triple bonds. Typically a $C_2$-$C_4$ alkynyl group is a $C_2$-$C_3$ alkynyl group. Examples of $C_2$ to $C_4$ alkynyl groups include ethynyl, propynyl and butynyl. For the avoidance of doubt, where two alkynyl groups are present, the alkynyl groups may be the same or different.

As used herein, a $C_1$ to $C_4$ alkylene group is an unsubstituted or substituted bidentate moiety obtained by removing two hydrogen atoms from a $C_1$ to $C_4$ alkane. The two hydrogen atoms may be removed from the same carbon atom or from different carbon atoms. Typically a $C_1$ to $C_4$ alkylene group is a $C_1$ to $C_3$ alkylene group. Examples of $C_1$ to $C_4$ alkylene groups include methylene, ethylene, n-propylene, iso-propylene, n-butylene, sec-butylene and tert-butylene. A $C_1$ to $C_4$ alkylene group is typically a $C_1$ to $C_2$ alkylene group. A $C_1$ to $C_2$ alkyl group is methylene or ethylene, typically methylene. For the avoidance of doubt, where two alkylene groups are present, the alkylene groups may be the same or different.

As used herein, a $C_2$ to $C_4$ alkenylene group is an unsubstituted or substituted bidentate moiety obtained by removing two hydrogen atoms from a $C_2$ to $C_4$ alkene. The two hydrogen atoms may be removed from the same carbon atom or from different carbon atoms. Typically a $C_2$ to $C_4$ alkenylene group is a $C_2$ to $C_3$ alkenylene group. Examples of $C_2$ to $C_4$ alkenylene groups include ethenylene, n-propenylene, iso-propenylene, n-butenylene, sec-butenylene and tert-butenylene. A $C_2$ to $C_3$ alkenylene group is typically a $C_2$ alkenylene, i.e. ethenylene. For the avoidance of doubt, where two alkenylene groups are present, the alkenylene groups may be the same or different.

As used herein, a $C_2$ to $C_4$ alkynylene group is an unsubstituted or substituted bidentate moiety obtained by removing two hydrogen atoms from a $C_2$ to $C_4$ alkyne. The two hydrogen atoms may be removed from the same carbon atom or from different carbon atoms. Typically a $C_2$ to $C_4$ alkynylene group is a $C_2$ to $C_3$ alkynylene group. Examples of $C_2$ to $C_4$ alkynylene groups include ethynylene, n-propynylene, iso-propynylene, n-butynylene, sec-butynylene and tert-butynylene. A $C_2$ to $C_3$ alkynylene group is typically a $C_2$ alkynylene, i.e. ethynylene. For the avoidance of doubt, where two alkynylene groups are present, the alkynylene groups may be the same or different.

An alkyl, alkenyl, alkynyl, alkylene, alkenylene or alkynylene group as used herein may be unsubstituted or substituted. Unless otherwise stated, substituted alkyl, alkenyl or alkynyl groups typically carry one or more, e.g. 1, 2, 3 or 4, such as one, two or three e.g. one, or two, e.g. one substituent selected from halogen, —CN, —$R^8$, —$OR^{10}$, and —$NR^{10}R^{11}$, wherein $R^{10}$ and $R^{11}$ are as defined herein. The substituents on a substituted alkyl, alkenyl or alkynyl group are typically themselves unsubstituted unless otherwise stated. Where more than one substituent is present, these may be the same or different.

As used herein, a halogen is typically chlorine, fluorine, bromine or iodine and is preferably chlorine, bromine or fluorine, especially chorine or fluorine, especially fluorine.

A 3- to 10-membered carbocyclic group is a cyclic hydrocarbon containing from 3 to 10 carbon atoms. A carbocyclic group may be saturated or partially unsaturated, but is typically saturated. A 3- to 10-membered partially unsaturated carbocyclic group is a cyclic hydrocarbon containing from 3 to 10 carbon atoms and containing 1 or 2, e.g. 1 double bond. A 3- to 10-membered carbocyclic group is typically a 4- to 10-membered carbocyclic group. Often, a 3- to 10-membered carbocyclic group is a 3- to 6-membered carbocyclic group, such as a 4- to 6-membered or 5- to 6-membered carbocyclic group. A 3- to 10-membered carbocyclic group may be a fused bicyclic group, as defined herein. A 3- to 10-membered carbocyclic group may be a saturated 4- to 6-membered, preferably 5- or 6-membered carbocyclic group. Examples of 3- to 6-membered saturated carbocyclic groups include cyclopropyl, cyclobutyl, cyclopentyl and cyclohexyl groups.

A 3- to 10-membered heterocyclic group is a cyclic group containing from 3 to 10 atoms selected from C, O, N and S in the ring, including at least one heteroatom, and typically one or two heteroatoms. The heteroatom or heteroatoms are typically selected from O, N, and S, most typically from S and N, especially N. For example, where the heterocyclic group is denoted a nitrogen-containing heterocyclic group, it contains one nitrogen atom and optionally a further heteroatom selected from O, N and S. A heterocyclic group may be saturated or partially unsaturated. A 3- to 10-membered partially unsaturated heterocyclic group is a cyclic group containing from 3 to 10 atoms selected from C, O, N and S in the ring and containing 1 or 2, e.g. 1 double bond.

A 3- to 10-membered heterocyclic group is typically a 4- to 10-membered heterocyclic group. Sometimes a 3- to 10-membered heterocyclic group is a 3- to 6-membered heterocyclic group, such as a monocyclic 4- to 6-membered heterocyclic group or a monocyclic 5- or 6-membered heterocyclic group. Alternatively, a 3- to 10-membered heterocyclic group may be a 9- or 10-membered fused bicyclic heterocyclic group (i.e. a fused heterobicyclic group).

Examples of 5- and 6-membered saturated heterocyclic groups include piperazine, piperidine, morpholine, 1,3-oxazinane, pyrrolidine, imidazolidine, and oxazolidine, including quaternised derivatives thereof, as defined herein. Examples of 5- and 6-membered partially saturated heterocyclic groups include tetrahydropyrazine, tetrahydropyridine, dihydro-1,4-oxazine, tetrahydropyrimidine, dihydro-1,3-oxazine, dihydropyrrole, dihydroimidazole and dihydrooxazole, including quaternised derivatives thereof, as defined herein.

Examples of 9- and 10-membered fused heterobicyclic groups include 9-membered fused heterobicyclic groups such as indoline, 2,3-dihydrobenzofuran, 2,3-dihydrobenzo[b]thiophene, 2,3-dihydro-1H-benzo[d]imidazole, 2,3-dihydrobenzo[d]oxazole, 2,3-dihydrobenzo[d]thiazole, benzo[d][1,3]dioxole, 4,5,6,7-tetrahydrothiazolo[5,4-c]pyridine and 4,5,6,7-tetrahydrothiazolo[4,5-c]pyridine, including quaternised derivatives thereof, as defined herein; and 10-membered heterobicyclic groups such as 1,2,3,4-tetrahydroquinoline, 1,2,3,4-tetrahydroisoquinoline, chromane, isochromane, thiochromane, isothiochromane, 1,2,3,4-tetrahydroquinoxaline, 1,2,3,4-tetrahydroquinazoline, 1,4-dihydro-2H-benzo[d][1,3]oxazine, 3,4-dihydro-2H-benzo[b][1,4]oxazine, 3,4-dihydro-2H-benzo[b][1,4]thiazine, 1,4-dihydro-2H-benzo[d][1,3]thiazine, 4H-benzo[d][1,3]dioxine and 2,3-dihydrobenzo[b][1,4]dioxine, including quaternised derivatives thereof. Often, the fused heterobicyclic group comprises 1, 2 or 3, preferably 1 or 2 nitrogen atoms.

For the avoidance of doubt, references to a heterocyclic group also include fused polycyclic ring systems, including for instance fused bicyclic systems in which a heterocyclic group is fused to an aryl group. When the heterocyclic group is such a fused heterocyclic group, preferred examples are fused ring systems wherein a 5- to 6-membered heterocyclic group is fused to a phenyl group.

As used herein, a $C_3$ to $C_6$ cycloalkylene group (also referred to as a $C_{3-6}$cycloalkylene group) is an unsubstituted or substituted bidentate moiety obtained by removing two hydrogen atoms from a saturated $C_3$ to $C_6$ carbocyclic group as defined herein. The two hydrogen atoms may be removed from the same carbon atom or from different carbon atoms. Examples of $C_{3-6}$cycloalkylene groups include cyclopropylene, cyclobutylene, cyclopentylene and cyclohexylene.

As used herein, a $C_6$ to $C_{10}$ aryl group is a substituted or unsubstituted, monocyclic or fused polycyclic aromatic group containing from 6 to 10 carbon atoms in the ring portion. Examples include monocyclic groups such as phenyl and fused bicyclic groups such as naphthyl and indenyl. Phenyl (benzene) is preferred.

As used herein, a 5- to 10-membered heteroaryl group is a substituted or unsubstituted monocyclic or fused polycyclic aromatic group containing from 5 to 10 atoms in the ring portion, including at least one heteroatom, for example 1, 2 or 3 heteroatoms, typically selected from O, S and N. A heteroaryl group is typically a 5- or 6-membered heteroaryl group or a 9- or 10-membered heteroaryl group, preferably a 5- or 6-membered heteroaryl group. Preferably, the heteroaryl group comprises 1, 2 or 3, preferably 1 or 2 nitrogen atoms.

Examples of 5- and 6-membered heteroaryl groups include pyrrole, furan, thiophene, imidazole, oxazole, thiazole, pyridine, pyridazine, pyrimidine, and pyrazine. Examples of 9- and 10-membered heteroaryl groups include 9-membered heteroaryl groups such as indole, benzothiophene, benzofuran, benzoxazole, benzothiazole, benzimidazole, imidazo[1,2-a]pyridine, [1,2,4]triazolo[1,5-a]pyridine and imidazo[1,2-a]pyrazine, including quaternised derivatives thereof; and 10-membered heteroaryl groups such as quinoline, isoquinoline, quinazoline, and quinoxaline.

For the avoidance of doubt, references to a heteroaryl group also include fused polycyclic ring systems, including for instance fused bicyclic systems in which a heteroaryl group is fused to an aryl group. When the heteroaryl group is such a fused heteroaryl group, preferred examples are fused ring systems wherein a 5- to 6-membered heteroaryl group is fused to a phenyl group.

As used herein, a fused bicyclic group is a group comprising two cyclic moieties sharing a common bond between two atoms.

A carbocyclic, heterocyclic, aryl or heteroaryl group may be unsubstituted or substituted as described herein. For example, a carbocyclic, heterocyclic, aryl or heteroaryl group may be unsubstituted or substituted with 1, 2 or 3, typically 1 or 2 such as e.g. 1 substituent. Suitable substituents include, halogen; —CN; $OR^{10}$ and —$NR^{10}R^{11}$ (wherein $R^{10}$ and $R^{11}$ are as defined herein) unsubstituted $C_1$ to $C_2$ alkyl and $R^2$ as depicted in Formula (I) and defined herein.

The substituents on a substituted carbocyclic, heterocyclic, aryl or heteroaryl group are typically themselves unsubstituted, unless otherwise stated.

Compounds of the invention may comprise heterocyclic or heteroaryl groups comprising at least one nitrogen atom. In such compounds, said nitrogen atom(s) are independently selected from secondary, tertiary and quaternary nitrogen atom(s). A quaternary nitrogen atom is present when the compound comprises a quaternised derivative of one or more monocyclic groups or fused bicyclic groups. As used herein, a quaternised derivative of a moiety such as a cyclic moiety is formed by bonding an additional alkyl group to a nitrogen atom in the moiety such that the valency of the said nitrogen atom increases from 3 to 4 and the nitrogen atom is positively charged.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as oxalic, citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines. Hydrochloride salts and acetate salts are preferred, in particular hydrochloride salts.

In Formula (I), the stereochemistry is not limited. In particular, compounds of Formula (I) containing one or more chiral centre may be used in enantiomerically or diastereoisomerically pure form, or in the form of a mixture of isomers. Further, for the avoidance of doubt, the compounds of the invention may be used in any tautomeric form. Typically, the agent or substance described herein contains at least 50%, preferably at least 60, 75%, 90% or 95% of a compound according to Formula (I) which is enantiomerically or diastereomerically pure. Typically, a compound of the invention comprises by weight at least 60%, such as at least 75%, 90%, or 95% of a single enantiomer or diastereomer. Preferably, the compound is substantially optically pure.

For the avoidance of doubt, the terms 'thiazole derivative' and 'thiazolyl derivative' may be used interchangeably and unless otherwise indicated refer to compounds of the invention, such as compounds of Formula (I).

Compounds of the Invention

Typically, in Formula (I), $R^1$ is selected from H and $R^{1a}$. More preferably, $R^1$ is H. $R^{1a}$ is typically an unsubstituted $C_1$ to $C_4$ alkyl group, such as an unsubstituted $C_1$ to $C_2$ alkyl group. More preferably, $R^{1a}$ is methyl or t-butyl.

In Formula (I), Ⓐ may preferably be a cyclic group selected from $C_6$ to $C_{10}$ aryl and 5- to 10-membered heteroaryl groups. Ⓐ is preferably a cyclic group selected from phenyl, 5- to 6-membered heteroaryl, and 5- to 6-membered carbocyclic and heterocyclic groups. Ⓐ is more preferably selected from phenyl and 5- to 6-membered heteroaryl groups. Still more preferably, Ⓐ is a phenyl.

When Ⓐ is a 5- to 10-membered heteroaryl group, it is preferably a 5- or 6-membered group. When Ⓐ is a 4- to 10-membered heterocyclic or carbocyclic group, it is preferably a 5- or 6-membered group. When Ⓐ is a heterocyclic or heteroaryl group, it preferably contains 1, 2 or 3, preferably 1 or 2 heteroatoms selected from O, N and S. When Ⓐ is a heterocyclic or heteroaryl group, it is preferably a nitrogen-containing group. When Ⓐ is a fused heteroaryl or heterocyclic group, Ⓐ preferably comprises a benzene ring fused to a 5- or 6-membered heterocyclic or heteroaryl group as defined herein.

Preferably, Ⓐ is selected from phenyl, cyclohexane, piperidine, pyridazine, pyridine and thiazole. More preferably, Ⓐ is selected from phenyl, pyridazine, pyridine and thiazole. Still more preferably, Ⓐ is phenyl.

In Formula (I), each $R^2$ is independently selected from:
(i) halo or $R^8$.
(ii) $C_{1-3}$ alkyl, $O(C_{1-3}$ alkyl), $S(C_{1-3}$ alkyl), $SO(C_{1-3}$ alkyl) or $SO_2(C_{1-3}$ alkyl), any of which may optionally be substituted with 1, 2 or 3 halo substituents and/or one $R^8$ substituent; and
(iii) $NR^aC(O)R^c$, and $NR^aC(O)NR^bR^c$, wherein each $R^a$ and $R^b$ is independently selected from hydrogen and unsubstituted $C_{1-2}$ alkyl and each $R^c$ is unsubstituted $C_{1-2}$ alkyl;
wherein $R^8$ is as defined herein.

When an $R^2$ group is according to option (i) above, preferably the group is a halo group. Fluorine is preferred.

When an $R^2$ group is according to option (ii) above, preferably the $C_{1-3}$ alkyl group in the $R^2$ moiety is a $C_{1-2}$ alkyl group, more preferably a $C_1$ alkyl (methyl) group. The $R^2$ group is preferably selected from $C_{1-2}$ alkyl, $O(C_{1-2}$ alkyl), $S(C_{1-2}$ alkyl) and $SO(C_{1-2}$ alkyl), more preferably from $C_{1-2}$ alkyl and $O(C_{1-2}$ alkyl), each of which may be unsubstituted or substituted as described above. When an $R^2$ group is according to option (ii) above, the $R^2$ group may optionally be substituted with 1, 2 or 3 halo substituents and/or one $R^8$ substituent; preferably with either 1, 2 or 3 halo substituents (of which one or more, preferably all are fluorine) or with one $R^8$ substituent. Preferred $R^2$ groups according to option (ii) above include $C_{1-2}$ alkyl and $O(C_{1-2}$ alkyl) each of which is unsubstituted or is substituted with 3 fluorine substitutents, such as —$CF_3$, —$OCF_3$ and —$OCH_3$. For the avoidance of doubt, when $R^2$ is according to option (ii) above and is substituted as described above, the one or more substituent(s) are each preferably present on the alkyl moiety of the $R^2$ group.

When an $R^2$ group is according to option (iii) above, each $R^a$ and $R^b$ is independently preferably selected from hydrogen and methyl. Each $R^c$ is preferably methyl. More preferably, each $R^a$ and $R^b$ is independently selected from hydrogen and methyl (preferably hydrogen) and $R^c$ is methyl.

Preferably, each $R^8$ group is independently selected from CN, OH, —C(O)$NR^fR^g$, —$NR^fR^g$, wherein each of $R^f$ and $R^g$ is independently H or methyl, preferably hydrogen. More preferably, each $R^8$ group is independently selected from CN and —C(O)$NR^fR^g$.

Accordingly, in Formula (I), each $R^2$ is preferably independently selected from:
halo or $R^8$.
$C_{1-2}$ alkyl, $O(C_{1-2}$ alkyl), $S(C_{1-2}$ alkyl), $SO(C_{1-2}$ alkyl) or $SO_2(C_{1-2}$ alkyl), any of which may optionally be substituted with 1, 2 or 3 halo substituents and/or one $R^8$ substituent; and
$NR^aC(O)R^c$, and $NR^aC(O)NR^bR^c$, wherein each $R^a$ and $R^b$ is independently selected from hydrogen and unsubstituted $C_{1-2}$ alkyl and each $R^c$ is unsubstituted $C_{1-2}$ alkyl; wherein each $R^8$ is independently selected from CN, OH, —C(O)$NR^fR^g$, and —$NR^fR^g$—; wherein each of $R^f$ and $R^g$ is independently H or unsubstituted $C_{1-2}$ alkyl.

More preferably, in Formula (I), each $R^2$ is independently selected from
halo, CN, OH, —C(O)$NR^fR^g$, —$NR^fR^g$; wherein each of $R^f$ and $R^g$ is independently H or methyl; and
$C_{1-2}$ alkyl, $O(C_{1-2}$ alkyl), $S(C_{1-2}$ alkyl), $SO(C_{1-2}$ alkyl) any of which may optionally be substituted with 1, 2 or 3 halo substituents and/or one substituent selected from CN and OH.

In Formula (I), m is preferably 0, 1 or 2. More preferably, m is 1 or 2. Sometimes m is 1. Sometimes m is 2.

Therefore, in Formula (I), preferably:
Ⓐ is a cyclic group selected from phenyl, 5- to 6-membered heteroaryl, and 5- to 6-membered carbocyclic and heterocyclic groups;
each $R^2$ is independently selected from:
halo or $R^8$;
$C_{1-2}$ alkyl, $O(C_{1-2}$ alkyl), $S(C_{1-2}$ alkyl), $SO(C_{1-2}$ alkyl) or $SO_2(C_{1-2}$ alkyl), any of which may optionally be substituted with 1, 2 or 3 halo substituents and/or one $R^8$ substituent; and
$NR^aC(O)R^c$, and $NR^aC(O)NR^bR^c$, wherein each $R^a$ and $R^b$ is independently selected from hydrogen and unsubstituted $C_{1-2}$ alkyl and each $R^c$ is unsubstituted $C_{1-2}$ alkyl;
wherein each $R^8$ is independently selected from CN, OH, —C(O)$NR^fR^g$, and —$NR^fR^g$;
wherein each of $R^f$ and $R^g$ is independently H or unsubstituted $C_{1-2}$ alkyl.
and
m is 0, 1 or 2.

More preferably, in Formula (I):
Ⓐ is selected from phenyl, cyclohexane, piperidine, pyridazine, pyridine and thiazole;
each $R^2$ is independently selected from
halo, CN, OH, —C(O)$NR^fR^g$, —$NR^fR^g$; wherein each of $R^f$ and $R^g$ is independently H or methyl; and
$C_{1-2}$ alkyl, $O(C_{1-2}$ alkyl), $S(C_{1-2}$ alkyl), $SO(C_{1-2}$ alkyl) any of which may optionally be substituted with 1, 2 or 3 halo substituents and/or one substituent selected from CN and OH;
and
m is 1 or 2.

Typically, in Formula (I), n is 0.

In Formula (I), if n is 1, $R^3$ is preferably selected from hydrogen and an unsubstituted $C_1$ to $C_3$ alkyl group such as methyl or ethyl, preferably methyl. More preferably, $R^3$ if present is hydrogen.

Typically, in Formula (I), Z is a bond or is selected from —$NR^1C(O)$—, —$C(O)NR^{10}$—, —$NR^{10}C(O)NR^{11}$—, —$NR^{10}C(O)O$—, —$OC(O)NR^{10}$, —$NR^{10}C(O)S$—, —$SC(O)NR^{10}$, —$NR^{10}C(NR^{11})$—, —$C(NR^{10})NR^{11}$—, —$NR^{10}C(NR^{11})NR^{12}$—, —$NR^{10}C(NR^{11})O$—, —$OC(NR^{10})NR^{11}$, —$NR^{10}C(NR^{11})S$—, —$SC(NR^{10})NR^{11}$, —$C(O)NR^{15}$—, —$NR^{10}C(O)NR^{15}$—, —$OC(O)NR^{15}$, —$SC(O)NR^{15}$, —$C(NR^{10})NR^{15}$—, —$NR^{10}C(NR^{11})NR^{15}$—, —$OC(NR^{10})NR^{15}$, and —$SC(NR^{10})NR^{15}$, wherein $R^{10}$, $R^{11}$, $R^{12}$ and R are as defined herein. Preferably, Z is a bond or is selected from —$NR^{10}C(O)$—, —$C(O)NR^{10}$—, —$NR^{10}C(O)NR^{11}$—, —$NR^{10}C(O)O$—, —$OC(O)NR^{10}$, —$NR^{10}C(O)S$—, —$SC(O)NR^{10}$, —$NR^{10}C(NR^{11})$—, —$C(NR^{10})NR^{11}$—, —$NR^{10}C(NR^{11})NR^{12}$—, —$NR^{10}C(NR^{11})O$—, —$OC(NR^{10})NR^{11}$, —$NR^{10}C(NR^{11})S$—, and —$SC(NR^{10})NR^{11}$, wherein $R^{10}$, $R^{11}$ and $R^{12}$ are as defined herein. More preferably, Z is a bond or is selected from —$NR^{10}C(O)$—, —$C(O)NR^{10}$—, —$NR^{10}C(O)NR^{11}$—, —$NR^{10}C(O)O$—, —$OC(O)NR^{10}$, —$NR^{10}C(O)S$—, —$SC(O)NR^{10}$, —$NR^{10}C(NR^{11})$—, —$C(NR^{10})NR^{11}$—, and —$NR^{10}C(NR^{11})NR^2$—. Still more preferably, Z is a bond or is selected from —$NR^{10}C(O)$—, —$C(O)NR^{10}$—, —$NR^{10}C$ (O)NR$^{11}$—, —NR$^{10}$C(O)O—, —NR$^{10}$C(O)S—, and —NR$^{10}$C(NR$^{11}$)—. Most preferably, Z is selected from —NR$^{10}$C(O)—, —C(O)NR$^{10}$—, and —NR$^{10}$C(O)NR$^{11}$—, preferably —NR$^{10}$C(O)—.

Typically, each R$^{15}$ is independently substituted C$_1$ to C$_3$ alkyl or unsubstituted C$_2$ to C$_3$ alkyl, more preferably each R$^{15}$ is independently substituted C$_1$ to C$_2$ alkyl or unsubstituted C$_2$ alkyl; still more preferably each R$^{15}$ is independently substituted or unsubstituted C$_2$ alkyl. When R$^{15}$ is a substituted alkyl group the alkyl group is typically substituted with 1, 2 or 3, preferably 1 or 2, more preferably 1 substituents independently selected from halogen, CN, and OR$^{10}$, more preferably from CN and —OR$^{10}$, most preferably from CN and OH.

In Formula (I), L is a bond or is selected from C$_{1-4}$ alkylene, C$_{2-4}$ alkenylene, C$_{2-4}$ alkynylene, C$_{1-3}$ alkylene-(C$_{3-6}$cycloalkylene)-C$_{1-3}$ alkylene, C$_{1-4}$ alkylene-(C$_{3-6}$cycloalkylene) and (C$_{3-6}$cycloalkylene)-C$_{1-4}$ alkylene, wherein L is unsubstituted or is substituted with 1 or 2 substituents selected from halogen, —OR$^{10}$, and —NR$^{10}$R$^{11}$; or L is —C(R$^{10}$)=N—. Typically, in Formula (I), L is unsubstituted or is substituted with 1 substituent selected from halogen, —OR$^{10}$, and —NR$^{10}$R$^{11}$; most typically L is unsubstituted. When L is other than a bond or —C(R$^{10}$)=N— and L is substituted by one or more substituents as described above, the one or more substituents are each preferably present on the alkylene, alkenylene or alkynylene group(s) of L. For the avoidance of doubt, when L is a bond L is unsubstituted.

L is preferably a bond or is selected from C$_{1-4}$ alkylene, C$_{2-4}$ alkenylene and C$_{2-4}$ alkynylene; or L is —C(R$^{10}$)=N—. More preferably, L is a bond or is selected from C$_{1-3}$ alkylene and C$_{2-3}$ alkenylene or is —C(R$^{10}$)=N—. Still more preferably, L is selected from C$_{1-3}$ alkylene and C$_{2-3}$ alkenylene.

Typically, in Formula (I), X is a bond or, when L is other than a bond or —C(R$^{10}$)=N—, X is a bond or is selected from —NR$^{10}$— and —O—. More preferably, X is a bond.

Preferably, therefore, in Formula (I):
Z is a bond or is selected from —NR$^{10}$C(O)—, —C(O)NR$^{10}$—, —NR$^{10}$C(O)NR$^{11}$—, —NR$^{10}$C(O)O—, —OC(O)NR$^{10}$, —NR$^{10}$C(O)S—, —SC(O)NR$^{10}$, —NR$^{10}$C(NR$^{11}$)—, —C(NR$^{10}$)NR$^{11}$—, and —NR$^{10}$C(NR$^{11}$)NR$^{12}$—;
L is a bond or is selected from C$_{1-4}$ alkylene, C$_{2-4}$ alkenylene and C$_{2-4}$ alkynylene; or L is —C(R$^{10}$)=N—;
and
X is a bond.

More preferably, in Formula (I):
Z is selected from —NR$^{10}$C(O)—, —C(O)NR$^{10}$—, and —NR$^{10}$C(O)NR$^{11}$—;
L is selected from C$_{1-3}$ alkylene and C$_{2-3}$ alkenylene each of which are preferably unsubstituted;
and
X is a bond.

In Formula (I), R$^4$ is:
(i) selected from H, —CN and C$_1$ to C$_3$ alkyl which is unsubstituted or is substituted with 1, 2 or 3 substituents selected from halogen, —OR$^{10}$, —NR$^{10}$R$^{11}$, and —CN;
or
(ii) R$^4$ is joined together with R$^5$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted C$_1$ to C$_2$ alkyl, halogen, —OR$^{10}$, —NR$^{10}$R$^{11}$, and —CN.

In Formula (I), R$^5$ is
(i) selected from H, —CN and C$_1$ to C$_3$ alkyl which is unsubstituted or is substituted with 1, 2 or 3 substituents selected from halogen, —OR$^{10}$, —NR$^{10}$R$^{11}$, and —CN;
or
(ii) is joined together with R$^4$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted C$_1$ to C$_2$ alkyl, halogen, —OR$^{10}$, —NR$^{10}$R$^{11}$, and —CN;
or
(iii) is joined together with R$^6$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted C$_1$ to C$_2$ alkyl, halogen, —OR$^{10}$, —NR$^{10}$R$^{11}$, and —CN;

When R$^4$ is C$_1$ to C$_3$ alkyl according to option (i) above, it is typically unsubstituted or is substituted with 1, 2 or 3 halo substituents or with 1 or 2 halo substituents and/or with one substituent selected from —OR$^{10}$, —NR$^{10}$R$^{11}$, and —CN. When R$^4$ is according to option (i) above, R$^4$ is preferably H or C$_1$ to C$_2$ alkyl which is unsubstituted or is substituted with 1, 2 or 3 halo substituents or with one —OR$^{10}$ substituent; more preferably R$^4$ is H or methyl, most preferably H.

When R$^5$ is C$_1$ to C$_3$ alkyl according to option (i) above, it is typically unsubstituted or is substituted with 1, 2 or 3 halo substituents or with 1 or 2 halo substituents and/or with one substituent selected from —OR$^{10}$, —NR$^{10}$R$^{11}$, and —CN. When R$^5$ is according to option (i) above, R$^5$ is preferably selected from H, —CN and C$_1$ to C$_2$ alkyl which is unsubstituted or is substituted with 1, 2 or 3 halo substituents or one —NR$^{10}$R$^{11}$ substituent; more preferably, R$^5$ is H or methyl, most preferably H.

When R$^4$ is according to option (ii) above and R$^5$ is according to option (ii) above so that R$^4$ and R$^5$ are joined together to form, together with the atoms to which they are attached, a 5- to 6-membered heterocyclic group comprising at least one saturated carbon atom in the ring, the heterocyclic group is preferably unsubstituted or is substituted with 1 substituent selected from unsubstituted C$_1$ to C$_2$ alkyl, halogen, and —OR$^{10}$; more preferably the heterocyclic group is unsubstituted or is substituted with 1 substituent selected from methyl and methoxy; most preferably the heterocyclic group is unsubstituted. Preferably, when R$^4$ is according to option (ii) above and R$^5$ is according to option (ii) above, R$^4$ and R$^5$ are joined together to form, together with the atoms to which they are attached, a 5-membered heterocyclic group, preferably 4,5-dihydro-1H-imidazole.

In Formula (I), R$^6$ is
(i) selected from H, —CN and C$_1$ to C$_3$ alkyl which is unsubstituted or is substituted with 1, 2 or 3 substituents selected from halogen, —OR$^{10}$, —NR$^{10}$R$^{11}$, and —CN;
or
(ii) is joined together with R$^5$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted $C_1$ to $C_2$ alkyl, halogen, —$OR^{10}$, —$NR^{10}R^{11}$, and —CN;

or (iii) is joined together with $R^7$ if present to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted $C_1$ to $C_2$ alkyl, halogen, —$OR^{10}$, —$NR^{10}R^{11}$, and —CN.

When $R^6$ is $C_1$ to $C_3$ alkyl according to option (i) above, it is typically unsubstituted or is substituted with 1, 2 or 3 halo substituents or with 1 or 2 halo substituents and/or with one substituent selected from —$OR^{10}$, —$NR^{10}R^{11}$, and —CN. When $R^6$ is according to option (i) above, $R^6$ is preferably selected from H, —CN and $C_1$ to $C_2$ alkyl which is unsubstituted or is substituted with 1, 2 or 3 halo substituents or one —$NR^{10}R^{11}$ substituent; more preferably, $R^6$ is H or methyl, most preferably H.

When $R^5$ is according to option (iii) above and $R^6$ is according to option (ii) above so that $R^5$ and $R^6$ are joined together to form, together with the atoms to which they are attached, a 5- to 6-membered heterocyclic group comprising at least one saturated carbon atom in the ring, the heterocyclic group is preferably unsubstituted or is substituted with 1 substituent selected from unsubstituted $C_1$ to $C_2$ alkyl, halogen, and —$OR^{10}$; more preferably the heterocyclic group is unsubstituted or is substituted with 1 substituent selected from methyl and methoxy; most preferably the heterocyclic group is unsubstituted. Preferably, when $R^5$ is according to option (iii) above and $R^6$ is according to option (ii) above, $R^5$ and $R^6$ are joined together to form, together with the atoms to which they are attached, a 6-membered heterocyclic group, preferably morpholine or piperazine, more preferably morpholine.

In Formula (I), p is 0 or 1.

In Formula (I), $R^7$ if present is (i) selected from H, —CN and $C_1$ to $C_3$ alkyl which is unsubstituted or is substituted with 1, 2 or 3 substituents selected from halogen, —$OR^{10}$, —$NR^{10}R^{11}$, and —CN;

or (ii) is joined together with $R^6$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted $C_1$ to $C_2$ alkyl, halogen, —$OR^{10}$, —$NR^{10}R^{11}$, and —CN;

When $R^7$ is present and is $C_1$ to $C_3$ alkyl according to option (i) above, it is typically unsubstituted or is substituted with 1, 2 or 3 halo substituents or with 1 or 2 halo substituents and/or with one substituent selected from —$OR^{10}$, —$NR^{10}R^{11}$, and —CN. When $R^7$ is present and is according to option (i) above, $R^7$ is preferably selected from H, —CN and $C_1$ to $C_2$ alkyl which is unsubstituted or is substituted with 1, 2 or 3 halo substituents or one —$NR^{10}R^{11}$ substituent; more preferably, $R^7$ if present is H or methyl, most preferably H.

When $R^7$ is present and $R^6$ is according to option (iii) above and $R^7$ is according to option (ii) above so that $R^6$ and $R^7$ are joined together to form, together with the atoms to which they are attached, a 5- to 6-membered heterocyclic group comprising at least one saturated carbon atom in the ring, the heterocyclic group is preferably unsubstituted or is substituted with 1 substituent selected from unsubstituted $C_1$ to $C_2$ alkyl, halogen, and —$OR^{10}$; more preferably the heterocyclic group is unsubstituted or is substituted with 1 substituent selected from methyl and methoxy; most preferably the heterocyclic group is unsubstituted. Preferably, when $R^7$ is present and is according to option (ii) above and $R^6$ is according to option (iii) above, $R^6$ and $R^7$ are joined together to form, together with the atoms to which they are attached, a 5-membered heterocyclic group, preferably imidazolidine.

Preferably, therefore, in Formula (I), p is 1 and $R^7$ is H or methyl or is joined together with $R^6$ to form, together with the atoms to which they are attached, an unsubstituted 5- to 6-membered heterocyclic group. Preferably, $R^4$ is H or is joined together with $R^5$ to form, together with the atoms to which they are attached, an unsubstituted 5- to 6-membered heterocyclic group. More preferably, in Formula (I), $R^5$ is selected from H, —CN and $C_1$ to $C_2$ alkyl which is unsubstituted or is substituted with 1, 2 or 3 halo substituents and/or one —$NR^{10}R^{11}$ substituent and $R^6$ is H or methyl. Most preferably, $R^4$, $R^5$, $R^6$ and $R^7$ if present are each selected from methyl and hydrogen, preferably hydrogen.

For the avoidance of doubt, a heterocyclic group comprising at least one saturated carbon atom in the ring comprises a —$CH_2$— group within the ring, wherein one or both of the hydrogen atoms of the —$CH_2$— group may be substituted as defined herein. Usually, the saturated carbon atom in the ring is unsubstituted; i.e., the a heterocyclic group comprising at least one saturated carbon atom in the ring usually comprises a —$CH_2$— group within the ring. A heterocyclic group comprising at least one saturated carbon atom in the ring is therefore saturated or partially saturated. A heterocyclic group comprising at least one saturated carbon atom in the ring is not aromatic.

In some preferred compounds of Formula (I), therefore, $R^1$ is H;

Ⓐ is a cyclic group selected from phenyl, 5- to 6-membered heteroaryl, and 5- to 6-membered carbocyclic and heterocyclic groups;

m is 0, 1 or 2;

each $R^2$ is independently selected from:

halo or $R^8$;

$C_{1-2}$ alkyl, $O(C_{1-2}$ alkyl), $S(C_{1-2}$ alkyl), $SO(C_{1-2}$ alkyl) or $SO_2(C_{1-2}$ alkyl), any of which may optionally be substituted with 1, 2 or 3 halo substituents and/or one $R^8$ substituent; and $NR^aC(O)R^c$, and $NR^aC(O)NR^bR^c$, wherein each $R^a$ and $R^b$ is independently selected from hydrogen and unsubstituted $C_{1-2}$ alkyl and each $R^c$ is unsubstituted $C_{1-2}$ alkyl;

each $R^8$ is independently selected from CN, OH; —C(O)$NR^fR^g$, and —$NR^fR^g$; wherein each of $R^f$ and $R^g$ is independently H or unsubstituted $C_{1-2}$ alkyl;

n is 0; or n is 1 and $R^3$ is H

Z is selected from —$NR^{10}C(O)$—, —$C(O)NR^{10}$—, —$NR^{10}C(O)NR^{11}$—, —$NR^{10}C(O)O$—, —$OC(O)NR^{10}$, —$NR^{10}C(O)S$—, —$SC(O)NR^{10}$, —$NR^{10}C(NR^{11})$—, —$C(NR^{10})NR^{11}$—, and —$NR^{10}C(NR^1)NR^{12}$—;

L is a bond or is selected from $C_{1-4}$ alkylene, $C_{2-4}$ alkenylene and $C_{2-4}$ alkynylene; or L is —$C(R^{10})$=N—;

X is a bond;

i) p is 0;

$R^4$ is H and $R^5$ is selected from H, —CN and $C_1$ to $C_2$ alkyl which is unsubstituted or is substituted with 1, 2 or 3 halo substituents and/or one —$NR^{10}R^{11}$ substituent; or $R^4$ is joined together with $R^5$ to form, together with the atoms to which they are attached, an unsubstituted 5- to 6-membered heterocyclic group; and
$R^6$ is H or methyl;
or
ii) p is 1; and
$R^4$ is H; $R^5$ is selected from H, —CN and $C_1$ to $C_2$ alkyl which is unsubstituted or is substituted with 1, 2 or 3 halo substituents and/or one —$NR^{10}R^{11}$ substituent; $R^6$ is H or methyl and $R^7$ is H or methyl; or $R^4$ is joined together with $R^5$ to form, together with the atoms to which they are attached, an unsubstituted 5- to 6-membered heterocyclic group; $R^6$ is H or methyl and $R^7$ is H;

In some even more preferred compounds of Formula (I), $R^1$ is H;
Ⓐ is selected from phenyl, cyclohexane, piperidine, pyridazine, pyridine and thiazole;
m is 1 or 2;
each $R^2$ is independently selected from:
halo, CN, OH, —C(O)$NR^fR^g$, —$NR^fR^g$; wherein each of $R^f$ and $R^g$ is independently H or methyl; and
$C_{1-2}$ alkyl, O($C_{1-2}$ alkyl), S($C_{1-2}$ alkyl), SO($C_{1-2}$ alkyl) any of which may optionally be substituted with 1, 2 or 3 substituents selected from halo, CN, OH;
n is 0;
Z is selected from —$NR^{10}C(O)$—, —$C(O)NR^{10}$—, and —$NR^{10}C(O)NR^{11}$—;
L is selected from $C_{1-3}$ alkylene and $C_{2-3}$ alkenylene.
X is a bond;
p is 0; or p is 1 and $R^7$ is H;
$R^4$ is H;
$R^5$ is selected from H, —CN and $C_1$ to $C_2$ alkyl which is unsubstituted or is substituted with 1, 2 or 3 halo substituents and/or one —$NR^{10}R^{11}$ substituent H; and
$R^6$ is H.

Particularly preferred compounds of the invention are
5-[[4-[(2-guanidinoacetyl)amino]-3-(trifluoromethoxy)phenyl]sulfonylamino]thiazole-4-carboxylic acid;
5-[[3-fluoro-4-[[(2-guanidinoacetyl)amino]methyl]phenyl]sulfonylamino]thiazole-4-carboxylic acid;
5-[[3-fluoro-4-(guanidinomethyl)phenyl]sulfonylamino]thiazole-4-carboxylic acid;
5-[[3-fluoro-4-(2-guanidinoethylsulfanylcarbonylamino)phenyl]sulfonylamino]thiazole-4-carboxylic acid;
5-[[4-[2-[(2-amino-2-imino-ethyl)amino]-2-oxo-ethyl]-3-fluoro-phenyl]sulfonylamino]thiazole-4-carboxylic acid;
5-[[3-carbamoyl-4-[(2-guanidinoacetyl)amino]phenyl]sulfonylamino]thiazole-4-carboxylic acid;
5-[[3-cyano-4-[(2-guanidinoacetyl)amino]phenyl]sulfonylamino]thiazole-4-carboxylic acid;
5-[[3-fluoro-4-(2-guanidinoethoxycarbonylamino)phenyl]sulfonylamino]thiazole-4-carboxylic acid;
5-[(4-guanidinophenyl)sulfonylamino]thiazole-4-carboxylic acid;
5-[[4-[2-(2-carbamimidoylhydrazino)-2-oxo-ethyl]-3-fluoro-phenyl]sulfonylamino]thiazole-4-carboxylic acid;
5-[[3-chloro-4-[(2-guanidinoacetyl)amino]phenyl]sulfonylamino]thiazole-4-carboxylic acid;
5-[[4-[(2-guanidinoacetyl)amino]-3-methoxy-phenyl]sulfonylamino]thiazole-4-carboxylic acid;
5-[[4-[[2-(2-carbamimidoylhydrazino)acetyl]amino]-3-fluoro-phenyl]sulfonylamino]thiazole-4-carboxylic acid;
5-[[4-[[(2E)-2-(carbamimidoylhydrazono)acetyl]amino]-3-fluoro-phenyl]sulfonylamino]thiazole-4-carboxylic acid;
5-[[4-[[2-(4,5-dihydro-1H-imidazol-2-ylamino)acetyl]amino]-3,5-difluoro-phenyl]sulfonylamino]thiazole-4-carboxylic acid;
5-[[6-[(2-guanidinoacetyl)amino]pyridazin-3-yl]sulfonylamino]thiazole-4-carboxylic acid;
5-[[4-[(2-amino-2-imino-ethyl)carbamoylamino]-3-fluoro-phenyl]sulfonylamino]thiazole-4-carboxylic acid;
5-[[3,5-difluoro-4-(guanidinocarbamoylamino)phenyl]sulfonylamino]thiazole-4-carboxylic acid;
5-[[4-[(3-amino-3-imino-propanoyl)amino]-3,5-difluoro-phenyl]sulfonylamino]thiazole-4-carboxylic acid;
5-[[4-[[3-(dimethylamino)-3-imino-propanoyl]amino]-3-fluoro-phenyl]sulfonylamino]thiazole-4-carboxylic acid;
5-[[3-fluoro-4-[(2-guanidinooxyacetyl)amino]phenyl]sulfonylamino]thiazole-4-carboxylic acid;
5-[[3-fluoro-4-[[3-imino-3-(methylamino)propanoyl]amino]phenyl]sulfonylamino]thiazole-4-carboxylic acid;
5-[[4-[3-(4,5-dihydro-1H-imidazol-2-yl)propanoylamino]-3-fluoro-phenyl]sulfonylamino]thiazole-4-carboxylic acid;
5-[[2-[(2-guanidinoacetyl)amino]thiazol-5-yl]sulfonylamino]thiazole-4-carboxylic acid;
5-[[4-[[2-[(N-cyanocarbamimidoyl)amino]acetyl]amino]-3-fluoro-phenyl]sulfonylamino]thiazole-4-carboxylic acid;
5-[[3-fluoro-4-(guanidinocarbamoylamino)phenyl]sulfonylamino]thiazole-4-carboxylic acid;
5-[[3-fluoro-4-[[2-(morpholine-4-carboximidoylamino)acetyl]amino]phenyl]sulfonylamino]thiazole-4-carboxylic acid;
5-[[4-[(3-amino-3-imino-2-methyl-propanoyl)amino]-3-fluoro-phenyl]sulfonylamino]thiazole-4-carboxylic acid;
5-[[4-[[2-(4,5-dihydro-1H-imidazol-2-yl)acetyl]amino]-3-fluoro-phenyl]sulfonylamino]thiazole-4-carboxylic acid;
5-[[4-(carbamimidoylcarbamoylamino)-3-fluoro-phenyl]sulfonylamino]thiazole-4-carboxylic acid;
5-[[4-[[(2R)-2-guanidinopropanoyl]amino]phenyl]sulfonylamino]thiazole-4-carboxylic acid;
5-[[3,5-difluoro-4-[(2-guanidinoacetyl)amino]phenyl]sulfonylamino]thiazole-4-carboxylic acid;
5-[[4-[(4-amino-4-imino-butanoyl)amino]-3-fluoro-phenyl]sulfonylamino]thiazole-4-carboxylic acid;
5-[[4-[[2-(4,5-dihydro-1H-imidazol-2-ylamino)acetyl]amino]-2,5-difluoro-phenyl]sulfonylamino]thiazole-4-carboxylic acid;
5-[[2,5-difluoro-4-[(2-guanidinoacetyl)amino]phenyl]sulfonylamino]thiazole-4-carboxylic acid;
5-[[3-fluoro-4-[[2-[(N-methylcarbamimidoyl)amino]acetyl]amino]phenyl]sulfonylamino]thiazole-4-carboxylic acid;
5-[[3-fluoro-4-[[2-(2-iminoimidazolidin-1-yl)acetyl]amino]phenyl]sulfonylamino]thiazole-4-carboxylic acid;
5-[[4-[[2-[carbamimidoyl(methyl)amino]acetyl]amino]-3-fluoro-phenyl]sulfonylamino]thiazole-4-carboxylic acid;
5-[[4-[[2-[[N-(2-aminoethyl)carbamimidoyl]amino]acetyl]amino]-3-fluoro-phenyl]sulfonylamino]thiazole-4-carboxylic acid;
5-[[5-fluoro-6-[(2-guanidinoacetyl)amino]-3-pyridyl]sulfonylamino]thiazole-4-carboxylic acid;
5-[[3-fluoro-4-(3-guanidinopropanoylamino)phenyl]sulfonylamino]thiazole-4-carboxylic acid;
5-[[4-[(3-amino-3-imino-propanoyl)amino]-3-fluoro-phenyl]sulfonylamino]thiazole-4-carboxylic acid;
5-[[3,5-difluoro-4-(guanidinocarbamoylamino)phenyl]sulfonylamino]thiazole-4-carboxylic acid;
5-[[3-fluoro-4-[(2-guanidinoacetyl)amino]phenyl]sulfonylamino]thiazole-4-carboxylic acid; and 5-[[4-[(2-guanidinoacetyl)amino]phenyl]sulfonylamino]thiazole-4-carboxylic acid; and pharmaceutically acceptable salts thereof.

Synthesis

The compounds of the invention can be prepared by any suitable method. Detailed general synthetic routes for representative compounds of the invention are set out below and in the Examples.

In summary, compounds of the invention can typically be prepared in a reaction according to the following scheme:

For example, Q can be bromine and —Z'—W can be —C(O)NH₂ so that Q and W react together via Buchwald chemistry (this is particularly suited to when n is 0). Alternatively, Q can be —NH₂ and —Z'—W can be —C(O)OH so that Q and W react together in a standard peptide coupling reaction using reagents such as HATU. Other methods of coupling compounds are well known to those skilled in the art. In compounds B and C the moiety —NR⁷—Pro represents a protected amine moiety which can be deprotected to yield the amine via standard methods such as acid-catalysed

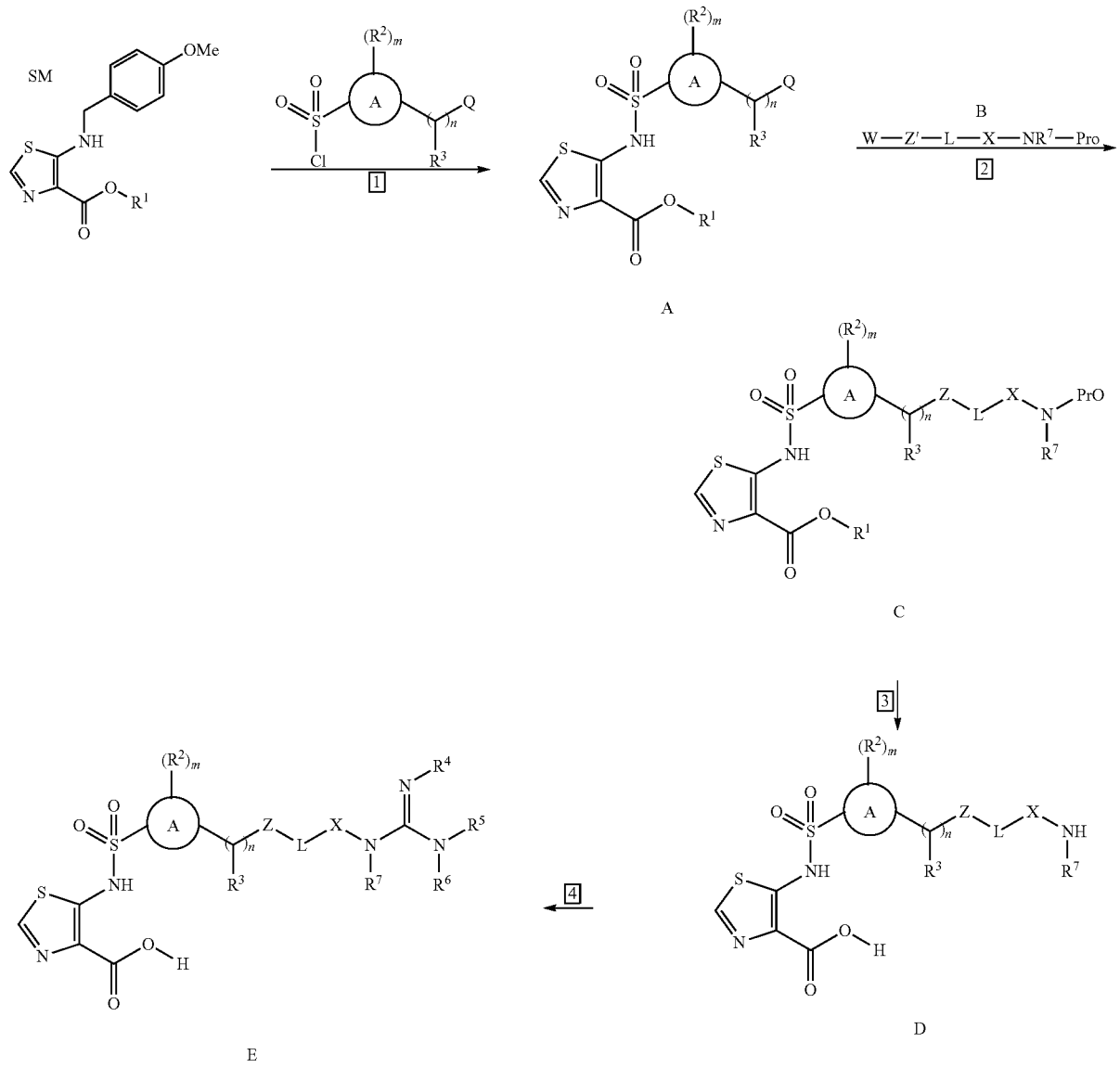

Starting material SM is readily available and can, for example, be prepared using the methods described in WO 2014/198849. The disclosure of WO 2014/198849 regarding the formation of compound SM and its analogues is incorporated by reference. Reaction of SM with a sulphonyl chloride derivative of Ⓐ (reaction step 1) yields a thiazole sulphonamide derivative of Ⓐ (A). Reaction of A with a W—Z-L-X-Pro moiety (B) yields intermediate C. In the above scheme, Q and W are complementary reactive groups which react together to couple A to B to yield compound C.

deprotection (compounds D). Suitable amine protecting groups are well known to those skilled in the art and include Boc (tert-butoxycarbonyl) protecting groups The amine can then be reacted to form a guanidine group as in compound E by reaction with known guanidinylating agents such as 1H-pyrazole-1-carboximidamide. In compounds of the invention wherein p is zero such that an amidine rather than a guanidine group is present, the synthesis shown above can be modified so that compound B comprises a protected amidine group rather than protected amine NR⁷-Pro. Suitable amidine protecting groups are well known to those skilled in the art and include Boc (tert-butoxycarbonyl) protecting groups. In these cases, reaction of A and B yields a compound C' which when deprotected yields the desired amidine product E'. Detailed synthetic routes to exemplary compounds of the invention are set out below.

Therapeutic Efficacy

The compounds of the present invention are therapeutically useful. The present invention therefore provides compounds as described herein, for use in medicine. The present invention provides compounds as described herein, for use in treating the human or animal body. For the avoidance of doubt, the compound of the invention may be administered in the form of a solvate.

Also provided is a pharmaceutical composition comprising a compound of the invention together with a pharmaceutically acceptable carrier or diluent and optionally further comprising an antibiotic agent. Typically, the composition contains up to 85 wt % of a compound of the invention. More typically, it contains up to 50 wt % of a compound of the invention. Preferred pharmaceutical compositions are sterile and pyrogen free. Further, when the pharmaceutical compositions provided by the invention contain a compound of the invention which is optically active, the compound of the invention is typically a substantially pure optical isomer.

The composition of the invention may be provided as a kit comprising instructions to enable the kit to be used in the methods described herein or details regarding which subjects the method may be used for.

As explained above, the compounds of the invention are useful in treating or preventing bacterial infection. In particular, they are inhibitors of metallo-β-lactamase (MBL) enzymes and are therefore useful for removing or reducing resistance of Gram-negative bacteria to antibiotics.

The compounds of the invention may be used as stand-alone therapeutic agents. For example, the compounds of the invention may be used as standalone adjuncts in antibacterial therapy, for example in chemotherapy regimes. Alternatively, they may be used in combination with antibiotic agents to enhance the action of the antibiotic agent. The compounds of the invention may find particular use in treating or preventing bacterial infection caused by bacteria which are resistant to treatment with antibiotic agents when administered alone, particularly where the resistance is caused by presence of metallo-β-lactamase and/or serine-β-lactamase enzymes. Treatment or prevention of such infection with β-lactam antibiotics alone may be unsuccessful.

The present invention therefore also provides a product comprising (i) a compound of the invention as described herein and (ii) an antibiotic agent. The compound of the invention and the antibiotic agent may be provided in a single formulation, or they may be separately formulated. Where separately formulated, the two agents may be administered simultaneously or separately. They may be provided in the form of a kit, optionally together with instructions for their administration. The products may also be referred to herein as combinations or pharmaceutical combinations.

Where formulated together, the two active agents may be provided as a pharmaceutical composition comprising (i) a compound of the invention as described herein and (ii) a further antibacterial compound; and (iii) a pharmaceutically acceptable carrier or diluent.

Preferably, the antibiotic agent is a β-lactam antibiotic. More preferably, the antibiotic agent is a β-lactam antibiotic is selected from carbapenems, penicillins, cephalosporins and penems. Examples of carbapenem antibiotics include Imipenem, Meropenem, Ertapenem, Doripenem and Biapenem. Examples of penicillins include Amoxicillin, Ampicillin, Ticarcillin, Piperacillin and Cloxacillin. Examples of cephalosporins include Cefazolin, Ceftriaxone, Ceftazidine and Ceftobiprole. Examples of penems include Faropenem. Other antibiotic agents include tobramycin, neomycin, streptomycin, gentamycin, tazobactam, rifampicin, ciprofloxacin, amikacin, colistin, aztreonam and levofloxacin. Preferably, the β-lactam antibiotic is a carbapenem antibiotic, more preferably imipenem or meropenem, most preferably meropenem.

The products of the invention may further comprise a serine-β-lactamase (SBL) inhibitor. Thus, the invention also provides a product comprising (i) a compound of the invention; (ii) a serine-β-lactamase (SBL) inhibitor; and (iii) an antibiotic agent. These products are referred to herein as "triple combinations". The triple combinations comprise the above three active agents (i) to (iii) but may also comprise further active agents if desired.

In the triple combination of the invention, the compound of the invention, the SBL inhibitor and the antibiotic agent may each be provided in a single formulation, or they may be separately formulated. Alternatively, two of the components may be provided in a single formulation and the remaining component may be provided separately. In other words, the compound of the invention may be formulated with the SBL inhibitor and the antibiotic agent; or the compound of the invention may be formulated with the SBL inhibitor whilst the antibiotic agent is provided separately; or the compound of the invention may be formulated with the antibiotic agent whilst the SBL inhibitor is provided separately; or the SBL inhibitor may be formulated with the antibiotic agent whilst the compound of the invention is provided separately; or the compound of the invention, the SBL inhibitor and the antibiotic agent may each be formulated separately. Where separately formulated, the components of the triple combination may be administered simultaneously or separately. They may be provided in the form of a kit, optionally together with instructions for their administration.

Where two or more active agents are formulated together, the two or more active agents may be provided as a pharmaceutical composition comprising (i) a compound of the invention as described herein; (ii) a pharmaceutically acceptable carrier or diluent; and one or both of (iii) an antibiotic agent; and (iv) a serine-β-lactamase (SBL) inhibitor.

In the triple combination of the invention, the SBL inhibitor is a compound of Formula (II) or a pharmaceutically acceptable salt thereof,

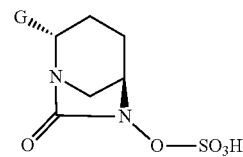

[FORMULA (II)]

wherein
G is selected from —CN and —C(O)NR$^j$R$^k$;
R$^k$ is selected from —W and -Q-W; wherein W is selected from 5- to 6-membered heterocyclyl, R$^j$ and —N(R$^j$)$_2$; and Q is selected from —NR$^j$C(O)—, —C(O)—NR$^j$—, $C_{1-3}$ alkylene, —O—$C_{1-3}$ alkylene and —N(R$^j$)—$C_{1-3}$ alkylene;

each $R^j$ is selected from H and unsubstituted $C_{1-3}$ alkyl, preferably H.

In Formula (II), when W is a 5- to 6-membered heterocyclyl, W is preferably a 6-membered heterocycle containing a nitrogen atom; more preferably W is piperidinyl. Preferably, in Formula (II), W is selected from 5- to 6-membered heterocyclyl and —N($R^j$)$_2$, more preferably W is selected from piperidinyl and NH$_2$. In formula (II), Q is preferably selected from —$NR^j$C(O)— and —O—$C_{1-3}$ alkylene. Preferably, in Formula (II), each $R^j$ is H. Thus, preferred definitions G in formula (II) are —CN and —C(O)NHR$^k$, wherein $R^k$ is selected from —W and -Q-W; wherein W is selected from 5- to 6-membered heterocyclyl, preferably pyridinyl, and —NH$_2$; and Q is selected from —NHC(O)— and —O—$C_{1-3}$ alkylene.

More preferably, in the pharmaceutical combination of the invention, the SBL inhibitor is selected from WCK4234, avibactam, relebactam, zidebactam and nacubactam, or pharmaceutically acceptable salts thereof. The structures of WCK4234, avibactam, relebactam, zidebactam and nacubactam are shown below. Such SBL inhibitors are commercially available and/or can be synthesized according to published protocols available to those skilled in the art. For example, WCK4234 and its synthesis is described in WO 2013/038330 and WO 2015/114595. Avibactam and its synthesis is described in Ball, M. et al, Org. Process Res. Dev., 2016, 20 (10), pp 1799-1805; and US 2012/323010. Relebactam and its synthesis is described in WO 2009/091856. Zidebactam and its synthesis is described in WO 2015/110885. Nacubactam and its synthesis is described in WO 2014/091268 and US 2016/272641.

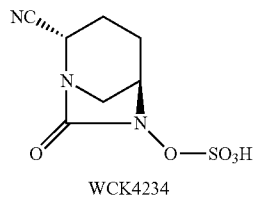

WCK4234

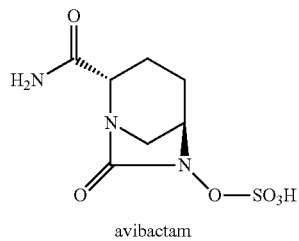

avibactam

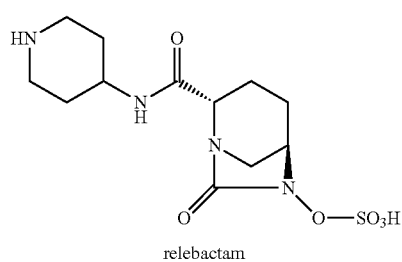

relebactam

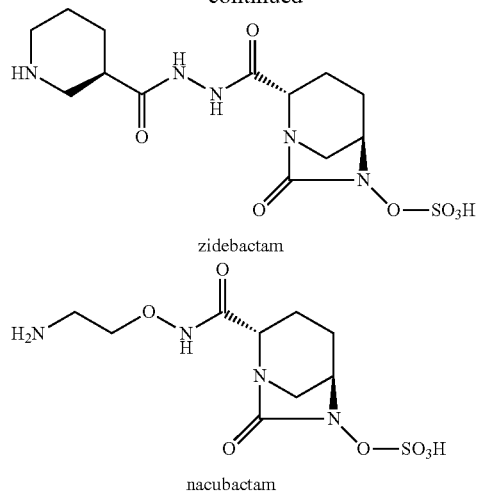

zidebactam nacubactam

More preferably, in the pharmaceutical combination of the invention, the SBL inhibitor is WCK4234 or a pharmaceutically acceptable salt thereof. Still more preferably, the SBL inhibitor is WCK4234 or the sodium salt thereof. A process for the preparation of the sodium salt of WCK4234 is described in WO 2015/114595.

In the triple combination of the invention, the antibiotic agent may be any antibiotic agent disclosed herein. Preferably, in the pharmaceutical combination of the invention, the antibiotic agent is a β-lactam antibiotic. Preferably, the β-lactam antibiotic is selected from carbapenems, penicillins, cephalosporins and penems, more preferably the β-lactam antibiotic is a carbapenem antibiotic, preferably imipenem or meropenem, most preferably meropenem.

Most preferably, therefore, the pharmaceutical combination of the invention comprises (i) a compound of the invention; (ii) an SBL inhibitor selected from WCK4234, avibactam, relebactam, zidebactam and nacubactam, and pharmaceutically acceptable salts thereof, preferably WCK4234 or a pharmaceutically acceptable salt thereof; and (iii) a carbapenem antibiotic, preferably meropenem.

The compounds of the invention are also useful in treating or preventing bacterial infection. The present invention therefore provides a compound of the invention for use in medicine. The invention also provides the use of a compound of the invention in the manufacture of a medicament. The invention also provides compositions and products comprising the compounds of the invention, as described here. Such compositions and products are also useful in treating or preventing bacterial infection. The present invention therefore provides a composition or product as defined herein for use in medicine. The invention also provides the use of a composition or product of the invention in the manufacture of a medicament.

As explained above, the compounds, compositions and products of the invention are useful in treating or preventing bacterial infection. The invention therefore also provides a method of treating or preventing bacterial infection in a subject, which method comprises administering to said subject an effective amount of a compound, composition or product as described herein. Further provided is a compound, composition or product of the invention as described herein for the manufacture of a medicament for use in treating or preventing bacterial infection; the compound of the invention is often used in combination with an antibiotic agent.

As further explained above, the compounds of the invention are useful in combination with a further antibacterial compound. The invention therefore provides a compound of the invention for use in treating or preventing bacterial infection, wherein such use comprises co-administering the compound of the invention with a further antibacterial compound. The invention also provides the use of a compound of the invention in the manufacture of a medicament for treating or preventing bacterial infection by co-administration of the compound of the invention with a further antibacterial compound. The invention also provides a method for treating or preventing bacterial infection by co-administering the compound of the invention and a further antibacterial compound to a subject in need thereof. The further antibacterial compound is preferably an antibacterial compound as described herein; more preferably a β-lactam antibiotic as described herein.

The compounds of the invention are also useful in combination with a serine-β-lactamase (SBL) inhibitor and an antibiotic agent, i.e. as a "triple combination". The invention therefore provides a compound of the invention for use in treating or preventing bacterial infection, wherein such use comprises co-administering (i) the compound of the invention with (ii) a serine-β-lactamase (SBL) inhibitor and (iii) an antibiotic agent. Also provided is an antibiotic agent for use in treating or preventing bacterial infection by co-administration with a compound of the invention and optionally an SBL inhibitor. Also provided is an SBL inhibitor for use in treating or preventing bacterial infection by co-administration with a compound of the invention and optionally an antibiotic agent. The invention also provides the use of a compound of the invention in the manufacture of a medicament for treating or preventing bacterial infection by co-administration of (i) the compound of the invention with (ii) a serine-β-lactamase (SBL) inhibitor and (iii) an antibiotic agent. Also provided is the use of an antibiotic agent in the manufacture of a medicament for use in treating or preventing bacterial infection by co-administration with a compound of the invention and optionally an SBL inhibitor. Also provided is the use of an SBL inhibitor in the manufacture of a medicament for use in treating or preventing bacterial infection by co-administration with a compound of the invention and optionally an antibiotic agent. The invention also provides a method for treating or preventing bacterial infection by co-administering (i) the compound of the invention; and (ii) a serine-β-lactamase (SBL) inhibitor and/or (iii) an antibiotic agent, to a subject in need thereof. The serine-β-lactamase (SBL) inhibitor is preferably a serine-β-lactamase (SBL) inhibitor described herein. The antibiotic agent is preferably an antibacterial compound as described herein; more preferably a β-lactam antibiotic as described herein.

In one aspect, the subject is a mammal, in particular a human. However, it may be non-human. Preferred non-human animals include, but are not limited to, primates, such as marmosets or monkeys, commercially farmed animals, such as horses, cows, sheep or pigs, and pets, such as dogs, cats, mice, rats, guinea pigs, ferrets, gerbils or hamsters. The subject can be any animal that is capable of being infected by a bacterium.

The compounds, compositions and combinations described herein are useful in the treatment of bacterial infection which occurs after a relapse following an antibiotic treatment. The compounds, compositions and combinations can therefore be used in the treatment of a patient who has previously received antibiotic treatment for the (same episode of) bacterial infection.

The bacterium causing the infection may be any bacterium expressing a metallo-β-lactamase enzyme or an analogue thereof. Typically the bacterium causing the infection expresses a MBL enzyme. The bacterium is typically Gram-negative. The bacterium may in particular be a pathogenic bacterium. Typically, the bacterial infection to be treated using the compounds of the invention is resistant to treatment with a conventional antibiotic when the conventional antibiotic is used alone.

The Gram-negative bacteria of which antibiotic resistance can be removed using the compounds of general formula (I) are bacteria which produce metallo-β-lactamases, which may be metallo-β-lactamases of subclasses B1, B2 or B3, for example IMP-type (including IMP-1), VIM-type (including VIM-1 and VIM-2) and NDM-type (including NDM-1) enzymes. Typically, the Gram-negative bacteria express NDM-type MBL enzymes, VIM-type MBL enzymes and/or IMP-type MBL enzymes; more typically the bacteria express NDM-type MBL enzymes and/or VIM-type MBL enzymes; most typically the bacteria express NDM-type MBL enzymes. The Gram-negative bacteria may express one or more of the following enzymes: ACT-TYPE, CMY-4, CTX-M-3, CTX-M-15, IMP-1, IMP-28, KPC-2, NDM-1, OXA-48, OXA-181, SHV-OSBL, SHV-11, SHV-12, TEM-OSBL, TEM-1, VIM-1, and/or VIM-19.

The bacterial infection may be caused by bacteria from the families Enterobacteriaceae, Pseudomonadaceae and/or Moraxellaceae, more typically the bacterial infection is caused by bacteria from the families Enterobacteriaceae and/or Pseudomonadaceae, and most typically the bacterial infection is caused by bacteria from the family Enterobacteriaceae. The bacterial infection may be caused by *Pseudomonas* (e.g. *Pseudomonas aeruginosa, Pseudomonas oryzihabitans*, or *Pseudomonas plecoglossicida*), *Klebsiella, Escherichia, Acinetobacter* or *Burkholderia*. For example, the bacterial infection may be caused by *Klebsiella pneumonia, Escherichia coli, Pseudomonas aeruginosa, Burkholderia cepacia* or *Acinetobacter baumannii*. The bacterial infection may be caused by *Escherichia coli, Klebsiella pneumonia*, or *Klebsiella oxytoca*. The bacterium may be an opportunistic pathogen.

The compounds, compositions and products of the invention are useful in the prevention or treatment of infection by the following strains:

NTBC020 (*E. coli* strain expressing NDM-1, TEM-1 and CTX-M-15); NTBC035-2 (*K. pneumoniae* strain expressing NDM-1, CMY-4 and SHV-11); NTBC104-1 (*K. pneumoniae* strain expressing NDM-1 and SHV-11); NTBC123 (*K. pneumoniae* strain expressing NDM-1); NTBC062 (*K. pneumoniae* strain expressing IMP-1 and TEM-1); NTBC024 (*K. pneumoniae* strain expressing VIM-19, TEM-1 and CTX-M-3); NTBC042 (*E. coli* strain expressing VIM-1, TEM-1, CTX-M-15, SHV-12); NTBC055 (*E. Coli* strain expressing VIM-1); and NTBC039 (*K. oxytoca* strain expressing IMP-28).

The compounds, compositions and products of the invention may also be useful in the prevention or treatment of infection by the following strains. The triple combination is particularly useful in the prevention or treatment of infection by these strains:

NTBC019 (*K. pneumonia* strain expressing NDM-1, CTX-M-15 and OXA-181); NTBC185 (*K. pneumonia* strain expressing SHV-OSBL, TEM-OSBL, NDM-1 and OXA-48); NTBC186 (*K. pneumonia* strain expressing ACT-TYPE, VIM-1 and OXA-48); NTBC187 (*K. pneumonia* strain expressing SHV-OSBL, NDM-1 and OXA-48); and NTBC188 (*K. pneumonia* strain expressing NDM-1 and KPC-2).

The compound, composition or combination of the invention may be used to treat or prevent infections and conditions caused by any one or a combination of the above-mentioned bacteria. In particular, the compound, composition or combination of the invention may be used in the treatment or prevention of pneumonia. The compound, composition or combination may also be used in the treatment of septic shock, urinary tract infection, and infections of the gastrointestinal tract, skin or soft tissue.

The compound, composition or combination of the invention may be used to treat patients with Carbapenem Resistant Enterobacteriaceae (CRE). CRE can be found in the community or in hospitals and other institutions which are commonly associated with long term patients and those that are undergoing significant medical interventions such as are commonly cared for in Intensive Care Units (ICUs).

A compound, composition or combination of the invention can be administered to the subject in order to prevent the onset or reoccurrence of one or more symptoms of the bacterial infection. This is prophylaxis. In this embodiment, the subject can be asymptomatic. The subject is typically one that has been exposed to the bacterium. A prophylactically effective amount of the agent or formulation is administered to such a subject. A prophylactically effective amount is an amount which prevents the onset of one or more symptoms of the bacterial infection.

A compound, composition or combination of the invention can be administered to the subject in order to treat one or more symptoms of the bacterial infection. In this embodiment, the subject is typically symptomatic. A therapeutically effective amount of the agent or formulation is administered to such a subject. A therapeutically effective amount is an amount effective to ameliorate one or more symptoms of the disorder.

The compound, composition or combination of the invention may be administered in a variety of dosage forms. Thus, it can be administered orally, for example as tablets, troches, lozenges, aqueous or oily suspensions, dispersible powders or granules. Formulation composition of the invention may also be administered parenterally, whether subcutaneously, intravenously, intramuscularly, intrasternally, transdermally or by infusion techniques. The compound, composition or combination may also be administered as a suppository. Preferably, the compound, composition or combination may be administered via inhaled (aerosolised) or intravenous administration, most preferably by inhaled (aerosolised) administration.

The compound, composition or combination of the invention is typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

The compound, composition or combination of the invention may be formulated for inhaled (aerosolised) administration as a solution or suspension. The compound, composition or combination of the invention may be administered by a metered dose inhaler (MDI) or a nebulizer such as an electronic or jet nebulizer. Alternatively, the compound, composition or combination of the invention may be formulated for inhaled administration as a powdered drug, such formulations may be administered from a dry powder inhaler (DPI). When formulated for inhaled administration, the compound, composition or combination of the invention may be delivered in the form of particles which have a mass median aerodynamic diameter (MMAD) of from 1 to 100 µm, preferably from 1 to 50 µm, more preferably from 1 to 20 µm such as from 3 to 10 µm, e.g. from 4 to 6 µm. When the compound, composition or combination of the invention is delivered as a nebulized aerosol, the reference to particle diameters defines the MMAD of the droplets of the aerosol. The MMAD can be measured by any suitable technique such as laser diffraction.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspension or solutions for intramuscular injections or inhalation may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for inhalation, injection or infusion may contain as carrier, for example, sterile water or preferably they may be in the form of sterile, aqueous, isotonic saline solutions. Pharmaceutical compositions suitable for delivery by needleless injection, for example, transdermally, may also be used.

A therapeutically or prophylactically effective amount of the compound of the invention is administered to a subject. The dose may be determined according to various parameters, especially according to the compound used; the age, weight and condition of the subject to be treated; the route of administration; and the required regimen. Again, a physician will be able to determine the required route of administration and dosage for any particular subject. A typical daily dose is from about 0.01 to 100 mg per kg, preferably from about 0.1 mg/kg to 50 mg/kg, e.g. from about 1 to 10 mg/kg of body weight, according to the activity of the specific inhibitor, the age, weight and conditions of the subject to be treated, the type and severity of the disease and the frequency and route of administration. Preferably, daily dosage levels are from 5 mg to 2 g.

When the compound of the invention is administered to a subject in combination with another active agent (for example in the form of a pharmaceutical combination comprising an antibiotic agent and optionally an SBL inhibitor), the dose of the other active agent (e.g. SBL inhibitor and/or antibiotic agent) can be determined as described above. The dose may be determined according to various parameters, especially according to the agent used; the age, weight and condition of the subject to be treated; the route of administration; and the required regimen. Again, a physician will be able to determine the required route of administration and dosage for any particular subject. A typical daily dose is from about 0.01 to 100 mg per kg, preferably from about 0.1 mg/kg to 50 mg/kg, e.g. from about 1 to 10 mg/kg of body weight, according to the activity of the specific inhibitor, the age, weight and conditions of the subject to be treated, the type and severity of the disease and the frequency and route of administration. Preferably, daily dosage levels are from 5 mg to 2 g.

The antibacterial properties of the compounds described herein mean that they are also useful in the treatment of bacterial infection in vitro, i.e. other than by the treatment of human or animal subjects. Thus, the invention also provides a cleaning composition comprising a thiazole derivative of Formula (I) or a salt thereof. The cleaning composition may further comprise, for example, a detergent, a surfactant (including ionic and non-ionic surfactants), a diluent, a bleach (including a hypochlorite such as sodium hypochlorite or calcium hypochlorite, chlorine, chlorine dioxide, hydrogen peroxide or an adduct thereof, sodium perborate, and sodium percarbonate), an alcohol (such as ethanol or isopropanol), or a disinfectant. Typically, the disinfectant may be selected from benzyl-4-chlorophenol, amylphenol, phenylphenol, glutaraldehyde, alkyl dimethyl benzyl ammonium chloride, alkyl dimethyl ethylbenzyl ammonium chloride, iodine, peracetic acid and chlorine dioxide. Typically, the detergent may be an alkaline detergent such as sodium hydroxide, sodium metasilicate, or sodium carbonate, or an acid detergent such as hydrochloric acid, nitric acid, sulfuric acid, phosphoric acid, citric acid, or tartaric acid.

The following Examples illustrate the invention. They do not however, limit the invention in any way. In this regard, it is important to understand that the particular assay used in the Examples section is designed only to provide an indication of biological activity. There are many assays available to determine biological activity, and a negative result in any one particular assay is therefore not determinative.

Experimental Details
General Synthetic Methodology

There are several related synthetic methods to this class of compounds described by Formula 1 and which are described below, where R is taken to mean any substituent on the phenyl ring.

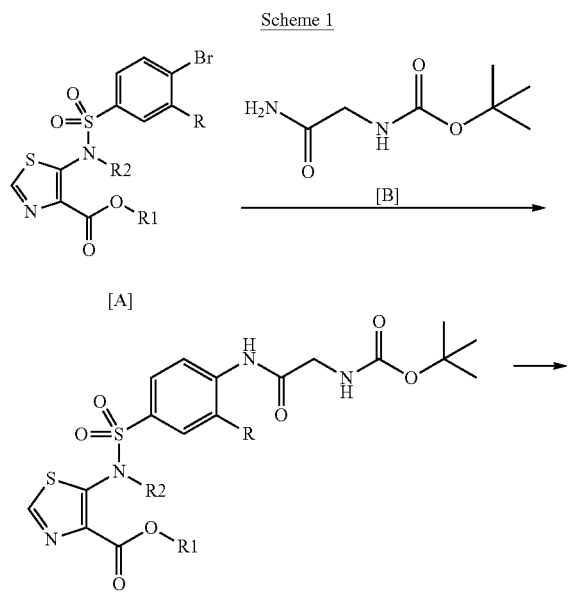

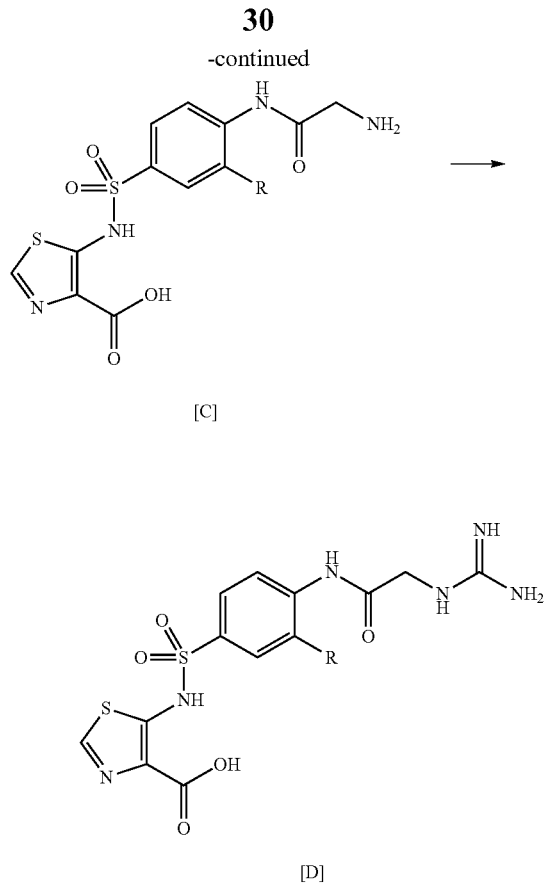

The preparation of the key thiazole intermediate tert-butyl 5-{[(4-methoxyphenyl) methyl]amino}-1,3-thiazole-4-carboxylate has been described previously (WO2014/198849) and is easily prepared on a 100 g scale. Reaction of this with a wide range of arylsulphonyl chlorides has been achieved using basic catalysis (such as pyridine, triethylamine or sodium hydride) giving sulphonamide intermediates such as [A]. Other versions of the thiazole starting material (eg R1=ethyl; R2=H) are also easily accessible or even commercially available. Many of the compounds described herein are accessible from the standard Buchwald reaction of bromophenylsulphonamide [A] with e.g. protected glycinamides such as [B]. Global acid-catalysed deprotection reveals the primary amine [C] which can be converted to the guanidine [D] if required (Scheme 1) using a guanidinylating reagent such as 1H-pyrazole-1-carboximidamide.

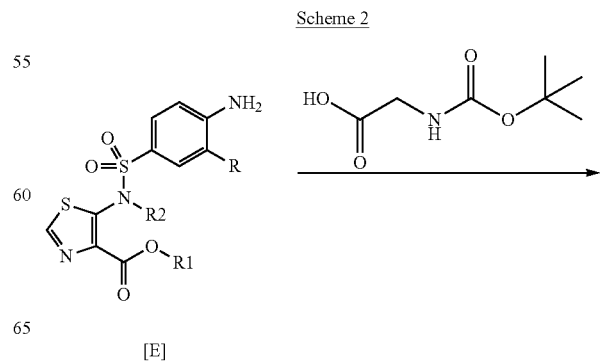

31
-continued

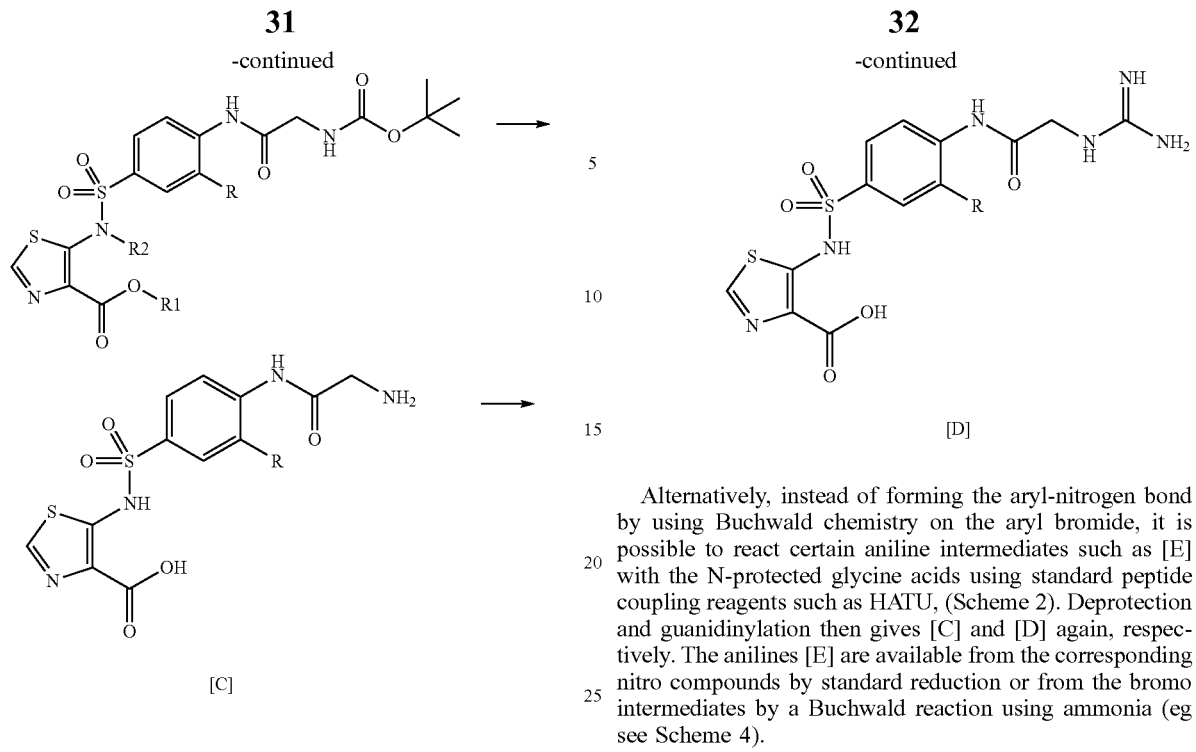

[C]

32
-continued

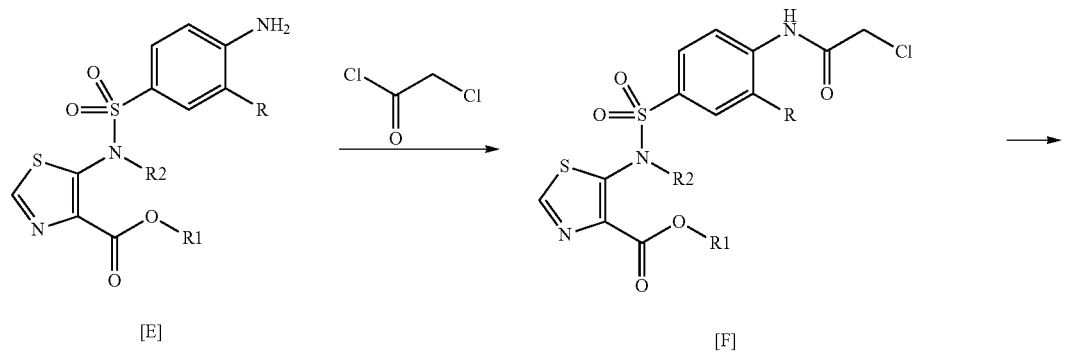

[D]

Alternatively, instead of forming the aryl-nitrogen bond by using Buchwald chemistry on the aryl bromide, it is possible to react certain aniline intermediates such as [E] with the N-protected glycine acids using standard peptide coupling reagents such as HATU, (Scheme 2). Deprotection and guanidinylation then gives [C] and [D] again, respectively. The anilines [E] are available from the corresponding nitro compounds by standard reduction or from the bromo intermediates by a Buchwald reaction using ammonia (eg see Scheme 4).

Scheme 3

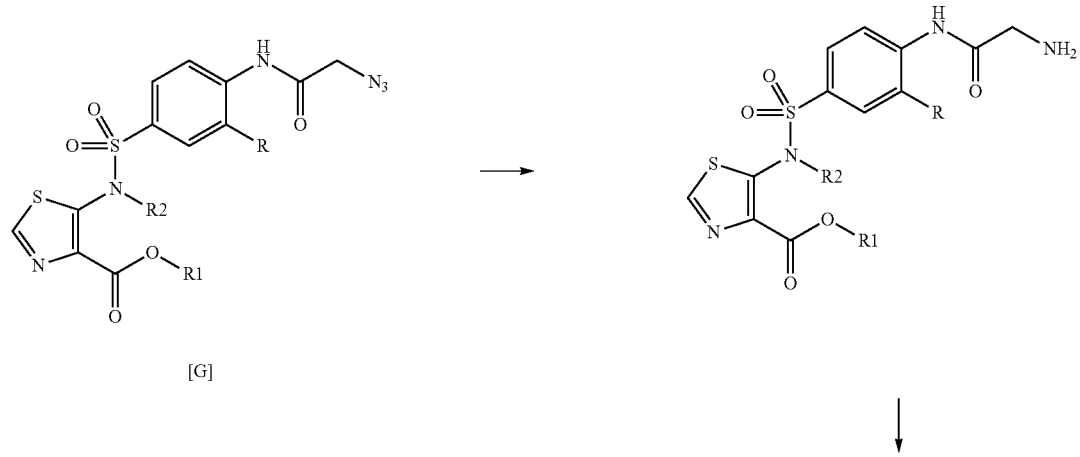

33 34

-continued

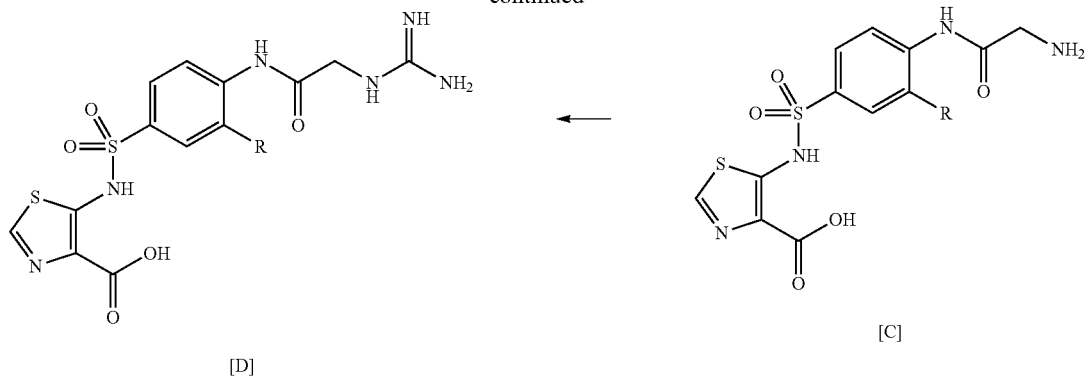

[D]　　　　[C]

In certain circumstances, eg where the substituents on the aryl ring are particularly electron-withdrawing, neither the Buchwald amidation nor the amide formation using protected glycine derivatives are successful. For these situations it is necessary to react the aniline with highly reactive chloroacetyl chloride to give intermediate [F]. Displacement with sodium azide then affords azidoacetamide [G] which can be reduced with standard reducing agents, accessing [C] and [D] in the usual manner, (Scheme 3).

Scheme 4

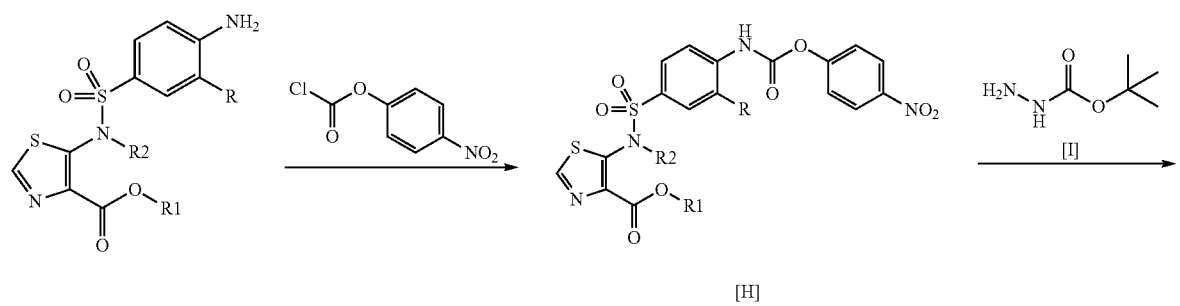

[H]

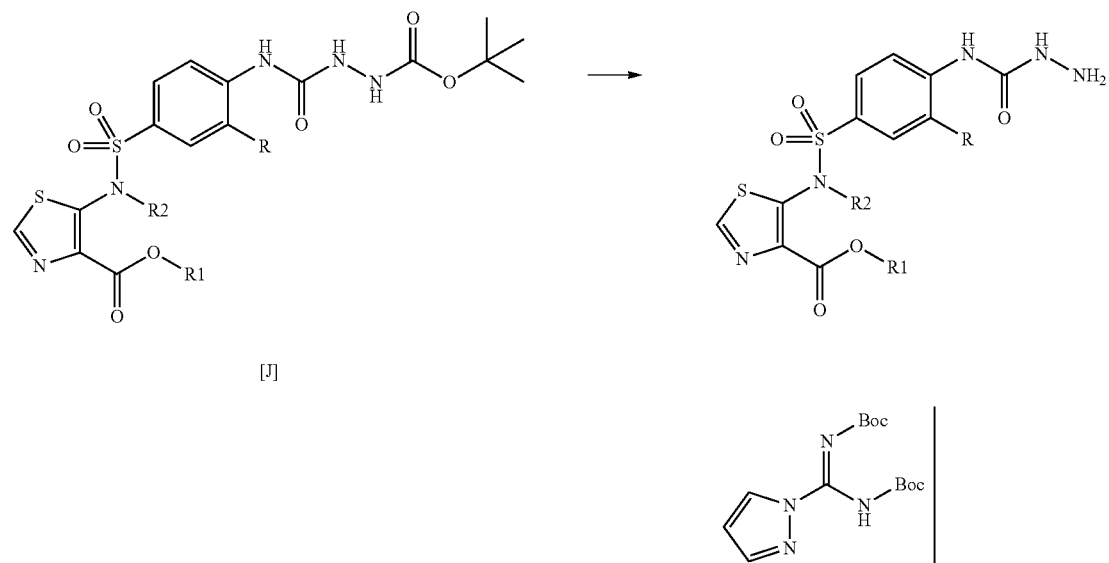

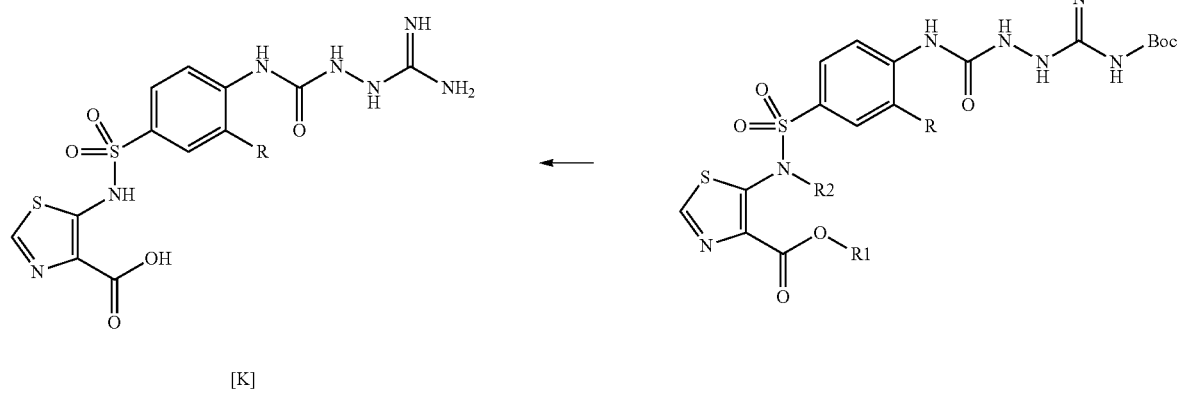

[K]

Certain ureido derivatives require bespoke syntheses (Scheme 4). For example Buchwald reaction of the usual bromoarylsulphonamide with ammonia itself as the nitrogen-containing component gives the corresponding aniline. Activation of this aniline with 4-nitrophenyl chloroformate gives [H] which reacts with BOC-protected hydrazine [I] to give coupled product [J], possibly by the intermediacy of the isocyanate derived from [H]. Mild acid treatment removes the BOC group which can be guanidinylated to afford a protected guanidine functionality. Global deprotection of BOC, p-methoxybenzyl and tert-butyl ester groups then affords guanidine [K].

Scheme 5

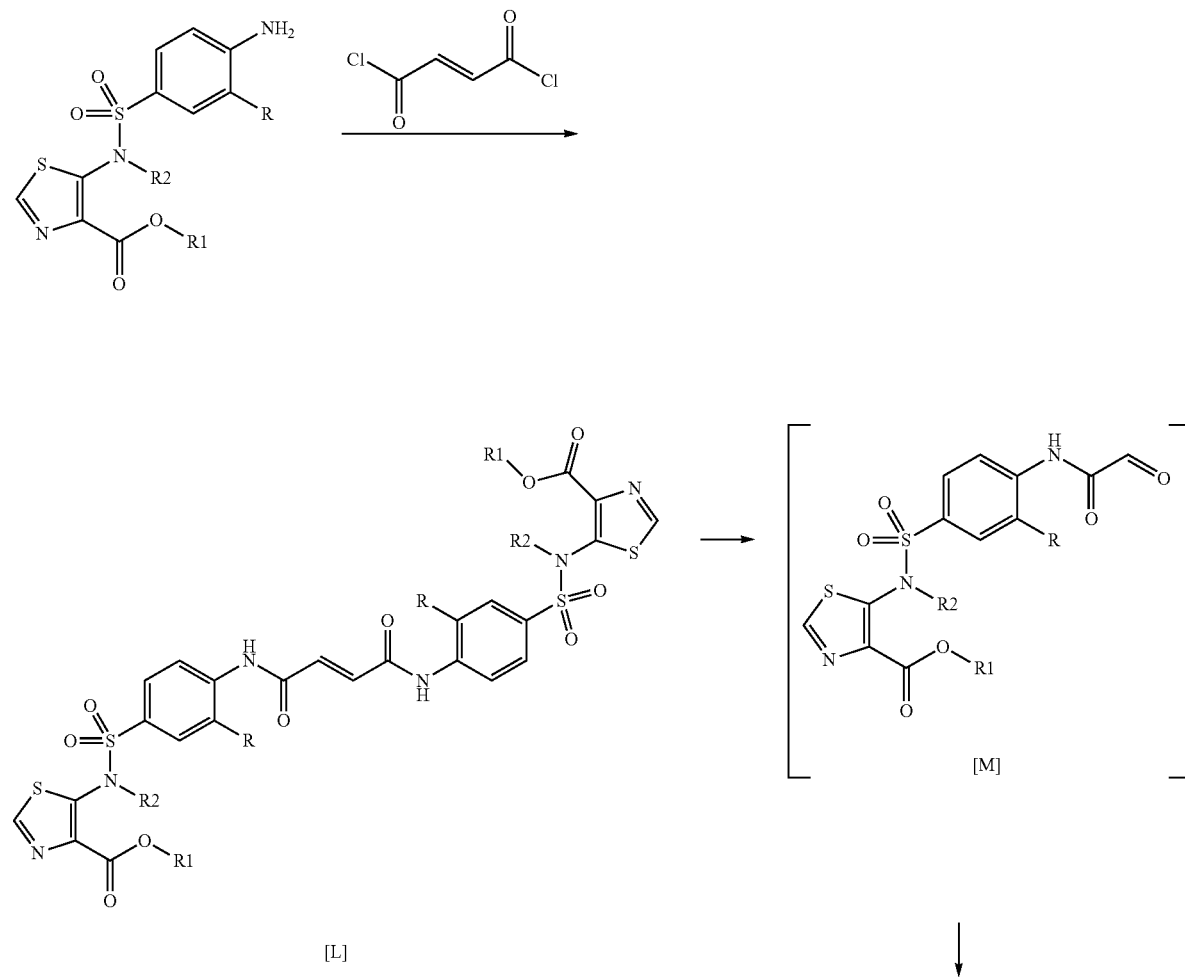

[L]     [M]

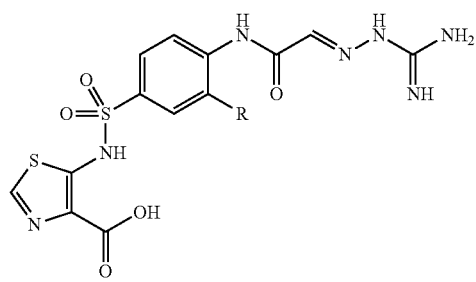

[O]

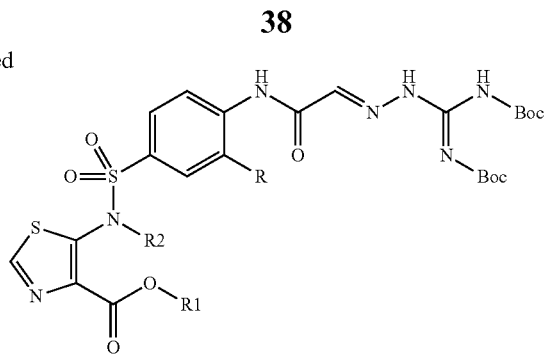

[N]

Certain analogues require a critical glyoxamide intermediate [M], which is synthesised by reacting the usual aniline with 0.5 equivalents of fumaryl chloride to give symmetrical bis amide [L]. Ozonolysis proceeds to give the labile glyoxamide [M] which can be reacted with a variety of nucleophiles including the bis-BOC protected aminoguanidine affording [N]. Global deprotection in the usual way then affords the corresponding imine [O], (Scheme 5).

Abbreviations

ACN Acetonitrile
AcOH Acetic acid
Ag(OTf) Silver triflate
AIBN Azobisisobutyronitrile
Boc Tert-butoxy-carbonyle
Boc2O Di-tert-butyl dicarbonate
$Cs_2CO_3$ Cesium carbonate
CFU Colony forming unit
CuI Copper iodide
DCM Dichloromethane
DIPEA N,N-Diisopropylethylamine
DMAP 4-Dimethylaminopyridine
DMF Dimethylformamide
DMS Dimethylsulfide
DMSO Dimethyl sulfoxide
dppf 1,1'-Bis(diphenylphosphino)ferrocene
EDC.HCl N-(3-Dimethylaminopropyl)-N'-ethylcarbodiimide hydrochloride
EtOAc Ethyl acetate
EtOH Ethanol
Et3N Triethylamine
HATU 1-[Bis(dimethylamino)methylene]-1H-1,2,3-triazolo[4,5-b]pyridinium 3-oxid hexafluorophosphate
HCl Hydrochloric acid
HOBt Hydroxybenzotriazole
$H_2SO_4$ Sulfuric Acid
IPA Iso-propyl alcohol
Km Michaelis constant
MeI Methyl iodide
MeOH Methanol
NBS N-bromo succinimide
$Na_2CO_3$ Sodium carbonate
$Na_2SO_4$ Sodium sulfate
$Pd_2(dba)_3$ Tris(dibenzylideneacetone)dipalladium(O)
$PdCl_2(PPh3)2$ Bis(triphenylphosphine)palladium(II) dichloride
$PdCl_2(dppf)$ [1,1'-Bis(diphenylphosphino)ferrocene]dichloropalladium(II)
PMB Paramethoxybenzyl
TEA Triethylamine
TES Triethylsilane
TMSOK Potassium trimethylsilanolate
TFA Trifluoroacetic acid
TMSOTf Trimethylsilyl trifluoromethanesulfonate
TFA Trifluoroacetic acid
THF Tetrahydrofurane
T3P Propylphosphinic anhydride
RT Room temperature The structure of (RuPhos) Palladium (II) phenethylamine chloride (1:1 MTBE adduct) used for Buchwald coupling steps (RuPhos Pd G1 complex) is shown below.

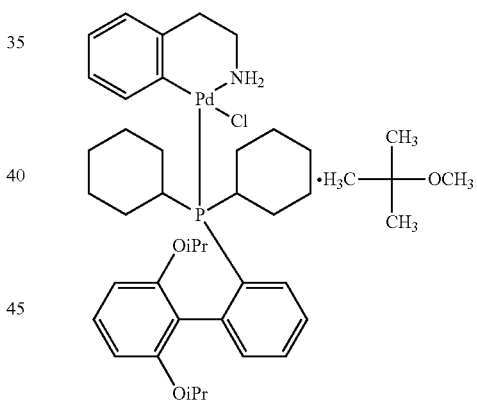

EXAMPLES

General Techniques

1H NMR spectra are reported at 300 or 400 MHz in DMSO-d6 solutions (δ in ppm), using chloroform as the reference standard (7.25 ppm). When peak multiplicities are reported, the following abbreviations are used: s (singlet), d (doublet), t (triplet), m (multiplet), bs (broadened singlet), dd (doublet of doublets), dt (doublet of triplets), q (quartet). Coupling constants, when given, are reported in hertz (Hz).

The term "purified by prep hplc (MDAP)" refers compound purification using a mass-directed auto purification system on an Agilent 1260 infinity machine with an XSelect CHS Prep C18 column, eluting with 0.1% formic acid in water/acetonitrile and detection with a Quadruploe LC/MS.

Example 1 tert-butyl 5-[(4-methoxyphenyl)methylamino]thiazole-4-carboxylate (Key Intermediate-1)

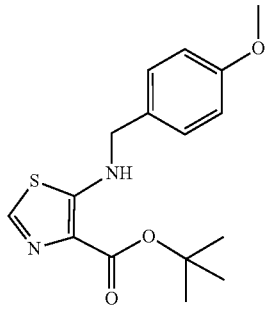 [SMILES: COc1ccc(CNc2scnc2C(=O)OC(C)(C)C)cc1]

A suspension of potassium tert-butoxide (874 mg, 7.79 mmol) in dry tetrahydrofuran (10 mL) was stirred vigorously at room temperature. To this, a solution of tert-butyl isocyanoacetate (1.0 g, 7.08 mmol) in dry tetrahydrofuran (5 mL) was added drop wise and the mixture stirred at room temperature for 10 minutes. To this, a solution of 4-methoxybenzyl isothiocyanate (1.27 g, 7.08 mmol) in dry tetrahydrofuran (5 mL) was added drop wise at room temperature. After 2 hours the solution was poured into saturated NaHCO3 solution and extracted with ethyl acetate. The organic layer was dried with Na2SO4, filtered and concentrated in vacuo to dryness. The residue was purified by silica gel chromatography (eluting with 0-50% ethyl acetate/cyclohexane) affording the title product as a pale yellow solid (852 mg).

1H NMR (CDC$_3$) δ: 7.81 (1H, m), 7.73 (1H, br s), 7.31-7.23 (2H, m), 6.92-6.85 (2H, m), 4.35 (2H, d), 3.80 (3H, s), 1.61 (9H, s).

M/z 321 (M+H)$^+$

Example 2

5-[[3,5-difluoro-4-[(2-guanidinoacetyl)amino]phenyl]sulfonylamino]thiazole-4-carboxylic acid

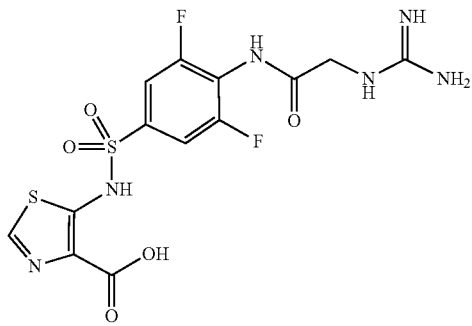 [SMILES: N=C(N)NCC(=O)Nc1c(F)cc(S(=O)(=O)Nc2scnc2C(=O)O)cc1F]

a. tert-butyl 5-[(4-bromo-3,5-difluoro-phenyl)sulfonyl-[(4-methoxyphenyl)methyl]amino]thiazole-4-carboxylate

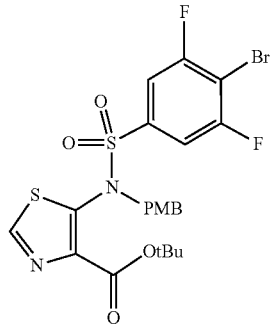

A solution of tert-butyl 5-[(4-methoxyphenyl)methylamino]thiazole-4-carboxylate (1 g, 3.12 mmol, 1 eq) in THF (15 mL) was added to NaH suspension in THF (10 mL) at 0° C. under argon atmosphere. After 30 minutes, a solution of 4-bromo-3,5-difluoro-benzenesulfonyl chloride (1.0 g, 3.43 mmol, 1.1 eq) in THF (15 mL) was added at 0° C. under argon atmosphere. The resulting reaction mixture was stirred at RT for 1 h, quenched with ice cold water (20 mL) and extracted with ethyl acetate (2×20 mL). The combined organic layer was dried over Na$_2$SO$_4$, filtered and concentrated. The crude material was purified by trituration with diethyl ether (2×5 mL) affording a pale yellow solid (800 mg, 44%).

M/z 577.0 (M+H)$^+$ b. tert-butyl 5-[[4-[[2-(tert-butoxycarbonylamino)acetyl]amino]-3,5-difluoro-phenyl]sulfonyl-[(4-methoxyphenyl)methyl]amino]thiazole-4-carboxylate

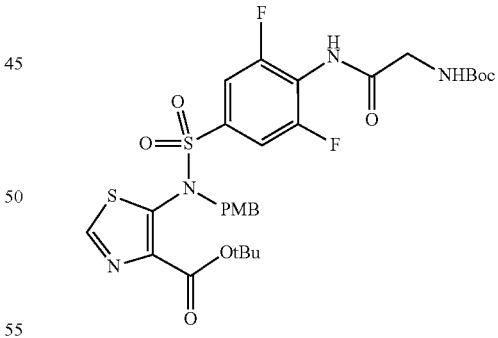

A solution of tert-butyl 5-[(4-bromo-3,5-difluoro-phenyl)sulfonyl-[(4-methoxyphenyl)methyl]amino]thiazole-4-carboxylate (100 mg, 0.173 mmol, 1 eq) in 1,4-dioxane (5 mL) was purged with argon for 15 minutes. Then tert-butyl N-(2-amino-2-oxo-ethyl)carbamate (45 mg, 0.26 mmol, 1.5 eq), K$_3$PO$_4$ (110 mg, 0.521 mmol, 3 eq), Pd$_2$(dba)$_3$ (16 mg, 0.17 mmol, 0.1 eq) and Xantphos (30 mg, 0.052 mmol, 0.3 eq) were added under argon atmosphere. The resulting reaction mixture was heated to 85° C. for 16 h in a closed vial. The temperature was allowed to cool to RT, and the reaction mixture was filtered through celite pad and the pad was washed with EtOAc (2×5 mL). The organic layer was concentrated under reduced pressure. The resulting crude compound was dissolved in ethyl acetate (25 mL), washed with water (10 mL) and brine solution (10 mL). The organic layer was dried over $Na_2SO_4$, filtered and concentrated. The crude material was purified by flash chromatography (eluting with 55% ethyl acetate in petroleum ether) affording a pale yellow solid (60 mg, 51%).

M/z 669.5 $(M+H)^+$ c. 5-[[4-[(2-aminoacetyl)amino]-3,5-difluoro-phenyl]sulfonylamino]thiazole-4-carboxylic acid, trifluoroacetate

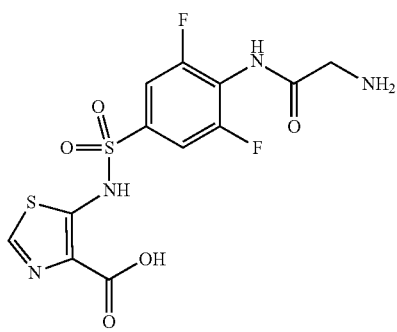 [SMILES: NCC(=O)Nc1c(F)cc(S(=O)(=O)Nc2scnc2C(=O)O)cc1F]

TFA (4 mL) was added to tert-butyl 5-[[4-[[2-(tert-butoxycarbonylamino)acetyl]amino]-3,5-difluoro-phenyl]sulfonyl-[(4-methoxyphenyl)methyl]amino]thiazole-4-carboxylate (300 mg, 0.448 mmol, 1 eq) at RT and stirred for 4 h. TFA was evaporated by reduced pressure. The resulting crude product was triturated with diethyl ether (2×5 mL) and dried under high vacuum to afford a pale yellow solid (150 mg, 85%).

M/z 393.3 $(M+H)^+$ d. 5-[[3,5-difluoro-4-[(2-guanidinoacetyl)amino]phenyl]sulfonylamino]thiazole-4-carboxylic acid

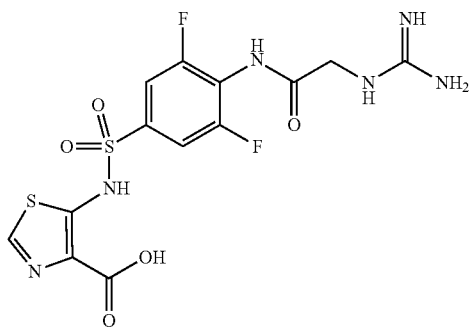 [SMILES: N=C(N)NCC(=O)Nc1c(F)cc(S(=O)(=O)Nc2scnc2C(=O)O)cc1F]

To a stirred solution of 5-[[4-[(2-aminoacetyl)amino]-3,5-difluoro-phenyl]sulfonylamino]thiazole-4-carboxylic acid, trifluoroacetate (150 mg, 0.382 mmol, 1 eq) in DMF (5 mL) was added pyrazole-1-carboxamidine; hydrochloride (84 mg, 0.573 mmol, 1.5 eq) and DIPEA (0.3 mL, 1.91 mmol, 5 eq) at RT. The resulting reaction mixture was stirred at RT for 16 h, and concentrated under reduced pressure. Water (5 mL) was added to the residue and the precipitate was filtered and washed with diethyl ether (2×5 mL). The crude product was purified by preparative HPLC to afford the title compound as a white solid (47 mg, 28%).

$^1$H NMR (400 MHz, DMSO-$d_6$) δ 13.20 (1H, s), 10.14 (1H, brs), 8.12 (1H, s), 7.55 (1H, brs), 7.43 (2H, d, J=7.2 Hz), 7.35-7.10 (3H, brs), 4.12 (2H, s).

M/z 434.9 $(M+H)^+$

LC-MS Condition:
Column: Acquity BEH C18 (50 mm×2.1 mm, 1.7 um);
Mobile Phase: A: 0.05% Formic Acid in water;
B: 0.05% Formic Acid in ACN;
Time (min)/% B: 0/3, 0.4/3, 2/98, 3.4/98, 3.5/3, 4/3;
Column Temp: 35° C., Flow Rate: 0.6 mL/min
Prep. HPLC Condition:
Column: Symmetry C18 (300*19) mm, 7 u;
Mobile phase: (A) 0.1% Formic Acid (B) Acetonitrile;
Flow: 19 mL/min;
Gradient (T/% B): 0/5, 1/5, 8/20, 11/20, 11.02/99, 12/99, 12.1/5, 15/5;
Solubility: ACN+$H_2O$+THF+FA Example 3

5-[[5-fluoro-6-[(2-guanidinoacetyl)amino]-3-pyridyl]sulfonylamino]thiazole-4-carboxylic acid

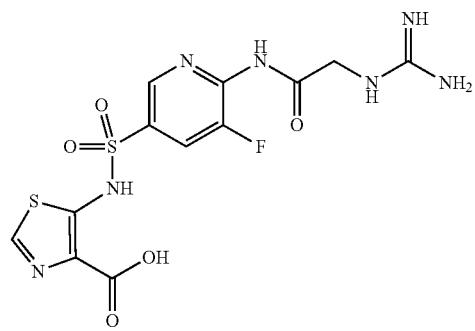 [SMILES: N=C(N)NCC(=O)Nc1ncc(S(=O)(=O)Nc2scnc2C(=O)O)cc1F]

a. 5-fluoro-6-hydroxy-pyridine-3-sulfonylchloride

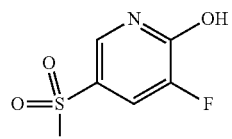

3-fluoropyridin-2-ol (2 g, 17.6 mmol) was added to chlorosulfonic acid (20 mL, 300.3 mmol) at 0° C. The reaction mixture was stirred at 160° C. for 2 h, cooled to RT and slowly poured into ice cold water (50 mL). The aqueous layer was extracted with EtOAc (3×50 mL). The organic layer was dried over $Na_2SO_4$, filtered and concentrated under reduced pressure. The crude compound was triturated with n-pentane (2×50 mL) to afford an off-white solid (2.7 g, 72%).

M/z 212.11 $(M+H)^+$ b. 6-chloro-5-fluoro-pyridine-3-sulfonylchloride

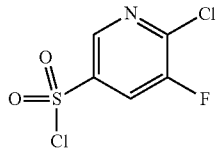 [SMILES: O=S(=O)(Cl)c1cnc(Cl)c(F)c1]

Thionyl chloride (5 mL, 68.9 mmol) was added to 5-fluoro-6-hydroxy-pyridine-3-sulfonyl chloride (1 g, 4.73 mmol) in toluene (25 mL) at 0° C. DMF (0.2 mL) was then added slowly at 0° C. The reaction mixture was refluxed for 3 h, cooled to RT and concentrated under reduced pressure. The resulting crude material was co-distilled with toluene (2×25 mL) to afford a pale yellow liquid which was used in the next step without further purification (0.9 g, crude).

$^1$H NMR (400 MHz, DMSO-$d_6$) δ 8.83 (1H, m), 8.04 (1H, m).

c. tert-butyl 5-[(6-chloro-5-fluoro-3-pyridyl)sulfonyl-[(4-methoxyphenyl)methyl]amino]thiazole-4-carboxylate

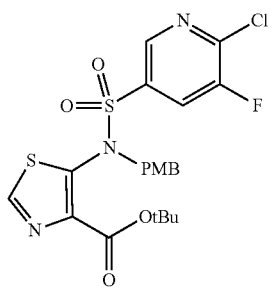

A solution of tert-butyl 5-[(4-methoxyphenyl)methylamino]thiazole-4-carboxylate (1.5 g, 4.68 mmol) in THF (25 mL) was added to NaH (1.12 g, 46.8 mmol) suspension in THF (10 mL) at 0° C. under argon atmosphere. After 15 minutes, a solution of 6-chloro-5-fluoro-pyridine-3-sulfonyl chloride (1.6 g, 7.0 mmol) in THF (15 mL) was added to the above reaction mixture at 0° C. under argon atmosphere. The resulting reaction mixture was stirred at RT for 0.5 h, quenched with ice cold water (20 mL) and extracted with ethyl acetate (3×20 mL). The combined organic layer was dried over Na$_2$SO$_4$, filtered and concentrated. The crude compound was purified by flash chromatography (eluting with 10-15% ethyl acetate in petroleum ether) to afford a yellow oil (1.3 g, 54%).

M/z 514.27 (M+H)$^+$ d. tert-butyl 5-[[6-[[2-(tert-butoxycarbonylamino)acetyl]amino]-5-fluoro-3-pyridyl]sulfonyl-[(4-methoxyphenyl)methyl]amino]thiazole-4-carboxylate

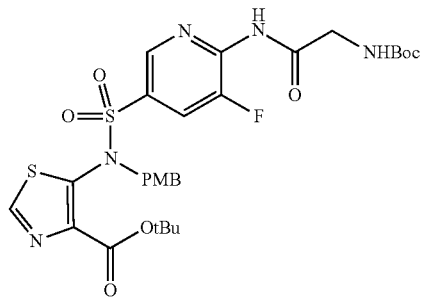

A solution of tert-butyl 5-[(6-chloro-5-fluoro-3-pyridyl)sulfonyl-[(4-methoxyphenyl)methyl]amino]thiazole-4-carboxylate (150 mg, 0.29 mmol) in 1,4-dioxane (5 mL) was purged with argon for 20 minutes. Then tert-butyl N-(2-amino-2-oxo-ethyl)carbamate (75 mg, 0.43 mmol), Cs$_2$CO3 (282 mg, 0.87 mmol), Pd$_2$(dba)$_3$ (26 mg, 0.02 mmol) and Xantphos (50 mg, 0.08 mmol) were added under argon atmosphere. The resulting reaction mixture was heated to 70° C. for 0.5 h in a sealed tube, allowed to cool to RT, filtered through celite pad and the pad was washed with ethyl acetate (2×3 mL). The organic layer was concentrated under reduced pressure. The crude material was purified by flash chromatography (eluting with 50% ethyl acetate in petroleum ether) to afford a pale yellow solid (75 mg, 39%).

M/z 652.41 (M+H)$^+$ e. 5-[[6-[(2-aminoacetyl)amino]-5-fluoro-3-pyridyl]sulfonylamino]thiazole-4-carboxylic acid, trifluoacetate

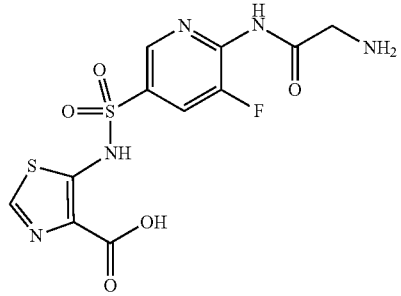 [SMILES: NCC(=O)Nc1ncc(S(=O)(=O)Nc2scnc2C(=O)O)cc1F]

TFA (1.5 mL) was added to a solution of tert-butyl 5-[[6-[[2-(tert-butoxycarbonylamino)acetyl]amino]-5-fluoro-3-pyridyl]sulfonyl-[(4-methoxyphenyl)methyl]amino]thiazole-4-carboxylate (150 mg, 0.23 mmol) in DCM (2 mL) at 0° C., allowed to stir at RT for 18 h and concentrated under reduced pressure. The residue was triturated with diethyl ether (2×2 mL), n-pentane (2×2 mL) and dried under high vacuum to afford an off white solid which was used in next step without further purification (60 mg, crude).

M/z 376.24 (M+H)$^+$ f. 5-[[5-fluoro-6-[(2-guanidinoacetyl)amino]-3-pyridyl]sulfonylamino]thiazole-4-carboxylic acid

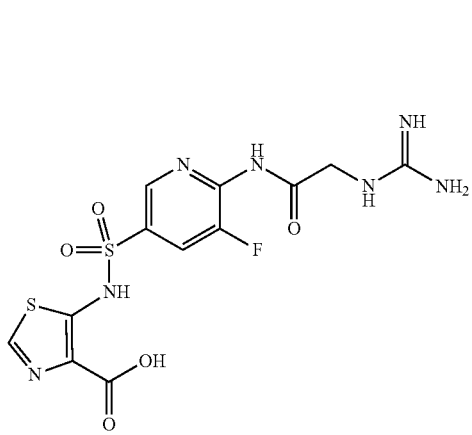 [SMILES: N=C(N)NCC(=O)Nc1ncc(S(=O)(=O)Nc2scnc2C(=O)O)cc1F]

Pyrazole-1-carboxamidine; hydrochloride (70 mg, 0.48 mmol) and DIPEA (0.27 mL, 1.6 mmol) were added to a stirred solution of 5-[[6-[(2-aminoacetyl)amino]-5-fluoro-3-pyridyl]sulfonylamino]thiazole-4-carboxylic acid, trifluoroacetate (120 mg, 0.32 mmol) in DMF (2 mL) at RT. The resulting reaction mixture was stirred at RT for 4 h, concentrated under reduced pressure and ice cold 1N HCl (2 mL) was added to the crude compound and stirred for 10 minutes. The resulting precipitate was filtered, washed with diethyl ether (2×5 mL) and dried under high vacuum. The crude product was purified by preparative. HPLC affording the title product as an off white solid (25 mg, 18%).

$^1$H NMR (400 MHz, DMSO-d$_6$) δ 13.20 (1H, brs), 10.8 (1H, brs), 8.51 (1H, d, J=1.6 Hz), 8.13 (1H, s), 7.99 (1H, dd, J=9.6 Hz, J=1.6 Hz), 7.52 (1H, brs), 7.26 (3H, brs), 4.20 (2H, d, J=4.4 Hz).

M/z 418.18 (M+H)$^+$

LC-MS Condition:

Column: Acquity BEH C18 (50 mm×2.1 mm, 1.7 um);

Mobile Phase: A: 0.05% Formic Acid in water; B: 0.05% Formic Acid in ACN;

Time (min)/% B: 0/3, 0.4/3, 3.2/98, 3.8/98, 4.2/3, 4.5/3;

Column Temp: 35° C.;

Flow Rate: 0.6 mL/min.

Prep. HPLC Condition:

Column used: PHENYL HEXYL (150*30) mm 5 u;

Mobile phase: (A) 0.1% Formic Acid, (B) Acetonitrile;

Flow: 19 mL/min;

Gradient –(T/% B): 0/5, 1/5, 6/30, 8.9/30, 8.95/99, 11/99, 11.1/5, 14/5;

Solubility: ACN+THF.

Example 4

5-[[4-[(3-amino-3-imino-propanoyl)amino]-3-fluoro-phenyl]sulfonylamino]thiazole-4-carboxylic acid

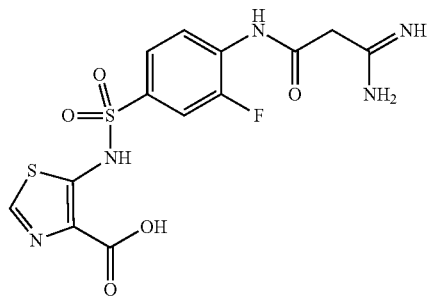 [SMILES: N=C(N)CC(=O)Nc1ccc(S(=O)(=O)Nc2scnc2C(=O)O)cc1F]

a. tert-butyl N-[3-amino-1-(tert-butoxycarbonylamino)-3-oxo-prop-1-enyl]carbamate

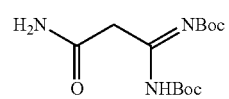

Saturated NaHCO$_3$ solution (10 mL was added to a stirred solution of 3-amino-3-imino-propanamide (3 g, 29.6 mmol) in dioxane (20 mL) at RT. Then (Boc)$_2$O (16.5 mL, 74.0 mmol) was added drop wise at 0° C. The resulting reaction mixture was stirred at RT for 16 h, concentrated under reduced pressure and water (30 mL) was added to the residue. The crude compound was extracted with ethyl acetate (2×50 mL). The combined organic layer was dried over Na$_2$SO$_4$, filtered and concentrated. The crude material was purified by flash column chromatography (eluting with 2% methanol in DCM) to afford an off-white solid (3.1 g, 34%).

M/z 302.36 (M+H)$^+$ b. tert-butyl 5-[[4-[3,3-bis(tert-butoxycarbonylamino)prop-2-enoylamino]-3-fluoro-phenyl]sulfonyl-[(4-methoxyphenyl)methyl]amino]thiazole-4-carboxylate

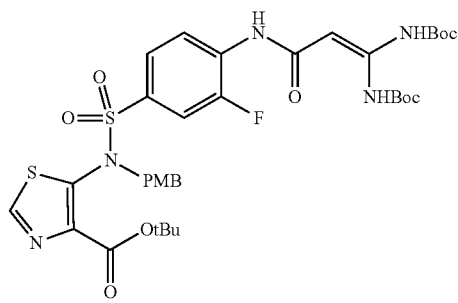

A solution of tert-butyl 5-[(4-bromo-3-fluoro-phenyl)sulfonyl-[(4-methoxyphenyl)methyl]amino]thiazole-4-carboxylate (1.1 g, 1.97 mmol) in 1,4-dioxane (15 mL) was purged with argon for 15 minutes. Then tert-butyl N-[3-amino-1-(tert-butoxycarbonylamino)-3-oxo-prop-1-enyl] carbamate (892 mg, 2.95 mmol), K$_3$PO$_4$ (837 mg, 3.94 mmol), Pd$_2$(dba)$_3$ (180 mg, 0.19 mmol) and Xantphos (342 mg, 0.59 mmol) were added under argon atmosphere. The resulting reaction mixture was heated to 65° C. for 3 h in a sealed tube, cooled to RT, filtered through a celite pad and the pad was washed with EtOAc (2×10 mL). The filtrate was concentrated under reduced pressure. The resulting crude compound was dissolved in ethyl acetate (50 mL), washed with water (30 mL) and brine solution (30 mL). The organic layer was dried over Na$_2$SO$_4$, filtered and concentrated under reduced pressure. The crude material was purified by flash chromatography (eluting with 55% ethyl acetate in petroleum ether) to afford a pale yellow solid (1.3 g, 85%).

M/z 778.52 (M+H)$^+$ c. 5-[[4-[(3-amino-3-imino-propanoyl)amino]-3-fluoro-phenyl]sulfonylamino]thiazole-4-carboxylic acid

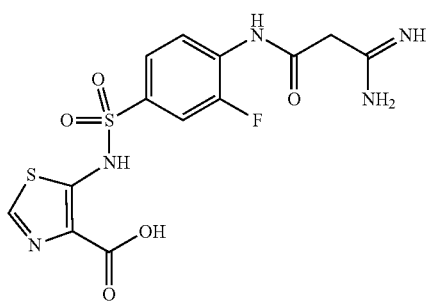

TFA (6 mL) was added to tert-butyl 5-[[4-[3,3-bis(tert-butoxycarbonylamino)prop-2-enoylamino]-3-fluoro-phenyl]sulfonyl-[(4-methoxyphenyl)methyl]amino]thiazole-4-carboxylate (600 mg, 0.77 mmol) at RT. The resulting mixture was stirred for 3 h and concentrated under reduced pressure. The resulting crude product was triturated with diethyl ether (2×10 mL) and dried under high vacuum. The crude product was purified by preparative HPLC affording the title product as an off-white solid (47 mg, 15%).

$^1$H NMR (400 MHz, DMSO-d$_6$) δ 13.42 (1H, brs), 10.34 (1H, brs), 8.99 (2H, brs), 8.62 (2H, brs), 8.14-8.02 (2H, m), 7.58-7.50 (2H, m), 3.68 (2H, s).

M/z 402.3 (M+H)$^+$

LC-MS Condition:

Column: Acquity BEH C18 (50 mm×2.1 mm, 1.7 um);

Mobile Phase: A: 0.05% Formic Acid in water; B: 0.05% Formic Acid in ACN;

Time (min)/% B: 0/3, 0.4/3, 3.2/98, 3.8/98, 4.2/3, 4.5/3;

Column Temp: 35° C.;

Flow Rate: 0.6 mL/min.

Prep. HPLC Condition:

Column used: PRONTOSIL (250*19) mm, 5 u;

Mobile phase: (A) 0.1% Formic Acid, (B) Acetonitrile;

Flow: 19 mL/min;

Gradient −(T/% B): 0/5, 1/5, 7.3/59, 7.4/99, 11/99, 11.1/5, 14/5;

Solubility: ACN+THF+H$_2$O+formic acid.

Examples 5 and 6

Example 5: 5-[[3-cyano-4-[(2-guanidinoacetyl)amino]phenyl]sulfonylamino]thiazole-4-carboxylic acid

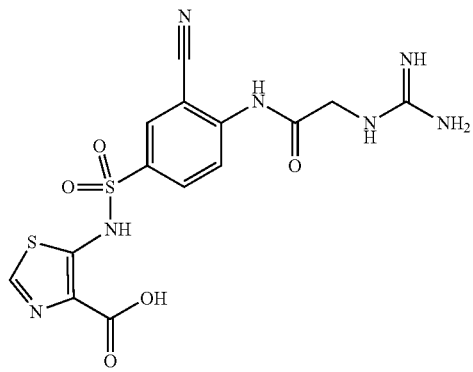 [SMILES: N#Cc1cc(S(=O)(=O)Nc2scnc2C(=O)O)ccc1NC(=O)CNC(=N)N]

Example 6: 5-[[3-carbamoyl-4-[(2-guanidinoacetyl)amino]phenyl]sulfonylamino]thiazole-4-carboxylic acid

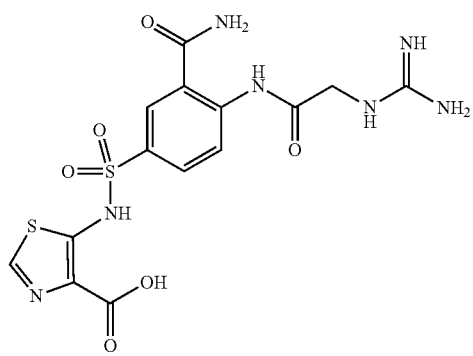 [SMILES: N=C(N)NCC(=O)Nc1ccc(S(=O)(=O)Nc2scnc2C(=O)O)cc1C(N)=O]

a. 4-bromo-3-cyano-benzenesulfonylchloride

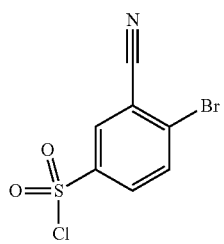 [SMILES: N#Cc1cc(S(=O)(=O)Cl)ccc1Br]

Solution-A: To a stirred solution of 5-amino-2-bromo-benzonitrile (2 g, 10.1 mmol) in AcOH (25 mL) was added conc. HCl (5 mL) at 0° C. and stirred for 10 minutes. Then NaNO$_2$ (770 mg, 11.1 mmol) in H$_2$O (10 mL) was added at the same temperature and stirred for 20 minutes.

Solution-B: SO2 gas was purged in AcOH (25 mL) for 30 minutes. Then a solution of CuCl$_2$ (1.62 g, 12.2 mmol) in H₂O (10 mL) was added at 0° C. and stirred for 20 minutes. After that, Solution-B was added drop wise to Solution-A. The reaction mixture was stirred at RT for 20 minutes and diluted with water (20 mL). The resulting precipitate was filtered, washed with n-pentane (2×20 mL) and dried under high vacuum to afford a yellow solid (1.7 g, 60%).

b. 5-[[3-cyano-4-[(2-hydroxyacetyl)amino]phenyl]sulfonyl-methyl-amino]thiazole-4-carboxylic acid

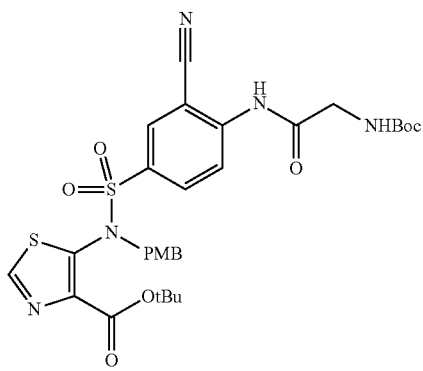

This compound was prepared following the procedure reported for Example 2 step b.

M/z 658.8 (M+H)⁺ c. 5-[[4-[(2-aminoacetyl)amino]-3,5-difluoro-phenyl]sulfonylamino]thiazole-4-carboxylic acid, trifluoroacetate

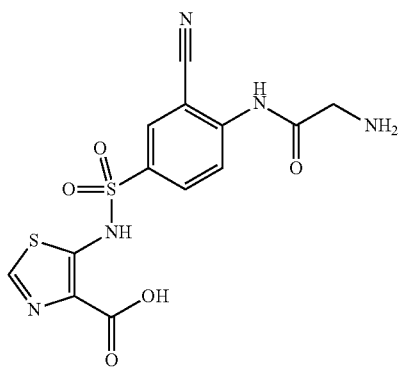 [SMILES: N#Cc1cc(S(=O)(=O)Nc2scnc2C(=O)O)ccc1NC(=O)CN]

This compound was prepared following the procedure reported for Example 2 step c.

M/z 382.4 (M+H)⁺ d. 5-[[4-[(2-aminoacetyl)amino]-3-cyano-phenyl]sulfonylamino]thiazole-4-carboxylic acid and 5-[[4-[(2-aminoacetyl)amino]-3-carbamoyl-phenyl]sulfonylamino]thiazole-4-carboxylic acid

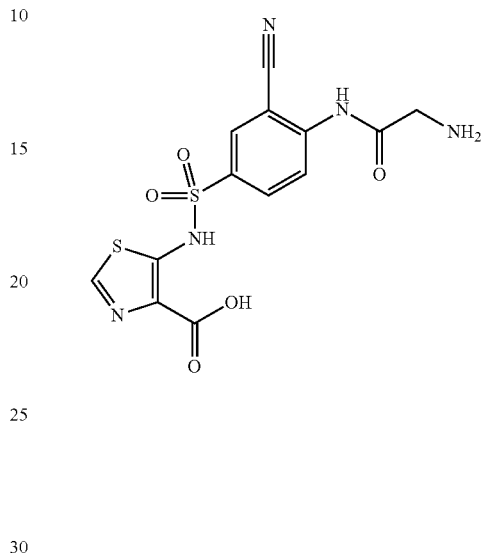

TFA: H₂O (9:1, 5 mL) was added to tert-butyl 5-[[4-[[2-(tert-butoxycarbonylamino)acetyl]amino]-3-cyano-phenyl]sulfonyl-[(4-methoxyphenyl)methyl]amino]thiazole-4-carboxylate (400 mg, 0.60 mmol) at RT. The reaction mixture was stirred for 6 h and concentrated under reduced pressure. The resulting material was triturated with diethyl ether (2×10 mL) and dried under high vacuum to obtain a yellow solid which was used in the next step without further purification (300 mg, crude) (72% of 5-[[4-[(2-aminoacetyl)amino]-3-cyano-phenyl]sulfonylamino]thiazole-4-carboxylic acid and 8% of 5-[[4-[(2-aminoacetyl)amino]-3-carbamoyl-phenyl]sulfonylamino]thiazole-4-carboxylic acid).

M/z 382.05 (M+H)⁺ and 400.01 (M+H)⁺ e. 5-[[3-cyano-4-[(2-guanidinoacetyl)amino]phenyl]sulfonylamino]thiazole-4-carboxylic acid and 5-[[3-carbamoyl-4-[(2-guanidinoacetyl)amino]phenyl]sulfonylamino]thiazole-4-carboxylic acid

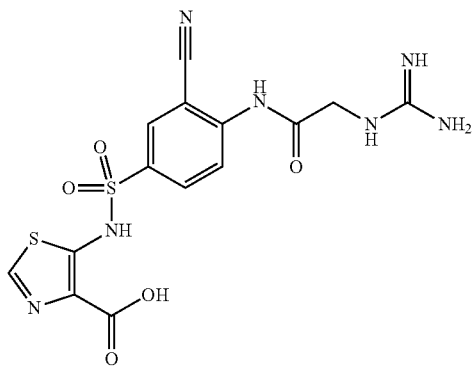

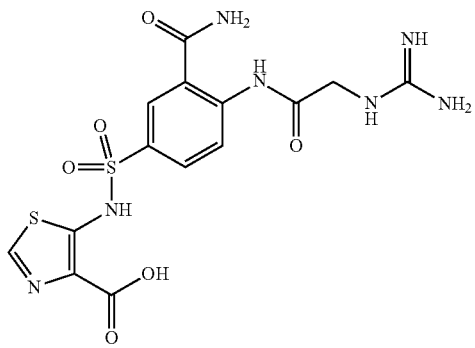

Pyrazole-1-carboxamidine (172 mg, 1.18 mmol) and DIPEA (0.3 mL, 1.57 mmol) were added to a stirred solution of 5-[[4-[(2-aminoacetyl)amino]-3-cyano-phenyl]sulfonylamino]thiazole-4-carboxylic acid and 5-[[4-[(2-aminoacetyl)amino]-3-carbamoyl-phenyl]sulfonylamino]thiazole-4-carboxylic acid (300 mg, 0.78 mmol) in DMF (5 mL) at RT. The resulting reaction mixture was stirred at RT for 16 h and concentrated under reduced pressure. Water (5 mL) was added to the residue. The resulting precipitate was filtered and washed with diethyl ether (2×5 mL). The crude product was purified by preparative HPLC affording the title products:

Example 5

(72 mg, off-white solid):
$^1$H NMR (400 MHz, DMSO-d$_6$) δ 13.30 (1H, brs), 10.50 (1H, brs), 8.09 (1H, s), 8.02 (1H, d, J=2.0 Hz), 7.99 (1H, dd, J=8.8 Hz, J=2.0 Hz), 7.82 (1H, d, J=8.8 Hz), 7.52 (2H, brs), 7.23 (3H, brs), 4.13 (2H, s).
M/z 424.34 (M+H)$^+$

Example 6

(5.2 mg, off-white solid):
$^1$H NMR (400 MHz, DMSO-d$_6$) δ 13.42 (1H, brs), 12.0 (1H, brs), 8.59 (1H, brs), 8.51 (1H, d), 8.20 (1H, d, J=2.0 Hz), 8.03 (1H, s), 7.83 (1H, dd, J=8.8 Hz, J=2.0 Hz), 7.80 (1H, brs), 7.44 (4H, brs), 4.07 (2H, s).
M/z 442.34 (M+H)$^+$
LC-MS Condition:
Column: Acquity BEH C18 (50 mm×2.1 mm, 1.7 um);
Mobile Phase: A: 0.05% Formic Acid in water; B: 0.05% Formic Acid in ACN;
Time (min)/% B: 0/3, 0.4/3, 3.2/98, 3.8/98, 4.2/3, 4.5/3;
Column Temp: 35° C.;
Flow Rate: 0.6 mL/min.
Prep. HPLC Condition:
Column: Symmetry C18 (150*25) mm, 10 u;
Mobile phase: (A) 0.05% Formic Acid (B) Acetonitrile;
Flow: 19 mL/min;
Gradient (T/% B): 0/5, 1/5, 5/20, 10.5/24, 10.52/99, 12/99, 12.02/5, 15/5;
Solubility: ACN+H$_2$O+THF+FA.

Compounds prepared using analogous methods to those described for Examples 2 to 6 and purified in a similar manner by preparative HPLC are shown in the Table below.

| Example | Structure | Name, NMR and mass |
|---|---|---|
| 7 | 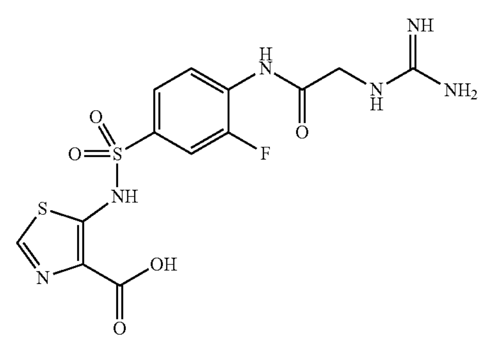 [SMILES: N=C(N)NCC(=O)Nc1ccc(S(=O)(=O)Nc2scnc2C(=O)O)cc1F] | 5-[[3-fluoro-4-[(2-guanidinoacetyl)amino]phenyl]sulfonylamino]thiazole-4-carboxylic acid<br>M/z 415.2 (M − Na)$^-$<br>$^1$H NMR (d6-DMSO) δ 13.1 (1H, s), 8.08 (1H, s), 7.93 (1H, brs), 7.48 (2H, d, J = 7 Hz), 3.88 (2H, s). |

| Example | Structure | Name, NMR and mass |
|---------|-----------|--------------------|
| 8 | 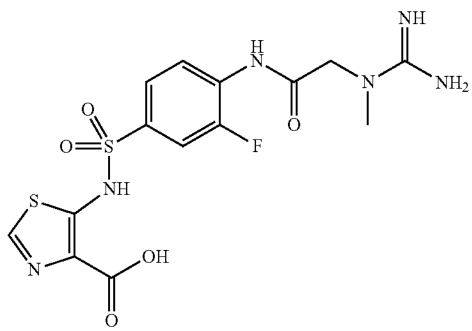 [SMILES: CN(CC(=O)Nc1ccc(S(=O)(=O)Nc2scnc2C(=O)O)cc1F)C(=N)N] | 5-[[4-[[2-[carbamimidoyl(methyl)amino]acetyl]amino]-3-fluoro-phenyl]sulfonylamino]thiazole-4-carboxylic acid<br>M/z 431.2 (M + H)$^+$<br>$^1$H NMR (d6-DMSO) δ 13.30 (1H, s), 10.14 (1H, brs), 8.44 (1H, s), 8.13 (1H, m), 8.07 (1H, s), 7.57-7.32 (5H, brs), 4.27 (2H, s), 2.95 (3H, s). |
| 9 | 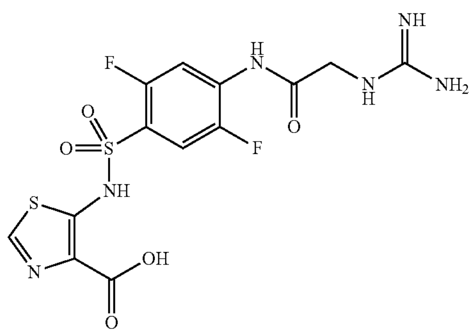 [SMILES: N=C(N)NCC(=O)Nc1cc(F)c(S(=O)(=O)Nc2scnc2C(=O)O)cc1F] | 5-[[2,5-difluoro-4-[(2-guanidinoacetyl)amino]phenyl]sulfonylamino]thiazole-4-carboxylic acid<br>M/z 435.3 (M + H)$^+$<br>$^1$H NMR (d6-DMSO) δ 13.3 (1H, s), 10.3 (1H, brs), 8.1 (1H, s), 8.04 (1H, m), 7.57 (2H, m), 7.39-7.09 (4H, brs), 4.10 (2H, s). |
| 10 | 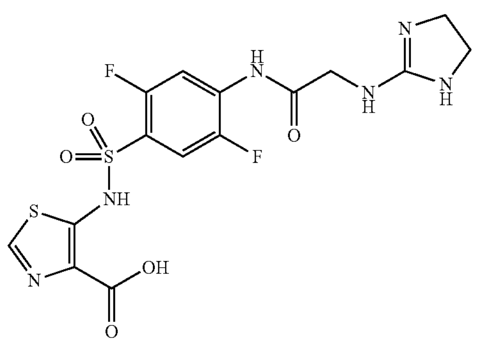 [SMILES: O=C(CNC1=NCCN1)Nc1cc(F)c(S(=O)(=O)Nc2scnc2C(=O)O)cc1F] | 5-[[4-[[2-(4,5-dihydro-1H-imidazol-2-ylamino)acetyl]amino]-2,5-difluoro-phenyl]sulfonylamino]thiazole-4-carboxylic acid<br>M/z 461.3 (M + H)+<br>$^1$H NMR (d6-DMSO) δ 13.19 (1H, s), 10.1 (1H, brs), 8.39 (2H, brs), 8.10 (1H, s), 8.03 (1H, m), 7.55 (1H, m), 4.09 (2H, s), 3.60 (4H, s). |
| 11 | 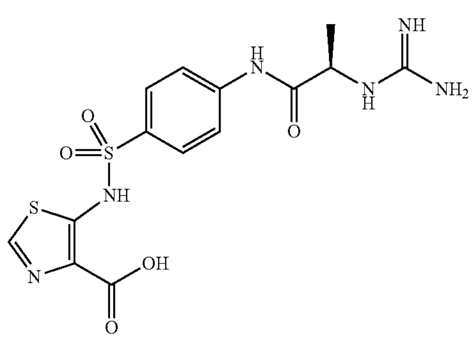 [SMILES: C[C@@H](NC(=N)N)C(=O)Nc1ccc(S(=O)(=O)Nc2scnc2C(=O)O)cc1] | 5-[[4-[[(2R)-2-guanidinopropanoyl]amino]phenyl]sulfonylamino]thiazole-4-carboxylic acid<br>M/z 413.3 (M + H)$^+$<br>$^1$H NMR (d6-DMSO) δ 13.6 (1H, s), 10.3 (1H, s), 8.03 (1H, s), 7.71 (5H, m), 7.25-6.96 (4H, brs), 4.25 (1H, t, J = 7.2 Hz), 1.40 (3H, d, J = 6.8 Hz). |

| Example | Structure | Name, NMR and mass |
|---|---|---|
| 12 | 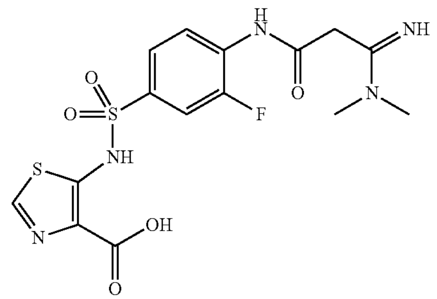 [SMILES: CN(C)C(=N)CC(=O)Nc1ccc(S(=O)(=O)Nc2scnc2C(=O)O)cc1F] | 5-[[4-[[3-(dimethylamino)-3-imino-propanyl]amino]-3-fluoro-phenyl]sulfonylamino]thiazole-4-carboxylic acid<br>M/z 430.3 (M + H)+<br>$^1$H NMR (d6-DMSO) δ 13.5 (1H, brs), 9.51 (1H, brs), 8.45 (1H, t, J = 8 Hz), 8.19 (1H, s), 7.91 (2H, m), 4.22 (2H, s), 3.42 (3H, s), 3.35 (3H, s). |
| 13 | 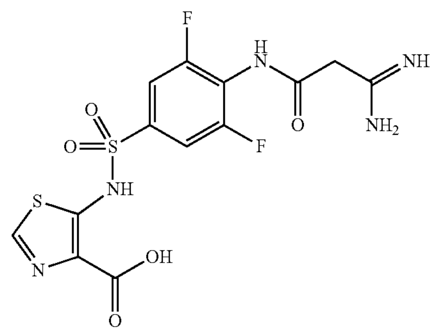 [SMILES: N=C(N)CC(=O)Nc1c(F)cc(S(=O)(=O)Nc2scnc2C(=O)O)cc1F] | 5-[[4-[(3-amino-3-imino-propanoyl)amino]-3,5-difluoro-phenyl]sulfonylamino]thiazole-4-carboxylic acid<br>M/z 420.3 (M + H)+<br>$^1$H NMR (d6-DMSO) δ 13.21 (1H, s), 9.01 (2H, brs), 8.58 (2H, brs), 8.12 (1H, s), 7.43 (2H, d, J = 7.2 Hz), 3.62 (2H, s). |
| 14 | 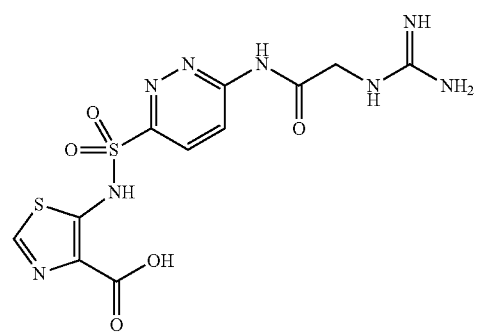 [SMILES: N=C(N)NCC(=O)Nc1ccc(S(=O)(=O)Nc2scnc2C(=O)O)nn1] | 5-[[6-[(2-guanidinoacetyl)amino]pyridazin-3-yl]sulfonylamino]thiazole-4-carboxylic acid<br>M/z 401.4 (M + H)+<br>$^1$H NMR (d6-DMSO) δ 13.1 (1H, brs), 11.5 (1H, brs), 8.45 (1H, s), 8.38 (1H, d, J = 9.6 Hz), 8.21 (1H, brs), 8.10 (1H, s), 8.07 (1H, m), 7.89-7.68 (4H, brs), 4.13 (2H, s).<br>Key intermediate 6-chloro-3-pyridazinesulfonyl chloride was prepared as described in the literature, K. Ashton et al, WO2013/123444. |
| 15 | 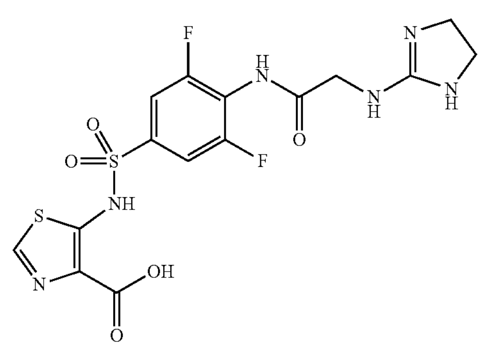 [SMILES: O=C(CNC1=NCCN1)Nc1c(F)cc(S(=O)(=O)Nc2scnc2C(=O)O)cc1F] | 5-[[4-[[2-(4,5-dihydro-1H-imidazol-2-ylamino)acetyl]amino]-3,5-difluoro-phenyl]sulfonylamino]thiazole-4-carboxylic acid<br>M/z 461.3 (M + H)+<br>$^1$H NMR (d6-DMSO) δ 13.1 (1H, brs), 10.1 (1H, brs), 8.12 (1H, s), 7.42 (2H, d, J = 9.6 Hz), 4.14 (2H, s), 3.59 (4H, s). |

| Example | Structure | Name, NMR and mass |
|---|---|---|
| 16 | | 5-[[4-[(2-guanidinoacetyl)amino]-3-methoxy-phenyl]sulfonylamino]thiazole-4-carboxylic acid<br>M/z 429.3 (M + H)+<br>1H NMR (d6-DMSO) δ 13.59 (1H, brs), 9.41 (1H, brs), 8.44 (1H, s), 8.10 (1H, d, J = 8.4 Hz), 8.04 (1H, s), 7.77 (1H, brs), 7.56-7.32 (4H, brs), 7.30 (2H, m), 4.09 (2H, s), 3.86 (3H, s).<br>The key intermediate 4-acetamido-3-methoxybenzenesulfonyl chloride was prepared by literature procedures, P. Patel et al, Bioorg Med Chem Lett, 2007, 17, 6610. |
| 17 | | 5-[[3-chloro-4-[(2-guanidinoacetyl)amino]phenyl]sulfonylamino]thiazole-4-carboxylic acid<br>M/z 433.3 (M + H)+<br>1H NMR (d6-DMSO) δ 13.4 (1H, brs), 9.81 (1H, brs), 8.43 (1H, s), 8.08 (1H, s), 7.95 (1H, d, J = 8.4 Hz), 7.38 (1H, d, J = 2 Hz), 7.67 (1H, m), 7.51-7.22 (4H, brs), 4.12 (2H, s).<br>The key intermediate 3-chloro-4-nitrobenzene-1-sulfonyl chloride is commercially available. |
| 16 | | 5-[[3-cyano-4-[(2-guanidinoacetyl)amino]phenyl]sulfonyl-amino]thiazole-4-carboxylic acid<br>M/z 424.3 (M + H)+<br>1H NMR (d6-DMSO) δ 13.26 (1H, brs), 10.51 (1H, brs), 8.09 (1H, s), 8.03 (1H, m), 7.99 (1H, m), 7.83 (1H, d, J = 8.8 Hz), 7.52 (1H, brs), 7.38-7.13 (4H, brs), 4.13 (2H, s). |
| 17 | | 5-[[3-carbamoyl-4-[(2-guanidinoacetyl)amino]phenyl]sulfonyl-amino]thiazole-4-carboxylic acid<br>M/z 442.3 (M + H)+<br>1H NMR (d6-DMSO) δ 13.41 (1H, brs), 12.01 (1H, brs), 8.59 (1H, brs), 8.51 (1H, d, J = 8.8 Hz), 8.41 (1H, s), 8.20 (1H, d, J = 2 Hz), 8.04 (1H, s), 7.84 (1H, m), 7.82 (1H, m), 7.54-7.30 (4H, brs), 4.07 (2H, s). |

| Example | Structure | Name, NMR and mass |
|---|---|---|
| 18 | 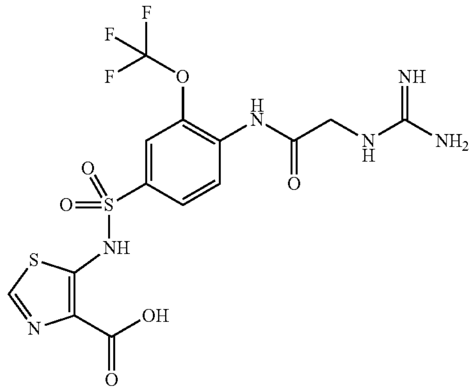 [SMILES: N=C(N)NCC(=O)Nc1ccc(S(=O)(=O)Nc2scnc2C(=O)O)cc1OC(F)(F)F] | 5-[[4-[(2-guanidinoacetyl)amino]-3-(trifluoromethoxy)phenyl]sulfonylamino]thiazole-4-carboxylic acid<br>M/z 483.0 (M + H)+<br>1H NMR (d6-DMSO) δ 13.38 (1H, s), 10.1 (1H, brs), 8.17 (1H, d, J = 9 Hz), 8.09 (1H, s), 7.72 (1H, m), 7.64 (1H, d, J = 1.5 Hz), 7.54 (1H, brs), 7.39-7.25 (4H, brs), 4.12 (2H, s).<br>Key intermediate 4-bromo-3-(trifluoromethoxy)benzenesulfonyl chloride was prepared according to literature procedures, C-M. Park et al, J Med Chem, 2008, 51, 6902 |
| 19 | 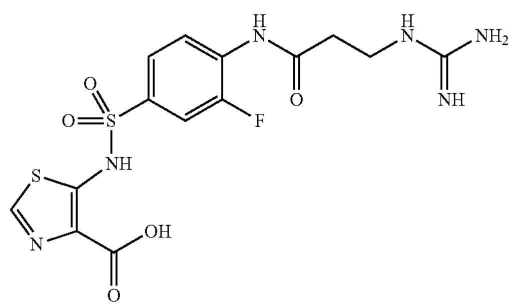 [SMILES: N=C(N)NCCC(=O)Nc1ccc(S(=O)(=O)Nc2scnc2C(=O)O)cc1F] | 5-[[3-fluoro-4-(3-guanidinopropanoylamino)phenyl]sulfonylamino]thiazole-4-carboxylic acid<br>M/z 431.2 (M + H)+<br>1H NMR (d6-DMSO) δ 10.19 (1H, s), 8.37 (1H, s), 8.18 (1H, t, J = 8.1 Hz), 7.60 (2H, m), 7.46 (1H, m), 7.35-6.81 (4H, brs), 3.40 (2H, m), 2.70 (2H, t, J = 6.3 Hz). |

Example 20

5-[[4-[(2-guanidinoacetyl)amino]phenyl]sulfonylamino]thiazole-4-carboxylic acid

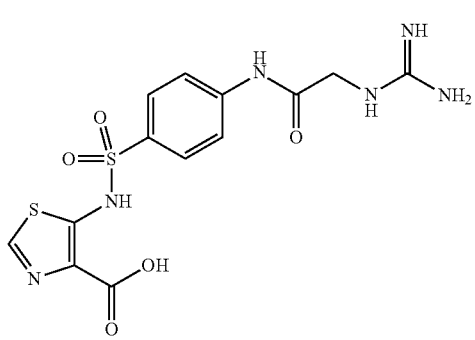 [SMILES: N=C(N)NCC(=O)Nc1ccc(S(=O)(=O)Nc2scnc2C(=O)O)cc1]

a. ethyl 5-[[4-[[2-(tert-butoxycarbonylamino)acetyl]amino]phenyl]sulfonylamino]thiazole-4-carboxylate

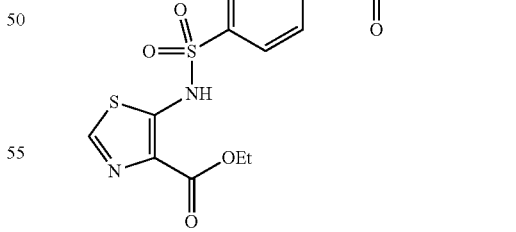

DIPEA (0.63 mL, 3.66 mmol) and HATU (696 mg, 1.83 mmol) were added to a stirred solution of 2-(tert-butoxycarbonylamino)acetic acid (321 mg, 1.83 mmol) in DMF (5 mL). The reaction mixture was stirred at RT for 15 minutes and then ethyl 5-[(4-aminophenyl)sulfonylamino]thiazole-4-carboxylate (400 mg, 1.22 mmol) was added at the same temperature under N2 atmosphere. The resulting reaction mixture was stirred at RT for 16 h and concentrated under reduced pressure. The resulting crude compound was dissolved in 10% MeOH in DCM (20 mL), washed with sat NH₄Cl (2×10 mL), water (10 mL) and brine solution (10 mL). The organic layer was dried over Na₂SO₄, filtered and concentrated under vacuum. The crude material was purified by column chromatography (eluting with 3% MeOH) affording an off-white solid (400 mg, 67%).

M/z 484.8 (M+H)⁺507.06 (M+Na)⁺ b. ethyl 5-[[4-[(2-aminoacetyl)amino]phenyl]sulfonylamino]thiazole-4-carboxylate

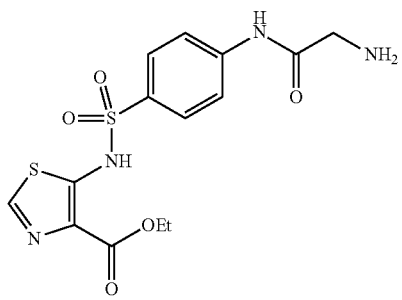 [SMILES: CCOC(=O)c1ncsc1NS(=O)(=O)c1ccc(NC(=O)CN)cc1]

2N HCl in Et₂O (4 mL) was added to ethyl 5-[[4-[[2-(tert-butoxycarbonylamino)acetyl]amino]phenyl]sulfonylamino]thiazole-4-carboxylate (400 mg, 0.82 mmol) in diethyl ether (5 mL) at 0° C. The reaction mixture was stirred for 5 h at RT and concentrated under reduced pressure. The crude product was purified by preparative HPLC (HCOOH/CH₃CN/H₂O) affording an off-white solid (300 mg, 94%).

M/z 385.13 (M+H)⁺ c. ethyl 5-[[4-[[2-[[N,N'-bis(tert-butoxycarbonyl)carbamimidoyl]amino]acetyl]amino]phenyl]sulfonylamino]thiazole-4-carboxylate

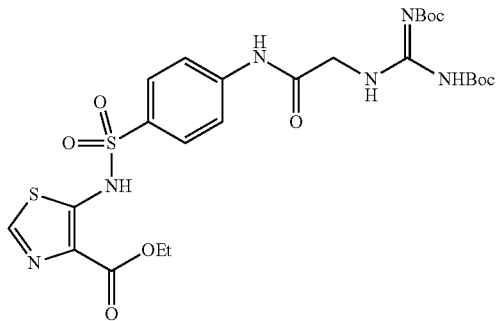

DIPEA (0.08 mL, 0.49 mmol) and tert-butyl N-[(tert-butoxycarbonylamino)-pyrazol-1-yl-methylene]carbamate (87 mg, 0.28 mmol) were added to a stirred solution of ethyl 5-[[4-[(2-aminoacetyl)amino]phenyl]sulfonylamino]thiazole-4-carboxylate (270 mg, 0.70 mmol) in DMF (5 mL) at RT. The resulting reaction mixture was stirred at RT for 16 h and concentrated under reduced pressure. The resulting crude compound was dissolved in 10% MeOH in DCM (20 mL), washed with water (10 mL) and brine solution (10 mL). The organic layer was dried over Na₂SO₄, filtered and concentrated under reduced pressure. The crude material was purified by column chromatography (eluting with 4% MeOH in DCM) affording an off white solid (250 mg, 56%).

M/z 626.97 (M+H)⁺ d. 5-[[4-[[2-[[(Z)—N,N'-bis(tert-butoxycarbonyl)carbamimidoyl]amino]acetyl]amino]phenyl]sulfonylamino]thiazol e-4-carboxylic acid

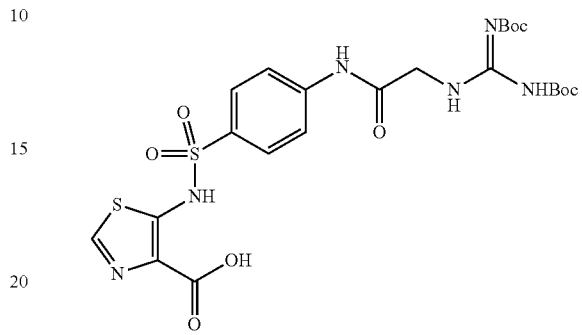

TMSOK (69 mg, 0.54 mmol) was added to a stirred solution of ethyl 5-[[4-[[2-[[N,N'-bis(tert-butoxycarbonyl)carbamimidoyl]amino]acetyl]amino]phenyl]sulfonylamino]thiazole-4-carboxylate (170 mg, 0.27 mmol) in THF (4 mL) at RT under N₂ atmosphere. The resulting reaction mixture was stirred at 40° C. for 5 h and concentrated under reduced pressure. The resulting crude product was triturated with diethyl ether (2×5 mL) and dried under high vacuum. The residue was dissolved in water (5 mL) and acidified with 1N HCl (adjusted pH2). The resulting solid was filtered, washed with n-pentane and dried under high vacuum to afford an off-white solid which was used to next step without further purification (70 mg crude, 43%).

M/z 598.92 (M+H)⁺ e. 5-[[4-[(2-guanidinoacetyl)amino]phenyl]sulfonylamino]thiazole-4-carboxylic acid

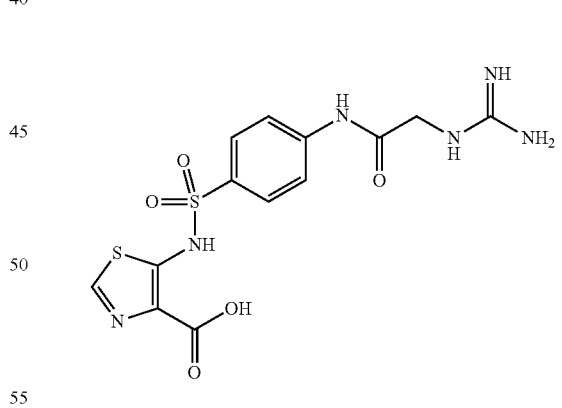

2N HCl in Ether (1 mL) was added to 5-[[4-[[2-[[(Z)—N,N'-bis(tert-butoxycarbonyl)carbamimidoyl]amino]acetyl]amino]phenyl]sulfonylamino]thiazole-4-carboxylic acid (70 mg, 0.11 mmol) in diethyl ether (2 mL) at 0° C. The reaction mixture was stirred at RT for 5 h and concentrated under reduced pressure. The crude product was purified by preparative HPLC to afford the title product as an off white solid (11 mg, 23%).

¹H NMR (500 MHz, DMSO-d₆) δ 13.59 (1H, s), 10.42 (1H, brs), 8.02 (1H, s), 7.68-7.63 (5H, m), 7.42 (4H, brs), 4.02 (2H, s).

M/z 398.78 (M+H)⁺

Example 21

5-[[4-[[2-(4,5-dihydro-1H-imidazol-2-yl)acetyl]amino]-3-fluoro-phenyl]sulfonylamino]thiazole-4-carboxylic acid

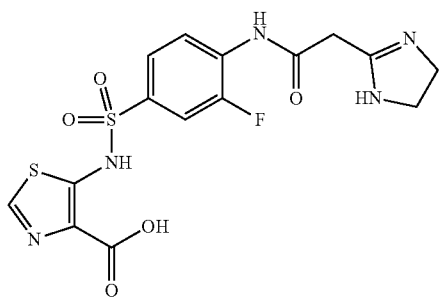 [SMILES: O=C(CC1=NCCN1)Nc1ccc(S(=O)(=O)Nc2scnc2C(=O)O)cc1F]

a. tert-butyl 5-[[4-[(2-cyanoacetyl)amino]-3-fluoro-phenyl]sulfonyl-[(4-methoxyphenyl)methyl]amino]thiazole-4-carboxylate

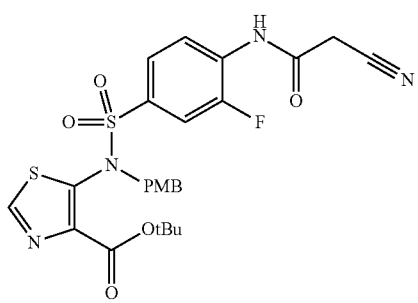

A solution of 2-cyanoacetic acid (86 mg, 1.01 mmol) and PCl$_5$ (210 mg, 1.01 mmol) in DCM (20 mL) was heated to reflux for 30 minutes. The reaction mixture temperature was cooled to RT and a solution of tert-butyl 5-[(4-amino-3-fluoro-phenyl)sulfonyl-[(4-methoxyphenyl)methyl]amino]thiazole-4-carboxylate (500 mg, 1.01 mmol) in DCM (30 mL) was added under nitrogen atmosphere. The resulting reaction mixture was heated to reflux for 2.5 h, cooled to RT, diluted with DCM (50 mL) and washed with aqueous NaHCO$_3$ solution (30 mL), water (30 mL) and brine (30 mL) solution. The organic layer was dried over Na$_2$SO$_4$, filtered and concentrated under reduced pressure. The crude material was purified by flash chromatography (eluting with 1-2% MeOH in DCM) to afford a pale yellow solid (180 mg, 31%).

M/z 561.43 (M+H)$^+$ b. tert-butyl 5-[[4-[[2-(4,5-dihydro-1H-imidazol-2-yl)acetyl]amino]-3-fluoro-phenyl]sulfonyl-[(4-methoxyphenyl)methyl]amino]thiazole-4-carboxylate

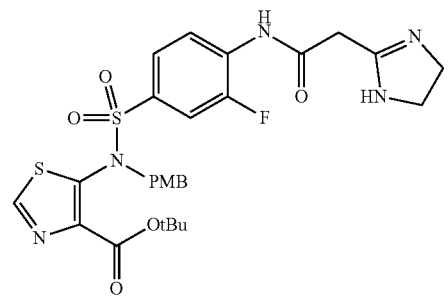

HCl gas was passed to a solution of tert-butyl 5-[[4-[(2-cyanoacetyl)amino]-3-fluoro-phenyl]sulfonyl-[(4-methoxyphenyl)methyl]amino]thiazole-4-carboxylate (300 mg, 0.53 mmol) in ethanol:Et$_2$O (1:2, 30 mL) at 0° C. for 2 h. The resulting reaction mixture was kept in refrigerator for 16 h. Then the volatile components were evaporated under reduced pressure at 40° C. The residue was dissolved in ethanol (10 mL) and ethylene diamine (48 mg, 0.80 mmol) was added at RT. The reaction mixture was stirred at RT for 16 h and concentrated under reduced pressure. The resulting crude product was triturated with diethyl ether (2×5 mL) and dried under high vacuum to afford a pale brown solid which was used in the next step without further purification (330 mg, crude).

M/z 548.29 (M-Boc+H)$^+$ c. 5-[[4-[[2-(4,5-dihydro-1H-imidazol-2-yl)acetyl]amino]-3-fluoro-phenyl]sulfonylamino]thiazole-4-carboxylic acid

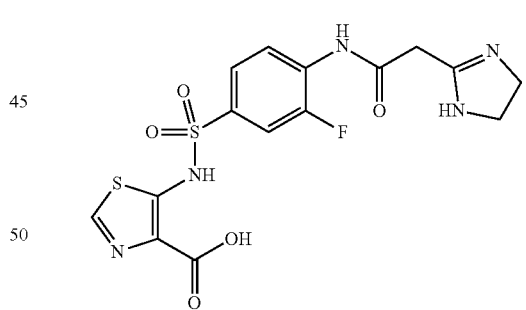

TFA (3 mL) was added to tert-butyl 5-[[4-[[2-(4,5-dihydro-1H-imidazol-2-yl)acetyl]amino]-3-fluoro-phenyl]sulfonyl-[(4-methoxyphenyl)methyl]amino]thiazole-4-carboxylate (300 mg, 0.54 mmol) at RT. The reaction mixture was stirred at RT for 4 h and concentrated under reduced pressure. The resulting crude product was triturated with diethyl ether (2×5 mL) and dried under high vacuum. The crude product was purified by preparative HPLC to afford the title product as an off-white solid (26 mg, 11%).

$^1$H NMR (400 MHz, DMSO-d$_6$) δ 13.50 (1H, brs), 10.30 (1H, brs), 8.29 (2H, brs), 8.08-8.04 (2H, m), 7.54-7.48 (2H, m), 3.40 (2H, s), 3.36-3.28 (2H, obs), 2.88-2.85 (2H, m).

M/z 428.37 (M+H)$^+$

Example 22

5-[[3-fluoro-4-[[3-imino-3-(methylamino)propanoyl]amino]phenyl]sulfonylamino]thiazole-4-carboxylic acid

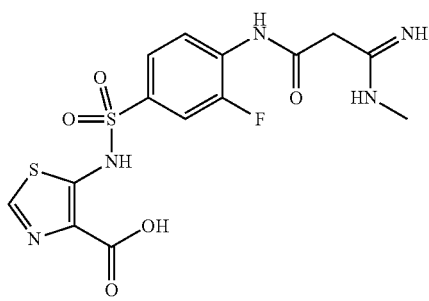 [SMILES: CNC(=N)CC(=O)Nc1ccc(S(=O)(=O)Nc2scnc2C(=O)O)cc1F]

a. tert-butyl 5-[[3-fluoro-4-[[3-[hydroxy(methyl)amino]-3-imino-propanoyl]amino]phenyl]sulfonyl-[(4-methoxyphenyl)methyl]amino]thiazole-4-carboxylate

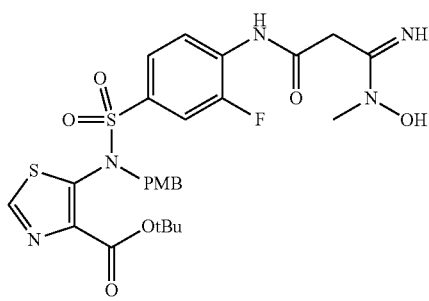

MeNHOH.HCl (298 mg, 3.56 mmol) and sodium carbonate (472 mg, 4.45 mmol) were added to a solution of tert-butyl 5-[[4-[(2-cyanoacetyl)amino]-3-fluoro-phenyl]sulfonyl-[(4-methoxyphenyl)methyl]amino]thiazole-4-carboxylate (1 g, 1.78 mmol) in ethanol (15 mL) at RT. The resulting reaction mixture was stirred at 60° C. for 3 h, cooled to RT, filtered and washed with ethanol (2×10 mL). The combined organic layer was concentrated under reduced pressure. The obtained crude compound was triturated with Et$_2$O (2×10 mL) and dried under high vacuum to afford a brown solid which was used in next step without further purification.

M/z 608.03 (M+H)$^+$ b. tert-butyl 5-[[3-fluoro-4-[[3-imino-3-(methylamino)propanoyl]amino]phenyl]sulfonyl-[(4-methoxyphenyl)methyl]amino]thiazole-4-carboxylate

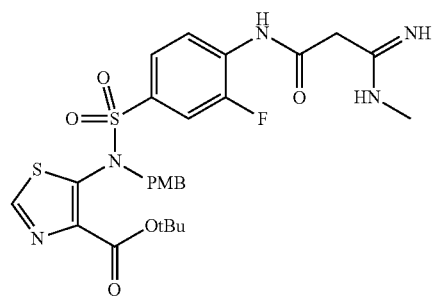

Bis(pinacolato)diboron (*Adv. Synth. catal.* 2015, 357, 451-462) (357 mg, 1.4 mmol) was added to a solution of tert-butyl 5-[[3-fluoro-4-[[3-[hydroxy(methyl)amino]-3-imino-propanoyl]amino]phenyl]sulfonyl-[(4-methoxyphenyl)methyl]amino]thiazole-4-carboxylate (570 mg, 0.93 mmol) in acetonitrile (10 mL) at RT. The resulting reaction mixture was stirred at RT for 1 h and concentrated under reduced pressure. The crude compound was purified by flash chromatography (eluting with 2% triethyl amine in 10% methanol and DCM) to afford a pale yellow solid (130 mg, 23%).

M/z 592.05 (M+H)$^+$ c. 5-[[3-fluoro-4-[[3-imino-3-(methylamino)propanoyl]amino]phenyl]sulfonylamino]thiazole-4-carboxylic acid

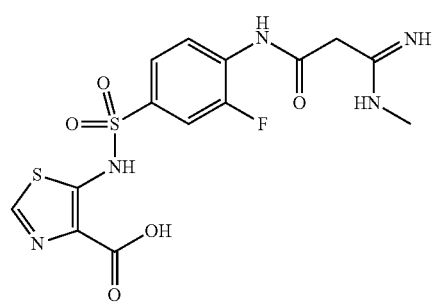 [SMILES: CNC(=N)CC(=O)Nc1ccc(S(=O)(=O)Nc2scnc2C(=O)O)cc1F]

TFA (3 mL) was added to tert-butyl 5-[[3-fluoro-4-[[3-imino-3-(methylamino)propanoyl]amino]phenyl]sulfonyl-[(4-methoxyphenyl)methyl]amino]thiazole-4-carboxylate (130 mg, 0.21 mmol) at RT. The reaction mixture was stirred for 2 h at RT and concentrated under reduced pressure. The resulting crude product was triturated with diethyl ether (2×5 mL) and dried under high vacuum. The crude product was purified by preparative HPLC affording the title product as yellow solid (20 mg, 22%).

$^1$H NMR (400 MHz, CF$_3$COOD) δ 9.53 (1H, brs), 8.42 (1H, t, J=8.0 Hz), 8.20 (1H, s), 7.92 (1H, d, J=8.8 Hz), 7.88 (1H, d, J=9.2 Hz), 4.08 (2H, s), 3.18 (3H, s).

M/z 416.34 (M+H)$^+$

LC-MS Condition:
Column: Acquity BEH C18 (50 mm×2.1 mm, 1.7 um);
Mobile Phase: A: 0.05% Formic Acid in water; B: 0.05% Formic Acid in ACN;
Time (min)/% B: 0/3, 0.4/3, 3.2/98, 3.8/98, 4.2/3, 4.5/3;
Column Temp: 35° C.;
Flow Rate: 0.6 mL/min.
Prep. HPLC Condition:
Column: Symmetry C18 (300*19) mm, 7 u;
Mobile phase: (A) 0.1% Formic Acid (B) Acetonitrile;
Flow: 19 mL/min;
Gradient (T/% B): 0/5, 1/5, 8.9/40, 8.92/99, 12/99, 12.1/5, 15/5;
Solubility: ACN+H$_2$O+THF.

Example 23

5-[[2-[(2-guanidinoacetyl)amino]thiazol-5-yl]sulfonylamino]thiazole-4-carboxylic acid

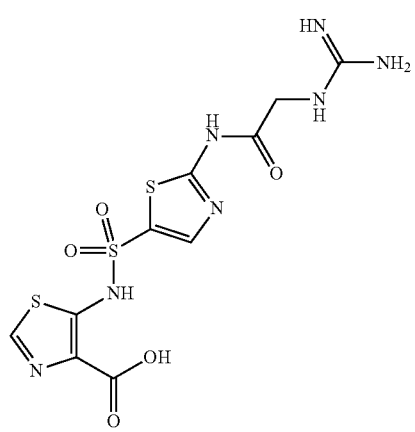 [SMILES: N=C(N)NCC(=O)Nc1ncc(S(=O)(=O)Nc2scnc2C(=O)O)s1]

a. 2-acetamidothiazole-5-sulfonylchloride

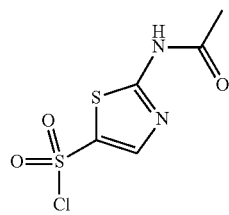

N-thiazol-2-ylacetamide (5 g, 35.2 mmol) was added portion wise to a solution of chlorosulfonic acid (11.7 mL, 176 mmol) at 0° C. The reaction mixture was stirred at 100° C. for 4 h, cooled to RT and poured into ice cold water (100 mL). The resulting precipitate was filtered and washed with water (20 mL). The precipitate was triturated with n-pentane (2×20 mL) and azeotroped with toluene to afford an off-white solid which was used in the next step without further purification (2 g crude, 23%).

M/z 241.23 (M+H)$^+$ b. ethyl 5-[(2-acetamidothiazol-5-yl)sulfonylamino]thiazole-4-carboxylate

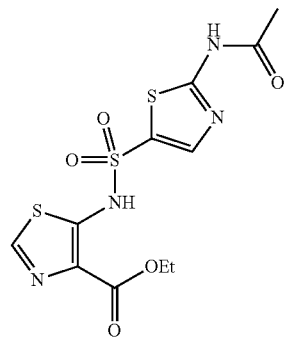 [SMILES: CCOC(=O)c1ncsc1NS(=O)(=O)c1cnc(NC(C)=O)s1]

A solution of ethyl 5-aminothiazole-4-carboxylate (300 mg, 1.74 mmol) in THF (10 mL) was added to a stirred solution of NaH (250 mg, 10.4 mmol) in THF (10 mL) at 0° C. and stirred for 5 minutes. Then a solution of 2-acetamidothiazole-5-sulfonyl chloride (502 mg, 2.0 mmol) in THF (10 mL) was added to the reaction mixture at 0° C. The reaction mixture was stirred at the same temperature for 1 h. Ice cold water (30 mL) was added to the reaction mixture which was then washed with EtOAc (2×15 mL). The aqueous layer was acidified to pH 2.0 using 1N HCl and extracted with EtOAc (3×15 mL). The organic layer was dried over Na$_2$SO$_4$, filtered and concentrated under reduced pressure to afford a pale brown solid which was used to next step without further purification (175 mg crude, 26%).

M/z 377.32 (M+H)$^+$ c. ethyl 5-[(2-aminothiazol-5-yl)sulfonylamino]thiazole-4-carboxylate, hydrochloride

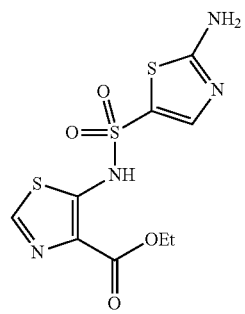 [SMILES: CCOC(=O)c1ncsc1NS(=O)(=O)c1cnc(N)s1]

Concentrated HCl (7 mL) was added to a solution of ethyl 5-[(2-acetamidothiazol-5-yl)sulfonylamino]thiazole-4-carboxylate (700 mg, 1.86 mmol) in ethanol (70 mL) at RT. The reaction mixture was refluxed for 5 h and concentrated under reduced pressure. The resulting crude compound was washed with diethyl ether (20 mL), n-pentane (20 mL) and dried under high vacuum to afford a brown solid which was used in the next step without further purification (600 mg, crude).

M/z 335.04 (M+H)$^+$ d. ethyl 5-[[2-[[2-(tert-butoxycarbonylamino)acetyl]amino]thiazol-5-yl]sulfonylamino]thiazole-4-carboxylate

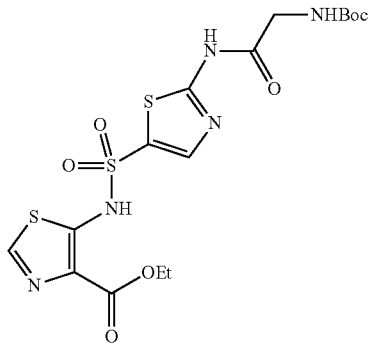 [SMILES: CC(C)(C)OC(=O)NCC(=O)Nc1ncc(S(=O)(=O)Nc2scnc2C(=O)O)s1]

HATU (1.36 g, 3.58 mmol) and DIPEA (2.5 mL, 14.3 mmol) were added to a stirred solution of 2-(tert-butoxycarbonylamino)acetic acid (628 mg, 3.58 mmol) in DMF (6 mL) at RT. The reaction mixture was stirred at RT for 15 minutes and then ethyl 5-[(2-aminothiazol-5-yl)sulfonylamino]thiazole-4-carboxylate, hydrochloride (600 mg, 1.79 mmol) was added at the same temperature under $N_2$ atmosphere. The resulting reaction mixture was stirred at RT for 18 h. Ice cold water (30 mL) was added and extracted with DCM (3×20 mL). The organic layer was dried over $Na_2SO_4$, filtered and concentrated under reduced pressure. The crude compound was purified by flash chromatography (eluting with using 60-80% of EtOAc in petroleum ether) affording a brown solid (400 mg, 45%).

M/z 492.34 $(M+H)^+$ e. 5-[[2-[[2-(tert-butoxycarbonylamino)acetyl]amino]thiazol-5-yl]sulfonylamino]thiazole-4-carboxylic acid

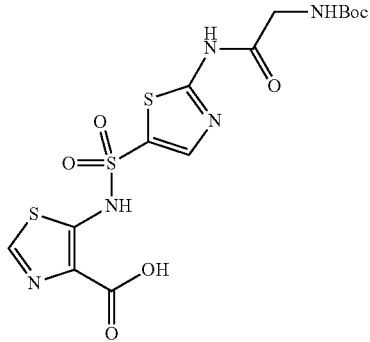

TMSOK (625 mg, 4.8 mmol) was added to a stirred solution of ethyl 5-[[2-[[2-(tert-butoxycarbonylamino)acetyl]amino]thiazol-5-yl]sulfonylamino]thiazole-4-carboxylate (400 mg, 0.8 mmol) in THF (40 mL) at RT. The reaction mixture was stirred at 40° C. for 1 h, concentrated under reduced pressure and water (2 mL) was added to the residue. The reaction mixture was acidified to pH 2 using 1N HCl. The resulting precipitate was filtered, washed with diethyl ether (2×10 mL), n-pentane (10 mL) and dried under high vacuum to afford a pale yellow solid (200 mg, 53%).

M/z 464.30 $(M+H)^+$ f. 5-[[2-[(2-aminoacetyl)amino]thiazol-5-yl]sulfonylamino]thiazole-4-carboxylic acid, hydrochloride

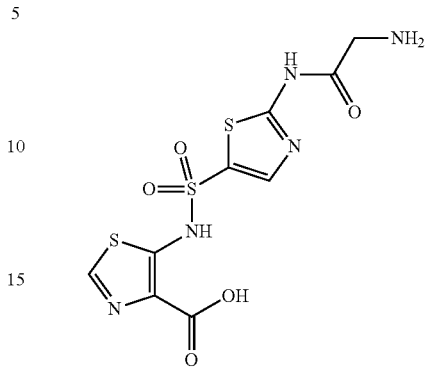

HCl in $Et_2O$ (2M, 10 mL) was added to 5-[[2-[[2-(tert-butoxycarbonylamino)acetyl]amino]thiazol-5-yl]sulfonylamino]thiazole-4-carboxylic acid (200 mg, 0.43 mmol) at RT. The reaction mixture was stirred at the same temperature for 3 h, concentrated under reduced pressure and the resulting residue was washed with diethyl ether (2×5 mL) and n-pentane (5 mL) affording a pale yellow solid which was used in the next step without further purification (150 mg, crude).

M/z 364.30 $(M+H)^+$ g. 5-[[2-[(2-guanidinoacetyl)amino]thiazol-5-yl]sulfonylamino]thiazole-4-carboxylic acid

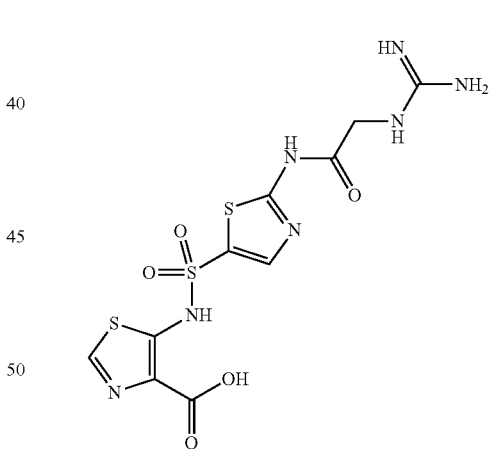

DIPEA (0.44 mL, 2.7 mmol) was added to a stirred solution of 5-[[2-[(2-aminoacetyl)amino]thiazol-5-yl]sulfonylamino]thiazole-4-carboxylic acid, hydrochloride (100 mg, 0.27 mmol) and pyrazole-1-carboxamidine, hydrochloride (80 mg, 0.55 mmol) in DMF (2 mL) at RT. The reaction mixture was stirred at the same temperature for 6 h. DMF was evaporated and then water (3 mL) was added to the resulting crude material, stirring for 5 minutes. The resulting precipitate was filtered and washed with water (2×2 mL) then dried under high vacuum. The crude compound was purified by preparative HPLC affording an off-white solid (16 mg, 14%).

$^1$H NMR (400 MHz, DMSO-d$_6$) δ 13.28 (1H, s), 12.6 (1H, brs), 8.15 (1H, s), 7.71 (1H, s), 7.44 (1H, t, J=6.4 Hz), 7.21 (4H, brs), 4.11 (2H, d, J=6.4 Hz).

M/z 405.9 (M+H)$^+$

LC-MS Condition:

Column: Acquity BEH C18 (50 mm×2.1 mm, 1.7 um)

Mobile Phase: A: 0.05% Formic Acid in water; B: 0.05% Formic Acid in ACN

Gradient: Time (min)/% B: 0/3, 0.4/3, 3.2/98, 3.8/98, 4.2/3, 4.5/3

Column Temp: 35° C.,

Flow Rate: 0.6 mL/min

Prep. HPLC Condition:

Column used: Atlantis T3 (250*19) mm, 5 u;

Mobile phase: (A) 0.1% Formic Acid (B) Acetonitrile

Flow: 19 mL/min

Gradient –(T/% B): 0/5, 1/5, 8.2/55, 8.21/99, 10/99, 10.1/5, 13/5

Diluent: ACN+H$_2$O+FA

Example 24

5-[[4-[2-(2-carbamimidoylhydrazino)-2-oxo-ethyl]-3-fluoro-phenyl]sulfonylamino]thiazole-4-carboxylic acid

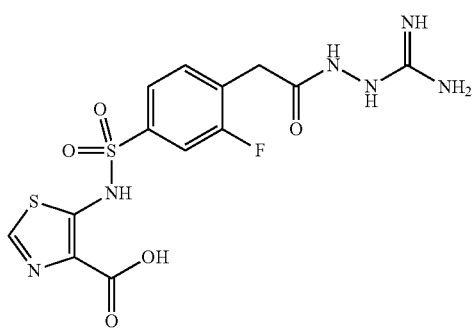 [SMILES: N=C(N)NNC(=O)Cc1ccc(S(=O)(=O)Nc2scnc2C(=O)O)cc1F]

a. tert-butyl 5-[[4-(2-ethoxy-2-oxo-ethyl)-3-fluoro-phenyl]sulfonyl-[(4-methoxyphenyl)methyl]amino] thiazole-4-carboxylate

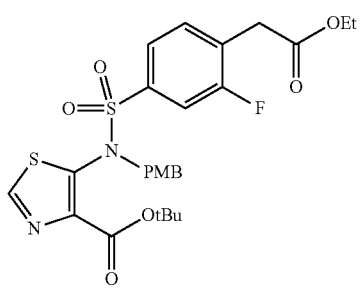

A mixture of tert-butyl 5-[(4-bromo-3-fluoro-phenyl) sulfonyl-[(4-methoxyphenyl)methyl]amino]thiazole-4-carboxylate (2 g, 3.58 mmol), potassium 3-ethoxy-3-oxo-propanoate (1.2 g, 7.16 mmol) and DMAP (43 mg, 0.35 mmol) in mesitylene (20 mL) was purged with argon gas for 30 minutes. BINAP (222 mg, 0.35 mmol) and Pd2(dba)3 (327 mg, 0.35 mmol) were then added at the same temperature. The reaction mixture was stirred at 120° C. for 18 h, cooled to RT and concentrated under reduced pressure. The crude product was purified by flash chromatography (eluting with 40% EtOAc in petroleum ether) to afford a yellow solid which was used in the next step without further purification (0.45 g, crude).

M/z 565.43 (M+H)$^+$ b. tert-butyl 5-[[3-fluoro-4-(2-hydrazino-2-oxo-ethyl)phenyl]sulfonyl-[(4-methoxyphenyl)methyl] amino]thiazole-4-carboxylate

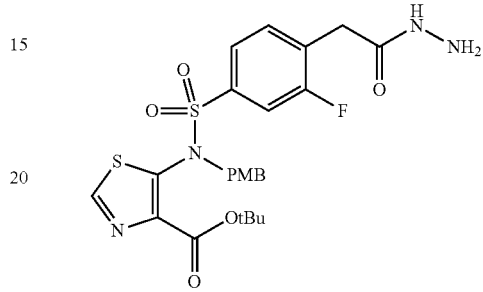

Hydrazine hydrate (709 mg, 14.1 mmol) was added to a stirred solution of tert-butyl 5-[[4-(2-ethoxy-2-oxo-ethyl)-3-fluoro-phenyl]sulfonyl-[(4-methoxyphenyl)methyl]amino] thiazole-4-carboxylate (400 mg, 0.7 mmol) in ethanol (20 mL) at RT. The reaction mixture was refluxed for 5 h and concentrated under reduced pressure to afford a brown solid which was used in the next step without further purification (350 mg, crude).

M/z 551.42 (M+H)$^+$ c. tert-butyl 5-[[4-[2-[2-N,N'-bis(tert-butoxycarbo-nyl)carbamimidoyl]hydrazino]-2-oxo-ethyl]-3-fluoro-phenyl]sulfonyl-[(4-methoxyphenyl)methyl] amino]thiazole-4-carboxylate

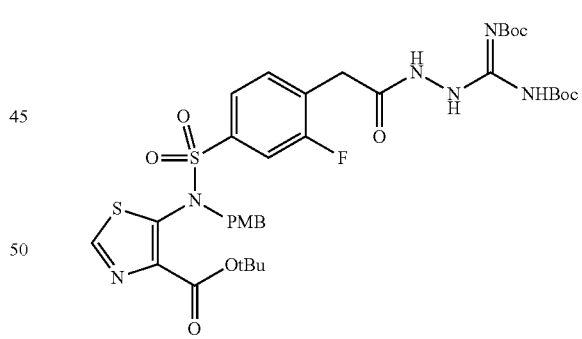

DIPEA (0.32 mL, 1.89 mmol) was added to a stirred solution of tert-butyl 5-[[3-fluoro-4-(2-hydrazino-2-oxo-ethyl)phenyl]sulfonyl-[(4-methoxyphenyl)methyl]amino] thiazole-4-carboxylate (350 mg, 0.63 mmol) and tert-butyl N—N-[(tert-butoxycarbonylamino)-pyrazol-1-yl-methyl-ene]carbamate (394 mg, 1.27 mmol) in DMF (5 mL) at RT. The reaction mixture was stirred at the same temperature for 18 h. Ice cold water was added to the reaction mixture and stirred for 10 minutes. The resulting precipitate was filtered, washed with water (2×5 mL) and dried under high vacuum. The crude product was purified by flash chromatography (eluting with 60% EtOAc in petroleum ether) to afford a yellow solid (120 mg, 23%).

M/z 793.53 (M+H)$^+$ d. 5-[[4-[2-(2-carbamimidoylhydrazino)-2-oxo-ethyl]-3-fluoro-phenyl]sulfonylamino]thiazole-4-carboxylic acid

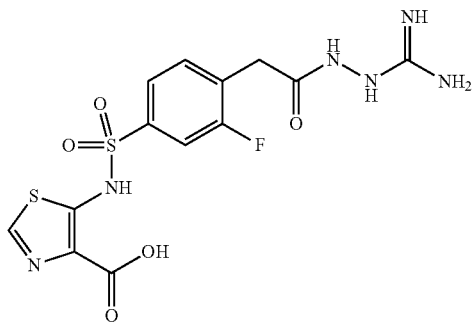 [SMILES: N=C(N)NNC(=O)Cc1ccc(S(=O)(=O)Nc2scnc2C(=O)O)cc1F]

Time (min)/% B: 0/3, 0.4/3, 3.2/98, 3.8/98, 4.2/3, 4.5/3;

Column Temp: 35° C.;

Flow Rate: 0.6 mL/min.

Prep. HPLC Condition:

Column used: Symmetry C18 (300*19) mm, 7 u;

Mobile phase: (A) 0.05% Formic Acid (B) Acetonitrile;

Flow: 19 mL/min;

Gradient (T/% B): 0/2, 1/2, 8/20, 10.5/20, 10.51/99, 12/99, 12.1/2, 15/2;

Solubility: ACN+$H_2O$+THF.

Compounds prepared by analogous methods to those described above for Examples 20 to 24 and purified in a similar manner by preparative HPLC are shown in the Table below:—

| Example | Structure | Name, NMR and Mass |
|---|---|---|
| 25 | 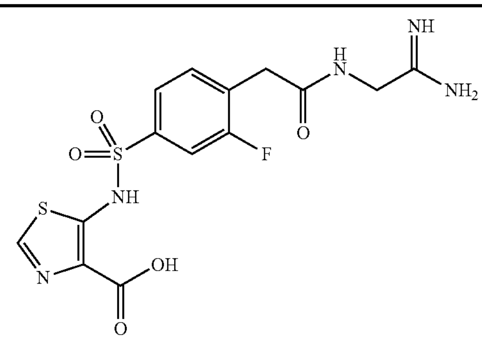 | 5-[[4-[2-[(2-amino-2-imino-ethyl)amino]-2-oxo-ethyl]-3-fluoro-phenyl]sulfonylamino]thiazole-4-carboxylic acid<br>M/z 416.1 (M + H)$^+$<br>$^1$H NMR (d6-DMSO) δ 13.1 (1H, s), 8.67 (1H, brs), 8.49 (3H, brs), 8.07 (1H, brs), 7.48 (1H, m), 7.43 (2H, m), 3.89 (2H, s), 3.61 (2H, s), 2.07 (1H, s). |

TFA (2 mL) was added to tert-butyl 5-[[4-[2-[2-[(Z)—N,N'-bis(tert-butoxycarbonyl)carbamimidoyl]hydrazino]-2-oxo-ethyl]-3-fluoro-phenyl]sulfonyl-[(4-methoxyphenyl)methyl]amino]thiazole-4-carboxylate (120 mg, 0.15 mmol) at RT. The reaction mixture was stirred for 3 h at the same temperature and concentrated under reduced pressure. The resulting crude material was triturated with diethyl ether (2×5 mL). The crude product was purified by preparative HPLC affording the title product as an off-white solid (23 mg).

$^1$H NMR (400 MHz, DMSO-d6) δ 13.40 (1H, brs), 8.06 (1H, s), 7.63 (3H, brs), 7.51-7.39 (3H, m), 3.56 (2H, s).

M/z 417.35 (M+H)$^+$

LC-MS Condition:

Column: Acquity BEH C18 (50 mm×2.1 mm, 1.7 um);

Mobile Phase: A: 0.05% Formic Acid in water; B: 0.05% Formic Acid in ACN;

Example 26

5-[[3,5-difluoro-4-(guanidinocarbamoylamino)phenyl]sulfonylamino]thiazole-4-carboxylic acid

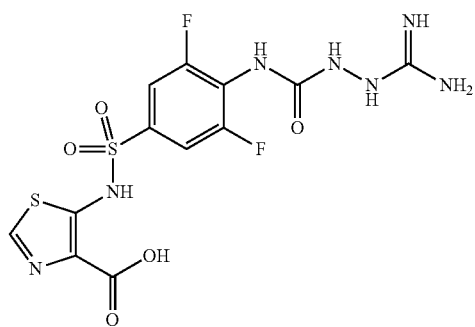 [SMILES: N=C(N)NNC(=O)Nc1c(F)cc(S(=O)(=O)Nc2scnc2C(=O)O)cc1F]

a. tert-butyl 5-[(4-amino-3,5-difluoro-phenyl)sulfonyl-[(4-methoxyphenyl)methyl]amino]thiazole-4-carboxylate

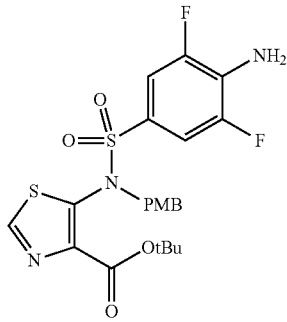

A saturated solution of NH₃ in dioxane (120 mL) was added to a mixture of tert-butyl 5-[(4-bromo-3,5-difluorophenyl)sulfonyl-[(4-methoxyphenyl)methyl]amino]thiazole-4-carboxylate (2 g, 3.47 mmol), Xantphos (0.6 g, 1.04 mmol), Pd₂(dba)₃ (0.317 g, 0.34 mmol) and K₃PO₄ (2.2 g, 10.4 mmol). The resulting mixture was stirred in sealed tube at 100° C. for 5 h, filtered through Celite pad and the pad was washed with ethyl acetate (2×25 mL). The filtrate was concentrated under reduced pressure. The crude material was purified by flash chromatography (eluting with 50% ethyl acetate in petroleum ether) affording a pale yellow solid (1.25 g, 70%).

M/z 512.4 (M+H)⁺; 534.56 (M+Na)⁺ b. tert-butyl 5-[[3,5-difluoro-4-[(4-nitrophenoxy)carbonylamino]phenyl]sulfonyl-[(4-methoxyphenyl)methyl]amino]thiazole-4-carboxylate

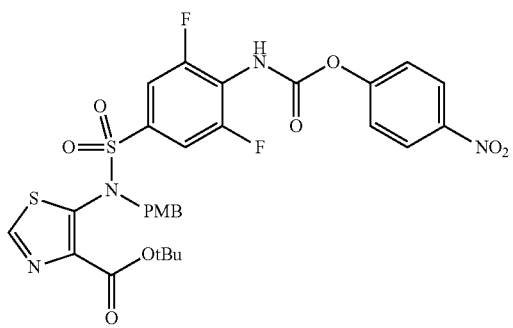

(4-nitrophenyl) carbonochloridate (1.57 g, 7.82 mmol) was added to a stirred solution tert-butyl 5-[(4-amino-3,5-difluoro-phenyl)sulfonyl-[(4-methoxyphenyl)methyl]amino]thiazole-4-carboxylate (2 g, 3.91 mmol) in toluene (120 mL) at room temperature and refluxed for 3 h. The reaction mixture was concentrated under reduced pressure. The crude product was used in the next step without further purification (3.5 g, crude).

c. tert-butyl 5-[[4-[(tert-butoxycarbonylamino)carbamoylamino]-3,5-difluoro-phenyl]sulfonyl-[(4-methoxyphenyl)methyl]amino]thiazole-4-carboxylate

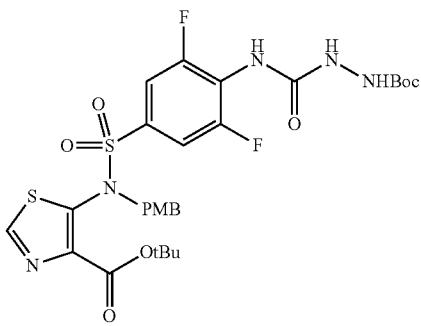

DIPEA (2.6 mL, 15.5 mmol) was added to a suspension of tert-butyl 5-[[3,5-difluoro-4-[(4-nitrophenoxy)carbonylamino]phenyl]sulfonyl-[(4-methoxyphenyl)methyl]amino]thiazole-4-carboxylate (3.5 g, 5.17 mmol) and tert-butyl N-aminocarbamate (1.36 g, 10.3 mmol) in THF (100 mL) at 0° C. The reaction mixture was stirred at RT for 3 h and concentrated under reduced pressure. The crude material was purified by flash chromatography (eluting with 70% ethyl acetate in petroleum ether) affording a pale yellow solid (1.5 g, 43%).

M/z 670.4 (M+H)⁺ d. 5-[[3,5-difluoro-4-(hydrazinecarbonylamino)phenyl]sulfonyl-[(4-methoxyphenyl)methyl]amino]thiazole-4-carboxylic acid, hydrochloride

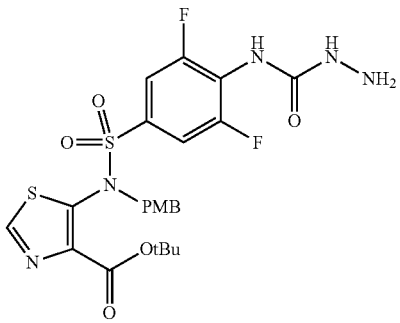

HCl in Et₂O (2M, 200 mL) was added to tert-butyl 5-[[4-[(tert-butoxycarbonylamino)carbamoylamino]-3,5-difluoro-phenyl]sulfonyl-[(4-methoxyphenyl)methyl]amino]thiazole-4-carboxylate (1.5 g, 2.24 mmol) at RT. The reaction mixture was stirred for 24 h, cooled to 0° C. for 30 minutes and Et₂O was decanted. The crude product was triturated with diethyl ether (2×40 mL) and dried under high vacuum affording an off-white solid (1 g, crude).

M/z 514.3 (M+H)⁺ e. 5-[[4-[[[N,N'-bis(tert-butoxycarbonyl)carbamimidoyl]amino]carbamoylamino]-3,5-difluoro-phenyl]sulfonyl-[(4-methoxyphenyl)methyl]amino]thiazole-4-carboxylic acid

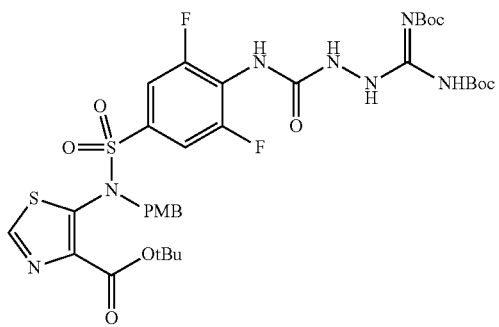

DIPEA (3.0 mL, 17.5 mmol) was added to a stirred solution of 5-[[3,5-difluoro-4-(hydrazinecarbonylamino)phenyl]sulfonyl-[(4-methoxyphenyl)methyl]amino]thiazole-4-carboxylic acid, hydrochloride (1 g, 1.75 mmol) and tert-butyl (NZ)—N-[(tert-butoxycarbonylamino)-pyrazol-1-yl-methylene]carbamate (0.54 g, 1.75 mmol) in DMF (6 mL) at RT. The reaction mixture was stirred for 5 h and DMF was removed. Then water was added to the crude product, stirring for 5 minutes. The resulting precipitate was filtered, washed with water (2×5 mL) and dried under high vacuum affording an off-white solid (1.25 g, crude).

M/z 756.1 (M+H)$^+$ f. 5-[[3,5-difluoro-4-(guanidinocarbamoylamino)phenyl]sulfonylamino]thiazole-4-carboxylic acid

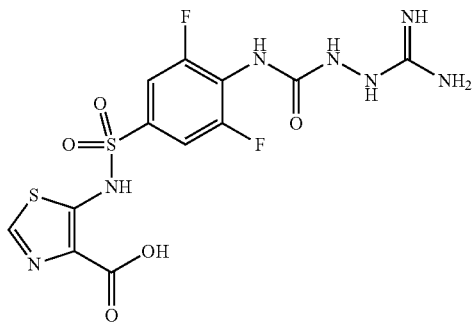

TFA (13 mL) was added to 5-[[4-[[[(Z)—N,N'-bis(tert-butoxycarbonyl)carbamimidoyl]amino]carbamoylamino]-3,5-difluoro-phenyl]sulfonyl-[(4-methoxyphenyl)methyl]amino]thiazole-4-carboxylic acid (1.25 g, 1.54 mmol) at RT. The reaction mixture was stirred for 3 h at RT and TFA was evaporated by flushing with N$_2$ gas. The resulting crude product was triturated with diethyl ether and purified by preparative HPLC to afford the title compound as a white solid (150 mg).

$^1$H NMR (300 MHz, DMSO-d$_6$) δ 13.28 (1H, brs), 8.70 (3H, br s), 8.12 (1H, s), 7.39 (2H, d, J=6.9 Hz), 7.0-7.37 (3H, br s).

M/z 436.0 (M+H)$^+$

LC-MS Condition:

Column: Aquity UPLC BEH C18 (50 mm×2.1 mm, 1.7 um);

Mobile phase: A: 0.1% of Formic Acid in Water, B: 0.1% of Formic acid in Acetonitrile;

Gradient: Time (min)/% B 0/2, 0.2/2, 1.5/98, 2.6/98, 2.61/2, 3.2/2;

Column Temp: 45° C., Flow rate: 0.8 mL/min

Prep. HPLC Condition:

Column: X select C18 (150*30 mm), 5 u;

Mobile Phase: 0.05% Formic acid in H$_2$O: Acetonitrile;

Flow: 25 mL/min;

Gradient (T/% B): 0/50, 8/50, 8/40, 9/40, 9.1/98, 11/98, 11.1/5, 14/40

Diluent: ACN+H$_2$O+MeOH+THF.

Example 27

5-[[3-fluoro-4-(2-guanidinoethoxycarbonylamino)phenyl]sulfonylamino]thiazole-4-carboxylic acid

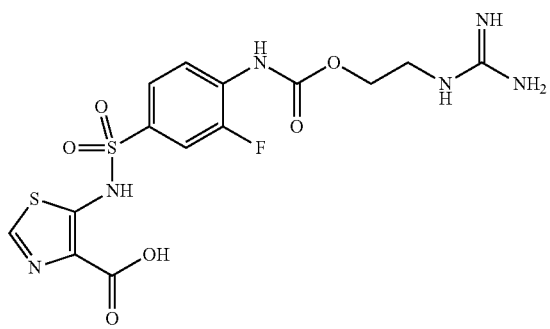 [SMILES: N=C(N)NCCOC(=O)Nc1ccc(S(=O)(=O)Nc2scnc2C(=O)O)cc1F]

a. tert-butyl 5-[[3-fluoro-4-[(4-nitrophenoxy)carbonylamino]phenyl]sulfonyl-[(4-methoxyphenyl)methyl]amino]thiazole-4-carboxylate

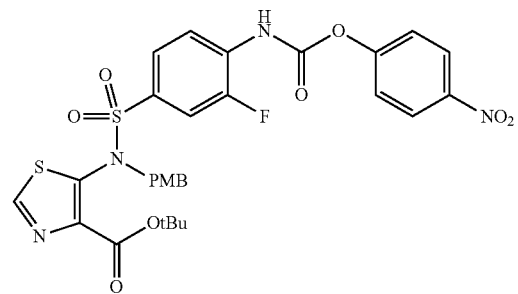

p-Nitrophenyl chloroformate (1.33 g, 6.0 mmol) was added to a stirred solution of tert-butyl 5-[(4-amino-3-fluoro-phenyl)sulfonyl-[(4-methoxyphenyl)methyl]amino]thiazole-4-carboxylate (1 g, 2.02 mmol) in toluene (30 mL) at RT. The resulting reaction mixture was stirred at 120° C. for 1 h and concentrated under reduced pressure. The resulting crude product was triturated with n-pentane (2×10 mL) and dried under high vacuum affording an off-white solid which was used in the next step without further purification (1.5 g, crude).

M/z 659.43 (M+H)$^+$ b. tert-butyl 5-[[4-[2-(tert-butoxycarbonylamino)
ethoxycarbonylamino]-3-fluoro-phenyl]sulfonyl-[(4-
methoxyphenyl)methyl]amino]thiazole-4-carboxy-
late

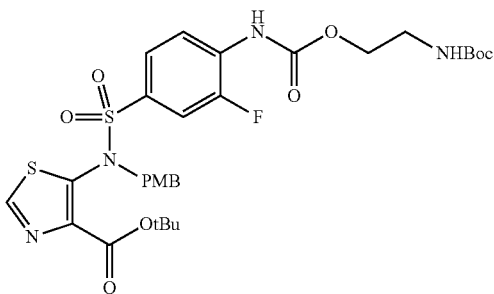

Tert-butyl N-(2-hydroxyethyl)carbamate (440 mg, 2.73 mmol) and DIPEA (0.97 mL, 5.46 mmol) were added to a stirred solution of tert-butyl 5-[[3-fluoro-4-[(4-nitrophenoxy)carbonylamino]phenyl]sulfonyl-[(4-methoxyphenyl)methyl]amino]thiazole-4-carboxylate (1.2 g, 1.82 mmol) in THF (20 mL) at RT. The resulting reaction mixture was stirred at RT for 2 h. Ice cold water was added followed by extraction with ethyl acetate (2×50 mL). The combined organic layer was dried over anhydrous Na$_2$SO$_4$, filtered and concentrated under reduced pressure. The crude material was purified by flash chromatography (eluting with 40% ethyl acetate in petroleum ether) affording an off-white solid (500 mg, 40%).
M/z 681.50 (M+H)$^+$ c. 5-[[4-(2-aminoethoxycarbonylamino)-3-fluoro-
phenyl]sulfonylamino]thiazole-4-carboxylic acid,
trifluoroacetate

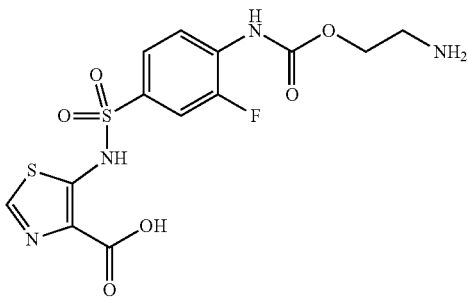 [SMILES: NCCOC(=O)Nc1ccc(S(=O)(=O)Nc2scnc2C(=O)O)cc1F]

TFA (5 mL) was added to tert-butyl 5-[[4-[2-(tert-butoxycarbonylamino)ethoxycarbonylamino]-3-fluoro-phenyl]sulfonyl-[(4-methoxyphenyl)methyl]amino]thiazole-4-carboxylate (450 mg, 0.66 mmol) at RT. The reaction mixture was stirred for 24 h at the same temperature and concentrated under reduced pressure. The resulting crude product was triturated with diethyl ether (2×10 mL) and dried under high vacuum to afford an off-white solid which was used in the next step without further purification (350 mg, crude).
M/z 405.36 (M+H)$^+$ d. 5-[[3-fluoro-4-(2-guanidinoethoxycarbonylamino)
phenyl]sulfonylamino]thiazole-4-carboxylic acid

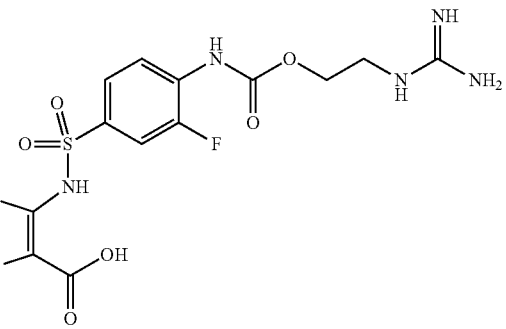

Pyrazole-1-carboxamidine, hydrochloride (136 mg, 0.92 mmol) and DIPEA (0.55 mL, 3.0 mmol) were added to a stirred solution of 5-[[4-(2-aminoethoxycarbonylamino)-3-fluoro-phenyl]sulfonylamino]thiazole-4-carboxylic acid, trifluoroacetate (250 mg, 0.61 mmol) in DMF (6 mL) at RT. The resulting reaction mixture was stirred at RT for 4 h concentrated under reduced pressure and water (5 mL) was added to the residue. The resulting precipitate was filtered, washed with diethyl ether (2×5 mL) and dried under high vacuum. The crude product was purified by preparative HPLC affording the title product as an off-white solid (45 mg, 16%).
$^1$H NMR (300 MHz, DMSO-d$_6$) δ 13.42 (1H, brs), 9.60 (1H, s), 8.07 (1H, s), 7.79 (1H, t, J=8.0 Hz), 7.62-7.56 (1H, m), 7.51 (1H, d, J=8.0 Hz, J=2.0 Hz), 7.46 (1H, dd, J=10.4 Hz, 2.0 Hz), 7.12 (4H, brs), 4.18 (2H, t, J=5.2 Hz), 3.48-3.40 (2H, m).
M/z 447.27 (M+H)$^+$ Compounds prepared using analogous methods to those described for Examples 26 and 27 and purified in a similar manner by preparative HPLC are shown in the Table below:

| Example | Structure | Name, NMR and Mass |
|---|---|---|
| 28 | 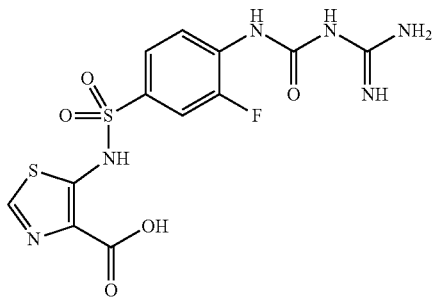 [SMILES: N=C(N)NC(=O)Nc1ccc(S(=O)(=O)Nc2scnc2C(=O)O)cc1F] | 5-[[4-(carbamimidoylcarbamoyl-amino)-3-fluoro-phenyl]sulfonylamino]thiazole-4-carboxylic acid<br>M/z 402.9 (M + H)$^+$<br>$^1$H NMR (d6-DMSO) δ 13.5 (1H, brs), 8.18 (1H, brs), 8.13 (1H, m), 8.04 (1H, s), 7.72 (1H, brs), 7.40 (2H, m), 6.96-6.61 (4H, m). |

| Example | Structure | Name, NMR and Mass |
|---|---|---|
| 29 | 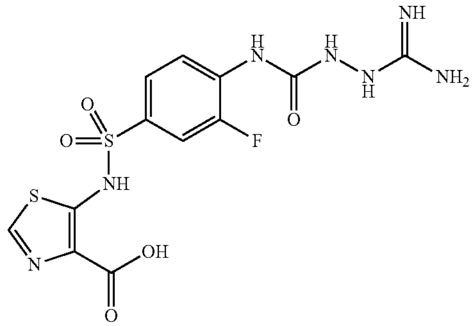 [SMILES: N=C(N)NNC(=O)Nc1ccc(S(=O)(=O)Nc2scnc2C(=O)O)cc1F] | 5-[[3-fluoro-4-(guanidinocarbamoylamino)phenyl]sulfonylamino]thiazole-4-carboxylic acid<br>M/z 416.3 (M + H)+<br>1H NMR (d6-DMSO) δ 8.49 (1H, s), 8.04 (1H, brs), 7.88 (1H, brs), 7.50 (4H, m), 3.94 (2H, brs). |
| 30 | 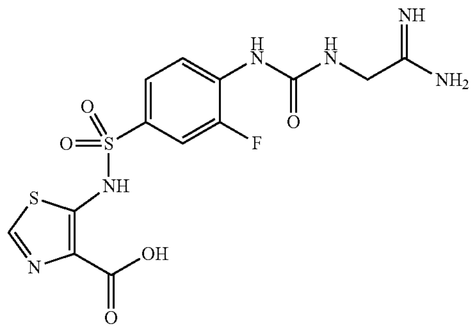 [SMILES: N=C(N)CNC(=O)Nc1ccc(S(=O)(=O)Nc2scnc2C(=O)O)cc1F] | 5-[[4-[(2-amino-2-imino-ethyl)carbamoylamino]-3-fluoro-phenyl]sulfonylamino]thiazole-4-carboxylic acid<br>M/z 417.3 (M + H)+<br>1H NMR (d6-DMSO) δ 13.5 (1H, brs), 9.01 (1H, s), 9.21-8.71 (4H, m), 8.43 (1H, s), 8.19 (1H, t, J = 8.4 Hz), 8.06 (1H, s), 7.46 (2H, t, J = 8.8 Hz), 7.29 (1H, m), 4.04 (2H, d, J = 5.2 Hz). |
| 31 | 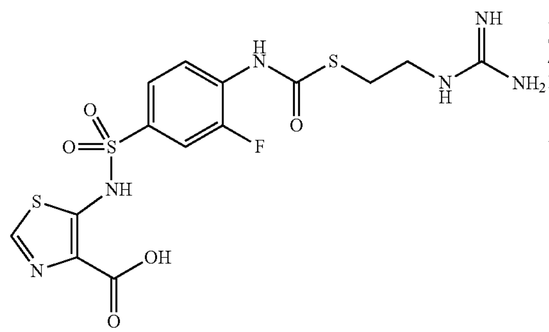 [SMILES: N=C(N)NCCSC(=O)Nc1ccc(S(=O)(=O)Nc2scnc2C(=O)O)cc1F] | 5-[[3-fluoro-4-(2-guanidinoethylsulfanyl-carbonylamino)phenyl]sulfonylamino]thiazole-4-carboxylic acid<br>M/z 463.1 (M + H)+<br>1H NMR (d6-DMSO) δ 13.42 (1H, s), 10.51 (1H, s), 8.16 (1H, s), 8.08 (1H, s), 7.79 (1H, t, J = 7.5 Hz), 7.61 (1H, s), 7.51 (2H, m), 7.31-6.79 (4H, m), 3.36 (2H, t, J = 6.5 Hz), 3.36 (2H, t, J = 6.5 Hz). |

Example 32

5-[[3,5-difluoro-4-(guanidinocarbamoylamino)phenyl]sulfonylamino]thiazole-4-carboxylic acid

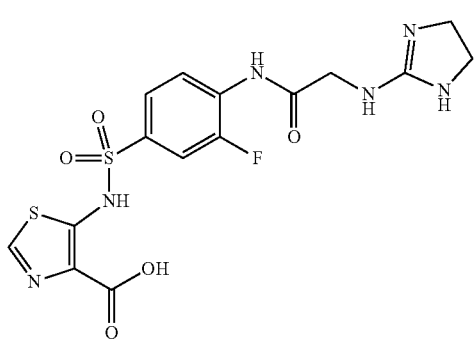 [SMILES: O=C(CNC1=NCCN1)Nc1ccc(S(=O)(=O)Nc2scnc2C(=O)O)cc1F]

a. tert-butyl 5-[[4-[(2-chloroacetyl)amino]-3-fluoro-phenyl]sulfonyl-[(4-methoxyphenyl)methyl]amino]thiazole-4-carboxylate

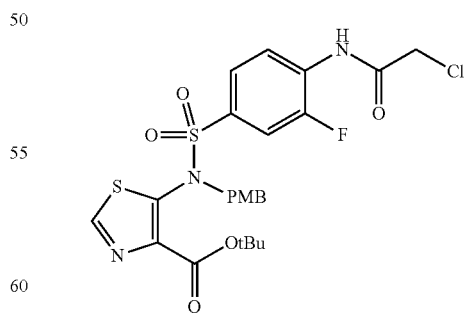

Et₃N (276 mg, 2.73 mmol) and chloroacetyl chloride (185 mg, 1.64 mmol) were added to a stirred solution of tert-butyl 5-[(4-amino-3-fluoro-phenyl)sulfonyl-[(4-methoxyphenyl)methyl]amino]thiazole-4-carboxylate (450 mg, 0.91 mmol) in DCM (5 mL) at 0° C. The resulting reaction mixture was stirred at RT for 2 h, quenched with ice cold water (5 mL) and extracted with DCM (2×10 mL). The combined organic layer was dried over Na2SO4, filtered and concentrated under reduced pressure. The crude material was purified by trituration with diethyl ether (2×5 mL) to afford a green solid which was used in the next step without further purification (400 mg, crude).

M/z 570.69 (M+H)+ b. tert-butyl 5-[[4-[(2-azidoacetyl)amino]-3-fluoro-phenyl]sulfonyl-[(4-methoxyphenyl)methyl]amino]thiazole-4-carboxylate

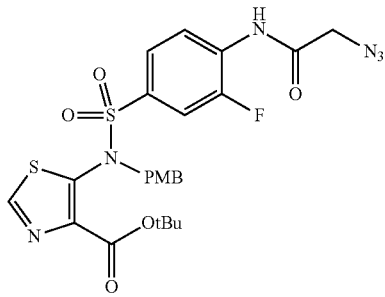

NaN3 (92 mg, 1.40 mmol) was added to a stirred solution of tert-butyl 5-[[4-[(2-chloroacetyl)amino]-3-fluoro-phenyl]sulfonyl-[(4-methoxyphenyl)methyl]amino]amino]thiazole-4-carboxylate (400 mg, 0.70 mmol) in DMF (5 mL) at RT. The resulting reaction mixture was stirred at RT for 16 h, quenched with ice cold water (10 mL) and extracted with ethyl acetate (2×10 mL). The combined organic extracts were dried over Na2SO4, filtered and concentrated under reduced pressure. The crude material was purified by trituration with diethyl ether (2×5 mL) to afford a light brown solid (370 mg, 91%).

M/z 577.23 (M+H)+ c. tert-butyl 5-[[4-[(2-aminoacetyl)amino]-3-fluoro-phenyl]sulfonyl-[(4-methoxyphenyl)methyl]amino]thiazole-4-carboxylate

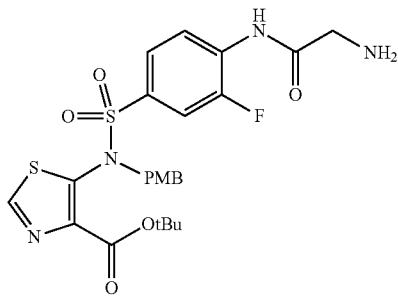

10% Pd/C (300 mg) was added to solution of tert-butyl 5-[[4-[(2-azidoacetyl)amino]-3-fluoro-phenyl]sulfonyl-[(4-methoxyphenyl)methyl]amino]thiazole-4-carboxylate (370 mg, 0.64 mmol) in EtOAc (10 mL) at RT under nitrogen atmosphere. The resulting reaction mixture was stirred at RT under a hydrogen atmosphere (balloon pressure) for 16 h, filtered through a pad of celite and washing with EtOAc (20 mL). The filtrate was concentrated under reduced pressure. The crude material was purified by trituration with diethyl ether (2×5 mL) to afford a brown solid (340 mg, 96%).

M/z 551.35 (M+H)+ d. tert-butyl 5-[[4-[[2-(4,5-dihydro-1H-imidazol-2-ylamino)acetyl]amino]-3-fluoro-phenyl]sulfonyl-[(4-methoxyphenyl)methyl]amino]thiazole-4-carboxylate

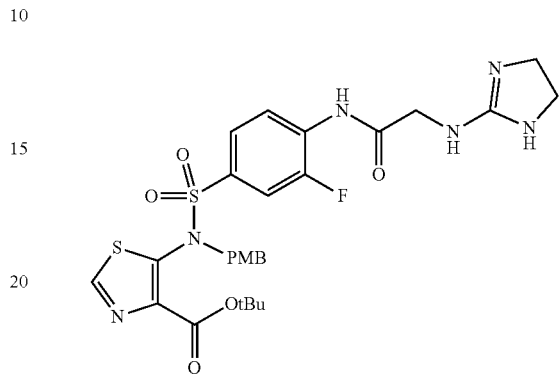

2-Methylsulfanyl-4,5-dihydro-1H-imidazole (124 mg, 0.50 mmol) was added to a stirred solution of tert-butyl 5-[[4-[(2-aminoacetyl)amino]-3-fluoro-phenyl]sulfonyl-[(4-methoxyphenyl)methyl]amino]thiazole-4-carboxylate (400 mg, 0.72 mmol) in THF (5 mL) at RT. The resulting reaction mixture was heated to 70° C. for 48 h in a closed vial and concentrated under reduced pressure to afford a yellow solid which was used in the next step without further purification (500 mg, crude).

M/z 619.36 (M+H)+ e. 5-[[3,5-difluoro-4-(guanidinocarbamoylamino)phenyl]sulfonylamino]thiazole-4-carboxylic acid

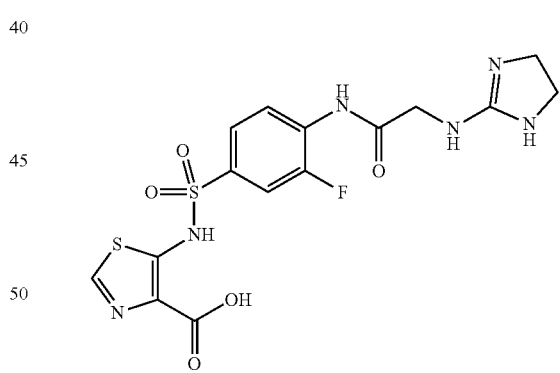

TFA (5 mL) was added to tert-butyl 5-[[4-[[2-(4,5-dihydro-1H-imidazol-2-ylamino)acetyl]amino]-3-fluoro-phenyl]sulfonyl-[(4-methoxyphenyl)methyl]amino]thiazole-4-carboxylate (500 mg, 0.50 mmol) at 0° C. and stirred at RT for 6 h. TFA was evaporated by reduced pressure and the resulting crude product was triturated with diethyl ether (2×5 mL) and dried under vacuum. The crude product was purified by preparative HPLC affording the title product as a white solid (37 mg, 18%).

$^1$H NMR (400 MHz, DMSO-d$_6$) δ 13.43 (1H, brs), 10.20 (1H, brs), 8.4 (3H, brs), 8.11-8.08 (2H, m), 7.55-7.48 (2H, m), 4.08 (2H, s), 3.60 (4H, s).

M/z 443.24 (M+H)+

LC-MS Condition:
Column: Acquity BEH C18 (50 mm×2.1 mm, 1.7 um);
Mobile Phase: A: 0.05% Formic Acid in water; B: 0.05% Formic Acid in ACN;
Time (min)/% B: 0/3, 0.4/3, 2/98, 3.8/98, 4.2/3, 4.5/3;
Column Temp: 35° C.,
Flow Rate: 0.6 mL/min.
Prep. HPLC Condition:
Column: Atlantis T3 (250*19) mm, 5 u;
Mobile phase: (A) 0.1% Formic Acid (B) Acetonitrile;
Flow: 19 mL/min;
Gradient (T/% B): 0/5, 1/5, 9/30, 10.31/99, 12/99, 12.1/5, 15/5;
Solubility: ACN+H₂O+THF.

Example 33

5-[[3-fluoro-4-[[2-(morpholine-4-carboximidoylamino)acetyl]amino]phenyl]sulfonylamino]thiazole-4-carboxylic acid

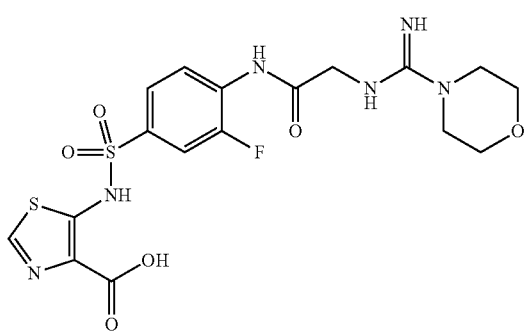 [SMILES: N=C(NCC(=O)Nc1ccc(S(=O)(=O)Nc2scnc2C(=O)O)cc1F)N1CCOCC1]

a. tert-butyl 5-[[3-fluoro-4-[[2-(morpholine-4-carbothioylamino)acetyl]amino]phenyl]sulfonyl-[(4-methoxyphenyl)methyl]amino]thiazole-4-carboxylate

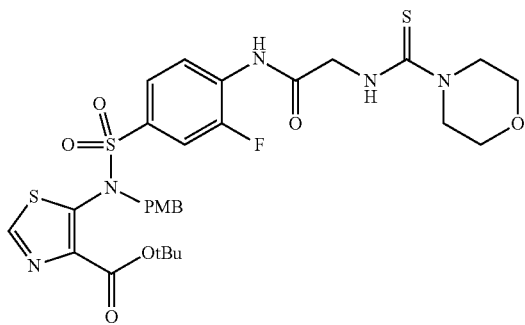

A solution of tert-butyl 5-[[4-[(2-aminoacetyl)amino]-3-fluoro-phenyl]sulfonyl-[(4-methoxyphenyl)methyl]amino]thiazole-4-carboxylate (500 mg, 0.9 mmol) and di(imidazol-1-yl)methanethione (242 mg, 1.36 mmol) in CH₂Cl₂ (15 mL) was stirred at RT for 30 minutes. Then morpholine (118 mg, 1.36 mmol) was added and the resulting reaction mixture was stirred at 40° C. for 1 h. The reaction mixture was concentrated under vacuum.

The crude compound was purified by flash chromatography eluting with 3% MeOH in CH₂Cl₂ to afford a pale pink gummy material (100 mg, 83%).
M/z 680.42 (M+H)⁺ b. tert-butyl 5-[[3-fluoro-4-[[2-(morpholine-4-carboximidoylamino)acetyl]amino]phenyl]sulfonyl-[(4-methoxyphenyl)methyl]amino]thiazole-4-carboxylate

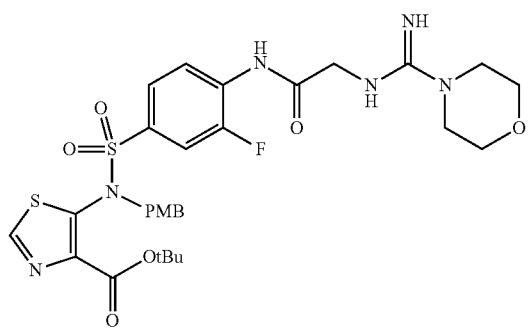

Ag(OTf) (255 mg, 0.99 mmol) was added to a solution of tert-butyl 5-[[3-fluoro-4-[[2-(morpholine-4-carbothioylamino)acetyl]amino]phenyl]sulfonyl-[(4-methoxyphenyl)methyl]amino]thiazole-4-carboxylate (450 mg, 0.66 mmol) in CH₂Cl₂:THF (1:1, 20 mL). The reaction mixture was cooled to −30° C. and NH₃ gas purged for 15 minutes. The reaction mixture was stirred at RT for 4 h, quenched with MeOH (1 mL) and concentrated under reduced pressure. Water (25 mL) was added and extracted with EtOAc (2×50 mL). The combined organic layer was dried over Na₂SO₄, filtered and concentrated. The crude material was purified by flash chromatography eluting with 3% MeOH in CH₂Cl₂ to afford a black gummy material (250 mg, 57%).
M/z 663.53 (M+H)⁺ c. 5-[[3-fluoro-4-[[2-(morpholine-4-carboximidoylamino)acetyl]amino]phenyl]sulfonylamino]thiazole-4-carboxylic acid

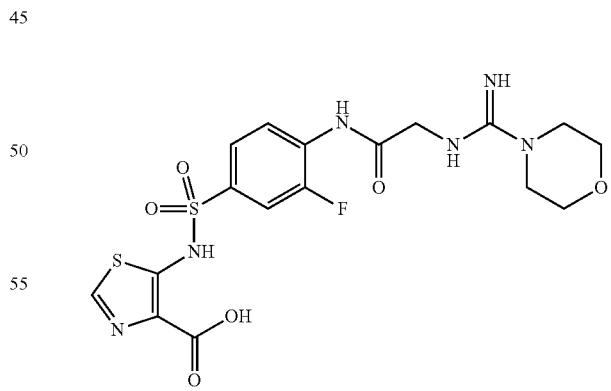

A solution of tert-butyl 5-[[3-fluoro-4-[[2-(morpholine-4-carboximidoylamino)acetyl]amino]phenyl]sulfonyl-[(4-methoxyphenyl)methyl]amino]thiazole-4-carboxylate in TFA: H₂O (95:5, 2 mL) was stirred at RT for 3 h. The reaction mixture was concentrated and the crude product was neutralised with methanolic ammonia. Then the reaction mixture was concentrated under reduced pressure. The crude material was purified by preparative HPLC affording the title product as an off-white solid (12.4 mg, 8%).

$^1$H NMR (400 MHz, DMSO-d6) δ 13.32 (1H, brs), 9.67 (1H, s), 8.13 (1H, s), 8.05-7.85 (3H, m), 7.63-7.61 (2H, m), 7.52-7.49 (1H, m), 4.18 (2H, brs), 3.63-3.55 (4H, m), 3.50-3.30 (4H, obs).

M/z 487.34 (M+H)$^+$

LC-MS Condition:
Column: Acquity BEH C18 (50 mm×2.1 mm, 1.7 um);
Mobile Phase: A: 0.05% Formic Acid in water; B: 0.05% Formic Acid in ACN;
Time (min)/% B: 0/3, 0.4/3, 3.2/98, 3.8/98, 4.2/3, 4.5/3;
Column Temp: 35° C.,
Flow Rate: 0.6 mL/min.
Prep. HPLC Condition:
Column used: Symmetry C18 (300*19) mm, 7 u;
Mobile phase: (A) 0.1% Formic Acid (B) Acetonitrile;
Flow: 19 mL/min;
Gradient –(T/% B): 0/5, 1/5, 7.1/56, 7.15/99, 10/99, 10.1/5, 13/5;
Solubility: CH$_3$CN+H$_2$O.

Example 34

5-[[4-[[2-[(N-cyanocarbamimidoyl)amino]acetyl]amino]-3-fluoro-phenyl]sulfonylamino]thiazole-4-carboxylic acid

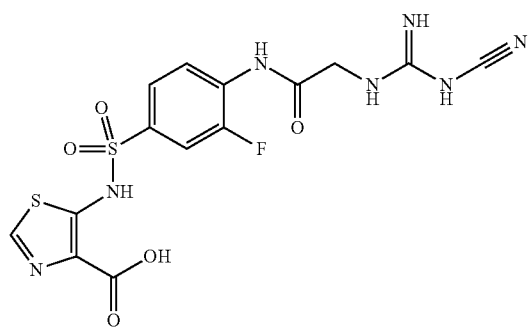 [SMILES: N#CNC(=N)NCC(=O)Nc1ccc(S(=O)(=O)Nc2scnc2C(=O)O)cc1F]

DIPEA (0.1 mL, 0.58 mmol) and NaN(CN)$_2$ (142 mg, 1.6 mmol) were added to a stirred solution of 5-[[4-[(2-aminoacetyl)amino]-3-fluoro-phenyl]sulfonylamino]thiazole-4-carboxylic acid (200 mg, 0.53 mmol) in DMF (5 mL) at RT under nitrogen atmosphere. The reaction mixture was stirred at 50° C. for 48 h and concentrated under reduced pressure. The crude compound was diluted with water (5 mL) and acidified to pH2-3 with 1N HCl. The resulting precipitate was filtered and dried under high vacuum. The crude product was purified by preparative HPLC affording the title product as an off-white solid (20.8 mg, 8%).

$^1$H NMR (400 MHz, DMSO-d$_6$) δ 12.8 (1H, brs), 10.0 (1H, s), 8.17 (1H, s), 8.13-8.09 (1H, m), 7.55-7.52 (2H, m), 6.96 (1H, brs), 6.87 (2H, s), 4.00 (2H, d, J=6.0 Hz).

M/z 442.18 (M+H)$^+$

LC-MS Condition:
Column: Acquity BEH C18 (50 mm×2.1 mm, 1.7 um);
Mobile Phase: A: 0.05% Formic Acid in water; B: 0.05% Formic Acid in ACN;
Time (min)/% B: 0/3, 0.4/3, 2/98, 3.4/98, 3.5/3, 4/3;
Column Temp: 35° C.,
Flow Rate: 0.6 mL/min.
Prep. HPLC Condition:
Column used: XBRIDGE C18 (150*19) mm, 5 u;
Mobile phase: (A) 0.1% Formic Acid (B) Acetonitrile;
Flow: 19 mL/min,
Gradient –(T/% B): 0/0, 2/0, 8/20, 10.9/20, 10.95/99, 13/99, 13.10/0, 16/0;
Solubility: ACN+H$_2$O+THF.

Example 35

5-[[4-[(4-amino-4-imino-butanoyl)amino]-3-fluoro-phenyl]sulfonylamino]thiazole-4-carboxylic acid

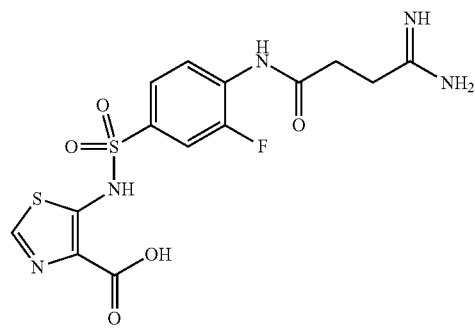 [SMILES: N=C(N)CCC(=O)Nc1ccc(S(=O)(=O)Nc2scnc2C(=O)O)cc1F]

a. 5-[[4-(3-chloropropanoylamino)-3-fluoro-phenyl]sulfonyl-[(4-methoxyphenyl)methyl]amino]thiazole-4-carboxylic acid

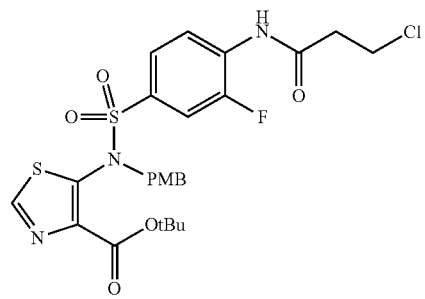

Acetic anhydride (5 mL) in DCM (5 mL) was added to a stirred solution of 3-chloropropanoyl chloride (1.5 g, 3.04 mmol) in DCM (5 mL) at 0° C. After 10 minutes, tert-butyl 5-[(4-amino-3-fluoro-phenyl)sulfonyl-[(4-methoxyphenyl)methyl]amino]thiazole-4-carboxylate (1.5 g) in DCM (10 mL) was added at 0° C. The resulting reaction mixture was stirred at RT for 2 h, quenched with ice cooled water (20 mL) and extracted with DCM (2×10 mL). The organic layer was dried over Na2SO$_4$, filtered and concentrated. The crude material was purified by flash chromatography (eluting with 60% ethyl acetate in petroleum ether) to afford an off-white solid (600 mg, 33%).

M/z 584.40 (M+H)$^+$ b. tert-butyl 5-[[4-(3-cyanopropanoylamino)-3-fluoro-phenyl]sulfonyl-[(4-methoxyphenyl)methyl]amino]thiazole-4-carboxylate

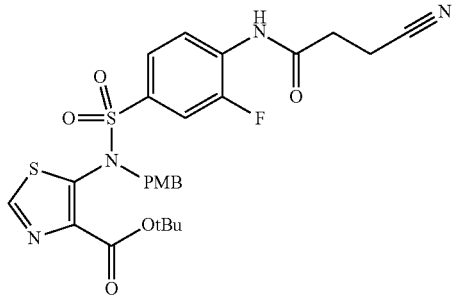

Sodium cyanide (76 mg, 1.54 mmol) was added to a stirred solution of 5-[[4-(3-chloropropanoylamino)-3-fluoro-phenyl]sulfonyl-[(4-methoxyphenyl)methyl]amino]thiazole-4-carboxylic acid (600 mg, 1.02 mmol) in DMF (5 mL) at RT. The resulting reaction mixture was stirred at RT for 6 h and quenched with ice cold water (10 mL). The resulting precipitate was filtered, washed with $Et_2O$ (2×10 mL) and dried under high vacuum to afford a brown solid (500 mg, 84%).

M/z 597.24 (M+Na)$^+$ c. tert-butyl 5-[[4-[(4-amino-4-imino-butanoyl)amino]-3-fluoro-phenyl]sulfonyl-[(4-methoxyphenyl)methyl]amino]thiazole-4-carboxylate

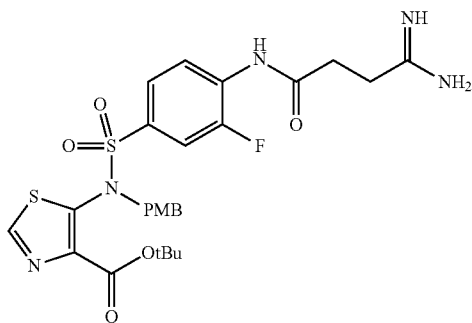

HCl gas was passed to a stirred solution of tert-butyl 5-[[4-(3-cyanopropanoylamino)-3-fluoro-phenyl]sulfonyl-[(4-methoxyphenyl)methyl]amino]thiazole-4-carboxylate (400 mg, 0.69 mmol) in ethanol:$Et_2O$ (1:4, 10 mL) at 0° C. for 2 h. The resulting reaction mixture was kept at 4° C. for 16 h. Then the volatile components were evaporated under reduced pressure. The residue was dissolved in ethanol (5 mL) and $NH_3$ gas was passed for 20 minutes. The volatile components were evaporated under reduced pressure. The resulting crude product was triturated with diethyl ether (2×5 mL) and dried under high vacuum to afford a brown solid which was used in the next step without further purification (350 mg, crude).

M/z 592.43 (M+H)$^+$ d. 5-[[4-[(4-amino-4-imino-butanoyl)amino]-3-fluoro-phenyl]sulfonylamino]thiazole-4-carboxylic acid

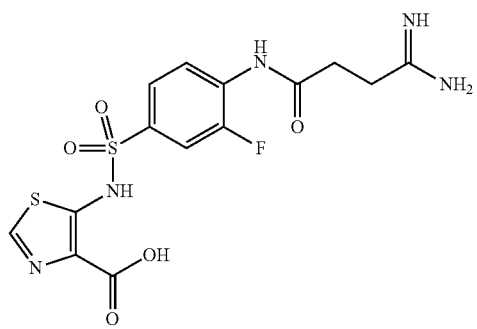 [SMILES: N=C(N)CCC(=O)Nc1ccc(S(=O)(=O)Nc2scnc2C(=O)O)cc1F]

TFA:$H_2O$ (95:5, 3 mL) was added to tert-butyl 5-[[4-[(4-amino-4-imino-butanoyl)amino]-3-fluoro-phenyl]sulfonyl-[(4-methoxyphenyl)methyl]amino]thiazole-4-carboxylate (350 mg, 0.592 mmol) at 0° C. The resulting reaction mixture was stirred at RT for 6 h and concentrated under reduced pressure. The resulting crude product was triturated with diethyl ether (2×5 mL) and dried under high vacuum. The crude product was purified by preparative HPLC affording the title product as an off-white solid (31 mg, 12%).

$^1$H NMR (400 MHz, DMSO-d$_6$) δ 13.40 (1H, s), 10.08 (1H, s), 8.99-8.71 (4H, m), 8.07 (1H, s), 8.05-8.01 (1H, m), 7.54-7.46 (2H, m), 2.85 (2H, t, J=7.2 Hz), 2.62 (2H, t, J=7.2 Hz).

M/z 415.93 (M+H)$^+$

LC-MS Condition:

Column: Acquity BEH C18 (50 mm×2.1 mm, 1.7 um);

Mobile Phase: A: 0.05% Formic Acid in water; B: 0.05% Formic Acid in ACN;

Time (min)/% B: 0/3, 0.4/3, 2/98, 3.4/98, 3.5/3, 4/3;

Column Temp: 35° C.;

Flow Rate: 0.6 mL/min.

Prep. HPLC Condition:

Column: Symmetry C18 (300*19) mm, 7 u;

Mobile phase: (A) 0.1% Formic Acid (B) Acetonitrile;

Flow: 19 mL/min;

Gradient (T/% B): 0/5, 1/5, 7/20, 10.1/20, 10.1/99, 13/99, 13.1/5, 16/5;

Solubility: ACN+$H_2O$+THF+DMSO+conc FA.

Example 36

5-[[4-[3-(4,5-dihydro-1H-imidazol-2-yl)propanoylamino]-3-fluoro-phenyl]sulfonylamino]thiazole-4-carboxylic acid a. 5-[[4-[3-(4,5-dihydro-1H-imidazol-2-yl)propanoylamino]-3-fluoro-phenyl]sulfonyl-[(4-methoxyphenyl)methyl]amino]thiazole-4-carboxylic acid

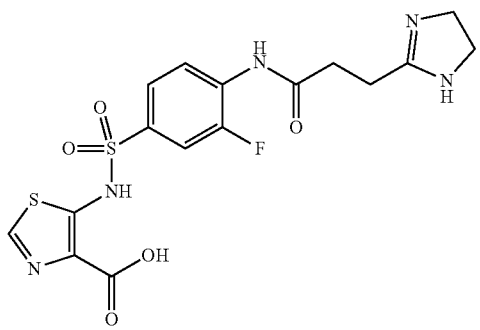 [SMILES: O=C(CCC1=NCCN1)Nc1ccc(S(=O)(=O)Nc2scnc2C(=O)O)cc1F]

HCl gas was passed to a stirred solution of tert-butyl 5-[[4-(3-cyanopropanoylamino)-3-fluoro-phenyl]sulfonyl-[(4-methoxyphenyl)methyl]amino]thiazole-4-carboxylate (310 mg, 0.53 mmol) in ethanol:Et$_2$O (1:4, 15 mL) at 0° C. for 2 h. The resulting reaction mixture was kept in refrigerator for 16 h. Then the volatile components were evaporated under reduced pressure. The resulting residue was dissolved in ethanol (5 mL). Then ethylene diamine (32 mg, 0.53 mmol) was added at RT. The resulting reaction mixture was stirred at RT for 8 h and concentrated under reduced pressure. The resulting crude product was triturated with n-pentane (2×5 mL) and dried under high vacuum to afford a brown solid which was used in the next step without further purification (400 mg, crude).

M/z 618.46 (M+H)$^+$ b. 5-[[4-[3-(4,5-dihydro-1H-imidazol-2-yl)propanoylamino]-3-fluoro-phenyl]sulfonylamino]thiazole-4-carboxylic acid TFA:H$_2$O (95:5, 3 mL) was added to 5-[[4-[3-(4,5-dihydro-1H-imidazol-2-yl)propanoylamino]-3-fluoro-phenyl]sulfonyl-[(4-methoxyphenyl)methyl]amino]thiazole-4-carboxylic acid (280 mg, 0.45 mmol) at 0° C. The resulting reaction mixture was stirred at RT for 4 h and concentrated under reduced pressure. The resulting crude product was triturated with diethyl ether (2×5 mL) and dried under high vacuum. The crude product was purified by preparative HPLC to afford the title product as an off-white solid (21 mg, 10%).

$^1$H NMR (300 MHz, DMSO-d$_6$) δ 13.45 (1H, brs), 9.80 (1H, brs), 8.12-8.04 (2H, m), 7.54-7.44 (2H, m), 3.65 (4H, s), 2.82-2.77 (2H, m), 2.62-2.58 (2H, m).

M/z 441.98 (M+H)$^+$

LC-MS Condition:

Column: Acquity BEH C18 (50 mm×2.1 mm, 1.7 um);

Mobile Phase: A: 0.05% Formic Acid in water; B: 0.05% Formic Acid in ACN;

Time (min)/% B: 0/3, 0.4/3, 3.2/98, 3.8/98, 4.2/3, 4.5/3;

Column Temp: 35° C.;

Flow Rate: 0.6 mL/min.

Prep. HPLC Condition:

Column: Symmetry C18 (300*19) mm, 7 u;

Mobile phase: (A) 0.1% Formic Acid (B) Acetonitrile;

Flow: 19 mL/min;

Gradient (T/% B): 0/5, 1/5, 7/30, 8.7/30, 8.75/99, 11/99, 11.1/5, 13/5;

Solubility: ACN+H$_2$O+THF.

Example 37

5-[[4-[(3-amino-3-imino-2-methyl-propanoyl)amino]-3-fluoro-phenyl]sulfonylamino]thiazole-4-carboxylic acid

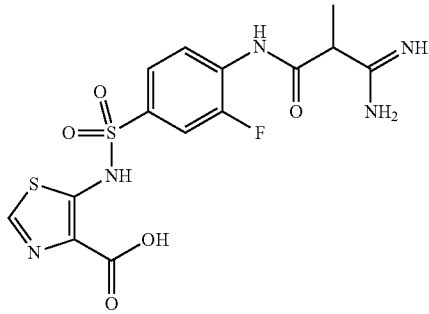 [SMILES: CC(C(=N)N)C(=O)Nc1ccc(S(=O)(=O)Nc2scnc2C(=O)O)cc1F]

a. tert-butyl 5-[[4-(2-chloropropanoylamino)-3-fluoro-phenyl]sulfonyl-[(4-methoxyphenyl)methyl]amino]thiazole-4-carboxylate

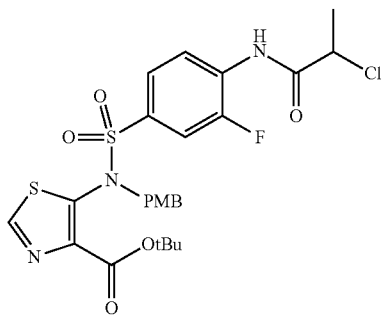

2-chloropropanoyl chloride (1.48 mL, 15.1 mmol) was added to a stirred solution of tert-butyl 5-[(4-amino-3-fluoro-phenyl)sulfonyl-[(4-methoxyphenyl)methyl]amino]thiazole-4-carboxylate (3 g, 6.0 mmol) in DCM (50 mL) at 0° C. The resulting reaction mixture was stirred at RT for 2 h and concentrated under reduced pressure. The residue was triturated with diethyl ether (2×50 mL), pentane (2×50 mL) and dried under reduced pressure to afford an off-white solid (3.4 g, 95%).

M/z 606.28 (M+Na)⁺; 582.75 (M−H)⁻ b. tert-butyl 5-[[4-(2-cyanopropanoylamino)-3-fluoro-phenyl]sulfonyl-[(4-methoxyphenyl)methyl]amino]thiazole-4-carboxylate

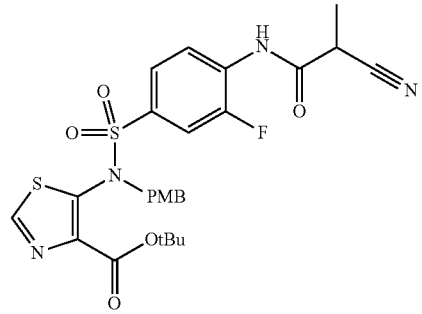

NaCN (570 mg, 11.6 mmol) was added to a solution of tert-butyl 5-[[4-(2-chloropropanoylamino)-3-fluoro-phenyl]sulfonyl-[(4-methoxyphenyl)methyl]amino]thiazole-4-carboxylate (3.4 g, 5.8 mmol) in DMF (35 mL) at RT. The resulting reaction mixture was stirred at RT for 16 h and quenched with ice cooled water. The resulting precipitate was filtered and dried under high vacuum. The crude product was purified by silica gel chromatography (eluting with 40% EtOAc in petroleum ether) to afford an off-white solid (1.5 g, 44%).

M/z 597.29 (M+Na)⁺; 573.62 (M−H)⁻ c. tert-butyl 5-[[3-fluoro-4-[[3-(hydroxyamino)-3-imino-2-methyl-propanoyl]amino]phenyl]sulfonyl-[(4-methoxyphenyl)methyl]amino]thiazole-4-carboxylate

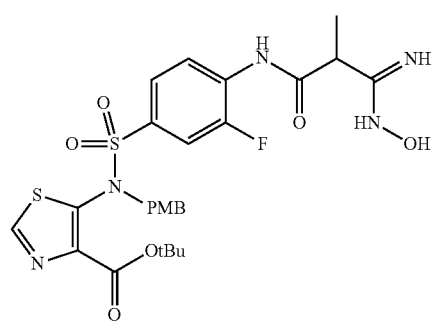

NH₂OH.HCl (362 mg, 5.22 mmol) and Na2CO3 (828 mg, 7.8 mmol) were added to a stirred solution of tert-butyl 5-[[4-(2-cyanopropanoylamino)-3-fluoro-phenyl]sulfonyl-[(4-methoxyphenyl)methyl]amino]thiazole-4-carboxylate (1.5 g, 2.61 mmol) in EtOH (30 mL) at RT. The resulting reaction mixture was stirred at 65° C. for 1 h, cooled to RT and filtered. The filtrate was concentrated under reduced pressure to afford a pale yellow gummy material which was used in the next step without further purification (1.5 g, crude).

M/z 608.48 (M+H)⁺ d. tert-butyl 5-[[4-[(3-amino-3-imino-2-methyl-propanoyl)amino]-3-fluoro-phenyl]sulfonyl-[(4-methoxyphenyl)methyl]amino]thiazole-4-carboxylate

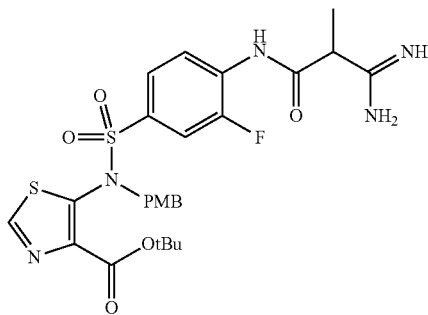

Iron powder (193 mg, 3.4 mmol) was added to tert-butyl 5-[[3-fluoro-4-[[3-(hydroxyamino)-3-imino-2-methyl-propanoyl]amino]phenyl]sulfonyl-[(4-methoxyphenyl)methyl]amino]thiazole-4-carboxylate (350 mg, 0.57 mmol) in ethanol:water (1:1, 3 mL) and heated to reflux for 30 minutes. Then 1N HCl (0.3 mL) in ethanol:water (1:1, 3 mL) was added to the reaction mixture over a period of 30 minutes. The reaction mixture was stirred for an additional 1 h at 70° C., cooled to RT and filtered through celite. The celite pad was washed with ethanol (2×10 mL). The filtrate was concentrated under reduced pressure to afford a pale yellow liquid which was used in the next step without further purification (340 mg, crude).

M/z 592.28 (M+H)$^+$ e. 5-[[4-[(3-amino-3-imino-2-methyl-propanoyl)amino]-3-fluoro-phenyl]sulfonylamino]thiazole-4-carboxylic acid

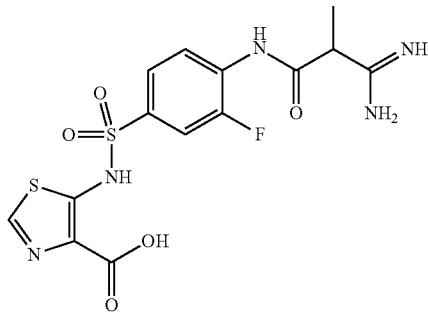 [SMILES: CC(C(=N)N)C(=O)Nc1ccc(S(=O)(=O)Nc2scnc2C(=O)O)cc1F]

Tert-butyl 5-[[4-[(3-amino-3-imino-2-methyl-propanoyl)amino]-3-fluoro-phenyl]sulfonyl-[(4-methoxyphenyl)methyl]amino]thiazole-4-carboxylate (340 mg, 0.57 mmol) was added to a solution of TFA:H$_2$O (9:1, 3 mL) at RT. The reaction mixture was stirred at RT for 3 h and concentrated under reduced pressure (below 30° C. of bath temperature). The residue was triturated with diethyl ether (2×5 mL) and dried under high vacuum. The crude product was purified by preparative HPLC to afford the title product as an off-white solid (48.2 mg).

$^1$H NMR (300 MHz, DMSO-d$_6$) δ 13.40 (1H, brs), 10.25 (1H, s), 8.89 (2H, s), 8.65 (2H, s), 8.11 (1H, s), 8.0 (1H, t, J=8.1 Hz), 7.60-7.50 (2H, m), 3.87 (1H, q, J=7.2 Hz), 1.49 (3H, d, J=7.2 Hz).

M/z 416.34 (M+H)$^+$

LC-MS Condition:
Column: Acquity BEH C18 (50 mm×2.1 mm, 1.7 um);
Mobile Phase: A: 0.05% Formic Acid in water; B: 0.05% Formic Acid in ACN;
Time (min)/% B: 0/3, 0.4/3, 3.2/98, 3.8/98, 4.2/3, 4.5/3;
Column Temp: 35° C.;
Flow Rate: 0.6 mL/min.
Prep. HPLC Condition:
Column used: Symmetry C18 (300*19) mm, 7 u;
Mobile phase: (A) 0.1% Formic Acid (B) Acetonitrile;
Flow: 19 mL/min;
Gradient –(T/% B): 0/5, 1/5, 8/50, 8.1/99, 11/99, 11.1/5, 14/5;
Solubility: ACN+H$_2$O+Concentrated FA.

Example 38

5-[[3-fluoro-4-[[2-(2-iminoimidazolidin-1-yl)acetyl]amino]phenyl]sulfonylamino]thiazole-4-carboxylic acid

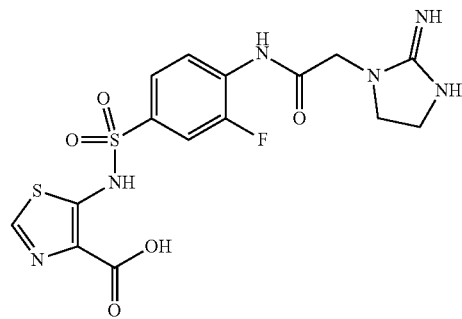 [SMILES: N=C1NCCN1CC(=O)Nc1ccc(S(=O)(=O)Nc2scnc2C(=O)O)cc1F]

a. tert-butyl 5-[[3-fluoro-4-[[2-(2-thioxoimidazolidin-1-yl)acetyl]amino]phenyl]sulfonyl-[(4-methoxyphenyl)methyl]amino]thiazole-4-carboxylate

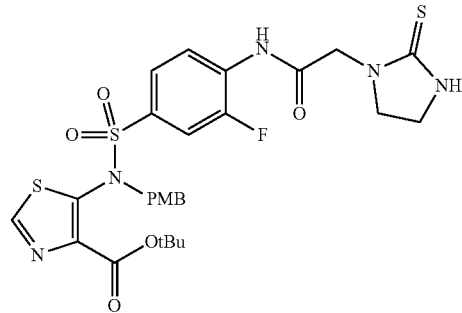

A solution of tert-butyl 5-[[4-[(2-chloroacetyl)amino]-3-fluoro-phenyl]sulfonyl-[(4-methoxyphenyl)methyl]amino]thiazole-4-carboxylate (500 mg, 0.87 mmol) in acetonitrile (50 mL) was added to a stirred solution of ethylenediamine (0.29 mL, 4.38 mmol) in acetonitrile (50 mL) over a period of 30 minutes at 75° C. The resulting reaction mixture was stirred at 75° C. for 2.5 h. Di(imidazol-1-yl)methanethione (1.56 g, 8.77 mmol) was then added at 75° C. and the reaction was stirred for 1 h at the same temperature then concentrated under reduced pressure. The resulting crude compound was diluted with EtOAc (50 mL), washed with water (10 mL) and brine solution (10 mL). The organic layer was dried over Na$_2$SO$_4$, filtered and concentrated under reduced pressure. The crude material was purified by flash chromatography (eluting with 60% EtOAc in petroleum ether) to afford a light brown solid (200 mg, 36%).

M/z 636.20 (M+H)$^+$ b. tert-butyl 5-[[3-fluoro-4-[[2-(2-iminoimidazolidin-1-yl)acetyl]amino]phenyl]sulfonyl-[(4-methoxyphenyl)methyl]amino]thiazole-4-carboxylate

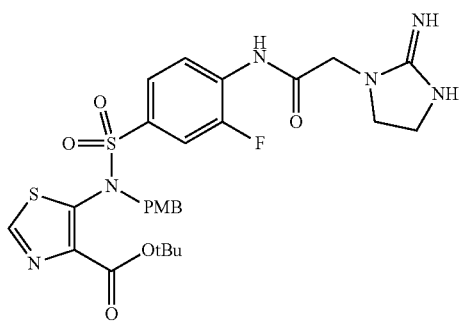

Ag(OTf) (121 mg, 0.47 mmol) and saturated NH$_3$ in THF (5 mL) were added to a stirred solution of tert-butyl 5-[[3-fluoro-4-[[2-(2-thioxoimidazolidin-1-yl)acetyl]amino]phenyl]sulfonyl-[(4-methoxyphenyl)methyl]amino]thiazole-4-carboxylate (200 mg, 0.31 mmol) in CH$_2$Cl$_2$ (10 mL) at −30° C. under nitrogen atmosphere. The resulting reaction mixture was stirred at RT for 16 h, quenched with MeOH (2 mL) and stirred at RT for 10 minutes. The reaction mixture was filtered through celite pad and the pad was washed with CH$_2$Cl$_2$ (2×10 mL). The filtrate was concentrated under reduced pressure to afford a dark brown liquid which was used in the next step without further purification (300 mg, crude).

M/z 619.48 (M+H)$^+$ c. 5-[[3-fluoro-4-[[2-(2-iminoimidazolidin-1-yl)acetyl]amino]phenyl]sulfonylamino]thiazole-4-carboxylic acid

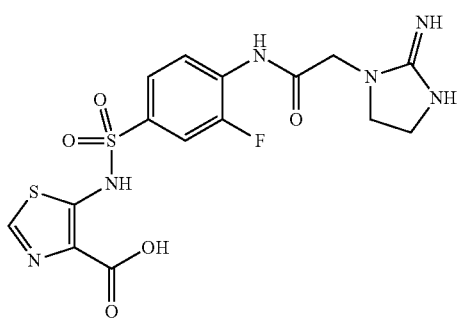 [SMILES: N=C1NCCN1CC(=O)Nc1ccc(S(=O)(=O)Nc2scnc2C(=O)O)cc1F]

TFA: H$_2$O (9:1, 5 mL) was added to tert-butyl 5-[[3-fluoro-4-[[2-(2-iminoimidazolidin-1-yl)acetyl]amino]phenyl]sulfonyl-[(4-methoxyphenyl)methyl]amino]thiazole-4-carboxylate (270 mg, 0.43 mmol) at 0° C. The resulting reaction mixture was stirred at RT for 3 h and concentrated under reduced pressure. The resulting crude product was triturated with diethyl ether (2×5 mL) and dried under high vacuum. The crude product was purified by preparative HPLC affording the title product as an off-white solid (10.6 mg).

$^1$H NMR (400 MHz, DMSO-d$_6$) δ 13.32 (1H, brs), 10.24 (1H, s), 8.70 (1H, brs), 8.12 (1H, s), 7.68-7.60 (3H, m), 7.47 (1H, dd, J=8.0 Hz, J=7.6 Hz), 7.38 (1H, s), 4.11 (2H, s), 3.74-3.67 (2H, m), 3.61-3.55 (2H, m).

M/z 443.24 (M+H)$^+$

LC-MS Condition:
Column: Acquity BEH C18 (50 mm×2.1 mm, 1.7 um);
Mobile Phase: A: 0.05% Formic Acid in water; B: 0.05% Formic Acid in ACN;
Time (min)/% B: 0/3, 0.4/3, 3.2/98, 3.8/98, 4.2/3, 4.5/3;
Column Temp: 35° C.,
Flow Rate: 0.6 mL/min
Prep. HPLC Condition:
Column used: Atlantis T3 (250*19) mm, 5 u;
Mobile phase: (A) 0.1% Formic Acid (B) Acetonitrile;
Flow: 19 mL/min;
Gradient −(T/% B): 0/5, 1/5, 7/30, 8.25/30, 8.3/99, 11/99, 11.1/5, 14/5;
Solubility: ACN+H$_2$O+THF Example 39

5-[[4-[[2-[[N-(2-aminoethyl)carbamimidoyl]amino]acetyl]amino]-3-fluoro-phenyl]sulfonylamino]thiazole-4-carboxylic acid

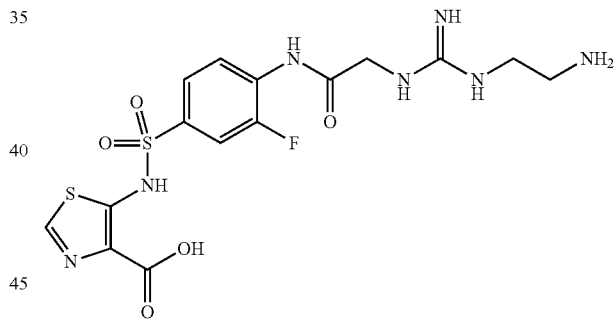

a. tert-butyl 5-[[4-[[2-[2-(tert-butoxycarbonylamino)ethylcarbamothioylamino]acetyl]amino]-3-fluorophenyl]sulfonyl-[(4-methoxyphenyl)methyl]amino]thiazole-4-carboxylate

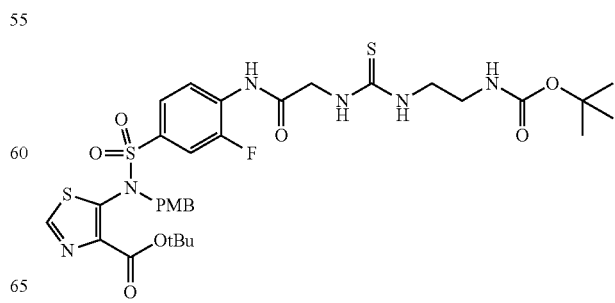

Di(imidazol-1-yl)methanethione (97 mg, 0.54 mmol) was added to a stirred solution of tert-butyl 5-[[4-[(2-aminoacetyl)amino]-3-fluoro-phenyl]sulfonyl-[(4-methoxyphenyl)methyl]amino]thiazole-4-carboxylate (200 mg, 0.36 mmol) in DCM (10 mL) at RT. The reaction mixture was stirred at RT for 4 h and NH$_2$CH$_2$CH$_2$NHBoc (174 mg, 1.08 mmol) was added. The reaction mixture was stirred at 40° C. for 6 h and concentrated under reduced pressure. The crude product was purified by column chromatography (eluting with 60% EtOAc in petroleum ether) to afford a brown solid (80 mg, 29%).

M/z 753.43 (M+H)$^+$ b. tert-butyl 5-[[4-[[2-[[N-[2-(tert-butoxycarbonylamino)ethyl]carbamimidoyl]amino]acetyl]amino]-3-fluoro-phenyl]sulfonyl-[(4-methoxyphenyl)methyl]amino]thiazole-4-carboxylate

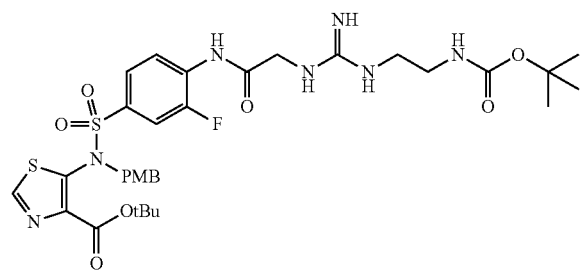

Ag(OTf) (107 mg, 0.47 mmol) was added to a stirred solution of tert-butyl 5-[[4-[[2-[2-(tert-butoxycarbonylamino)ethylcarbamothioylamino]acetyl]amino]-3-fluoro-phenyl]sulfonyl-[(4-methoxyphenyl)methyl]amino]thiazole-4-carboxylate (220 mg, 0.27 mmol) in CH$_2$Cl$_2$ (10 mL) at RT. The reaction mixture was stirred at RT for 15 minutes and saturated NH$_3$ in THF (5 mL) was added at −30° C. under nitrogen atmosphere. The resulting reaction mixture was stirred at RT for 6 h, filtered through celite pad and the pad was washed with CH$_2$Cl$_2$ (10 mL). The filtrate was concentrated and the obtained crude material was triturated with n-pentane (10 mL) to afford a brown solid which was used in the next step without further purification.

M/z 736.40 (M+H)$^+$ c. 5-[[4-[[2-[[N-(2-aminoethyl)carbamimidoyl]amino]acetyl]amino]-3-fluoro-phenyl]sulfonylamino]thiazole-4-carboxylic acid

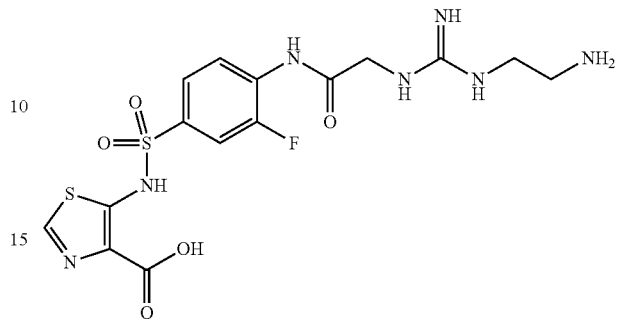

TFA: H$_2$O (9:1, 2 mL) was added to tert-butyl 5-[[4-[[2-[[N-[2-(tert-butoxycarbonylamino)ethyl]carbamimidoyl]amino]acetyl]amino]-3-fluoro-phenyl]sulfonyl-[(4-methoxyphenyl)methyl]amino]thiazole-4-carboxylate (210 mg, 0.28 mmol) at 0° C. The reaction mixture was stirred at RT for 4 h and concentrated under reduced pressure. The resulting crude product was triturated with diethyl ether (2×5 mL) and dried under high vacuum. The crude product was purified by preparative HPLC affording the title product as brown solid (25 mg).

$^1$H NMR (300 MHz, DMSO-d$_6$) δ 8.13 (1H, brs), 8.09 (1H, s), 7.42-7.30 (2H, m), 6.96 (1H, dd, J=8.7 Hz, J=8.4 Hz), 6.20-6.00 (1H, m), 5.70-5.40 (1H, m), 3.82 (2H, s), 3.27 (2H, brs), 2.80-2.75 (2H, m).

M/z 460.30 (M+H)$^+$

LC-MS Condition:
Column: Acquity BEH C18 (50 mm×2.1 mm, 1.7 um);
Mobile Phase: A: 0.05% Formic Acid in water; B: 0.05% Formic Acid in ACN;
Time (min)/% B: 0/3, 0.4/3, 3.2/98, 3.8/98, 4.2/3, 4.5/3;
Column Temp: 35° C.;
Flow Rate: 0.6 mL/min.
Prep. HPLC Condition:
Column: Atlantis T3 (250*19) mm, 5 u;
Mobile phase: (A) 0.1% Formic Acid (B) Acetonitrile;
Flow: 19 mL/min;
Gradient (T/% B): 0/5, 1/5, 7/25, 12/30, 12.1/99, 15/99, 15.1/5, 18/5;
Solubility: ACN+H$_2$O+THF+FA.

Compounds prepared using methods analogous to those described above for Example 39 by using methyl-amine in step-a and purified in a similar manner by preparative HPLC are shown in the Table below:—

| Example | Structure | Name, NMR and Mass |
|---|---|---|
| 40 | 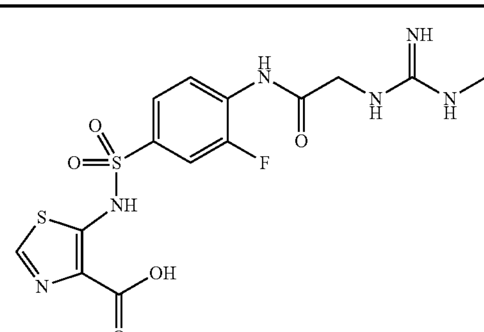 | 5-[[3-fluoro-4-[[2-[(N-methylcarbamimidoyl)amino]acetyl]amino]phenyl]sulfonylamino]thiazole-4-carboxylic acid<br>M/z 431.2 (M + H)$^+$<br>$^1$H NMR (d6-DMSO) δ 13.39 (1H, s), 9.65 (1H, s), 8.11 (1H, m), 8.05 (1H, m), 7.94 (3H, m), 7.61 (2H, m), 7.49 (1H, d, J = 8.4 Hz), 3.88 (2H, d, J = 5.2 Hz), 2.65 (3H, d, J = 4.4 Hz). |

Example 41

5-[[4-[[2-(2-carbamimidoylhydrazino)acetyl]amino]-3-fluoro-phenyl]sulfonylamino]thiazole-4-carboxylic acid

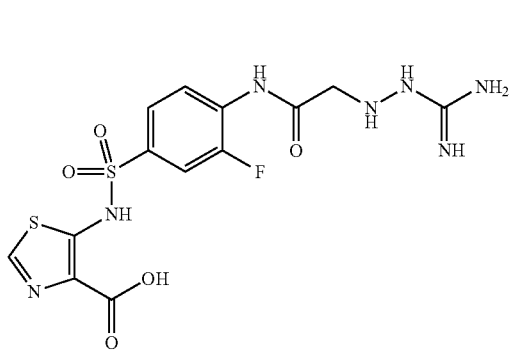 [SMILES: N=C(N)NNCC(=O)Nc1ccc(S(=O)(=O)Nc2scnc2C(=O)O)cc1F]

a. tert-butyl 5-[[4-[[2-(2-tert-butoxycarbonylhydrazino)acetyl]amino]-3-fluoro-phenyl]sulfonyl-[(4-methoxyphenyl)methyl]amino]thiazole-4-carboxylate

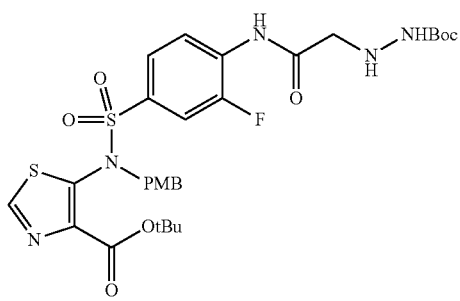

KI (1.17 g, 7.01 mmol) was added to a solution of tert-butyl 5-[[4-[(2-chloroacetyl)amino]-3-fluoro-phenyl]sulfonyl-[(4-methoxyphenyl)methyl]amino]thiazole-4-carboxylate (2 g, 3.50 mmol) in DMF (20 mL) at RT. After 10 minutes, tert-butyl N-aminocarbamate (695 mg, 5.26 mmol) was added to the reaction mixture at the same temperature. The resulting reaction mixture was stirred at RT for 16 h and concentrated under reduced pressure. Water (25 mL) was added to the crude compound and stirred for 20 minutes. The resulting precipitate was filtered, washed with diethyl ether and dried under high vacuum to afford a pale yellow solid which was used in the next step without further purification (1.2 g, 52%).

M/z 666.48 (M+H)$^+$ b. 5-[[3-fluoro-4-[(2-hydrazinoacetyl)amino]phenyl]sulfonylamino]thiazole-4-carboxylic acid

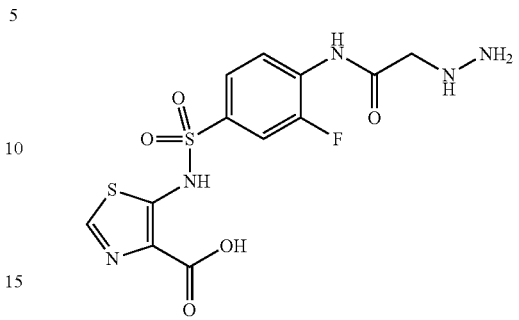

TFA (4 mL) was added to tert-butyl 5-[[4-[[2-(2-tert-butoxycarbonylhydrazino)acetyl]amino]-3-fluoro-phenyl]sulfonyl-[(4-methoxyphenyl)methyl]amino]thiazole-4-carboxylate (1.2 g, 1.80 mmol) at RT. The reaction mixture was stirred at RT for 16 h and concentrated under reducing pressure. The resulting crude product was triturated with diethyl ether (3×10 mL) to afford a pale yellow solid which was used in the next step without further purification (1 g, crude).

M/z 390.32 (M+H)$^+$ c. 5-[[4-[[2-(2-carbamimidoylhydrazino)acetyl]amino]-3-fluoro-phenyl]sulfonylamino]thiazole-4-carboxylic acid

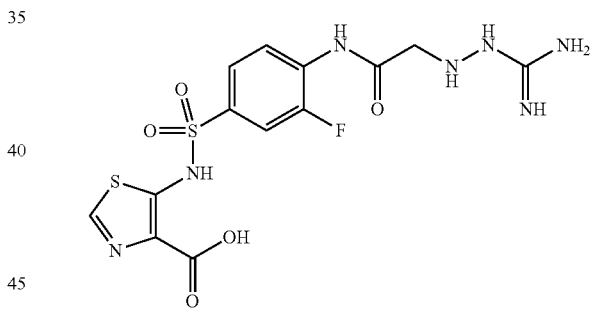

DIPEA (1.1 mL, 6.42 mmol) and pyrazole-1-carboxamidine; hydrochloride (212 mg, 1.92 mmol) were added to a stirred solution of 5-[[3-fluoro-4-[(2-hydrazinoacetyl)amino]phenyl]sulfonylamino]thiazole-4-carboxylic acid (500 mg, 1.28 mmol) in DMF (5 mL) at RT. The resulting reaction mixture was stirred at RT for 16 h, concentrated under reduced pressure and water (5 mL) was added to the residue. The resulting precipitate was filtered and washed with Et$_2$O (2×10 mL) and dried under high vacuum. The crude product was purified by preparative HPLC affording the title product as an off-white solid (15 mg).

$^1$H NMR (400 MHz, DMSO-d$_6$) δ 13.40 (1H, brs), 10.0 (1H, brs), 9.00 (1H, brs), 8.48 (1H, s), 8.05 (1H, m), 7.55-7.49 (2H, m), 7.45-7.22 (3H, brs), 5.67 (1H, brs), 3.62 (2H, d, J=4.4 Hz).

M/z 432.37 (M+H)$^+$

LC-MS Condition:

Column: Acquity BEH C18 (50 mm×2.1 mm, 1.7 um);

Mobile Phase: A: 0.05% Formic Acid in water; B: 0.05% Formic Acid in ACN;

Time (min)/% B: 0/3, 0.4/3, 3.2/98, 3.8/98, 4.2/3, 4.5/3;
Column Temp: 35° C.;
Flow Rate: 0.6 mL/min.
Prep. HPLC Condition:
Column: X BRIDGE C18 (150*19) mm, 5 u;
Mobile phase (A) 0.1% Formic Acid (B) Acetonitrile;
Flow: 19 mL/min;
Gradient (T/% B): (T/% B): 0/0, 3/0, 8.8/33, 9/33, 9.10/99, 12/99, 12.10/0, 15/0;
Solubility: ACN+H$_2$O+THF+DMSO+FA.

Example 42

5-[[3-fluoro-4-[(2-guanidinooxyacetyl)amino]phenyl]sulfonylamino]thiazole-4-carboxylic acid

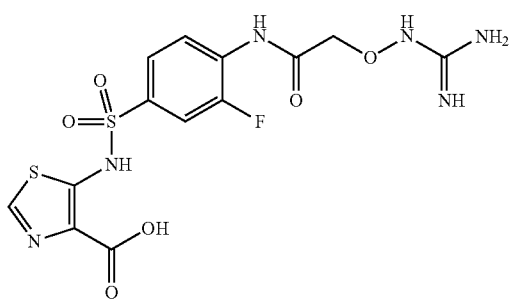 [SMILES: N=C(N)NOCC(=O)Nc1ccc(S(=O)(=O)Nc2scnc2C(=O)O)cc1F]

a. tert-butyl 5-[[4-[[2-(tert-butoxycarbonylamino)oxyacetyl]amino]-3-fluoro-phenyl]sulfonyl-[(4-methoxyphenyl)methyl]amino]thiazole-4-carboxylate

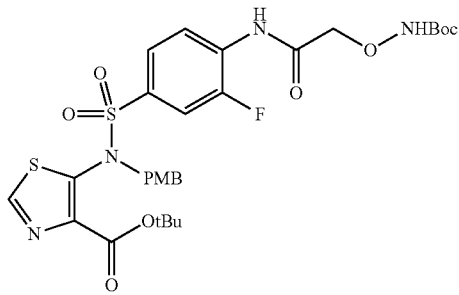

A solution of tert-butyl N-hydroxycarbamate (175 mg, 1.31 mmol) in THF (10 mL) was added to NaH (195 mg, 4.38 mmol) suspension in THF (10 mL) at 0° C. under argon atmosphere and stirred at RT for 30 minutes. Then tert-butyl 5-[[4-[(2-chloroacetyl)amino]-3-fluoro-phenyl]sulfonyl-[(4-methoxyphenyl)methyl]amino]thiazole-4-carboxylate (500 mg, 0.87 mmol) in THF (10 mL) was added to above reaction mixture at 0° C. under argon atmosphere. The resulting reaction mixture was stirred at RT for 1.5 h, quenched with ice cold water (20 mL) and extracted with ethyl acetate (2×20 mL). The combined organic layer was dried over Na$_2$SO$_4$, filtered and concentrated under reduced pressure. The crude material was purified by column chromatography (eluting with 30% ethyl acetate in petroleum ether) to afford a yellow solid (350 mg, 59%).

M/z 667.10 (M+H)$^+$ b. 5-[[4-[(2-aminooxyacetyl)amino]-3-fluoro-phenyl]sulfonylamino]thiazole-4-carboxylic acid

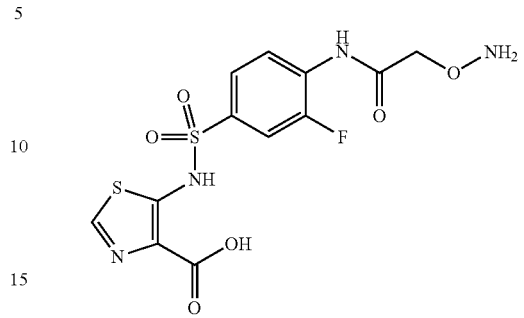

TFA: H$_2$O (9:1, 3 mL) was added to tert-butyl 5-[[4-[[2-(tert-butoxycarbonylamino)oxyacetyl]amino]-3-fluoro-phenyl]sulfonyl-[(4-methoxyphenyl)methyl]amino]thiazole-4-carboxylate (300 mg, 0.44 mmol) at 0° C. The reaction mixture was stirred at RT for 4 h and concentrated under reduced pressure. The resulting crude product was triturated with diethyl ether (3×10 mL) to afford an off-white solid which was used in next step without further purification (200 mg, crude).

M/z 390.95 (M+H)$^+$ c. 5-[[3-fluoro-4-[(2-guanidinooxyacetyl)amino]phenyl]sulfonylamino]thiazole-4-carboxylic acid

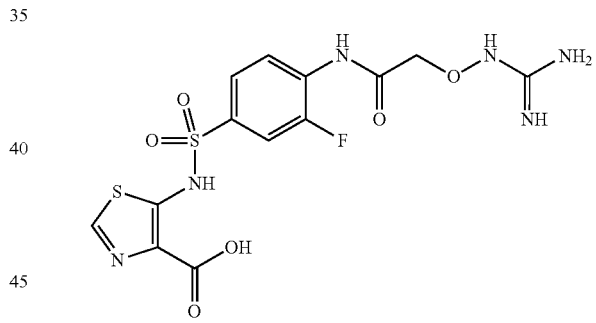

DIPEA (0.26 mL, 1.53 mmol) and pyrazole-1-carboxamidine; hydrochloride (149 mg, 0.92 mmol) were added to a stirred solution of 5-[[4-[(2-aminooxyacetyl)amino]-3-fluoro-phenyl]sulfonylamino]thiazole-4-carboxylic acid (200 mg, 0.51 mmol) in DMF (6 mL) at 0° C. The resulting reaction mixture was stirred at RT for 6 h, concentrated under reduced pressure and water (5 mL) was added to the residue. The resulting precipitate was filtered, washed with Et$_2$O (2×10 mL) and dried under high vacuum. The crude product was purified by preparative HPLC affording the title product as an off-white solid (70 mg, 31%).

$^1$H NMR (300 MHz, DMSO-d$_6$) δ 13.50 (1H, brs), δ 9.60 (1H, s), 8.37 (2H, brs), 8.17-8.12 (1H, m), 8.07 (1H, s), 7.58-7.51 (2H, m), 5.45 (2H, brs), 4.62 (2H, brs), 4.22 (2H, s).

M/z 433.30 (M+H)$^+$

LC-MS Condition:

Column: Acquity BEH C18 (50 mm×2.1 mm, 1.7 um);

Mobile Phase: A: 0.05% Formic Acid in Water B: 0.05% Formic Acid in Acetonitrile;
Time (min)/% B: 0/3, 0.4/3, 3.2/98, 3.8/98, 4.2/3, 4.5/3;
Column Temp: 35° C.;
Flow Rate: 0.6 mL/min.
Prep. HPLC Condition:
Column: X BRIDGE C18 (150*19) mm, 5 u;
Mobile phase (A) 0.1% Formic Acid (B) Acetonitrile;
Flow: 19 mL/min;
Gradient (T/% B): –(T/% B):0/0, 3/0, 8.8/33, 9/33, 9.10/99, 12/99, 12.10/0, 15/0;
Solubility: ACN+H$_2$O+THF+DMSO+FA.

Example 43

5-[[4-[[(2E)-2-(carbamimidoylhydrazono)acetyl]amino]-3-fluoro-phenyl]sulfonylamino]thiazole-4-carboxylic acid

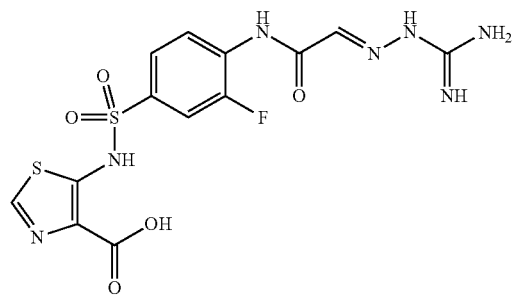 [SMILES: N=C(N)N/N=C/C(=O)Nc1ccc(S(=O)(=O)Nc2scnc2C(=O)O)cc1F]

a. tert-butyl 5-[[4-[[4-[4-[(4-tert-butoxycarbonylthiazol-5-yl)-[(4-methoxyphenyl)methyl]sulfamoyl]-2-fluoro-anilino]-4-oxo-but-2-enoyl]amino]-3-fluoro-phenyl]sulfonyl-[(4-methoxyphenyl)methyl]amino]thiazole-4-carboxylate

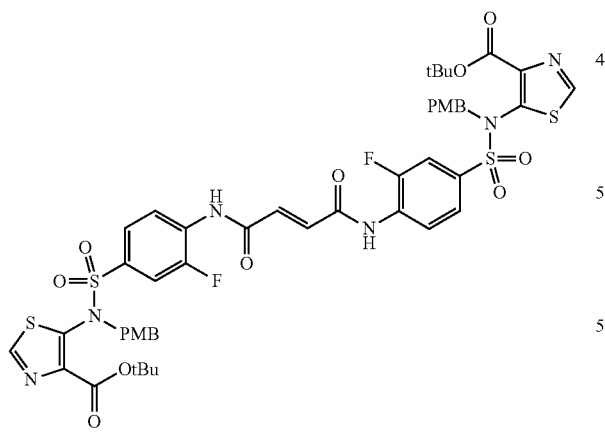

But-2-enedioyl dichloride (0.18 g, 1.2 mmol) in DCM (20 mL) was added to a solution of tert-butyl 5-[(4-amino-3-fluoro-phenyl)sulfonyl-[(4-methoxyphenyl)methyl]amino]thiazole-4-carboxylate (1 g, 2.0 mmol) in DCM (10 mL) at 0° C. The resulting reaction mixture was stirred at RT for 6 h, diluted with DCM and washed with water (2×10 mL) and brine (2×10 mL) solution. The combined organic layer was dried over Na$_2$SO$_4$, filtered and concentrated under reduced pressure. The crude material was purified by flash chromatography (eluting with 50% ethyl acetate in petroleum ether) to afford a pale yellow solid (500 mg, 23%).

M/z 1067.05 (M+H)$^+$ b. tert-butyl 5-[[3-fluoro-4-(oxaldehydoylamino)phenyl]sulfonyl-[(4-methoxyphenyl)methyl]amino]thiazole-4-carboxylate

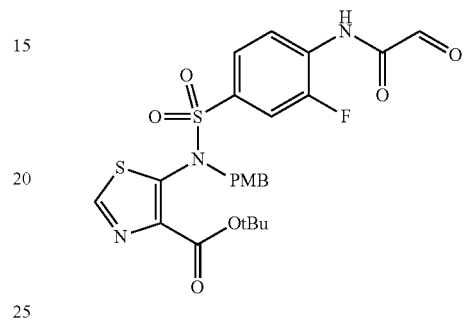

A solution of tert-butyl 5-[[4-[[4-[4-[(4-tert-butoxycarbonylthiazol-5-yl)-[(4-methoxyphenyl)methyl]sulfamoyl]-2-fluoro-anilino]-4-oxo-but-2-enoyl]amino]-3-fluoro-phenyl]sulfonyl-[(4-methoxyphenyl)methyl]amino]thiazole-4-carboxylate (500 mg, 0.46 mmol) in DCM/MeOH (3:1, 40 mL) was purged with ozone gas for 1 h at –78° C. Then DMS (2 mL) was added to the reaction mixture at the same temperature and the resulting mixture was stirred at RT for 2 h. The crude reaction mixture was used in next step without further purification.

c. tert-butyl 5-[[4-[[(2E)-2-(carbamimidoylhydrazono)acetyl]amino]-3-fluoro-phenyl]sulfonyl-[(4-methoxyphenyl)methyl]amino]thiazole-4-carboxylate

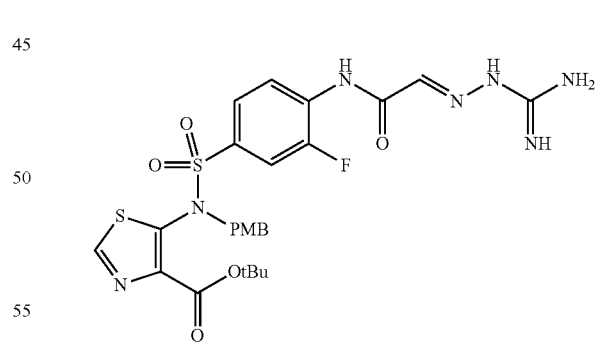

1-aminoguanidine; hydrochloride (30 mg, 0.27 mmol) was added to a stirred solution of tert-butyl 5-[[3-fluoro-4-(oxaldehydoylamino)phenyl]sulfonyl-[(4-methoxyphenyl)methyl]amino]thiazole-4-carboxylate (100 mg, 0.18 mmol) in DCM/MeOH (1:1, 10 mL) at RT. The resulting reaction mixture was stirred at RT for 16 h and concentrated under reduced pressure. The crude product was used in next step without further purification (100 mg, crude).

M/z 522.1 (M+H)$^+$ d. 5-[[4-[[(2E)-2-(carbamimidoylhydrazono)acetyl]amino]-3-fluoro-phenyl]sulfonylamino]thiazole-4-carboxylic acid

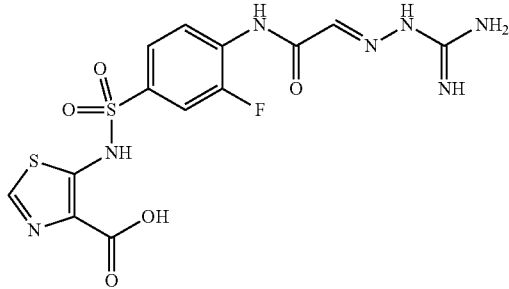 [SMILES: N=C(N)N/N=C/C(=O)Nc1ccc(S(=O)(=O)Nc2scnc2C(=O)O)cc1F]

TFA/H$_2$O (9:1, 1.0 mL) was added to tert-butyl 5-[[4-[[(2E)-2-(carbamimidoylhydrazono)acetyl]amino]-3-fluoro-phenyl]sulfonyl-[(4-methoxyphenyl)methyl]amino]thiazole-4-carboxylate (80 mg, 0.13 mmol) at 0° C., stirred at RT for 4 h and concentrated under reduced pressure. The resulting crude product was triturated with diethyl ether (2×5 mL) and dried under high vacuum. The crude product was purified by preparative HPLC affording the title product as an off-white solid (11 mg).

$^1$H NMR (400 MHz, DMSO-d$_6$) δ 9.68 (1H, brs), 8.05 (1H, s), 7.80 (1H, dd, J=8.4 Hz, J=8.0 Hz), 7.53-7.47 (2H, m), 7.19 (1H, s), 6.80-6.00 (4H, brs).

M/z 430.31 (M+H)$^+$

LC-MS Condition:
Column: Acquity BEH C18 (50 mm×2.1 mm, 1.7 um);
Mobile Phase: A: 0.05% Formic Acid in water; B: 0.05% Formic Acid in ACN;
Time (min)/% B: 0/3, 0.4/3, 3.2/98, 3.8/98, 4.2/3, 4.5/3;
Column Temp: 35° C.;
Flow Rate: 0.6 mL/min.
Prep. HPLC Condition:
Column: Atlantis T3 (250*19) mm, 5 u;
Mobile phase: (A) 0.1% Formic Acid (B) Acetonitrile;
Flow: 19 mL/min;
Gradient (T/% B): 0/5, 1/5, 7/25, 12/30, 12.1/99, 15/99, 15.1/5, 18/5;
Solubility: ACN+H$_2$O+THF+FA

Example 44

5-[(4-guanidinophenyl)sulfonylamino]thiazole-4-carboxylic acid

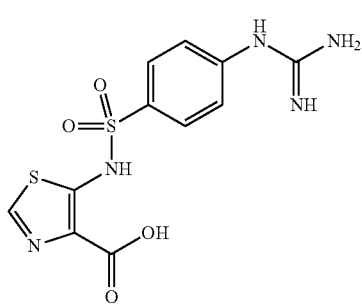 [SMILES: N=C(N)Nc1ccc(S(=O)(=O)Nc2scnc2C(=O)O)cc1]

a. tert-butyl 5-[[4-[[N,N'-bis(tert-butoxycarbonyl)carbamimidoyl]amino]phenyl]sulfonyl-[(4-methoxyphenyl)methyl]amino]thiazole-4-carboxylate

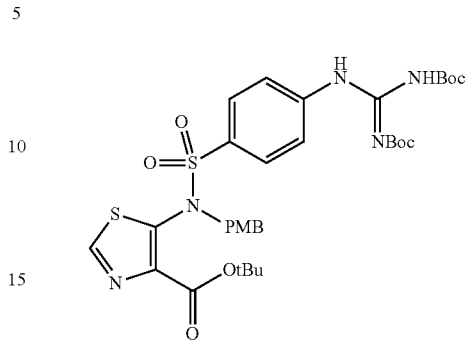

A solution of tert-butyl 5-[(4-aminophenyl)sulfonyl-[(4-methoxyphenyl)methyl]amino]thiazole-4-carboxylate (500 mg, 1.05 mmol) in THF (20 mL) was added to NaH (250 mg, 10.5 mmol) suspension in THF (20 mL) at 0° C. under argon atmosphere. After 30 minutes, a solution of tert-butyl N-[(tert-butoxycarbonylamino)-pyrazol-1-yl-methylene]carbamate (1.0 g, 3.43 mmol) in THF (10 mL) was added at 0° C. under argon atmosphere. The resulting reaction mixture was stirred at RT for 16 h, quenched with ice cold water (20 mL) and extracted with ethyl acetate (2×20 mL). The combined organic layer was dried over Na$_2$SO$_4$, filtered and concentrated under reduced pressure. The crude material was purified by trituration with diethyl ether (2×5 mL) to afford a pale yellow solid which was used in the next step without further purification (150 mg, crude).

M/z 662.03 (M+H-Boc)$^+$ b. 5-[(4-guanidinophenyl)sulfonylamino]thiazole-4-carboxylic acid

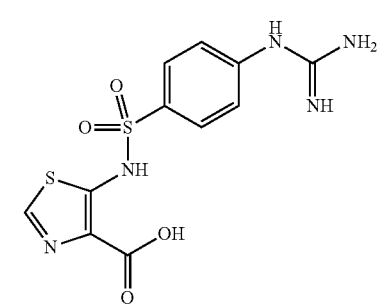 [SMILES: N=C(N)Nc1ccc(S(=O)(=O)Nc2scnc2C(=O)O)cc1]

TFA:H$_2$O (9:1, 2 mL) was added to tert-butyl 5-[[4-[[N,N'-bis(tert-butoxycarbonyl)carbamimidoyl]amino]phenyl]sulfonyl-[(4-methoxyphenyl)methyl]amino]thiazole-4-carboxylate (150 mg, 0.22 mmol) at RT. The resulting mixture was stirred for 4 h and concentrated under reduced pressure. The resulting crude product was triturated with diethyl ether (2×5 mL) and dried under high vacuum. The crude product was purified by preparative HPLC affording the title product as an off-white solid (22 mg, 28%).

$^1$H NMR (400 MHz, DMSO-d$_6$) δ 13.60 (1H, brs), 8.05 (1H, s), 7.74 (2H, d, J=8.8 Hz), 7.47 (3H, brs), 7.25 (2H, d, J=8.8 Hz).

M/z 342.29 (M+H)$^+$

LC-MS Condition:
Column: Acquity BEH C18 (50 mm×2.1 mm, 1.7 um);
Mobile Phase: A: 0.05% Formic Acid in water; B: 0.05% Formic Acid in ACN;
Time (min)/% B: 0/3, 0.4/3, 3.2/98, 3.8/98, 4.2/3, 4.5/3;
Column Temp: 35° C.,
Flow Rate: 0.6 mL/min.
Prep. HPLC Condition:
Column: Symmetry C18 (300*19) mm, 7 u;
Mobile phase: (A) 0.1% Formic Acid (B) Acetonitrile;
Flow: 19 mL/min;
Gradient (T/% B): 0/2, 1/2, 8/30, 9.10/99, 12/99, 12.10/2, 15/2;
Solubility: ACN+H$_2$O+DMSO.

Example 45

5-[[3-fluoro-4-[[(2-guanidinoacetyl)amino]methyl]phenyl]sulfonylamino]thiazole-4-carboxylic acid

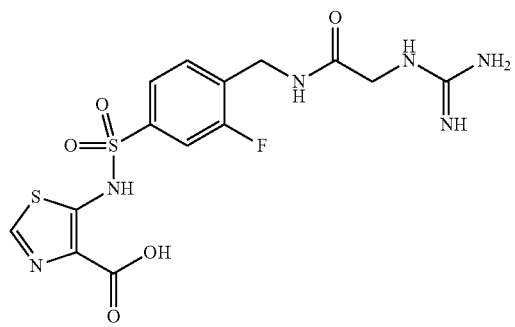 [SMILES: N=C(N)NCC(=O)NCc1ccc(S(=O)(=O)Nc2scnc2C(=O)O)cc1F]

a. tert-butyl 5-[(3-fluoro-4-vinyl-phenyl)sulfonyl-[(4-methoxyphenyl)methyl]amino]thiazole-4-carboxylate

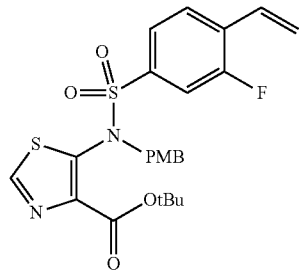

A solution of tert-butyl 5-[(4-bromo-3-fluoro-phenyl)sulfonyl-[(4-methoxyphenyl)methyl]amino]thiazole-4-carboxylate (3 g, 5.38 mmol) in 1,4-dioxane (40 mL) was purged with argon for 15 minutes. Then 4,4,5,5-tetramethyl-2-vinyl-1,3,2-dioxaborolane (0.99 g, 6.45 mmol), K$_2$CO3 (1.11 g, 8.07 mmol), PdCl$_2$(PPh$_3$)$_2$ (0.37 g, 0.53 mmol) were added under argon atmosphere. The resulting reaction mixture was heated to 85° C. for 24 h in a closed vial. The reaction mixture temperature was allowed to cool to RT, filtered through a celite pad (washed with EtOAc (2×50 mL)). The organic layer was concentrated under reduced pressure. The resulting crude compound was dissolved in ethyl acetate (50 mL), washed with water (50 mL) and brine solution (50 mL). The organic layer was dried over Na$_2$SO$_4$, filtered and concentrated under vacuum. The crude compound was purified by flash chromatography (eluting with 20% ethyl acetate in petroleum ether) affording an off-white solid (1.5 g, 55%).
M/z 505.1 (M+H)$^+$ b. tert-butyl 5-[(3-fluoro-4-formyl-phenyl)sulfonyl-[(4-methoxyphenyl)methyl]amino]thiazole-4-carboxylate

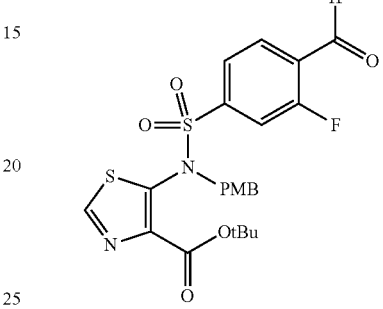

NaIO$_4$ (8.51 g, 39.8 mmol) and OSO$_4$ (1.68 g, 6.63 mmol) were added to a solution of tert-butyl 5-[(3-fluoro-4-vinyl-phenyl)sulfonyl-[(4-methoxyphenyl)methyl]amino]thiazole-4-carboxylate (6.7 g, 13.2 mmol) in acetonitrile:H$_2$O:CCl4 (1:1:1, 60 mL). The resulting reaction mixture was stirred at RT for 4 h. Water (30 mL) was added and the mixture was extracted with ethyl acetate (2×100 mL). The combined organic extracts were dried over Na$_2$SO$_4$, filtered and concentrated. The crude material was purified by flash chromatography (eluting with 22% ethyl acetate in petroleum ether) affording an off-white solid (4.5 g, 66%).
M/z 507.4 (M+H)$^+$ c. tert-butyl 5-[[3-fluoro-4-[hydroxyiminomethyl]phenyl]sulfonyl-[(4-methoxyphenyl)methyl]amino]thiazole-4-carboxylate

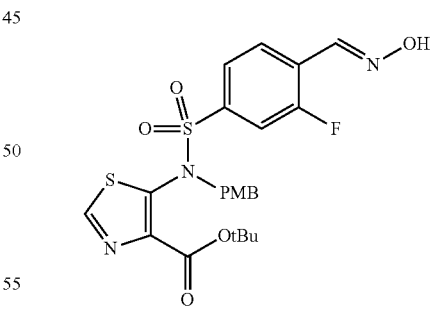

Tert-butyl 5-[(3-fluoro-4-formyl-phenyl)sulfonyl-[(4-methoxyphenyl)methyl]amino]thiazole-4-carboxylate (3.6 g, 7.10 mmol) solution in EtOH (20 mL) was added to a stirred solution of hydroxylamine hydrochloride (593.8 mg, 8.52 mmol) and ammonium chloride (454.9 mg, 8.52 mmol) in H$_2$O:EtOH (4:1, 30 mL). The resulting reaction mixture was stirred at RT for 4 h. Water (20 mL) was added and the mixture extracted with ethyl acetate (2×50 mL). The combined organic extracts were dried over Na$_2$SO$_4$, filtered and concentrated. The crude material was purified by flash chromatography (eluting with 40% ethyl acetate in petroleum ether) affording an off-white solid (2.8 g, 75%).

M/z 522.1 (M+H)+ d. tert-butyl 5-[[4-(aminomethyl)-3-fluoro-phenyl]sulfonyl-[(4-methoxyphenyl)methyl]amino]thiazole-4-carboxylate

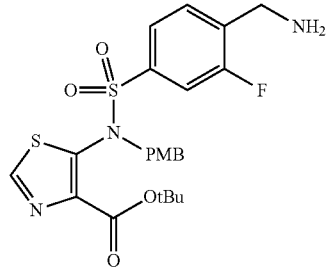

Zn dust (0.52 g, 8.04 mmol) was added to a stirred solution of tert-butyl 5-[[3-fluoro-4-[hydroxyiminomethyl]phenyl]sulfonyl-[(4-methoxyphenyl)methyl]amino]thiazole-4-carboxylate (2.8 g, 5.36 mmol) in AcOH (20 mL) at RT. The resulting reaction mixture was stirred at RT for 16 h. Ice cold water was added and the mixture was extracted with ethyl acetate (2×50 mL). The combined organic extracts were dried over $Na_2SO_4$, filtered and concentrated. The crude material was purified by trituration with diethyl ether (2×10 mL) affording a yellow solid (2 g, 73%).

M/z 508.1 (M+H)+ e. tert-butyl 5-[[4-[[[2-(tert-butoxycarbonylamino)acetyl]amino]methyl]-3-fluoro-phenyl]sulfonyl-[(4-methoxyphenyl)methyl]amino]thiazole-4-carboxylate

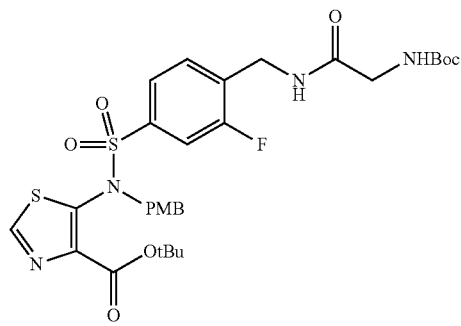

DIPEA (0.61 mL, 3.54 mmol) and HATU (0.67 g, 1.77 mmol) were added to a solution of tert-butyl 5-[[4-(aminomethyl)-3-fluoro-phenyl]sulfonyl-[(4-methoxyphenyl)methyl]amino]thiazole-4-carboxylate (0.6 g, 1.18 mmol) and 2-(tert-butoxycarbonylamino)acetic acid (0.31 g, 1.77 mmol) in DMF (20 mL) under argon atmosphere. The resulting reaction mixture was stirred at RT for 4 h. Ice cold water (10 mL) was added and the mixture was extracted with ethyl acetate (2×20 mL). The combined organic extracts were dried over $Na_2SO_4$, filtered and concentrated. The crude material was purified by flash chromatography (eluting with 50% ethyl acetate in petroleum ether) affording an off-white solid (500 mg, 63%).

M/z 508.1 (M+H)+ f. 5-[[4-[[(2-aminoacetyl)amino]methyl]-3-fluoro-phenyl]sulfonylamino]thiazole-4-carboxylic acid, trifluoroacetate

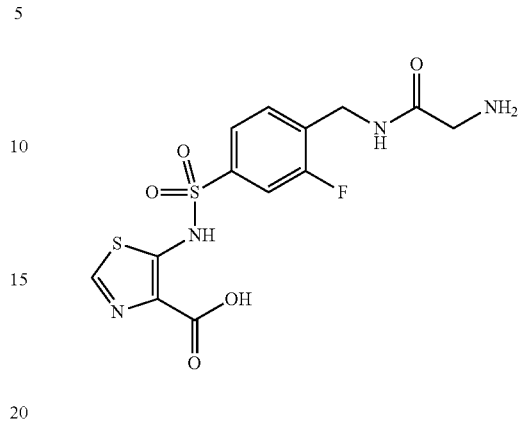

TFA (5 mL) was added to tert-butyl 5-[[4-[[[2-(tert-butoxycarbonylamino)acetyl]amino]methyl]-3-fluoro-phenyl]sulfonyl-[(4-methoxyphenyl)methyl]amino]thiazole-4-carboxylate (500 mg, 0.75 mmol) at RT and stirred for 4 h. TFA was evaporated by reduced pressure. The resulting crude product was triturated with diethyl ether (2×10 mL) and dried under high vacuum affording an off-white solid (250 mg, 85%).

M/z 389.1 (M+H)+ g. 5-[[3-fluoro-4-[[(2-guanidinoacetyl)amino]methyl]phenyl]sulfonylamino]thiazole-4-carboxylic acid

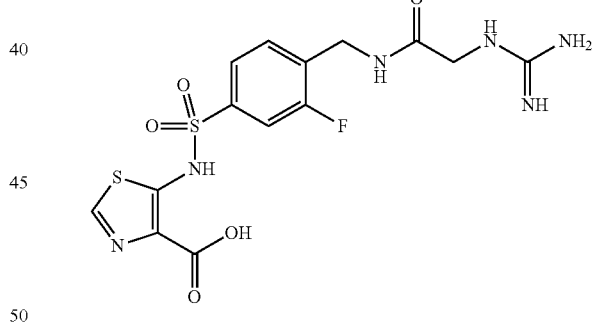

Pyrazole-1-carboxamidine, hydrochloride (141.2 mg, 0.96 mmol) and DIPEA (0.55 mL, 3.21 mmol) were added to a stirred solution of 5-[[4-[[(2-aminoacetyl)amino]methyl]-3-fluoro-phenyl]sulfonylamino]thiazole-4-carboxylic acid, trifluoroacetate (250 mg, 0.64 mmol) in DMF (6 mL) at RT. The resulting reaction mixture was stirred at RT for 18 h and concentrated under reduced pressure. Water (5 mL) was added to the residue. The resulting precipitate was filtered and washed with diethyl ether (2×5 mL). The crude product was purified by preparative HPLC to afford the title compound as a white solid (70 mg, 25%).

$^1$H NMR (500 MHz, DMSO-$d_6$) δ 13.43 (1H, brs), 8.60 (1H, brs), 8.08 (1H, s), 7.51-7.42 (3H, m), 7.50-7.10 (4H, brs), 4.33 (2H, s), 3.85 (2H, s).

M/z 431.0 (M+H)+

LC-MS Condition:
Column: Acquity UPLC BEH C18 (50 mm×2.1 mm, 1.7 um);
Mobile Phase: A: 0.1% Formic Acid in Water; B: 0.1% Formic Acid in Acetonitrile;
Flow Rate: 0.8 mL/min
Time (min)/% B: 0/2, 0.4/2, 2.2/98, 2.6/98, 2.61/2, 3.0/2.
Column Temp: 60° C.
Prep. HPLC Condition:
Column: KROMASIL-C18 (150*25 MM), 10 u;
Mobile phase: 0.05% Formic acid in $H_2O$: ACETONITRILE;
Flow: 25 mL/min
Gradient (T/% B): 0/5, 1/5, 7/40, 7.1/98, 9/98, 9.1/5, 11/5;
Solubility: ACN+$H_2O$+THF+DMSO Compounds prepared using methods analogous to those described above for Example 45 and purified in a similar manner by preparative HPLC are shown in the Table below:—

Mean Ki values from multiple experiments are presented below. Experimental results are shown given using the following bands:

For NDM-1 the Ki values of <0.05 μM are designated (A); Ki values of 0.05-0.2 μM are designated (B); Ki values of >0.2 μM (0.2-2 μM) are designated (C).

For VIM-1 the Ki values of <0.2 μM are designated (A); Ki values of 0.2-0.5 μM are designated (B); Ki values of >0.5 μM (0.5-1 μM) are designated (C).

For VIM-2 the Ki values of <0.02 μM are designated (A); Ki values of 0.02-0.05 μM are designated (B); Ki values of >0.05 μM (0.05-0.15 μM) are designated (C).

For IMP-1 the Ki values of <0.5 μM are designated (A); Ki values of 0.5-1 μM are designated (B); Ki values of >1 μM (1-10 μM) are designated (C).

Ki Values for Compounds of the Invention.

| Example | Structure | Name, NMR and Mass |
|---|---|---|
| 46 | 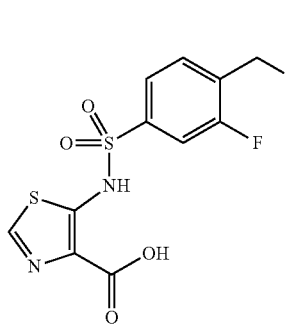 | 5-[[3-fluoro-4-(guanidinomethyl)phenyl]sulfonylamino]thiazole-4-carboxylic acid<br>M/z 374.0 (M + H)$^+$<br>$^1$H NMR (d6-DMSO) δ 13.40 (1H, s), 8.09 (1H, s), 7.59 (1H, d, J = 7.5 Hz), 7.47 (1H, d, J = 10 Hz), 7.59 (1H, d, J = 7.5 Hz), 7.50-7.25 (4H, brs), 4.41 (2H, s). |

Example 47: Activity of Compounds of the Invention

Experiments were conducted to determine:
(1) The inhibitory activity of the compounds of the invention against MBL enzymes;
(2) The plasma protein binding for compounds of the invention; and
(3) The plasma stability of compounds of the invention.

Details of the protocols used for each of the sets of experiments are set out below:

1. Enzymatic Inhibition

In Vitro Enzyme Inhibition Assays

Enzyme inhibition assays were performed using purified MBL enzymes (NDM-1; VIM-1; VIM-2; IMP-1) in 10 mM HEPES buffer pH 7.5 in 96-well microtiter plates. Imipenem (300 μM) was used as substrate and its hydrolysis was followed at UV 299 nm during 10 mn every 30 seconds using a Perkin Elmer Envision UV fluorescence plate reader. Hydrolysis rate data in presence of a range of inhibitors was analysed using Dotmatics database software and calculated $IC_{50}$ values were converted to Ki values using the Cheng-Prusoff equation:

$$Ki = IC_{50}/(1+([S]/K_m)$$

where the $K_m$ values for NDM-1, VIM-2 and IMP-1 are 70 μM, 1.5 μM, 9 μM and 25 μM respectively. Compound dilution was performed in DMSO.

| | Ki/μM | | | |
|---|---|---|---|---|
| Example | NDM-1 | VIM-1 | VIM-2 | IMP-1 |
| 2 | (A) | (B) | (C) | (C) |
| 3 | (B) | (B) | (B) | (C) |
| 4 | (A) | (B) | (B) | (C) |
| 5 | (B) | (A) | (B) | (A) |
| 6 | (C) | (B) | | (C) |
| 7 | (B) | (B) | (C) | (C) |
| 8 | (B) | (B) | | (C) |
| 9 | (B) | (B) | (A) | (C) |
| 10 | (A) | (A) | (A) | (B) |
| 11 | (C) | (B) | | (C) |
| 12 | (B) | (B) | | (B) |
| 13 | (A) | (A) | (C) | (B) |
| 14 | (C) | (B) | | (C) |
| 15 | (B) | (C) | | (C) |
| 16 | (B) | (A) | (A) | (B) |
| 17 | (B) | (A) | (A) | (A) |
| 18 | (B) | (A) | (A) | (A) |
| 19 | (B) | (B) | (B) | (C) |
| 20 | (B) | (B) | | |
| 21 | (A) | (B) | | (B) |
| 22 | (A) | (B) | (C) | (C) |
| 23 | (A) | (A) | (B) | (C) |
| 24 | (B) | (C) | | (C) |
| 25 | (B) | (B) | | (B) |
| 26 | (A) | (B) | (B) | (C) |
| 27 | (A) | (A) | (A) | (B) |
| 28 | (B) | (A) | (A) | (A) |
| 29 | (A) | (B) | (B) | (C) |
| 30 | (A) | (B) | (B) | (C) |
| 31 | (A) | (A) | (B) | (A) |
| 32 | (B) | (B) | (B) | (C) |

-continued

| Example | NDM-1 | VIM-1 | VIM-2 | IMP-1 |
|---|---|---|---|---|
| 33 | (C) | (B) | | (C) |
| 34 | (A) | (C) | (B) | (A) |
| 35 | (A) | (A) | (B) | (B) |
| 36 | (A) | (B) | (C) | (C) |
| 37 | (C) | (A) | | (C) |
| 38 | (C) | (B) | | (C) |
| 39 | (C) | (A) | (B) | (C) |
| 40 | (C) | (B) | | (C) |
| 41 | (A) | (B) | (B) | (B) |
| 42 | (C) | (C) | | (C) |
| 43 | (B) | (B) | | (A) |
| 44 | (C) | (B) | (C) | (C) |
| 45 | (C) | (C) | (C) | (C) |
| 46 | (B) | (B) | (C) | (C) |

2. Antimicrobial Susceptibility Testing

Antibiotic Activity of β-Lactam Antibiotics on MBL Expressing Bacteria in the Presence of the Compounds of the Invention The experiments were carried out using the 'broth microdilution method' according to the protocols M07-A8 established by the Clinical Laboratory Standards Institute (CLSI). Serial dilutions of the β-lactam antibiotic (Meropenem) were prepared in 96-well plates in cation-adjusted Mueller-Hinton broth (CAMHB); the concentration range was defined from 0.03 mg/L to 512 mg/L. The compounds were added at a constant concentration of 8 μg/mL. A bacterial inoculum of each strain (clinical isolates) was adjusted to a 0.5 McFarland turbidity standard in physiologic serum (0.9% NaCl), then diluted 1:100 in CAMHB and added to each well to give a final bacterial cell number of $5 \times 10^5$ CFU/well. After incubation for 18-20 hours in a heating chamber at 37° C., the growth inhibition was evaluated by the absence of any bacterial development.

Minimal inhibitory concentrations (MIC) are taken as the lowest concentration of antibiotic at which the test organism did not show visible growth; results were confirmed by measuring the optical density (OD) at 600 nm in a spectrophotometer.

Compounds of the invention were tested at a constant concentration of 8 μg/mL. The clinical strains used in these potentiation experiments were NTBC020 (*E. coli* strain expressing NDM-1, TEM-1 and CTX-M-15); NTBC035-2 (*K. pneumoniae* strain expressing NDM-1, CMY-4 and SHV-11); NTBC104-1 (*K. pneumoniae* strain expressing NDM-1 and SHV-11); NTBC123 (*K. pneumoniae* strain expressing NDM-1); NTBC018 (*C. freundii* strain expressing VIM-2); NTBC024 (*K. pneumoniae* strain expressing VIM-19, TEM-1 and CTX-M-3); NTBC042 (*E. coli* strain expressing VIM-1, TEM-1, CTX-M-15, SHV-12); NTBC055 (*E. Coli* strain expressing VIM-1); NTBC062 (*K. pneumoniae* strain expressing IMP-1 and TEM-1) and NTBC039 (*K. oxytoca* strain expressing IMP-28).

Results are shown below. Data are banded as follows: MIC values of <1 μg/mL are designated (A); MIC values of 1-2 μg/mL are designated (B); MIC values of >2 g/mL (2-200 μg/mL) are designated (C).

| Example | NTBC020 | NTBC035-2 | NTBC104-1 | NTBC123 | NTBC018 | NTBC024 | NTBC042 | NTBC055 | NTBC062 | NTBC039 |
|---|---|---|---|---|---|---|---|---|---|---|
| 2 | (B) | (B) | (C) | (C) | (A) | (B) | (A) | (B) | (B) | (B) |
| 3 | (C) | (B) | (B) | (C) | (A) | (B) | (A) | (B) | (B) | (C) |
| 4 | (B) | (B) | (C) | (C) | (A) | (B) | (A) | (B) | (B) | (B) |
| 5 | (B) | (B) | (C) | (C) | (A) | (A) | (A) | (B) | (B) | (A) |
| 7 | (B) | (B) | (B) | (C) | (A) | (B) | (A) | (B) | (B) | (B) |
| 10 | (C) | (B) | (C) | (C) | (A) | (A) | (A) | (B) | (B) | (B) |
| 13 | (B) | (B) | (C) | (C) | (A) | (B) | (A) | (B) | (B) | (B) |
| 15 | (C) | (C) | (C) | (C) | (B) | (C) | (C) | (C) | (C) | (C) |
| 16 | (C) | (C) | (C) | (C) | (A) | (A) | (A) | (A) | (B) | (B) |
| 17 | (C) | (C) | (C) | (C) | (A) | (A) | (A) | (B) | (B) | (A) |
| 19 | (B) | (B) | (C) | (C) | (A) | (B) | (A) | (B) | (B) | (A) |
| 20 | (C) | (C) | (C) | (C) | (A) | (C) | (A) | (B) | (B) | (B) |
| 22 | (B) | (B) | (C) | (C) | (A) | (C) | (B) | (C) | (B) | (B) |
| 23 | (C) | (B) | (A) | (C) | (A) | (B) | (B) | (B) | (B) | (C) |
| 24 | (C) | (C) | (C) | (C) | (A) | (B) | (A) | (B) | (C) | (C) |
| 25 | (C) | (C) | (C) | (C) | (A) | (C) | (B) | (B) | (B) | (B) |
| 26 | (A) | (A) | (B) | (C) | (A) | (A) | (A) | (B) | (B) | (C) |
| 27 | (C) | (C) | (C) | (C) | (B) | (B) | (A) | (B) | (B) | (B) |
| 29 | (C) | (B) | (C) | (C) | (A) | (B) | (A) | (C) | (B) | (B) |
| 30 | (C) | (C) | (B) | (C) | (A) | (A) | (A) | (B) | (B) | (B) |
| 32 | (B) | (B) | (C) | (C) | (A) | (B) | (A) | (B) | (B) | (B) |
| 34 | (C) | (C) | (C) | (C) | (A) | (B) | (A) | (B) | (B) | (B) |
| 35 | (C) | (B) | (B) | (C) | (A) | (B) | (A) | (B) | (B) | (B) |
| 36 | (C) | (C) | (C) | (C) | (A) | (C) | (A) | (B) | (B) | (B) |
| 38 | (C) | (C) | (C) | (C) | (B) | (C) | (B) | (C) | (B) | (C) |
| 41 | (B) | (B) | (C) | (C) | (A) | (B) | (A) | (B) | (B) | (B) |
| 43 | (C) | (C) | (C) | (C) | (A) | (B) | (B) | (B) | (B) | (C) |
| 44 | (C) | (C) | (C) | (C) | (A) | (B) | (A) | (A) | (B) | (C) |
| 45 | (C) | (C) | (C) | (C) | (B) | (C) | (B) | (B) | (B) | (B) |
| 46 | (C) | (B) | (C) | (C) | (B) | (B) | (A) | (A) | (B) | (C) |

Example 48: Comparative Study

3. Plasma Protein Binding

Protocol Summary

| | |
|---|---|
| Method | Rapid equilibrium dialysis |
| Species | Human Plasma |
| Plasma | 100% plasma |
| Test compound concentration | 10 μM |
| Buffer | Phosphate buffer saline pH 7.4 |
| Incubation Time | 5 h |
| No of replicates | 2 |
| QC Compounds | Warfarin |
| Final DMSO Concentration | <0.1% |
| Analytical Method | LC-MS/MS |

Assay Procedure

Test compound was spiked in plasma to a final concentration of 10 μM. An aliquot of 300 μL of plasma was placed in red chamber of the insert and 500 μL of PBS was placed into white chamber of the insert. The plate was incubated at 37° C. in thermomixer at 400 rpm for 5 hours. After incubation, the samples were matrix equilibrated with opposite matrix (10 μL of plasma/100 μL of buffer sample was matched with 100 μL of blank buffer/10 μL of plasma). Matrix matched samples were precipitated with 200 μL of acetonitrile containing internal standard. Samples were vortexed at 1000 rpm for 5 min and centrifuged at 4000 rpm for 10 min. Supernatant was separated, diluted 2 fold with water and analyzed on LC-MS/MS. Blank control samples were processed immediately after the preparation of plasma working stock solutions. These samples served as a measure for calculating the % recovery of test compounds.

Data Analysis and Calculation

The percent plasma bound fraction was calculated by the following equations:

$$\% \text{ Unbound} = 100 * F_C/T_C$$

$$\% \text{ Recovery} = 100 * (F_C + T_C)/T_0$$

where $T_C$=Total compound concentration as determined by the calculated concentration on the plasma side of the membrane $F_C$=Free compound concentration as determined by the calculated concentration on the buffer side of the membrane $T_0$=Total compound concentration as determined before dialysis For each set of duplicates/compound, the percentage bound, percentage unbound and percentage recovery was determined. Results are as shown below.

4. Plasma Stability of Test Compounds

Protocol Summary

| | |
|---|---|
| Test compound concentration | 1 μM |
| Matrix | Human Plasma |
| Incubation Time | 0, 1, 3 and 5 h |
| No of replicates | 2 per each time point |
| QC Compounds | Propantheline |
| Analytical Method | LC-MS/MS |
| End point | % Remaining of the test compound |

Assay Procedure

Test compound and QC compound were incubated at a final concentration of 1 μM in plasma at 37° C. in shaker water bath with gentle shaking. At predetermined time points, reaction was terminated with 200 μL of acetonitrile containing internal standard and centrifuged at 4000×RCF, 4° C. for 20 minutes. Supernatant was separated and analyzed by LC-MS/MS.

Data Analysis and Calculation

The following equation was used to determine the percentage remaining of test/QC compound following the procedure above:

$$\% \text{ remaining of the test substance} = \frac{\text{Peak Area ratio at time (min)}}{\text{Peak Area Ratio at 0 min}} \times 100$$

Results are as shown below.

Studies were undertaken to compare the compounds of the invention with structurally similar compounds ("Comp. x"). Experiments were conducted as described above. Data were banded as set out below.

For VIM-1 the Ki values of <0.15 μM are designated (++++); Ki values of 0.15-0.3 μM are designated (+++); Ki values of 0.3-0.5 μM are designated (++); Ki values of >0.5 μM (0.5-1 μM) are designated (+).

For IMP-1 the Ki values of <0.15 μM are designated (++++); Ki values of 0.15-0.6 μM are designated (+++); Ki values of 0.6-5 μM are designated (++); Ki values of >5 μM (5-10 μM) are designated (+).

For VIM-2 the Ki values of <0.02 μM are designated (++++); Ki values of 0.02-0.05 μM are designated (+++); Ki values of 0.05-0.1 μM are designated (++); Ki values of >0.1 μM (0.1-0.15 μM) are designated (+).

For NDM-1 the Ki values of <0.03 μM are designated (++++); Ki values of 0.03-0.1 μM are designated (+++); Ki values of 0.1-0.3 are designated (++); Ki values of >0.5 μM (0.3-2 μM) are designated (+).

| Example | Structure | Stability in human plasma | Human plasma protein binding |
|---|---|---|---|
| Comp. A | (sulfonamide-thiazole-carboxylic acid with glycinamide on fluorophenyl) | 29% remaining after 2 hours | 90.3% |
| Example 7 | (sulfonamide-thiazole-carboxylic acid with guanidinoacetamide on fluorophenyl) | 100% remaining after 5 hours | 60.8% |
| Comp. B | (sulfonamide-thiazole-carboxylic acid with glycinamide on difluorophenyl) | 0% remaining after 5 hours | Not available |
| Example 2 | (sulfonamide-thiazole-carboxylic acid with guanidinoacetamide on difluorophenyl) | 73% remaining after 2 hours | 81% |

| Example | Structure | Stability in human plasma | Human plasma protein binding |
|---|---|---|---|
| Comp. E | (thiazole-4-carboxylic acid with sulfonamide linked to methoxyphenyl-NH-C(O)-CH2-NH2) | 29% remaining after 2 hours | Not available |
| Example 16 | (thiazole-4-carboxylic acid with sulfonamide linked to methoxyphenyl-NH-C(O)-CH2-NH-C(=NH)NH2) | 89% remaining after 2 hours | Not available |

MBL-inhibitory efficacy was observed for the compound of Example 7.

| Example | Structure | Ki/μM | | | |
|---|---|---|---|---|---|
| | | VIM-1 | IMP-1 | VIM-2 | NDM-1 |
| Comp. B | (difluorophenyl glycinamide thiazole sulfonamide) | ++ | ++ | + | ++++ |
| Example 2 | (difluorophenyl guanidinoacetamide thiazole sulfonamide) | ++ | ++ | ++ | ++++ |

-continued

| Example | | Ki/μM | | | |
|---|---|---|---|---|---|
| | | VIM-1 | IMP-1 | VIM-2 | NDM-1 |
| Comp. C | (structure) | + | ++ | + | ++ |
| Example 3 | (structure) | ++ | ++ | +++ | ++ |
| Comp. D | (structure) | + | +++ | +++ | +++ |
| Example 5 | (structure) | +++ | +++ | +++ | +++ |

-continued
| Example | | Ki/μM | | | |
| --- | --- | --- | --- | --- | --- |
| | | VIM-1 | IMP-1 | VIM-2 | NDM-1 |
| Comp. E | 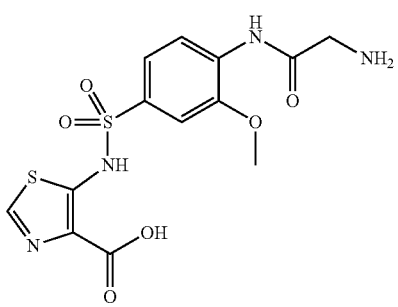 [SMILES: COc1cc(S(=O)(=O)Nc2scnc2C(=O)O)ccc1NC(=O)CN] | ++ | ++ | ND | ++ |
| Example 16 | 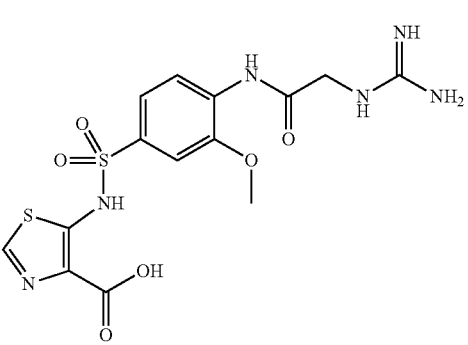 [SMILES: COc1cc(S(=O)(=O)Nc2scnc2C(=O)O)ccc1NC(=O)CNC(=N)N] | ++++ | +++ | ++++ | +++ |
| Comp. F | 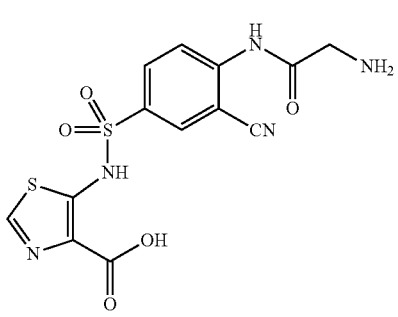 [SMILES: N#Cc1cc(S(=O)(=O)Nc2scnc2C(=O)O)ccc1NC(=O)CN] | +++ | ND | +++ | +++ |
| Example 17 | 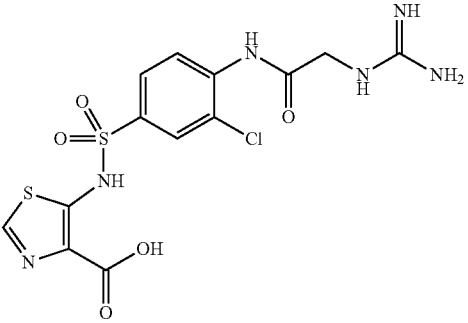 [SMILES: N=C(N)NCC(=O)Nc1ccc(S(=O)(=O)Nc2scnc2C(=O)O)cc1Cl] | ++++ | ++++ | ++++ | +++ |

-continued

| Example | | Ki/μM | | | |
|---|---|---|---|---|---|
| | | VIM-1 | IMP-1 | VIM-2 | NDM-1 |
| Comp. G | [structure] | ++ | +++ | +++ | +++ |
| Example 18 | [structure] | ++++ | ++++ | ++++ | +++ |
| Comp. H | [structure] | + | + | +++ | ++ |
| Example 20 | [structure] | +++ | ND | ND | ++ |

| Example | | Ki/μM | | | |
|---|---|---|---|---|---|
| | | VIM-1 | IMP-1 | VIM-2 | NDM-1 |
| Comp. I | [structure: thiazole-carboxylic acid with sulfonamide linked to fluorophenyl bearing urea-NH-NH₂] | + | ++ | ND | ++ |
| Example 29 | [structure: thiazole-carboxylic acid with sulfonamide linked to fluorophenyl bearing semicarbazide-guanidine] | +++ | ++ | +++ | ++++ |

ND: Not determined

The compounds of the invention were also found to exhibit better enzyme inhibition (lower Ki values) and better potentiation (lower MIC values) against the above mentioned MBL enzymes (VIM/IMP/NDM) and strains of bacteria as compared to the structurally related analogues lacking a —C(NR)—NR₂ motif.

As can be readily seen, the compounds of the invention are associated with improved properties compared with structurally analogous compounds. This finding is surprising, not least because the —C(NR)—NR₂ motif common to the compounds of the invention can be associated with rapid hydrolysis, so may have been expected to render the compounds unsuitable for the type of use described herein. The fact that this motif can be introduced not only without prejudicing the efficacy of the compounds, but also with an enhancement of plasma stability and efficacy, is thus unexpected.

5. PK (Pharmacokinetic) Studies.

Compound A and Example 7 were dosed i.v. at 1 mg/kg to male Swiss albino mice. The measured PK parameters are shown in the Table below:—

| Compound | $C_0$ (ng/mL) | AUC (ng · h/mL) | Cl (mL/min/kg) |
|---|---|---|---|
| Compound A | 17 | 9 | 819 |
| Example 7 | 1814 | 1036 | 16 |

$C_0$ = plasma concentration
AUC = area under the curve
Cl = clearance

Note that for the same dosage:
1. Example 7 achieves over a 100-fold maximum concentration compared to Compound A;
2. Example 7 achieves over a 100-fold exposure (AUC, integration of concentration vs time) compared to Compound A; and
3. Example 7 is cleared from the blood about 50-fold slower than Compound A.

This data is in accord with the in vitro data generated on plasma stability and confirms plasma stability as the limiting factor with regard to the potential of Compound A to be useful in animal efficacy studies.

6. In Vivo Efficacy Studies

Mice were infected in the thigh with *K. pneumoniae* NTBC104. The MIC of meropenem against this strain is 64 ug/mL due to the strain producing NDM-1. The MIC of meropenem in the presence of 8 ug/mL of the compound of Example 2 is 4 ug/mL.

At the end of the experiment (9 hours post infection) the animals were sacrificed and the numbers of colony forming units (CFUs) were measured in order to quantify bacterial load (extent of the infection). Meropenem at 30 mg/kg reduced bacterial load slightly whereas meropenem at 30 mg/kg plus the compound of Example 2 at 30 mg/kg significantly reduced the bacterial load compared to meropenem alone, showing a 1.6 $Log_{10}$ reduction in CFUs. Results are shown in FIG. 1.

Under the same experimental conditions the compound of Example 7 effected a 1.7 $Log_{10}$ reduction in CFUs compared to meropenem alone. Compound A was not progressed to efficacy studies as the in vitro and PK studies predicted this compound would fail in efficacy studies so it is not ethical to carry out such an experiment.

Under the same conditions the compound of Example 26 effected a 1.8 $Log_{10}$ reduction in CFUs compared to meropenem alone.

7. Extended MIC Profiling Vs MBL-Expressing Clinical Strains

To assess the coverage and potentiation of meropenem by compounds of the invention, the susceptibility of around 200 clinical isolates was examined. The criteria for selection into the panel was that the clinical strain was resistant to carbapenems, but only expressing NDM enzyme variants and not serine betalactamase enzymes with carbapenemase activity such as KPC or OXA.

Figure 2:
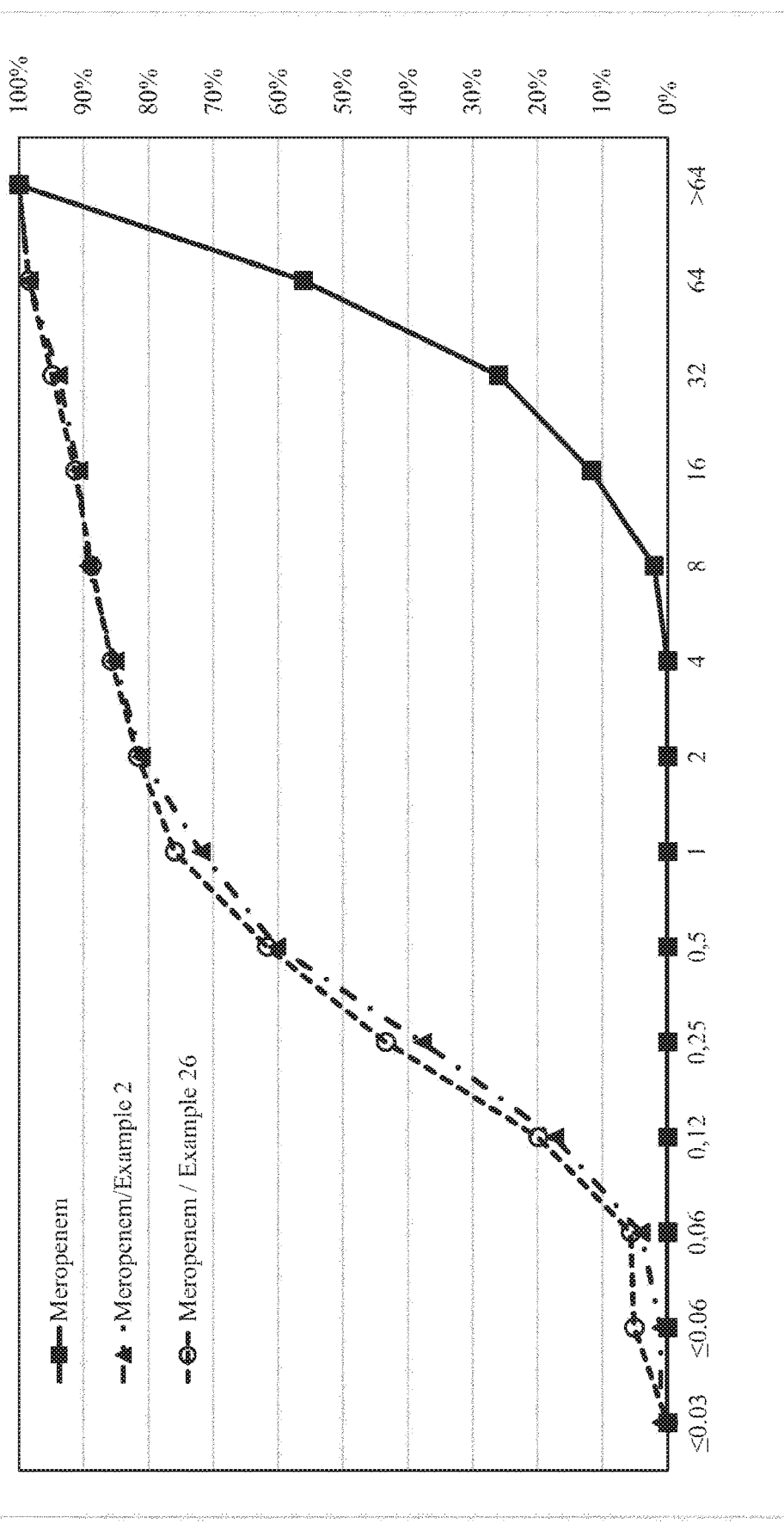
FIG. 2 shows cumulative MIC-meropenem potentiation using the compounds of Example 2 and Example 26 in a panel of clinical Enterobacteriacae strains expressing NDM enzymes (196 isolates). Data show that at an 8 µg/mL concentration of either Example 2 or Example 26, meropenem is potentiated to the extent that just under 90% of strains exhibit a meropenem MIC of 8 ug/mL. By contrast, the same concentration of meropenem alone is only capable of stopping the growth of <1% of the strains and within the parameters of the experiment the cessation of growth of 90% of all strains could not be achieved with meropenem alone.

At 8 μg/mL concentration of either Example 2 or Example 26, meropenem is potentiated to the extent that just under 90% of strains exhibit a meropenem MIC of 8 ug/mL, whereas the same concentration of meropenem alone is only stopping the growth of <1% of the strains and within the parameters of this experiment the cessation of growth of 90% of all strains could not be achieved with meropenem alone. Results are shown in FIG. 2.

Example 49

1. Combination Therapy by Compounds of the Invention with SBL Inhibitors and Antibiotic Agents As discussed above, bacteria exhibit resistance to antibiotics by mechanisms including both the modification of the biological target such that binding affinity for the antibiotic is reduced, and the production of enzymes which deactivate the antibacterial drug, such as beta-lactamase enzymes (including both serine-β-lactamases, SBL, and metallo-β-lactamases, MBL). A proposed strategy to address such resistance is to administer combination therapies comprising agents which inhibit the enzymes which deactivate the antibiotic together with the antibiotic itself. In other words, it may be possible to rescue the antibacterial activity of the drug by using a dual combination approach of antibiotic plus a drug that inhibits the deactivating enzyme Combinations of serine β-lactamase inhibitors with antibiotics are known. For example, the *Streptomyces* natural product clavulanic acid, a serine β-lactamase inhibitor, was developed as a dual combination together with the β-lactam antibiotic amoxicillin under the name Augmentin. More recently avibactam, a serine β-lactamase inhibitor with an improved spectrum of serine β-lactamase inhibition over clavulanic acid, has been introduced into the clinic in combination with the cephalosporin β-lactam antibiotic ceftazidime (known together as Avycaz). However, these combinations are ineffective at treating bacterial infection caused by bacteria which express MBL enzymes, as the SBL inhibitors are typically inactive against such enzymes.

A further complication of having two distinct categories of β-lactamase enzymes present in bacterial infections arises as neither diagnostic tests to very rapidly ascertain the precise mechanism of β-lactamase resistance nor dual inhibitors of both serine and metallo β-lactamase enzymes are currently available in the clinic. Indeed, at present no clinically-approved metallo β-lactamase inhibitor to address the problem of metallo β-lactamase enzymes exists, even if a rapid diagnostic test was available to allow resistance due to SBL enzymes to be distinguished from that due to MBL enzymes.

The inventors have now recognised that a product which is a pharmaceutical combination of an antibiotic, serine β-lactamase inhibitor and a metallo β-lactamase inhibitor (a so-called triple combination) could overcome the need to identify if a resistant bacterium causing a particular infection was producing a serine β-lactamase or a metallo β-lactamase enzyme (or both, in an increasing number of very resistant strains). In this regard, there are three possible scenarios for the β-lactamase profile of carbapenem-resistant enterobacteriaceae (CRE). Group 1 organisms have either exclusively metallo β-lactamase enzymes or a mixture of metallo β-lactamase and serine β-lactamase enzymes but the resistance is primarily due to the metallo β-lactamase. Group 2 organisms have serine β-lactamase enzymes only. Group 3 organisms have both metallo β-lactamase and serine β-lactamase enzymes and both enzymes play a significant role in resistance.

The following abbreviations are used in this Example:—

CMY: Class C β-lactamase

TEM: Class A β-lactamase

SHV: Class A B-lactamase (sulfhydryl variable)

CTX-M: Class A β-lactamase (CTX for cefotaximase and M for Munich)

OSBL: "older-spectrum" β-lactamases

OXA: Class D β-lactamase (oxacillinase)

ACT-TYPE: Class C β-lactamase (AmpC-type beta-lactamase)

KPC: Class A β-lactamase (*K. pneumoniae* carbapenemase)

VIM: Verona integron-encoded metallo-β-lactamase

NDM: New Delhi metallo-β-lactamase

IMP: Imipenemase metallo-β-lactamase

Experiments were carried out using the 'broth microdilution method' according to the protocols M07-A8 established by the Clinical Laboratory Standards Institute (CLSI). Serial dilutions of meropenem (mero) were prepared in 96-well plates in cation-adjusted Mueller-Hinton broth (CAMHB); the concentration range was defined from 0.03 mg/L to 512 mg/L. The compounds (the compound of Example 2, above, and/or WCK4234) were added at the concentration indicated in the table below. A bacterial inoculum of each strain (clinical isolates) was adjusted to a 0.5 McFarland turbidity standard in physiologic serum (0.9% NaCl), then diluted 1:100 in CAMHB and added to each well to give a final bacterial cell number of $5 \times 10^5$ CFU/well. After incubation for 18-20 hours in a heating chamber at 37° C., the growth inhibition was evaluated by the absence of any bacterial development.

Minimum inhibitory concentrations (MIC) are taken as the lowest concentration of antibiotic at which the test organism did not show visible growth; results were confirmed by measuring the optical density (OD) at 600 nm in a spectrophotometer.

The SBL inhibitor WCK4234 was synthesized according to the procedure described in WO 2015/114595.

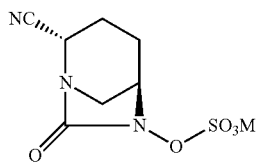

WCK4234
M: H (WCK4234) or Na (sodium salt of WCK4234)

In brief, WCK4234 and its sodium salt were synthesised following published procedures (WO2105114595), the latter stages of which are shown below:—

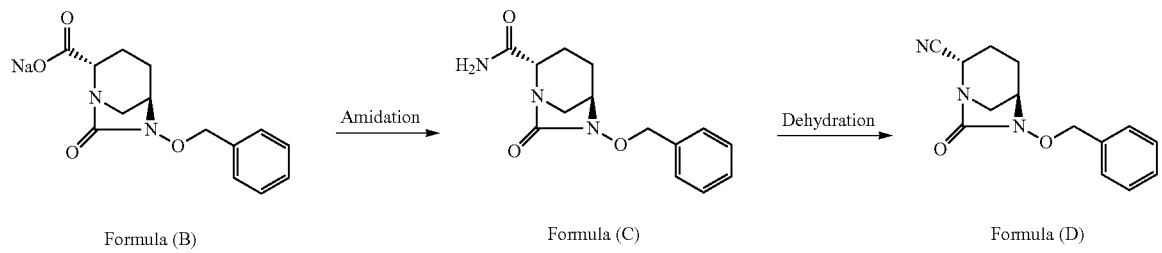

Formula (B) → Amidation → Formula (C) → Dehydration → Formula (D)

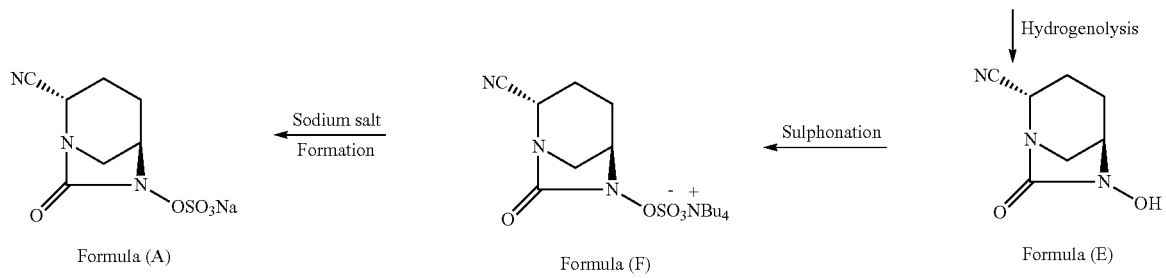

Formula (A) ← Sodium salt Formation ← Formula (F) ← Sulphonation ← Formula (E) ← Hydrogenolysis The compound of Formula (B) was prepared by the synthesis described in detail by Ball, M. et al in Organic Process Research and Development, (2016), 1799.

The clinical strains used in these experiments were as follows:

Group 1 (Strains where the Resistance is Primarily Due to Metallo β-Lactamase Enzymes):

NTBC020 (*E. coli* strain expressing NDM-1, TEM-1 and CTX-M-15); NTBC035-2 (*K. pneumoniae* strain expressing NDM-1, CMY-4 and SHV-11); NTBC104-1 (*K. pneumoniae* strain expressing NDM-1 and SHV-11); NTBC123 (*K. pneumoniae* strain expressing NDM-1); NTBC062 (*K. pneumoniae* strain expressing IMP-1 and TEM-1); NTBC024 (*K. pneumoniae* strain expressing VIM-19, TEM-1 and CTX-M-3); NTBC042 (*E. coli* strain expressing VIM-1, TEM-1, CTX-M-15, SHV-12); NTBC055 (*E. Coli* strain expressing VIM-1); and NTBC039 (*K. oxytoca* strain expressing IMP-28).

Group 2 (Strains where the Resistance is Due to Serine β-Lactamase Enzymes):

NTBC091-1 (*E. coli* strain expressing KPC-2 and TEM-1); NTBC093 (*E. cloacae* strain expressing KPC-2 and TEM-1); NTBC096-1 (*K. pneumonia* strain expressing OXA-181 and SHV-11); NTBC099 (*K. pneumonia* strain expressing KPC-3, SHV-11 and TEM-1); and NTBC189 (*K. pneumonia* strain expressing TEM-OSBL, CTX-M-14 and OXA-48).

Group 3 (Strains where the Resistance is Due to Both Serine and Metallo β-Lactamase Enzymes):

NTBC019 (*K. pneumonia* strain expressing NDM-1, CTX-M-15 and OXA-181); NTBC185 (*K. pneumonia* strain expressing SHV-OSBL, TEM-OSBL, NDM-1 and OXA-48); NTBC186 (*K. pneumonia* strain expressing ACT-TYPE, VIM-1 and OXA-48); NTBC187 (*K. pneumonia* strain expressing SHV-OSBL, NDM-1 and OXA-48); and NTBC188 (*K. pneumonia* strain expressing NDM-1 and KPC-2).

Results are shown below. Data are banded as follows: MIC values of <1 μg/mL are designated (A); MIC values of 1 or 2 g/mL are designated (B); MIC values of 4 or 8 μg/mL are designated (C); and MIC values ≥16 μg/mL are designated (D).

| Strain | MIC mero/ μg/mL | mero + WCK4234 (4 μg/mL) | mero + Ex. 2 (8 μg/mL) | mero + WCK4234 (4 ug/mL) + Ex. 2 (8 μg/mL) |
|---|---|---|---|---|
| Group 1 | | | | |
| NTBC020 | 128 | (D) | (A) | (A) |
| NTBC035-2 | 64 | (D) | (B) | (B) |
| NTBC104-1 | 64 | (D) | (A) | (A) |
| NTBC123 | 128 | (D) | (C) | (C) |
| NTBC062 | 4 | (C) | (B) | (B) |
| NTBC024 | 16 | (D) | (A) | (A) |
| NTBC042 | 8 | (C) | (B) | (B) |
| NTBC055 | 4 | (C) | (B) | (B) |
| Group 2 | | | | |
| NTBC091-1 | 4 | (A) | | |
| NTBC093 | 128 | (A) | | |
| NTBC096-1 | 16 | (A) | | |
| NTBC099 | 128 | (A) | | |
| NTBC189 | 16 | (A) | | |
| Group 3 | | | | |
| NTBC019 | 64 | (D) | (B) | (A) |
| NTBC185 | 128 | (D) | (D) | (C) |
| NTBC186 | 16 | (C) | (C) | (C) |
| NTBC187 | 128 | (D) | (D) | (C) |
| NTBC188 | 32 | (C) | (C) | (A) |

As can be seen for Group 1 and Group 2 strains, the dual combination of meropenem and appropriate β-lactamase inhibitor reduces the MIC required.

For Group 3 organisms the results indicate that the combination of a MBL inhibitor according to the invention and a SBL inhibitor (WCK4234) together with meropenem was capable of reducing the MIC required.

Discussion

In the antibacterial field there is no known example of triple therapy specifically for the eradication of bacterial infection. There is one known example of triple therapy for the management of gastro-oesophageal reflux disease (GORD) where *H. pylori* infection is suspected to be a component in the disorder as well as gastric ulcers, but in this case the National Institute of Clinical Excellence (NICE) guidelines recommend treatment with a triple combination of an anti-ulcer proton pump inhibitor with two antibiotics (amoxicillin and clarithromycin). Neither in development nor in the clinic are there any triple combination of antibacterial drugs or antibacterial drugs plus adjuvants such as a β-lactamase enzyme inhibitor.

One significant advantage offered by the triple combination of the invention is that when a CRE strain is encountered and rapid treatment is essential for the survival of the patient, the use of the triple combination means that in principle it is not essential to wait for microbiological and molecular characterisation of the resistance elements before commencing treatment. Thus, the triple combination described herein is useful in the prevention or treatment of any bacterial infection since it avoids the need for prior identification of the bacterial strain.

2. Further Data

Additional experiments were performed to demonstrate the advantages of the triple combination of the invention.

Experiments were conducted as described above. Compounds (the compounds of Examples 2 and 26) were tested at 8 µg/mL. Avibactam and Wck4234 were tested at 4 µg/mL. MIC values were determined for Strains tested expressed both carbapenemase one from class B (MBL) and one from class A or D (serine beta lactamase).

NTBC19 is *K. pneumoniae* expressing NDM-1; CTXM-15 and OXA-181.

NTBC188 is an *E. cloacae* expressing NDM-1 and KPC-2.

Data are banded as follows: MIC values of <0.5 µg/mL are designated (A); MIC values of 1-4 µg/mL are designated (B); MIC values of >8 µg/mL (8-512 µg/mL) are designated (C). Results are shown in the Table below.

|  | NTBC19 | NTBC188 |
|---|---|---|
| Meropenem | (C) | (C) |
| Meropenem + Avibactam | (C) | (C) |
| Meropenem + Wck4234 | (C) | (C) |
| Meropenem + Example 2 | (B) | (C) |
| Meropenem + Example 2 + Avibactam | (A) | (A) |
| Meropenem + Example 2 + WCK4234 | (A) | (A) |
| Meropenem + Example 26 | (B) | (C) |
| Meropenem + Example 26 + Avibactam | (A) | (A) |
| Meropenem + Example 26 + WCK4234 | (A) | (A) |

The data clearly show that the triple combination of (i) meropenem; (ii) a compound of the invention such as the compound of Example 2 or the compound of Example 26; and (iii) an SBL inhibitor such as avibactam or WCK4234 beneficially leads to decreased MIC values in both strains tested.

The invention claimed is:

1. A compound of Formula (I), or a pharmaceutically acceptable salt thereof,

[FORMULA (I)]

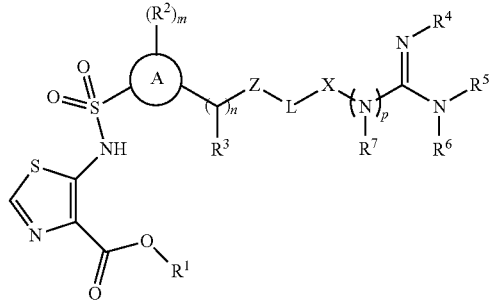

wherein
R$^1$ is selected from H, R$^{1a}$ and —CH$_2$OC(O)R$^{1a}$, wherein R$^{1a}$ is selected from an unsubstituted C$_1$ to C$_4$ alkyl group and phenyl;

Ⓐ is a cyclic group selected from C$_6$ to C$_{10}$ aryl and 5- to 10-membered heteroaryl;

each R$^2$ is independently selected from:
(i) halo or R$^8$;
(ii) C$_{1-3}$ alkyl, O(C$_{1-3}$ alkyl), S(C$_{1-3}$ alkyl), SO(C$_{1-3}$ alkyl) or SO$_2$(C$_{1-3}$ alkyl), any of which may optionally be substituted with 1, 2 or 3 halo substituents and/or one R'substituent; and
(iii) NR$^a$C(O)R$^c$, and NR$^a$C(O)NR$^b$R$^c$, wherein each R$^a$ and R$^b$ is independently selected from hydrogen and unsubstituted C$_{1-2}$ alkyl and each R$^c$ is unsubstituted C$_{1-2}$ alkyl;

and each R$^8$ is independently selected from CN, OH, —C(O)NR$^f$R$^g$, —NR$^f$R$^g$, —NR$^{10}$C(NR$^{11}$)R$^{12}$, —C(NR$^{10}$)NR$^{11}$R$^{12}$, and —NR$^{10}$C(NR$^{11}$)NR$^{12}$R$^{13}$; wherein each of R$^f$ and R$^g$ is independently H or unsubstituted C$_{1-2}$ alkyl;

m is 0, 1, 2 or 3

R$^3$ is selected from hydrogen and a C$_1$ to C$_3$ alkyl group which is unsubstituted or is substituted with 1, 2 or 3 substituents selected from halogen, —OR$^{10}$, and —NR$^{10}$R$^{11}$;

n is 0 or 1

Z is a bond or is selected from —NR$^{10}$C(O)—, —C(O)NR$^{10}$—, —NR$^{10}$C(O)NR$^{11}$—, —NR$^{10}$C(O)O—, —OC(O)NR$^{10}$, —NR$^{10}$C(O)S—, —SC(O)NR$^{10}$, —NR$^{10}$C(NR$^{11}$)—, —C(NR$^{10}$)NR$^{11}$—, —NR$^{10}$C(NR$^{11}$)NR$^{12}$—, —NR$^{10}$C(N$^+$R$^{11}$R$^{12}$)—, —C(N$^+$R$^{10}$R$^{11}$)NR$^{12}$—, —NR$^{10}$C(N$^+$R$^{11}$R$^{12}$)NR$^{13}$—, —NR$^{10}$C(NR$^{11}$)O—, —OC(NR$^{10}$)NR$^{11}$, —NR$^{10}$C(N$^+$R$^{11}$R$^{12}$)O—, —OC(N$^+$R$^{10}$R$^{11}$)NR$^{12}$—, —NR$^{10}$C(NR$^{11}$)S—, —SC(NR$^{10}$)NR$^{11}$, —NR$^{10}$C(N$^+$R$^{11}$R$^{12}$)S—, —SC(N$^+$R$^{10}$R$^{11}$)NR$^{12}$—, —C(O)NR$^{15}$—, —NR$^{10}$C(O)NR$^{15}$—, —OC(O)NR$^{15}$, —SC(O)NR$^{15}$, —C(NR$^{10}$)NR$^{15}$—, —NR$^{10}$C(NR$^{11}$)NR$^{15}$—, —C(N$^+$R$^{10}$R$^{11}$)NR$^{15}$—, —NR$^{10}$C(N$^+$R$^{11}$R$^{12}$)NR$^{15}$—, —OC(NR$^{10}$)NR$^{15}$, —OC(N$^+$R$^{10}$R$^{11}$)NR$^{15}$, —SC(NR$^{10}$)NR$^{15}$, and —SC(N$^+$R$^{10}$R$^{11}$)NR$^{15}$—;

L is a bond or is selected from C$_{1-4}$ alkylene, C$_{2-4}$ alkenylene, C$_{2-4}$ alkynylene, C$_{1-3}$ alkylene-(C$_{3-6}$cycloalkylene)-C$_{1-3}$ alkylene, C$_{1-4}$ alkylene-(C$_{3-6}$cycloalkylene) and (C$_{3-6}$cycloalkylene)-C$_{1-4}$ alkylene, wherein L is unsubstituted or is substituted with 1 or 2 substituents selected from halogen, —OR$^{10}$, and —NR$^{10}$R$_{11}$; or L is —C(R$^{10}$)=N—;

X is a bond or, when L is other than a bond or —C($R^{10}$)=N—, X is a bond or is selected from —$NR^{10}$—, —O—, —$NR^{10}$C($NR^{11}$)—, and —C($NR^{10}$)—;
p is 0 or 1;
$R^4$ is selected from H, —CN and $C_1$ to $C_3$ alkyl which is unsubstituted or is substituted with 1, 2 or 3 substituents selected from halogen, —$OR^{10}$, —$NR^{10}R^{11}$, and —CN;
$R^5$ is selected from H, —CN and $C_1$ to $C_3$ alkyl which is unsubstituted or is substituted with 1, 2 or 3 substituents selected from halogen, —$OR^{10}$, —$NR^{10}R^{11}$, and —CN;
$R^6$ is selected from H, —CN and $C_1$ to $C_3$ alkyl which is unsubstituted or is substituted with 1, 2 or 3 substituents selected from halogen, —$OR^{10}$, —$NR^{10}R^{11}$, and —CN;
$R^7$ if present is selected from H, —CN and $C_1$ to $C_3$ alkyl which is unsubstituted or is substituted with 1, 2 or 3 substituents selected from halogen, —$OR^{10}$, —$NR^{10}R^{11}$, and —CN;
each $R^{10}$, $R^{11}$, $R^{12}$, and $R^{13}$ is independently H or methyl;
each $R^{15}$ is independently substituted $C_1$ to $C_4$ alkyl or unsubstituted $C_2$ to $C_4$ alkyl, wherein when $R^{15}$ is a substituted $C_1$ to $C_4$ alkyl group, the alkyl group is substituted with 1, 2 or 3 substituents independently selected from halogen, CN, $OR^{10}$ and —$NR^{10}R^{11}$.

2. The compound according to claim 1 wherein $R^1$ is H.

3. The compound according to claim 1, wherein (A) is a cyclic group selected from phenyl and 5- to 6-membered heteroaryl.

4. The compound according to claim 1 wherein (A) is selected from phenyl, pyridazine, pyridine and thiazole.

5. The compound according to claim 1 wherein each $R^2$ is independently selected from:
 (i) halo, CN, OH, —C(O)$NR^fR^g$, or —$NR^fR^g$; wherein each of $R^f$ and $R^g$ is independently H or methyl; and
 (ii) $C_{1-2}$ alkyl, O($C_{1-2}$ alkyl), S($C_{1-2}$ alkyl), or SO($C_{1-2}$ alkyl); any of which may optionally be substituted with 1, 2 or 3 halo substituents and/or one substituent selected from CN and OH.

6. The compound according to claim 1 wherein $R^3$ is H.

7. The compound according to claim 1 wherein n is 0.

8. The compound according to claim 1 wherein Z is a bond or is selected from —$NR^{10}$C(O)—, —C(O)$NR^{10}$—, —$NR^{10}$C(O)$NR^{11}$—, —$NR^{10}$C(O)O—, —OC(O)$NR^{10}$, —$NR^{10}$C(O)S—, —SC(O)$NR^{10}$—, —$NR^{10}$C($NR^{11}$)—, —C($NR^{10}$)$NR^{11}$—, and —$NR^{10}$C($NR^{11}$)$NR^{12}$—.

9. The compound according to claim 1 wherein Z is selected from —$NR^{10}$C(O)—, —C(O)$NR^{10}$—, and —$NR^{10}$C(O)$NR^{11}$—.

10. The compound according to claim 1 wherein L is a bond or is selected from $C_{1-4}$ alkylene, $C_{2-4}$ alkenylene, and $C_{2-4}$ alkynylene;
or L is —C($R^{10}$)=N—.

11. The compound according to claim 1 wherein L is selected from $C_{1-3}$ alkylene and $C_{2-3}$ alkenylene.

12. The compound according to claim 1 wherein X is a bond.

13. The compound according to claim 1 wherein p is 1 and $R^7$ is H or methyl.

14. The compound according to claim 1 wherein $R^4$ is H.

15. The compound according to claim 1 wherein $R^5$ is selected from H, —CN and $C_1$ to $C_2$ alkyl which is unsubstituted or is substituted with 1, 2 or 3 halo substituents and/or one —$NR^{10}R^{11}$ substituent and $R^6$ is H or methyl.

16. The compound according to claim 1 wherein:
$R^1$ is H; (A) is a cyclic group selected from phenyl and 5- to 6-membered heteroaryl;
m is 0, 1 or 2;
each $R^2$ is independently selected from:
 halo or $R^8$;
 $C_{1-2}$ alkyl, O($C_{1-2}$ alkyl), S($C_{1-2}$ alkyl), SO($C_{1-2}$ alkyl) or $SO_2$($C_{1-2}$ alkyl), any of which may optionally be substituted with 1, 2 or 3 halo substituents and/or one $R^8$ substituent; and
 $NR^aC(O)R^c$, and $NR^aC(O)NR^bR^c$, wherein each $R^a$ and $R^b$ is independently selected from hydrogen and unsubstituted $C_{1-2}$ alkyl and each $R^c$ is unsubstituted $C_{1-2}$ alkyl;
each $R^8$ is independently selected from CN, OH, —C(O)$NR^fR^g$, and —$NR^fR^g$; wherein each of $R^f$ and $R^g$ is independently H or unsubstituted $C_{1-2}$ alkyl;
n is 0; or n is 1 and $R^3$ is H
Z is selected from —$NR^{10}$C(O)—, —C(O)$NR^{10}$—, —$NR^{10}$C(O)$NR^{11}$—, —$NR^{10}$C(O)O—, —OC(O)$NR^{10}$, —$NR^{10}$C(O)S—, —SC(O)$NR^{10}$, —$NR^{10}$C($NR^{11}$)—, —C($NR^{10}$)$NR^{11}$—, and —$NR^{10}$C($NR^{11}$)$NR^{12}$—;
L is a bond or is selected from $C_{1-4}$ alkylene, $C_{2-4}$ alkenylene and $C_{2-4}$ alkynylene; or L is —C($R^{10}$)=N—;
X is a bond;
i) p is 0;
 $R^4$ is H and $R^5$ is selected from H, —CN and $C_1$ to $C_2$ alkyl which is unsubstituted or is substituted with 1, 2 or 3 halo substituents and/or one —$NR^{10}R^{11}$ substituent; and
 $R^6$ is H or methyl;
or
ii) p is 1; and
 $R^4$ is H; $R^5$ is selected from H, —CN and $C_1$ to $C_2$ alkyl which is unsubstituted or is substituted with 1, 2 or 3 halo substituents and/or one —$NR^{10}R^{11}$ substituent; $R^6$ is H or methyl and $R^7$ is H or methyl.

17. The compound according to claim 1 wherein:
$R^1$ is H; (A) is selected from phenyl, pyridazine, pyridine and thiazole;
m is 1 or 2;
each $R^2$ is independently selected from:
or
 halo, CN, OH, —C(O)$NR^fR^g$, or —$NR^fR^g$; wherein each of $R^f$ and $R^9$ is independently H or methyl; and
 $C_{1-2}$ alkyl, O($C_{1-2}$ alkyl), S($C_{1-2}$ alkyl), or SO($C_{1-2}$ alkyl); any of which may optionally be substituted with 1, 2 or 3 substituents selected from halo, CN, OH;
n is 0;
Z is selected from —$NR^{10}$C(O)—, —C(O)$NR^{10}$—, and —$NR^{10}$C(O)$NR^{11}$—;
L is selected from $C_{1-3}$ alkylene and $C_{2-3}$ alkenylene;
X is a bond;
p is 0; or p is 1 and $R^7$ is H;
$R^4$ is H;
$R^5$ is selected from H, —CN and $C_1$ to $C_2$ alkyl which is unsubstituted or is substituted with 1, 2 or 3 halo substituents and/or one —$NR^{10}R^{11}$ substituent; and
$R^6$ is H.

18. The compound according to claim 1 wherein $R^4$, $R^5$, $R^6$ and $R^7$ if present are each hydrogen.

19. The compound according to claim 1, wherein:
R$^1$ is selected from H, R$^{1a}$ and —CH$_2$OC(O)R$^{1a}$, wherein R$^{1a}$ is selected from an unsubstituted C$_1$ to C$_4$ alkyl group and phenyl;
A is phenyl;
m is 2;
each R$^2$ is independently a halo group;
n is 0;
Z is —NR$^{10}$C(O)NR$^{11}$—;
L is a bond;
X is a bond;
p is 1;
R$^7$ is H;
R$^4$ is H;
R$^5$ is H;
R$^6$ is H; and
R$^{10}$ and R$^{11}$ are each H.

20. The compound according to claim 1, which compound is selected from:
5-[[4-[(2-guanidinoacetyl)amino]-3-(trifluoromethoxy)phenyl]sulfonylamino] thiazole-4-carboxylic acid;
5-[[3-fluoro-4-[[(2-guanidinoacetyl)amino]methyl]phenyl]sulfonylamino]thiazole-4-carboxylic acid;
5-[[3-fluoro-4-(guanidinomethyl)phenyl]sulfonylamino] thiazole-4-carboxylic acid;
5-[[3-fluoro-4-(2-guanidinoethylsulfanylcarbonylamino)phenyl]sulfonylamino] thiazole-4-carboxylic acid;
5-[[4-[2-[(2-amino-2-imino-ethyl)amino]-2-oxo-ethyl]-3-fluoro-phenyl]sulfonylamino]thiazole-4-carboxylic acid;
5-[[3-carbamoyl-4-[(2-guanidinoacetyl)amino]phenyl]sulfonylamino]thiazole-4-carboxylic acid;
5-[[3-cyano-4-[(2-guanidinoacetyl)amino]phenyl]sulfonylamino]thiazole-4-carboxylic acid;
5-[[3-fluoro-4-(2-guanidinoethoxycarbonylamino)phenyl]sulfonylamino]thiazole-4-carboxylic acid;
5-[(4-guanidinophenyl)sulfonylamino]thiazole-4-carboxylic acid;
5-[[4-[2-(2-carbamimidoylhydrazino)-2-oxo-ethyl]-3-fluoro-phenyl]sulfonylamino]thiazole-4-carboxylic acid;
5-[[3-chloro-4-[(2-guanidinoacetyl)amino]phenyl]sulfonylamino]thiazole-4-carboxylic acid;
5-[[4-[(2-guanidinoacetyl)amino]-3-methoxy-phenyl]sulfonylamino]thiazole-4-carboxylic acid;
5-[[4-[[2-(2-carbamimidoylhydrazino)acetyl]amino]-3-fluoro-phenyl]sulfonylamino]thiazole-4-carboxylic acid;
5-[[4-[[(2E)-2-(carbamimidoylhydrazono)acetyl]amino]-3-fluoro-phenyl]sulfonylamino]thiazole-4-carboxylic acid;
5-[[4-[[2-(4,5-dihydro-1H-imidazol-2-ylamino)acetyl]amino]-3,5-difluoro-phenyl]sulfonylamino]thiazole-4-carboxylic acid;
5-[[6-[(2-guanidinoacetyl)amino]pyridazin-3-yl]sulfonylamino]thiazole-4-carboxylic acid;
5-[[4-[(2-amino-2-imino-ethyl)carbamoylamino]-3-fluoro-phenyl]sulfonylamino]thiazole-4-carboxylic acid;
5-[[4-[(3-amino-3-imino-propanoyl)amino]-3,5-difluoro-phenyl]sulfonylamino] thiazole-4-carboxylic acid;
5-[[4-[[3-(dimethylamino)-3-imino-propanoyl]amino]-3-fluoro-phenyl]sulfonylamino]thiazole-4-carboxylic acid;
5-[[3-fluoro-4-[(2-guanidinooxyacetyl)amino]phenyl]sulfonylamino]thiazole-4-carboxylic acid;
5-[[3-fluoro-4-[[3-imino-3-(methylamino)propanoyl]amino]phenyl]sulfonylamino]thiazole-4-carboxylic acid;
5-[[4-[3-(4,5-dihydro-1H-imidazol-2-yl)propanoylamino]-3-fluoro-phenyl]sulfonylamino]thiazole-4-carboxylic acid;
5-[[2-[(2-guanidinoacetyl)amino]thiazol-5-yl]sulfonylamino]thiazole-4-carboxylic acid;
5-[[4-[[2-[(N-cyanocarbamimidoyl)amino]acetyl]amino]-3-fluoro-phenyl]sulfonylamino]thiazole-4-carboxylic acid;
5-[[3-fluoro-4-(guanidinocarbamoylamino)phenyl]sulfonylamino]thiazole-4-carboxylic acid;
5-[[3-fluoro-4-[[2-(morpholine-4-carboximidoylamino)acetyl]amino]phenyl]sulfonylamino]thiazole-4-carboxylic acid;
5-[[4-[(3-amino-3-imino-2-methyl-propanoyl)amino]-3-fluoro-phenyl]sulfonylamino]thiazole-4-carboxylic acid;
5-[[4-[[2-(4,5-dihydro-1H-imidazol-2-yl)acetyl]amino]-3-fluoro-phenyl]sulfonylamino]thiazole-4-carboxylic acid;
5-[[4-(carbamimidoylcarbamoylamino)-3-fluoro-phenyl]sulfonylamino]thiazole-4-carboxylic acid;
5-[[4-[[(2R)-2-guanidinopropanoyl]amino]phenyl]sulfonylamino]thiazole-4-carboxylic acid;
5-[[3,5-difluoro-4-[(2-guanidinoacetyl)amino]phenyl]sulfonylamino]thiazole-4-carboxylic acid;
5-[[4-[(4-amino-4-imino-butanoyl)amino]-3-fluoro-phenyl]sulfonylamino]thiazole-4-carboxylic acid;
5-[[4-[[2-(4,5-dihydro-1H-imidazol-2-ylamino)acetyl]amino]-2,5-difluoro-phenyl]sulfonylamino]thiazole-4-carboxylic acid;
5-[[2,5-difluoro-4-[(2-guanidinoacetyl)amino]phenyl]sulfonylamino]thiazole-4-carboxylic acid;
5-[[3-fluoro-4-[[2-[(N-methylcarbamimidoyl)amino]acetyl]amino]phenyl]sulfonylamino]thiazole-4-carboxylic acid;
5-[[3-fluoro-4-[[2-(2-iminoimidazobdin-1-yl)acetyl]amino]phenyl]sulfonylamino]thiazole-4-carboxylic acid;
5-[[4-[[2-[carbamimidoyl(methyl)amino]acetyl]amino]-3-fluoro-phenyl]sulfonylamino]thiazole-4-carboxylic acid;
5-[[4-[[2-[[N-(2-aminoethyl)carbamimidoyl]amino]acetyl]amino]-3-fluoro-phenyl]sulfonylamino]thiazole-4-carboxylic acid;
5-[[5-fluoro-6-[(2-guanidinoacetyl)amino]-3-pyridyl]sulfonylamino]thiazole-4-carboxylic acid;
5-[[3-fluoro-4-(3-guanidinopropanoylamino)phenyl]sulfonylamino]thiazole-4-carboxylic acid;
5-[[4-[(3-amino-3-imino-propanoyl)amino]-3-fluoro-phenyl]sulfonylamino]thiazole-4-carboxylic acid;
5-[[3-fluoro-4-[(2-guanidinoacetyl)amino]phenyl]sulfonylamino]thiazole-4-carboxylic acid; and
5-[[4-[(2-guanidinoacetyl)amino]phenyl]sulfonylamino] thiazole-4-carboxylic acid;
and pharmaceutically acceptable salts thereof.

21. A pharmaceutical composition comprising the compound according to claim 1 together with at least one pharmaceutically acceptable carrier or diluent.

22. The pharmaceutical composition according to claim 21 further comprising an antibiotic agent.

23. The pharmaceutical composition according to claim 22 wherein the antibiotic agent is a β-lactam antibiotic.

24. The pharmaceutical composition according to claim 23 wherein the β-lactam antibiotic is selected from carbapenems, penicillins, cephalosporins and penems.

25. The pharmaceutical composition according to claim 23 wherein the β-lactam antibiotic is meropenem.

26. The pharmaceutical composition according to claim 21 further comprising a serine-β-lactamase inhibitor.

27. The pharmaceutical composition according to claim 26 wherein the serine-β-lactamase inhibitor is a compound of Formula (II) or a pharmaceutically acceptable salt thereof,

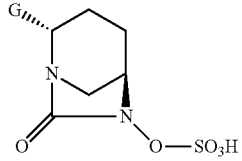

[FORMULA (II)]

wherein
  G is selected from —CN and —C(O)NR$^j$R$^k$;
  R$^k$ is selected from —W and -Q-W; wherein W is selected from 5- to 6-membered heterocyclyl, R$^j$ and —N(R$^j$)$_2$; and Q is selected from —NR$^j$C(O)—, —C(O)—NR$^j$—, C$_{1-3}$ alkylene, —O—C$_{1-3}$ alkylene and —N(R$^j$)—C$_{1-3}$ alkylene;
  each R$^j$ is selected from H and unsubstituted C$_{1-3}$ alkyl.

28. The pharmaceutical composition according to claim 26 wherein the serine-β-lactamase inhibitor is selected from WCK4234, avibactam, relebactam, zidebactam and nacubactam, or pharmaceutically acceptable salts thereof.

* * * * *

UNITED STATES PATENT AND TRADEMARK OFFICE
CERTIFICATE OF CORRECTION

| | | |
|---|---|---|
| PATENT NO. | : 11,299,467 B2 | Page 1 of 5 |
| APPLICATION NO. | : 16/631218 | |
| DATED | : April 12, 2022 | |
| INVENTOR(S) | : David Thomas Davies et al. | |

It is certified that error appears in the above-identified patent and that said Letters Patent is hereby corrected as shown below:

In the Claims

Column 135, Lines 66-67 and Column 136, Lines 1-67 and Column 137, Lines 1-27:
Claim 1 should read:
-- 1. A compound of Formula (I), or a pharmaceutically acceptable salt thereof,

[FORMULA (I)]

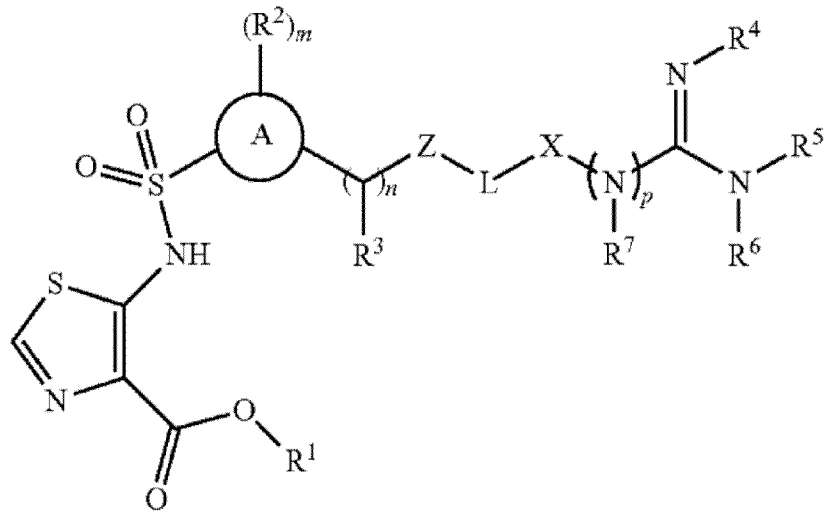

wherein
    $R^1$ is selected from H, $R^{1a}$ and $-CH_2OC(O)R^{1a}$, wherein
        $R^{1a}$ is selected from an unsubstituted $C_1$ to $C_4$ alkyl group and phenyl;
    Ⓐ is a cyclic group selected from $C_6$ to $C_{10}$ aryl and 5- to 10-membered heteroaryl;
    each $R^2$ is independently selected from:
    (i) halo or $R^8$;

Signed and Sealed this
Third Day of January, 2023

*Katherine Kelly Vidal*

Katherine Kelly Vidal
*Director of the United States Patent and Trademark Office*

CERTIFICATE OF CORRECTION (continued)

(ii) $C_{1-3}$ alkyl, $O(C_{1-3}$ alkyl), $S(C_{1-3}$ alkyl), $SO(C_{1-3}$ alkyl) or $SO_2(C_{1-3}$ alkyl), any of which may optionally be substituted with 1, 2 or 3 halo substituents and/or one $R^8$ substituent;

and (iii) $NR^aC(O)R^c$, and $NR^aC(O)NR^bR^c$, wherein each $R^a$ and $R^b$ is independently selected from hydrogen and unsubstituted $C_{1-2}$ alkyl and each $R^c$ is unsubstituted $C_{1-2}$ alkyl;

and each $R^8$ is independently selected from CN, OH, $-C(O)N^fR^g$, $-NR^fR^g$, $-NR^{10}C(NR^{11})R^{12}$, $-C(NR^{10})NR^{11}R^{12}$, and $-NR^{10}C(NR^{11})NR^{12}R^{13}$;

wherein each of $R^f$ and $R^g$ is independently H or unsubstituted $C_{1-2}$ alkyl;

m is 0, 1, 2 or 3

$R^3$ is selected from hydrogen and a $C_1$ to $C_3$ alkyl group which is unsubstituted or is substituted with 1, 2 or 3 substituents selected from halogen, $-OR^{10}$, and $-NR^{10}R^{11}$;

n is 0 or 1

Z is a bond or is selected from $-NR^{10}C(O)-$, $-C(O)NR^{10}-$, $-NR^{10}C(O)NR^{11}-$, $-NR^{10}C(O)O-$, $-OC(O)NR^{10}$, $-NR^{10}C(O)S-$, $-SC(O)NR^{10}$, $-NR^{10}C(NR^{11})-$, $-C(NR^{10})NR^{11}-$, $-NR^{10}C(NR^{11})NR^{12}-$, $-NR^{10}C(N^+R^{11}R^{12})-$, $-C(N^+R^{10}R^{11})NR^{12}-$, $-NR^{10}C(N^+R^{11}R^{12})NR^{13}-$, $-NR^{10}C(NR^{11})O-$, $-OC(NR^{10})NR^{11}$, $-NR^{10}C(N^+R^{11}R^{12})O-$, $-OC(N^+R^{10}R^{11})NR^{12}-$, $-NR^{10}C(NR^{11})S-$, $-SC(NR^{10})NR^{11}$, $-NR^{10}C(N^+R^{11}R^{12})S-$, $-SC(N^+R^{10}R^{11})NR^{12}-$, $-C(O)NR^{15}-$, $-NR^{10}C(O)NR^{15}-$, $-OC(O)NR^{15}$, $-SC(O)NR^{15}$, $-C(NR^{10})NR^{15}-$, $-NR^{10}C(NR^{11})NR^{15}-$, $-C(N^+R^{10}R^{11})NR^{15}-$, $-NR^{10}C(N^+R^{11}R^{12})NR^{15}-$, $-OC(NR^{10})NR^{15}$, $-OC(N^+R^{10}R^{11})NR^{15}-$, $-SC(NR^{10})NR^{15}$, and $-SC(N^+R^{10}R^{11})NR^{15}-$;

L is a bond or is selected from $C_{1-4}$ alkylene, $C_{2-4}$ alkenylene, $C_{2-4}$ alkynylene, $C_{1-3}$ alkylene-($C_{3-6}$cycloalkylene)-$C_{1-3}$ alkylene, $C_{1-4}$ alkylene-($C_{3-6}$cycloalkylene) and ($C_{3-6}$cycloalkylene)-$C_{1-4}$ alkylene, wherein L is unsubstituted or is substituted with 1 or 2 substituents selected from halogen, $-OR^{10}$, and $-NR^{10}R^{11}$; or L is $-C(R^{10})=N-$;

X is a bond or, when L is other than a bond or $-C(R^{10})=N-$, X is a bond or is selected from $-NR^{10}-$, $-O-$, $-NR^{10}C(NR^{11})-$, and $-C(NR^{10})-$;

p is 0 or 1;

$R^4$ is selected from H, -CN and $C_1$ to $C_3$ alkyl which is unsubstituted or is substituted with 1, 2 or 3 substituents selected from halogen, $-OR^{10}$, $-NR^{10}R^{11}$, and -CN;

$R^5$ is selected from H, -CN and $C_1$ to $C_3$ alkyl which is unsubstituted or is substituted with 1, 2 or 3 substituents selected from halogen, $-OR^{10}$, $-NR^{10}R^{11}$, and -CN;

$R^6$ is selected from H, -CN and $C_1$ to $C_3$ alkyl which is unsubstituted or is substituted with 1, 2 or 3 substituents selected from halogen, $-OR^{10}$, $-NR^{10}R^{11}$, and -CN;

$R^7$ if present is selected from H, -CN and $C_1$ to $C_3$ alkyl which is unsubstituted or is substituted with 1, 2 or 3 substituents selected from halogen, $-OR^{10}$, $-NR^{10}R^{11}$, and -CN;

each $R^{10}$, $R^{11}$, $R^{12}$, and $R^{13}$ is independently H or methyl;

each $R^{15}$ is independently substituted $C_1$ to $C_4$ alkyl or unsubstituted $C_2$ to $C_4$ alkyl, wherein when $R^{15}$ is a substituted $C_1$ to $C_4$ alkyl group, the alkyl group is substituted with 1, 2 or 3 substituents independently selected from halogen, CN, $OR^{10}$ and $-NR^{10}R^{11}$. --

Column 138, Lines 42-65:
Claim 17 should read:
-- 17. The compound according to claim 1 wherein:

CERTIFICATE OF CORRECTION (continued)
U.S. Pat. No. 11,299,467 B2

Page 3 of 5

$R^1$ is H; Ⓐ is selected from phenyl, pyridazine, pyridine and thiazole;
m is 1 or 2;
each $R^2$ is independently selected from:
    halo, CN, OH, -C(O)NR$^f$R$^g$, or -N$^f$R$^g$; wherein each of R$^f$ and R$^g$ is independently H or methyl; and
    $C_{1-2}$ alkyl, O($C_{1-2}$ alkyl), S($C_{1-2}$ alkyl), or SO($C_{1-2}$ alkyl); any of which may optionally be substituted with 1, 2 or 3 substituents selected from halo, CN, OH;
n is 0;
Z is selected from -NR$^{10}$C(O)-, -C(O)NR$^{10}$-, and -NR$^{10}$C(O)NR$^{11}$-;
L is selected from $C_{1-3}$ alkylene and $C_{2-3}$ alkenylene;
X is a bond;
p is 0; or p is 1 and $R^7$ is H;
$R^4$ is H;
$R^5$ is selected from H, -CN and $C_1$ to $C_2$ alkyl which is unsubstituted or is substituted with 1, 2 or 3 halo substituents and/or one -NR$^{10}$R$^{11}$ substituent; and
$R^6$ is H. --

Column 139, Lines 19-67 and Column 140, Lines 1-60:
Claim 20 should read:
-- 20. The compound according to claim 1, which compound is selected from:
    5-[[4-[ (2-guanidinoacetyl)amino]-3-(trifluoromethoxy)phenyl]sulfonylamino]thiazole-4-carboxylic acid;
    5-[[3-fluoro-4-[[(2-guanidinoacetyl)amino]methyl]phenyl]sulfonylamino]thiazole-4-carboxylic acid;
    5-[[3-fluoro-4-(guanidinomethyl)phenyl]sulfonylamino]thiazole-4-carboxylic acid;
    5-[[3-fluoro-4-(2-guanidinoethylsulfanylcarbonylamino)phenyl]sulfonylamino]thiazole-4-carboxylic acid;
    5-[[ 4-[2-[(2-amino-2-imino-ethyl)amino ]-2-oxo-ethyl]-3-fluoro-phenyl]sulfonylamino]thiazole-4-carboxylic acid;
    5-[[3-carbamoyl-4-[(2-guanidinoacetyl)amino]phenyl]sulfonylamino]thiazole-4-carboxylic acid;
    5-[[3-cyano-4-[(2-guanidinoacetyl)amino]phenyl]sulfonylamino]thiazole-4-carboxylic acid;
    5-[[3-fluoro-4-(2-guanidinoethoxycarbonylamino)phenyl]sulfonylamino]thiazole-4-carboxylic acid;
    5-[(4-guanidinophenyl)sulfonylamino]thiazole-4-carboxylic acid;
    5-[[ 4-[2-(2-carbamimidoylhydrazino)-2-oxo-ethyl ]-3-fluoro-phenyl]sulfonylamino]thiazole-4-carboxylic acid;
    5-[[3-chloro-4-[ (2-guanidinoacetyl)amino]phenyl]sulfonylamino]thiazole-4-carboxylic acid;
    5-[[4-[(2-guanidinoacetyl)amino]-3-methoxy-phenyl]sulfonylamino]thiazole-4-carboxylic acid;
    5-[[4-[[2-(2-carbamimidoylhydrazino)acetyl]amino]-3-fluoro-phenyl]sulfonylamino]thiazole-4-carboxylic acid;
    5-[[4-[[(2E)-2-(carbamimidoylhydrazono)acetyl]amino]-3-fluoro-phenyl]sulfonylamino]thiazole-4-carboxylic acid;
    5-[[4-[[2-(4,5-dihydro-1H-imidazol-2-ylamino)acetyl]amino]-3,5-difluoro-phenyl]

sulfonylamino]thiazole-4-carboxylic acid;

5-[[6-[(2-guanidinoacetyl)amino]pyridazin-3-yl]sulfonylamino]thiazole-4-carboxylic acid;

5-[[4-[(2-amino-2-imino-ethyl)carbamoylamino]-3-fluoro-phenyl]sulfonylamino]thiazole-4-carboxylic acid;

5-[[4-[(3-amino-3-imino-propanoyl)amino]-3,5-difluorophenyl]sulfonylamino]thiazole-4-carboxylic acid;

5-[[4-[[3-(dimethylamino)-3-imino-propanoyl]amino]-3-fluoro-phenyl]sulfonylamino]thiazole-4-carboxylic acid;

5-[[3-fluoro-4-[(2-guanidinooxyacetyl)amino]phenyl]sulfonylamino]thiazole-4-carboxylic acid;

5-[[3-fluoro-4-[[3-imino-3-(methylamino)propanoyl]amino]phenyl]sulfonylamino]thiazole-4-carboxylic acid;

5-[[4-[3-(4,5-dihydro-lH-imidazol-2-yl)propanoylamino]-3-fluoro-phenyl]sulfonylamino]thiazole-4-carboxylic acid;

5-[[2-[(2-guanidinoacetyl)amino]thiazol-5-yl]sulfonylamino]thiazole-4-carboxylic acid;

5-[[4-[[2-[(N-cyanocarbamimidoyl)amino]acetyl]amino]-3-fluoro-phenyl]sulfonylamino]thiazole-4-carboxylic acid;

5-[[3-fluoro-4-(guanidinocarbamoylamino)phenyl]sulfonylamino]thiazole-4-carboxylic acid;

5-[[3-fluoro-4-[[2-(morpholine-4-carboximidoylamino)acetyl]amino]phenyl]sulfonylamino]thiazole-4-carboxylic acid;

5-[[4-[(3-amino-3-imino-2-methyl-propanoyl)amino]-3-fluoro-phenyl]sulfonylamino]thiazole-4-carboxylic acid;

5-[[4-[[2-(4,5-dihydro-lH-imidazol-2-yl)acetyl]amino]-3-fluoro-phenyl]sulfonylamino]thiazole-4-carboxylic acid;

5-[[4-(carbamimidoylcarbamoylamino)-3-fluoro-phenyl]sulfonylamino]thiazole-4-carboxylic acid;

5-[[4-[[(2R)-2-guanidinopropanoyl]amino]phenyl]sulfonylamino]thiazole-4-carboxylic acid;

5-[[3,5-difluoro-4-[(2-guanidinoacetyl)amino]phenyl]sulfonylamino]thiazole-4-carboxylic acid;

5-[[4-[(4-amino-4-imino-butanoyl)amino]-3-fluoro-phenyl]sulfonylamino]thiazole-4-carboxylic acid;

5-[[4-[[2-(4,5-dihydro-lH-imidazol-2-ylamino)acetyl]amino]-2,5-difluoro-phenyl]sulfonylamino]thiazole-4-carboxylic acid;

5-[[2,5-difluoro-4-[(2-guanidinoacetyl)amino]phenyl]sulfonylamino]thiazole-4-carboxylic acid;

5-[[3-fluoro-4-[[2-[(N-methylcarbamimidoyl)amino]acetyl]amino]phenyl]sulfonylamino]thiazole-4-carboxylic acid;

5-[[3-fluoro-4-[[2-(2-iminoimidazolidin-1-yl)acetyl]amino]phenyl]sulfonylamino]thiazole-4-carboxylic acid;

5-[[4-[[2-[carbamimidoyl(methyl)amino]acetyl]amino]-3-fluoro-phenyl]sulfonylamino]thiazole-4-carboxylic acid;

5-[[4-[[2-[[N-(2-aminoethyl)carbamimidoyl]amino]acetyl]amino]-3-fluoro-phenyl]sulfonylamino]thiazole-4-carboxylic acid;

5-[[5-fluoro-6-[(2-guanidinoacetyl)amino]-3-pyridyl]sulfonylamino]thiazole-4-carboxylic acid;

5-[[3-fluoro-4-(3-guanidinopropanoylamino)phenyl]sulfonylamino]thiazole-4-carboxylic acid;

5-[[4-[(3-amino-3-imino-propanoyl)amino]-3-fluorophenyl]sulfonylamino]thiazole-4-carboxylic acid;

5-[[3-fluoro-4-[(2-guanidinoacetyl)amino]phenyl]sulfonylamino]thiazole-4-carboxylic acid; and 5-[[4-[(2-guanidinoacetyl)amino]phenyl]sulfonylamino]thiazole-4-carboxylic acid;

and pharmaceutically acceptable salts thereof. --